(12) United States Patent
Petrassi et al.

(10) Patent No.: US 11,427,560 B2
(45) Date of Patent: Aug. 30, 2022

(54) COMPOSITION AND METHODS FOR INHIBITING MAMMALIAN STERILE 20-LIKE KINASE 1

(71) Applicants: The Scripps Research Institute, La Jolla, CA (US); Universität Bremen, Bremen (DE)

(72) Inventors: Hank Michael James Petrassi, San Diego, CA (US); Murali Mohan Reddy Peram Surakattula, San Diego, CA (US); Kathrin Maedler, Bremen (DE); Amin Ardestani, Bremen (DE); Jason T. Roland, San Diego, CA (US); Tyler D. Baguley, San Diego, CA (US); Matthew S. Tremblay, San Diego, CA (US); Weijun Shen, San Diego, CA (US); Peter G. Schultz, La Jolla, CA (US); Arnab K. Chatterjee, San Diego, CA (US)

(73) Assignees: THE SCRIPPS RESEARCH INSTITUTE, La Jolla, CA (US); UNIVERSITÄT BREMEN, Bremen (DE)

( * ) Notice: Subject to any disclaimer, the term of this patent is extended or adjusted under 35 U.S.C. 154(b) by 0 days.

(21) Appl. No.: 16/998,963

(22) Filed: Aug. 20, 2020

(65) Prior Publication Data
US 2021/0061784 A1    Mar. 4, 2021

Related U.S. Application Data

(63) Continuation of application No. 15/738,986, filed as application No. PCT/US2016/039388 on Jun. 24, 2016, now Pat. No. 10,774,068.

(60) Provisional application No. 62/258,634, filed on Nov. 23, 2015, provisional application No. 62/184,781, filed on Jun. 25, 2015, provisional application No. 62/184,813, filed on Jun. 25, 2015.

(51) Int. Cl.
| | |
|---|---|
| *C07D 401/12* | (2006.01) |
| *A61K 31/47* | (2006.01) |
| *C12N 9/12* | (2006.01) |
| *A61K 31/517* | (2006.01) |
| *A61K 31/4709* | (2006.01) |
| *C07D 215/44* | (2006.01) |
| *C07D 215/46* | (2006.01) |
| *C07D 413/12* | (2006.01) |
| *C07D 471/04* | (2006.01) |
| *C07D 491/052* | (2006.01) |
| *C07D 491/056* | (2006.01) |

(52) U.S. Cl.
CPC ............ *C07D 401/12* (2013.01); *A61K 31/47* (2013.01); *A61K 31/4709* (2013.01); *A61K 31/517* (2013.01); *C07D 215/44* (2013.01); *C07D 215/46* (2013.01); *C07D 413/12* (2013.01); *C07D 471/04* (2013.01); *C07D 491/052* (2013.01); *C07D 491/056* (2013.01); *C12N 9/12* (2013.01); *C12Y 207/11001* (2013.01)

(58) Field of Classification Search
CPC .. C07D 401/12; C07D 215/44; C07D 215/46; C07D 413/12; C07D 471/04; C07D 491/052; C07D 491/056; A61K 31/47; A61K 31/4709
See application file for complete search history.

(56) References Cited

U.S. PATENT DOCUMENTS

| | | |
|---|---|---|
| 6,821,988 B2 | 11/2004 | Wissner et al. |
| 8,747,421 B2 | 6/2014 | Balbierz et al. |
| 10,774,068 B2 | 9/2020 | Petrassi et al. |
| 2014/0051681 A1 | 2/2014 | Augeri et al. |
| 2015/0030588 A1 | 1/2015 | Jessen et al. |

FOREIGN PATENT DOCUMENTS

| | | |
|---|---|---|
| CN | 103965120 A | 8/2014 |
| WO | WO-2009052264 A2 | 4/2009 |
| WO | WO-2014187964 A2 | 11/2014 |

OTHER PUBLICATIONS

Song,PNAS, Jan. 2010, vol. 107(4), p. 1431-1436. (Year: 2010).*
International Application No. PCT/US2016/039388 International Preliminary Report on Patentability dated Dec. 26, 2017.
International Application No. PCT/US2016/039388 International Search Report and Written Opinion dated Sep. 8, 2016.
PubChem SID 243568820 Mar. 16, 2015 [Retrieved from internet:<https://pubchem.ncbi.nim.nih.gov/substance/243568820#section=Top> (entire document).
Tsou et al., Optimization of 6,7-Disubstituted-4-(arylamino)quinoline-3-carbonitriles as Orally Active, Irreversible Inhibitors of Human Epidermal Growth Factor Receptor-2 Kinase Activity. Journal of Medicinal Chemistry. 48(4):1107-1131 (2005).
U.S. Appl. No. 15/738,986 Final Office Action dated Jan. 22, 2020.
U.S. Appl. No. 15/738,986 Office Action dated Jul. 17, 2019.
Fan et al., Pharmacological targeting of kinases MST1 and MST2 augments tissue repair and regeneration. Science Translational Medicine 8(325): 1-14 (2016).
Gao et al., Constitutive androstane receptor induced-hepatomegaly and liver regeneration is partially via yes-associated protein activation. Acta Pharm Sin B. Mar. 2021;11(3):727-737.
Liu et al., Macrophage MST1/2 Disruption Impairs Post-Infarction Cardiac Repair via LTB4. Circ Res. Oct. 29, 2021;129(10):909-926.
Wang et al., The Hippo pathway in tissue homeostasis and regeneration. Protein Cell. May 2017;8(5):349-359.

\* cited by examiner

*Primary Examiner* — D Margaret M Seaman
(74) *Attorney, Agent, or Firm* — Wilson Sonsini Goodrich & Rosati

(57) ABSTRACT

Disclosed herein are compounds, compositions, and methods of their use for the treatment of diabetes.

19 Claims, 5 Drawing Sheets

COMPOSITION AND METHODS FOR INHIBITING MAMMALIAN STERILE 20-LIKE KINASE 1

CROSS-REFERENCE

This application is a continuation of U.S. patent application Ser. No. 15/738,986, filed on Dec. 21, 2017, which is a U.S. National Stage entry of International Application No. PCT/US2016/039388, filed on Jun. 24, 2016, which claims benefit of U.S. Provisional Application No. 62/184,813, filed on Jun. 25, 2015, U.S. Provisional Application No. 62/184,781, filed on Jun. 25, 2015, and U.S. Provisional Application No. 62/258,634, filed on Nov. 23, 2015, which are herein incorporated by reference in their entirety.

BACKGROUND OF THE INVENTION

Beta cells of the pancreas produce insulin, which is required for cells to take up glucose. Under normal conditions, blood glucose levels rise after eating, triggering pancreatic insulin release. However, in subjects with insulin dependent diabetes mellitus (type 1 diabetes (T1D)), beta cells are damaged by autoimmune inflammation, leading to an insufficiency of insulin. In contrast, subjects with non-insulin-dependent diabetes mellitus (type 2 diabetes (T2D)), have normal or high levels of insulin, but a resistance to insulin in peripheral tissues. Beta cells are not able increase secretion of insulin to overcome this resistance. Apoptosis of beta cells occurs in both type I and type II diabetes. Therapies for both T1D and T2D include those that require strict dietary regimens and/or drugs that are often not well tolerated long term, both of which make adherence to these therapies challenging for patients. Thus, additional and/or alternative therapies are desirable.

SUMMARY OF THE INVENTION

Disclosed herein are compounds, or a pharmaceutically acceptable salt, solvate, or prodrug thereof, that modulate an activity of a mammalian sterile 20-like kinase 1 (MST1), a cleaved product thereof, or a homolog thereof. Further disclosed herein are compounds, or a pharmaceutically acceptable salt, solvate, or prodrug thereof, that inhibit the activity of a mammalian sterile 20-like kinase 1 (MST1), a cleaved product thereof, or a homolog thereof. Also disclosed herein are methods of treating a metabolic condition in a subject comprising administering to the subject a compound described herein that modulates an activity of a mammalian sterile 20-like kinase 1 (MST1), a cleaved product thereof, or a homolog thereof. In some embodiments, the metabolic condition is diabetes mellitus. In some embodiments, the metabolic condition is selected from type 1 diabetes mellitus and type 2 diabetes mellitus. In some embodiments, the metabolic condition is type 1 diabetes mellitus. In some embodiments, the metabolic condition is type 2 diabetes mellitus. In some embodiments, the compound inhibits the activity of a mammalian sterile 20-like kinase 1 (MST1), a cleaved product thereof, or a homolog thereof. In some embodiments, the activity is selected from a phosphorylation activity, an inflammatory activity, a cleavage activity, an apoptotic activity, a ubiquinating activity, a mitochondrial activity, and combinations thereof. In some embodiments, the compound inhibits phosphorylation of a protein downstream of the activity of the mammalian sterile 20-like kinase 1, the cleaved product thereof, or the homolog thereof. In some embodiments, the protein downstream is selected from a transcription factor, a kinase, and a histone. In some embodiments, the transcription factor is pancreatic and duodenal homeobox 1 (PDX-1) or a homolog thereof. In some embodiments, the histone is histone 2B (H2B). In some embodiments, the kinase is a Janus kinase (JNK). In some embodiments, the compound inhibits cleavage of a protein downstream of the activity of the mammalian sterile 20-like kinase 1, the cleaved product thereof, or the homolog thereof. In some embodiments, the protein downstream is a caspase. In some embodiments, the caspase is selected from caspase 9, caspase 3 and MST1. In some embodiments, the compound inhibits apoptotic activity of a protein downstream of the activity of the mammalian sterile 20-like kinase 1, the cleaved product thereof, or the homolog thereof. In some embodiments, the protein downstream is selected from JNK, Bim, Bax, Bcl-2, homologs thereof, and combinations thereof. In some embodiments, the compound is neratinib.

Further disclosed herein are methods of treating an inflammatory condition in a subject comprising administering to the subject a compound that inhibits an activity of a mammalian sterile 20-like kinase 1 (MST1), a cleaved product thereof, or a homolog thereof. Also disclosed herein are methods of treating an autoimmune disorder in a subject comprising administering to the subject a compound that inhibits an activity of a mammalian sterile 20-like kinase 1 (MST1), a cleaved product thereof, or a homolog thereof. In some embodiments, the compound is neratinib.

In some embodiments of the methods described herein, the compound is a compound of Formula (I) having the structure:

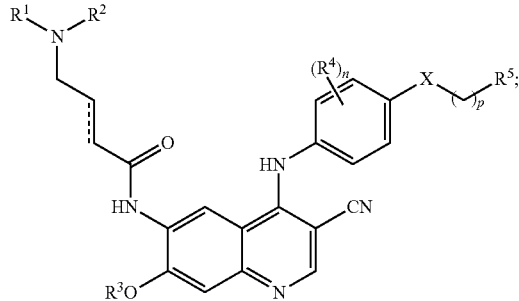

Formula (I)

wherein:
$=\!\!=\!\!=$ is a single or double bond;
X is —O—, —N(H)—, or —CH$_2$—;
R$^1$ and R$^2$ are each independently C$_{1-6}$alkyl; or R$^1$ and R$^2$ together with the nitrogen to which they are attached are combined to form a heterocycloalkyl ring;
R$^3$ is C$_{1-6}$alkyl;
each R$^4$ is independently halogen, C$_{1-6}$alkyl, C$_{1-6}$alkoxy, C$_{1-6}$haloalkyl, or —CN;
R$^5$ is aryl or heteroaryl, wherein aryl and heteroaryl are unsubstituted or substituted by one or more substituents selected from halogen, C$_{1-6}$alkyl, C$_{1-6}$alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl;
R$^6$ is H or C$_{1-6}$alkyl;
n is 0, 1, 2, or 3; and
p is 1, 2, or 3;
or a pharmaceutically acceptable salt, solvate, or prodrug thereof.

In some embodiments of the methods described herein, the compound is a compound of Formula (I) wherein p is 1. In some embodiments of the methods described herein, the compound is a compound of Formula (I) wherein n is 1 or 2. In some embodiments of the methods described herein, the compound is a compound of Formula (I) wherein each $R^4$ is independently halogen or $C_{1-6}$ alkyl. In some embodiments of the methods described herein, the compound is a compound having the structure of Formula (Ia):

Formula (Ia)

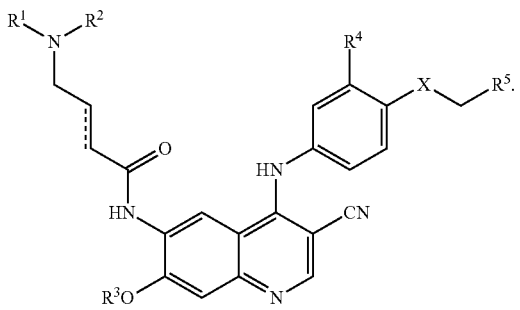

In some embodiments of the methods described herein, the compound is a compound having the structure of Formula (Ib):

Formula (Ib)

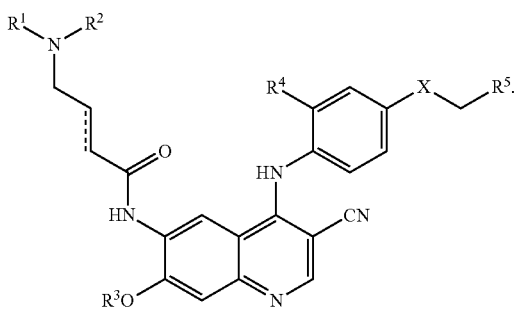

In some embodiments of the methods described herein, the compound is a compound of Formula (I), (Ia), or (Ib) wherein $R^1$ and $R^2$ are each independently $C_{1-6}$alkyl. In some embodiments of the methods described herein, the compound is a compound of Formula (I), (Ia), or (Ib) wherein $R^1$ and $R^2$ are each —CH3. In some embodiments of the methods described herein, the compound is a compound of Formula (I), (Ia), or (Ib) wherein $R^1$ and $R^2$ together with the nitrogen to which they are attached are combined to form a heterocycloalkyl ring. In some embodiments of the methods described herein, the compound is a compound of Formula (I), (Ia), or (Ib) wherein $R^5$ is heteroaryl and wherein heteroaryl is unsubstituted or substituted by one or more substituents selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments of the methods described herein, the compound is a compound of Formula (I), (Ia), or (Ib) wherein $R^5$ is unsubstituted pyridyl. In some embodiments of the methods described herein, the compound is a compound of Formula (I), (Ia), or (Ib) wherein $R^5$ is pyridyl substituted by one substituent selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments of the methods described herein, the compound is a compound of Formula (I), (Ia), or (Ib) wherein $R^5$ is pyridyl substituted by $C_{1-6}$alkyl. In some embodiments of the methods described herein, the compound is a compound of Formula (I), (Ia), or (Ib) wherein $R^5$ is pyridyl substituted by —CH$_3$. In some embodiments of the methods described herein, the compound is a compound of Formula (I), (Ia), or (Ib) wherein $R^5$ is aryl and wherein aryl is unsubstituted or substituted by one or more substituents selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments of the methods described herein, the compound is a compound of Formula (I), (Ia), or (Ib) wherein $R^5$ is unsubstituted phenyl. In some embodiments of the methods described herein, the compound is a compound of Formula (I), (Ia), or (Ib) wherein $R^5$ is phenyl substituted by one substituent selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments of the methods described herein, the compound is a compound of Formula (I), (Ia), or (Ib) wherein $R^4$ is halogen or $C_{1-6}$alkyl. In some embodiments of the methods described herein, the compound is a compound of Formula (I), (Ia), or (Ib) wherein $R^4$ is halogen. In some embodiments of the methods described herein, the compound is a compound of Formula (I), (Ia), or (Ib) wherein $R^4$ is —Cl. In some embodiments of the methods described herein, the compound is a compound of Formula (I), (Ia), or (Ib) wherein X is —O—. In some embodiments of the methods described herein, the compound is a compound of Formula (I), (Ia), or (Ib) wherein X is —N(H)—. In some embodiments of the methods described herein, the compound is a compound of Formula (I), (Ia), or (Ib) wherein X is —CH$_2$—. In some embodiments of the methods described herein, the compound is a compound of Formula (I), (Ia), or (Ib) wherein $R^3$ is —CH$_2$CH$_3$. In some embodiments of the methods described herein, the compound is a compound of Formula (I), (Ia), or (Ib) wherein ═ is a single bond. In some embodiments of the methods described herein, the compound is a compound of Formula (I), (Ia), or (Ib) wherein ═ is a double bond.

Also disclosed herein is a method of treating a metabolic condition in a subject comprising administering neratinib to the subject. Further disclosed herein is a method of treating diabetes mellitus in a subject comprising administering neratinib to the subject.

Also disclosed herein is a compound of Formula (II) having the structure:

Formula (II)

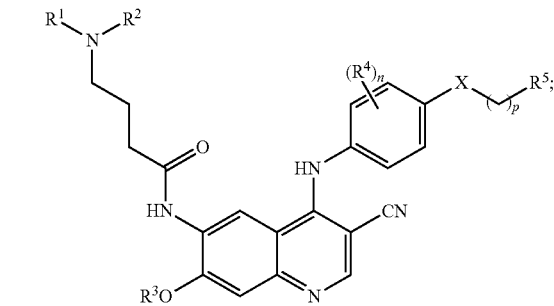

wherein:
  X is —O—, —N(H)—, or —CH$_2$—;
  R$^1$ and R$^2$ are each independently C$_{1-6}$alkyl; or R$^1$ and R$^2$ together with the nitrogen to which they are attached are combined to form a heterocycloalkyl ring;
  R$^3$ is C$_{1-6}$alkyl;
  each R$^4$ is independently halogen, C$_{1-6}$alkyl, C$_{1-6}$alkoxy, C$_{1-6}$haloalkyl, or —CN;
  R$^5$ is aryl or heteroaryl, wherein aryl and heteroaryl are unsubstituted or substituted with one or more substituents selected from halogen, C$_{1-6}$alkyl, C$_{1-6}$alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl;
  R$^6$ is H or C$_{1-6}$alkyl;
  n is 0, 1, 2, or 3; and
  p is 1, 2, or 3;
or a pharmaceutically acceptable salt, solvate, or prodrug thereof.

In some embodiments is a compound of Formula (II), wherein p is 1. In some embodiments is a compound of Formula (II), wherein n is 1 or 2. In some embodiments is a compound of Formula (II), wherein each R$^4$ is independently halogen or C$_{1-6}$alkyl. In some embodiments is a compound having the structure of Formula (IIa):

Formula (IIa)

In some embodiments is a compound having the structure of Formula (IIb):

Formula (IIb)

In some embodiments is a compound of Formula (II), (IIa), or (IIb), wherein R$^1$ and R$^2$ are each independently C$_{1-6}$alkyl. In some embodiments is a compound of Formula (II), (IIa), or (IIb), wherein R$^1$ and R$^2$ are each —CH$_3$. In some embodiments is a compound of Formula (II), (IIa), or (IIb), wherein R$^1$ and R$^2$ together with the nitrogen to which they are attached are combined to form a heterocycloalkyl ring. In some embodiments is a compound of Formula (II), (IIa), or (IIb), wherein R$^5$ is heteroaryl and wherein heteroaryl is unsubstituted or substituted by one or more substituents selected from halogen, C$_{1-6}$alkyl, C$_{1-6}$alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl. In some embodiments is a compound of Formula (II), (IIa), or (IIb), wherein R$^5$ is unsubstituted pyridyl. In some embodiments is a compound of Formula (II), (IIa), or (IIb), wherein R$^5$ is pyridyl substituted by one substituent selected from halogen, C$_{1-6}$alkyl, C$_{1-6}$alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl. In some embodiments is a compound of Formula (II), (IIa), or (IIb), wherein R$^5$ is pyridyl substituted by C$_{1-6}$alkyl. In some embodiments is a compound of Formula (II), (IIa), or (IIb), wherein R$^5$ is pyridyl substituted by —CH$_3$. In some embodiments is a compound of Formula (II), (IIa), or (IIb), wherein R$^5$ is aryl and wherein aryl is unsubstituted or substituted by one or more substituents selected from halogen, C$_{1-6}$alkyl, C$_{1-6}$alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl. In some embodiments is a compound of Formula (II), (IIa), or (IIb), wherein R$^5$ is unsubstituted phenyl. In some embodiments is a compound of Formula (II), (IIa), or (IIb), wherein R$^5$ is phenyl substituted by one substituent selected from halogen, C$_{1-6}$alkyl, C$_{1-6}$alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl. In some embodiments is a compound of Formula (II), (IIa), or (IIb), wherein R$^4$ is halogen or C$_{1-6}$alkyl. In some embodiments is a compound of Formula (II), (IIa), or (IIb), wherein R$^4$ is halogen. In some embodiments is a compound of Formula (II), (IIa), or (IIb), wherein R$^4$ is —Cl. In some embodiments is a compound of Formula (II), (IIa), or (IIb), wherein X is —O—. In some embodiments is a compound of Formula (II), (IIa), or (IIb), wherein X is —N(H)—. In some embodiments is a compound of Formula (II), (IIa), or (IIb), wherein X is —CH$_2$—. In some embodiments is a compound of Formula (II), (IIa), or (IIb), wherein R$^3$ is —CH$_2$CH$_3$.

Also provided herein is a pharmaceutical composition comprising a compound described herein, or a pharmaceutically acceptable salt, solvate, or prodrug thereof, and a pharmaceutically acceptable excipient.

Further disclosed herein is a method of treating cancer in a subject comprising administering to the subject a compound described herein, or a pharmaceutically acceptable salt, solvate, or prodrug thereof, and a pharmaceutically acceptable excipient.

DETAILED DESCRIPTION OF THE INVENTION

Figure 1:
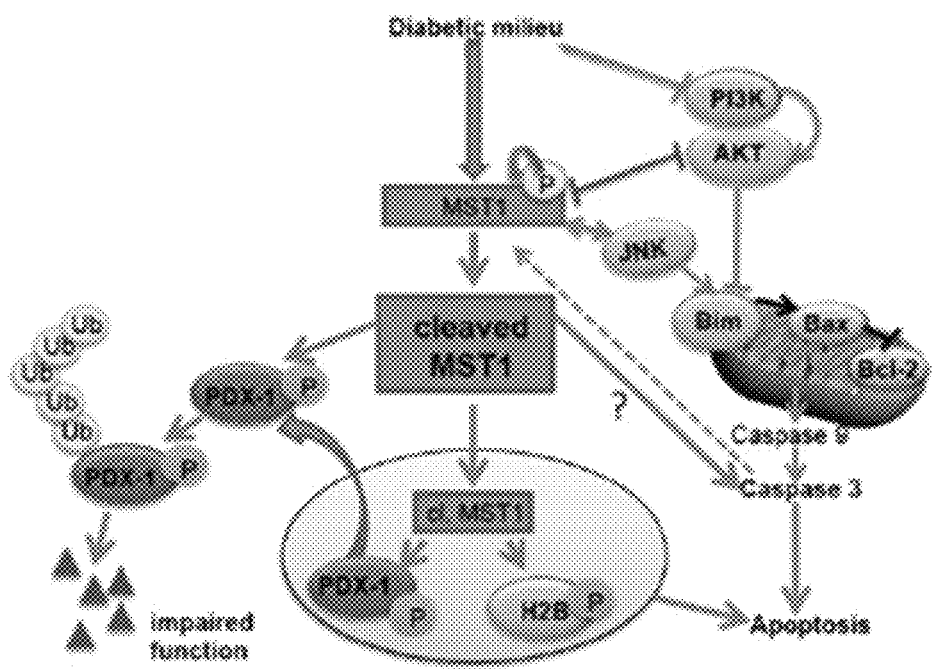
FIG. 1 depicts a pathway of MST1 molecular activity.
Figure 2:
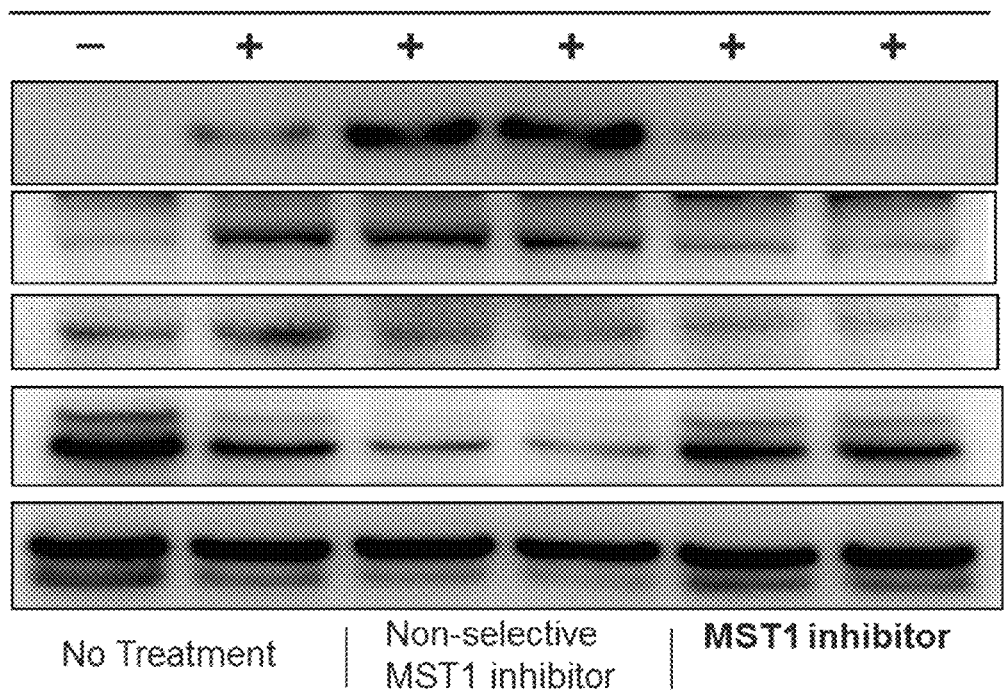
FIG. 2 shows expressions of apoptotic proteins downstream of MST1 activity were modulated by a non-selective MST1 inhibitor and a selective MST1 inhibitor.

Mammalian Sterile 20-like Kinase 1 (MST1) is upregulated in beta cells of islets in the pancreas that are exposed to a diabetogenic milieu, such as islets of type 2 diabetes patients and mice with mutant leptin receptors (db/db mice). Beta cell specific MST1 deficiency prevents loss of glucose regulation and beta cell mass induced by streptozotocin. MST1 mediates beta cell death via effects on mitochondria, pancreatic and duodenal homeobox 1 (PDX-1), and histone targets (see, e.g. FIG. 1). Therefore, MST1 inhibitors can serve as a therapeutic agent for patients with diabetes. In some embodiments, the MST1 inhibitor is neratinib.

Neratinib (also known as HKI-272) was identified as an inhibitor of MST1 kinase activity. Neratinib has been previously developed as an EGFR/HER-2 inhibitor, its use intended for breast cancer. Desirable pharmacokinetics and safety have been confirmed in human patients. However, neratinib as a modulator of MST1 and its use for treating diabetes, inflammatory conditions and autoimmune disorders is unprecedented.

Figure 3:
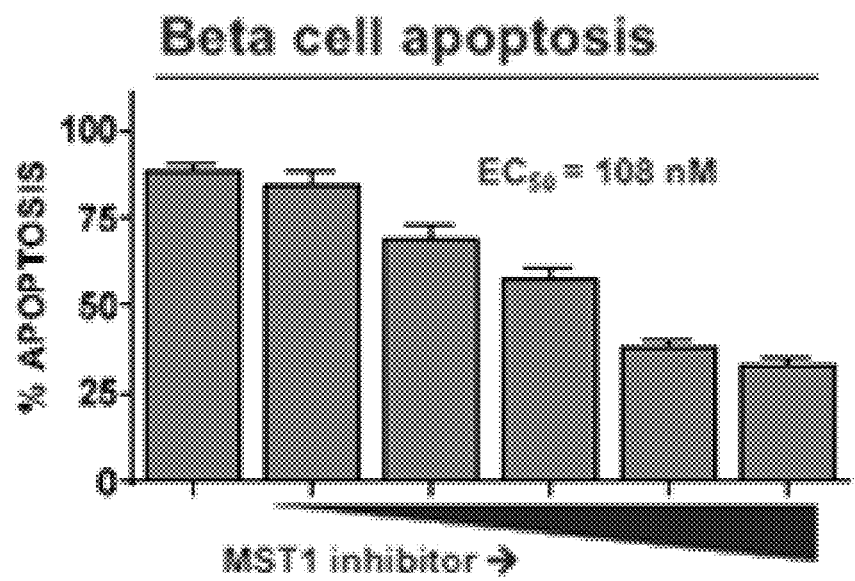
FIG. 3 shows beta cell apoptosis decreased with exposure to increasing concentrations of neratinib.
Figure 4:
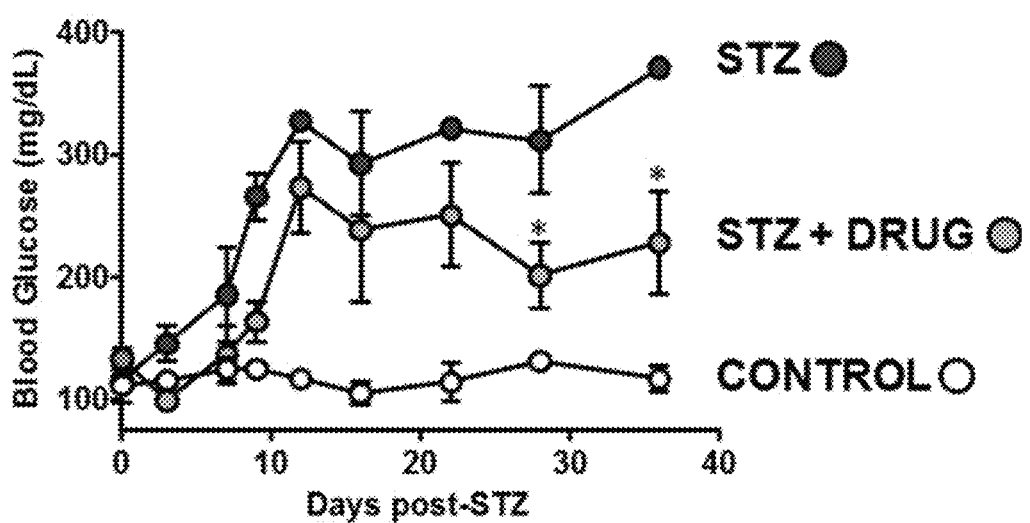
FIG. 4 shows neratinib attenuated hyperglycemia in T1D model mice.
Figure 5:
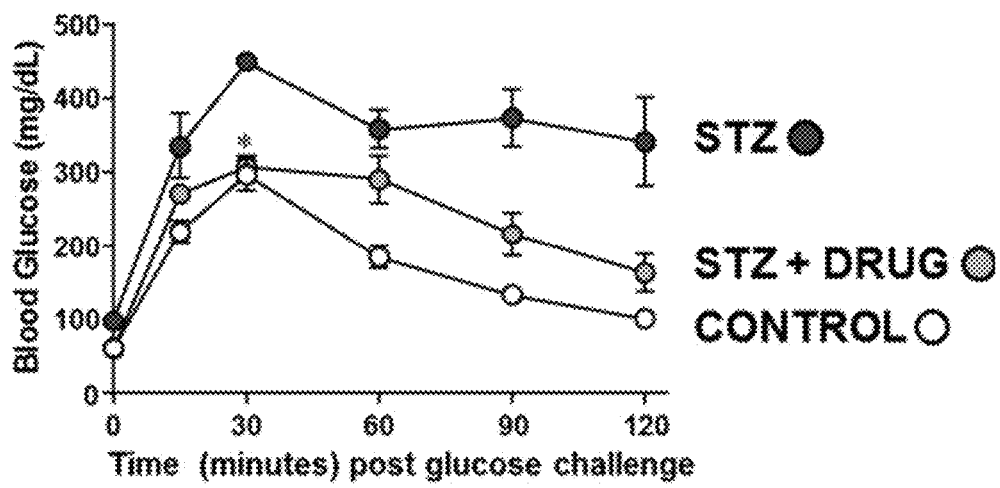
FIG. 5 shows neratinib improved responses to acute glucose challenge in T1D model mice.
Figure 6:
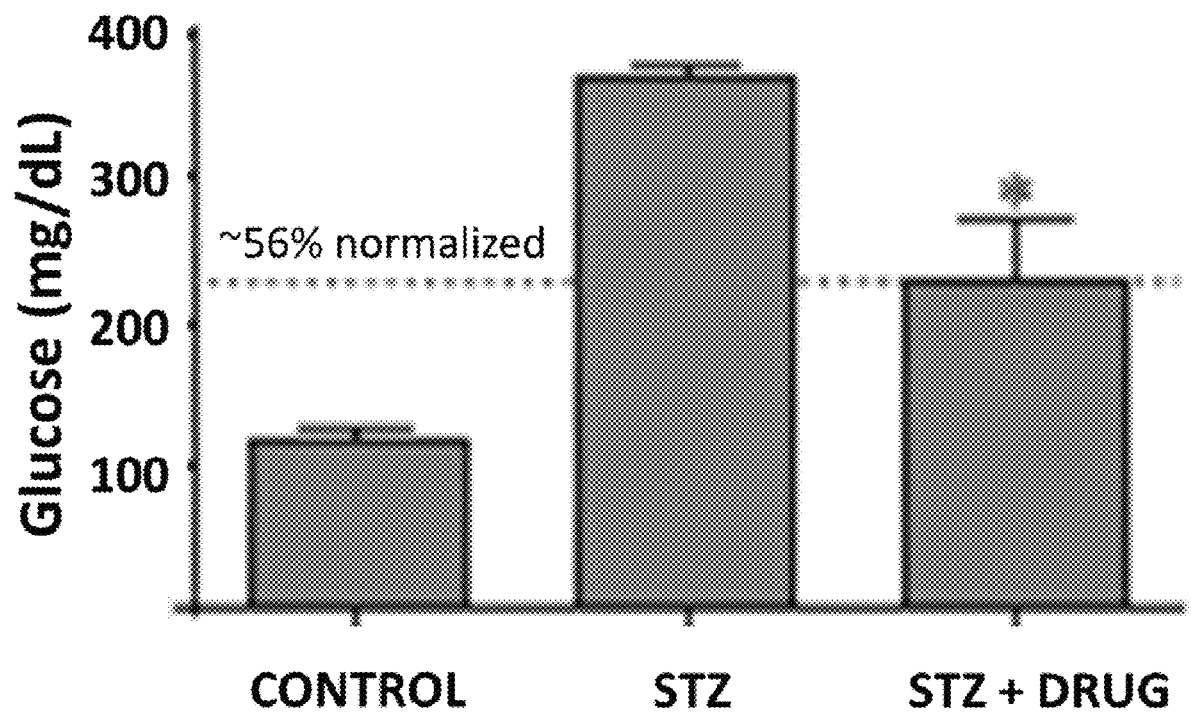
FIG. 6 shows neratinib reduced blood glucose in T1D model mice.
Figure 7:
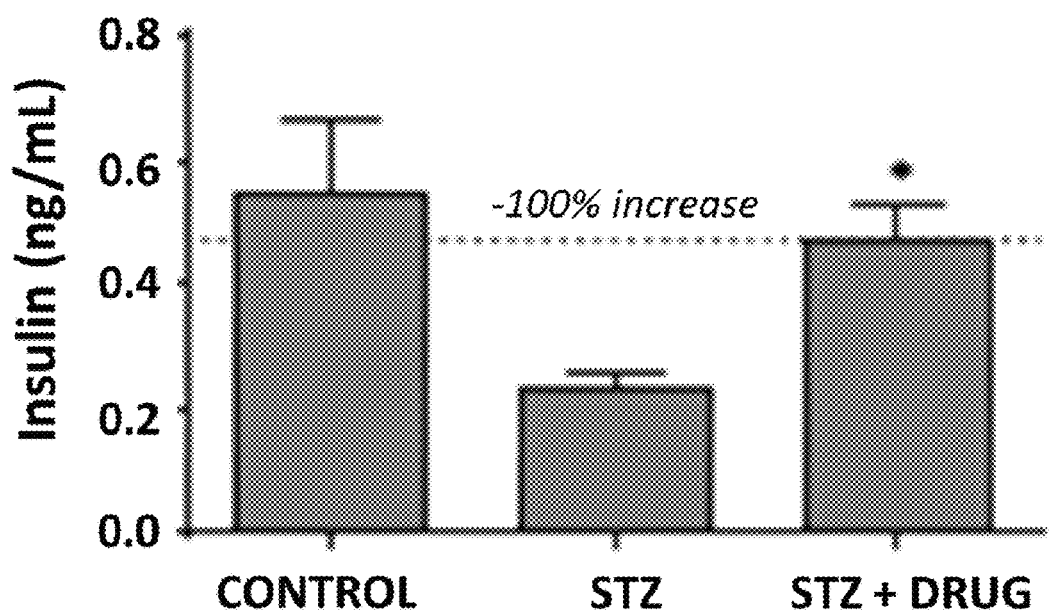
FIG. 7 shows neratinib increased serum insulin in T1D model mice.

Beta cell apoptosis was found to decrease with exposure to increasing concentrations of neratinib (see FIG. 3). Neratinib attenuated hyperglycemia in T1D model mice treated with streptozotocin (STZ) (see FIG. 4) and improved responses to acute glucose challenge in the T1D model mice (see FIG. 5). Neratinib reduced blood glucose and increased serum insulin in T1D model mice (see FIGS. 6-7).

Since diabetes is associated with and may be at least partially caused by autoimmune and inflammatory activity, the compounds described herein may have therapeutic potential for non-diabetes autoimmune and inflammatory conditions as well. In some embodiments, the MST1 inhibitor is neratinib.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a", "an", and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —$NH_2$ radical.
"Cyano" or "nitrile" refers to the —CN radical.
"Hydroxy" or "hydroxyl" refers to the —OH radical.
"Nitro" refers to the —$NO_2$ radical.
"Oxo" refers to the =O substituent.
"Oxime" refers to the =N—OH substituent.
"Thioxo" refers to the =S substituent.

"Alkyl" refers to a straight or branched hydrocarbon chain radical, has from one to twelve carbon atoms, and is attached to the rest of the molecule by a single bond. Alkyls comprising any number of carbon atoms from 1 to 12 are included. An alkyl comprising up to 12 carbon atoms is referred to as a $C_1$-$C_{12}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, vinyl, allyl, propynyl, and the like. Alkyl comprising unsaturations include alkenyl and alkynyl groups. Unless stated otherwise specifically in the specification, an alkyl group may be optionally substituted as described below.

"Alkylene" or "alkylene chain" refers to a straight or branched divalent hydrocarbon chain, as described for alkyl above. Unless stated otherwise specifically in the specification, an alkylene group may be optionally substituted as described below.

"Alkoxy" refers to a radical of the formula —$OR_a$ where $R_a$ is an alkyl radical as defined. Unless stated otherwise specifically in the specification, an alkoxy group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Cycloalkyl" or "carbocycle" refers to a stable, non-aromatic, monocyclic or polycyclic carbocyclic ring, which may include fused or bridged ring systems, which is saturated or unsaturated. Representative cycloalkyls or carbocycles include, but are not limited to, cycloalkyls having from three to fifteen carbon atoms, from three to ten carbon atoms, from three to eight carbon atoms, from three to six carbon atoms, from three to five carbon atoms, or three to four carbon atoms. Monocyclic cycloalkyls or carbocycles include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0] nonane, cis-decalin, trans-decalin, bicyclo[2.1.1]hexane, bicyclo[2.2.1]heptane, bicyclo[2.2.2]octane, bicyclo[3.2.2] nonane, and bicyclo[3.3.2]decane, and 7,7-dimethyl-bicyclo [2.2.1]heptanyl. Unless otherwise stated specifically in the specification, a cycloalkyl or carbocycle group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" similarly refers to a radical of the formula —OR$_a$ where R$_a$ is a haloalkyl radical as defined. Unless stated otherwise specifically in the specification, a haloalkoxy group may be optionally substituted as described below.

"Heterocycloalkyl" or "heterocyclyl" or "heterocyclic ring" or "heterocycle" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

The term "heteroaryl" as used herein, alone or in combination, refers to optionally substituted aromatic monoradicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidiazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, azepinyl, phenazinyl, benzimidazolyl, benzindolyl, benzofuranyl, benzofuranonyl, benzoxazolyl, benzothiazolyl, benzothiadiazolyl, benzothiophenyl, benzoxadiazolyl, benzodioxolyl, benzo[b][1,4]dioxepinyl, 1,4-benzodioxanyl, benzonaphthofuranyl, benzotriazolyl, benzodioxolyl, benzodioxinyl, benzopyranyl, benzopyranonyl, benzothienyl (benzothiophenyl), benzo[4,6]imidazo [1,2-a]pyridinyl, carbazolyl, cinnolinyl, dibenzofuranyl, dibenzothiophenyl, furanonyl, imidazolyl, indolyl, isoxazolyl, isoquinolinyl, indolizinyl, indazolyl, isoindolyl, indolinyl, isoindolinyl, indolizinyl, isothiazolyl, isoindolyloxadiazolyl, indazolyl, naphthyridinyl, oxadiazolyl, 2-oxoazepinyl, oxiranyl, 1-oxidopyridinyl, 1-oxidopyrimidinyl, 1-oxidopyrazinyl, 1-oxidopyridazinyl, 1-phenyl-1H-pyrrolyl, phenothiazinyl, phenoxazinyl, pyridinyl, pyridazinyl, pyrimidinyl, pyrazinyl, pyrrolyl, pyrazinyl, pyrazolyl, purinyl, phthalazinyl, pteridinyl, quinolinyl, quinazolinyl, quinoxalinyl, quinuclidinyl, triazolyl, tetrazolyl, thiazolyl, triazinyl, thiadiazolyl, tetrahydroquinolinyl, thiazolyl, and thiophenyl and the like, and their oxides, such as for example pyridyl-N-oxide. Illustrative examples of heteroaryl groups include the following moieties:

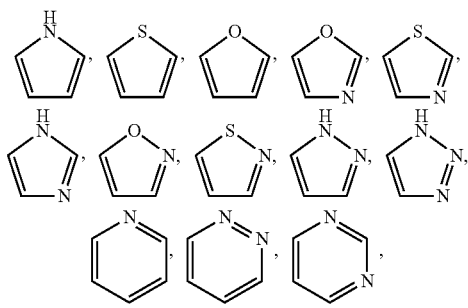

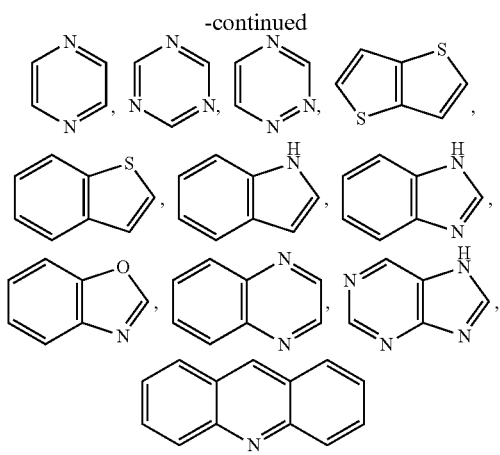

and the like.

All the above groups may be either substituted or unsubstituted. The term "substituted" as used herein means any of the above groups (e.g, alkyl, alkylene, alkoxy, aryl, cycloalkyl, haloalkyl, heterocyclyl and/or heteroaryl) may be further functionalized wherein at least one hydrogen atom is replaced by a bond to a non-hydrogen atom substituent. Unless stated specifically in the specification, a substituted group may include one or more substituents selected from: oxo, amino, —$CO_2H$, nitrile, nitro, hydroxyl, thiooxy, alkyl, alkylene, alkoxy, aryl, cycloalkyl, heterocyclyl, heteroaryl, dialkylamines, arylamines, alkylarylamines, diarylamines, trialkylammonium (—$N^+R_3$), N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NH_2$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen, sulfur, or nitrogen atoms. For example, an alkyl group may be substituted with one or more internal oxygen atoms to form an ether or polyether group. Similarly, an alkyl group may be substituted with one or more internal sulfur atoms to form a thioether, disulfide, etc.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —$CH_2CH_3$), fully substituted (e.g., —$CF_2CF_3$), mono-substituted (e.g., —$CH_2CH_2F$) or substituted at a level anywhere in-between fully substituted and mono-substituted (e.g., —$CH_2CHF_2$, —$CH_2CF_3$, —$CF_2CH_3$, —$CFHCHF_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

As used herein, MST1, a cleaved product thereof, a homolog thereof, a modification thereof (e.g. phosphorylation), complexes thereof, and a splice variant thereof, may be used interchangeably, unless otherwise specified. MST1, also known as Stk4, is a serine/threonine kinase. Homologs thereof may be selected from mammalian sterile 20-like kinase 2, Ste-20, and p21-activated kinase (Pak).

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition. In other embodiments, treatment also includes prophylactic treatment (e.g., administration of a composition described herein when an individual is suspected to be suffering from a bacterial infection).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

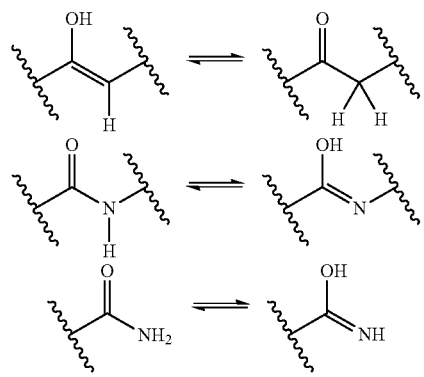

-continued

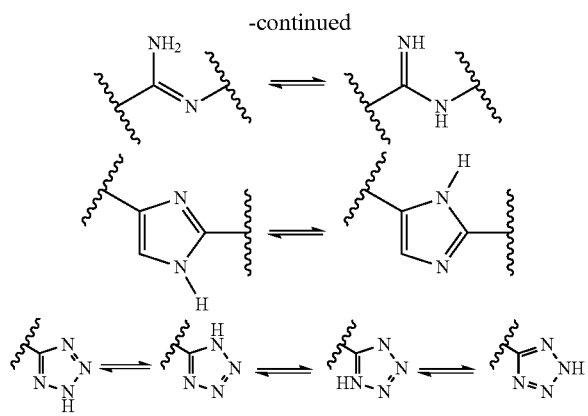

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

Compounds

In some embodiments is a compound of Formula (I), (Ia), (Ib), (II), (IIa), or (IIb) that modulates an activity of a mammalian sterile 20-like kinase 1 (MST1), a cleaved product thereof, or a homolog thereof. In some embodiments is a compound of Formula (I), (Ia), (Ib), (II), (IIa), or (IIb) that inhibits an activity of a mammalian sterile 20-like kinase 1 (MST1), a cleaved product thereof, or a homolog thereof. In some embodiments is a compound of Formula (I), (Ia), (Ib), (II), (IIa), or (IIb) that inhibits an activity of a mammalian sterile 20-like kinase 1 (MST1), a cleaved product thereof, or a homolog thereof wherein the activity is selected from a phosphorylation activity, an inflammatory activity, a cleavage activity, an apoptotic activity, a ubiquitinating activity, a mitochondrial activity, and combinations thereof. In some embodiments is a compound of Formula (I), (Ia), (Ib), (II), (IIa), or (IIb) that inhibits an activity of a mammalian sterile 20-like kinase 1 (MST1), a cleaved product thereof, or a homolog thereof; wherein the compound inhibits phosphorylation of a protein downstream of the activity of the mammalian sterile 20-like kinase 1, the cleaved product thereof, or the homolog thereof. In some embodiments is a compound of Formula (I), (Ia), (Ib), (II), (IIa), or (IIb) that inhibits an activity of a mammalian sterile 20-like kinase 1 (MST1), a cleaved product thereof, or a homolog thereof; wherein the compound inhibits cleavage of a protein downstream of the activity of the mammalian sterile 20-like kinase 1, the cleaved product thereof, or the homolog thereof. In some embodiments is a compound of Formula (I), (Ia), (Ib), (II), (IIa), or (IIb) that inhibits an activity of a mammalian sterile 20-like kinase 1 (MST1), a cleaved product thereof, or a homolog thereof; wherein the compound inhibits apoptotic activity of a protein downstream of the activity of the mammalian sterile 20-like kinase 1, the cleaved product thereof, or the homolog thereof.

In some embodiments provided herein, is a compound of Formula (I) having the structure:

Formula (I)

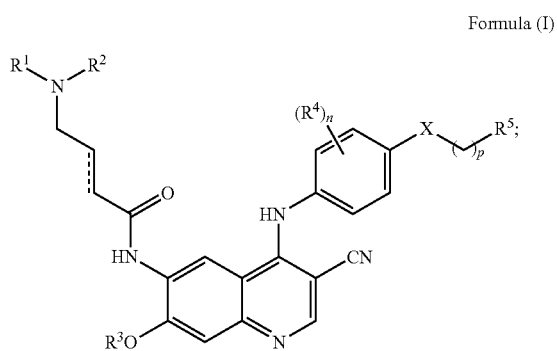

wherein:
=== is a single or double bond;
X is —O—, —N(H)—, or —CH$_2$—;
R$^1$ and R$^2$ are each independently C$_{1-6}$alkyl; or R$^1$ and R$^2$ together with the nitrogen to which they are attached are combined to form a heterocycloalkyl ring;
R$^3$ is C$_{1-6}$alkyl;
each R$^4$ is independently halogen, C$_{1-6}$alkyl, C$_{1-6}$alkoxy, C$_{1-6}$haloalkyl, or —CN;
R$^5$ is aryl or heteroaryl, wherein aryl and heteroaryl are unsubstituted or substituted by one or more substituents selected from halogen, C$_{1-6}$alkyl, C$_{1-6}$alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl;
R$^6$ is H or C$_{1-6}$alkyl;
n is 0, 1, 2, or 3; and
p is 1, 2, or 3;
or a pharmaceutically acceptable salt, solvate, or prodrug thereof.

In some embodiments is a compound of Formula (I), wherein p is 1. In some embodiments is a compound of Formula (I), wherein p is 2. In some embodiments is a compound of Formula (I), wherein p is 3. In some embodiments is a compound of Formula (I), wherein n is 0. In some embodiments is a compound of Formula (I), wherein n is 1. In some embodiments is a compound of Formula (I), wherein n is 2. In some embodiments is a compound of Formula (I), wherein n is 1 or 2. In some embodiments is a compound of Formula (I), wherein n is 3. In some embodiments is a compound of Formula (I), wherein each $R^4$ is halogen. In some embodiments is a compound of Formula (I), wherein each $R^4$ is independently —Cl or —Br. In some embodiments is a compound of Formula (I), wherein each $R^4$ is —Cl. In some embodiments is a compound of Formula (I), wherein each $R^4$ is —Br. In some embodiments is a compound of Formula (I), wherein each $R^4$ is $C_{1-6}$alkyl. In some embodiments is a compound of Formula (I), wherein each $R^4$ is —$CH_3$. In some embodiments is a compound of Formula (I), wherein each $R^4$ is independently halogen or $C_{1-6}$alkyl. In some embodiments is a compound of Formula (I), wherein each $R^4$ is independently —Cl or —$CH_3$. In some embodiments is a compound of Formula (I), wherein each $R^4$ is $C_{1-6}$alkoxy. In some embodiments is a compound of Formula (I), wherein each $R^4$ is $C_{1-6}$haloalkyl. In some embodiments is a compound of Formula (I), wherein each $R^4$ is —CN. In some embodiments is a compound of Formula (I), wherein $R^1$ and $R^2$ are each independently $C_{1-6}$alkyl. In some embodiments is a compound of Formula (I), wherein $R^1$ and $R^2$ are each —$CH_3$. In some embodiments is a compound of Formula (I), wherein $R^1$ and $R^2$ together with the nitrogen to which they are attached are combined to form a heterocycloalkyl ring. In some embodiments is a compound of Formula (I), wherein $R^1$ and $R^2$ together with the nitrogen to which they are attached are combined to form a piperidine ring. In some embodiments is a compound of Formula (I), wherein $R^1$ and $R^2$ together with the nitrogen to which they are attached are combined to form an optionally substituted piperazine ring. In some embodiments is a compound of Formula (I), wherein $R^1$ and $R^2$ together with the nitrogen to which they are attached are combined to form a morpholine ring. In some embodiments is a compound of Formula (I), wherein $R^5$ is heteroaryl and wherein heteroaryl is unsubstituted or substituted by one or more substituents selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl. In some embodiments is a compound of Formula (I), wherein $R^5$ is heteroaryl and wherein heteroaryl is substituted by one substituent selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl. In some embodiments is a compound of Formula (I), wherein $R^5$ is unsubstituted pyridyl. In some embodiments is a compound of Formula (I), wherein $R^5$ is pyridyl substituted by one or more substituents selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl. In some embodiments is a compound of Formula (I), wherein $R^5$ is pyridyl substituted by one substituent selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl. In some embodiments is a compound of Formula (I), wherein $R^5$ is pyridyl substituted by $C_{1-6}$alkyl. In some embodiments is a compound of Formula (I), wherein $R^5$ is pyridyl substituted by —$CH_3$. In some embodiments is a compound of Formula (I), wherein $R^5$ is pyridyl substituted by halogen. In some embodiments is a compound of Formula (I), wherein $R^5$ is pyridyl substituted by —Cl. In some embodiments is a compound of Formula (I), wherein $R^5$ is pyridyl substituted by —Br. In some embodiments is a compound of Formula (I), wherein $R^5$ is pyridyl substituted by $C_{1-6}$alkoxy. In some embodiments is a compound of Formula (I), wherein $R^5$ is pyridyl substituted by $C_{1-6}$haloalkyl. In some embodiments is a compound of Formula (I), wherein $R^5$ is pyridyl substituted by $C_{1-6}$haloalkoxy. In some embodiments is a compound of Formula (I), wherein $R^5$ is pyridyl substituted by —OH. In some embodiments is a compound of Formula (I), wherein $R^5$ is pyridyl substituted by —$CH_2OH$. In some embodiments is a compound of Formula (I), wherein $R^5$ is pyridyl substituted by —CN. In some embodiments is a compound of Formula (I), wherein $R^5$ is pyridyl substituted by —$CO_2R^6$. In some embodiments is a compound of Formula (I), wherein $R^5$ is pyridyl substituted by $C_{3-6}$cycloalkyl. In some embodiments is a compound of Formula (I), wherein $R^5$ is pyridyl substituted by phenyl. In some embodiments is a compound of Formula (I), wherein $R^5$ is aryl and wherein aryl is unsubstituted or substituted by one or more substituents selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl. In some embodiments is a compound of Formula (I), wherein $R^5$ is unsubstituted phenyl. In some embodiments is a compound of Formula (I), wherein $R^5$ is phenyl substituted by one or more substituents selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl. In some embodiments is a compound of Formula (I), wherein $R^5$ is phenyl substituted by one substituent selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl. In some embodiments is a compound of Formula (I), wherein $R^5$ is phenyl substituted by $C_{1-6}$alkyl. In some embodiments is a compound of Formula (I), wherein $R^5$ is phenyl substituted by —$CH_3$. In some embodiments is a compound of Formula (I), wherein $R^5$ is phenyl substituted by halogen. In some embodiments is a compound of Formula (I), wherein $R^5$ is phenyl substituted by —Cl. In some embodiments is a compound of Formula (I), wherein $R^5$ is phenyl substituted by —Br. In some embodiments is a compound of Formula (I), wherein $R^5$ is phenyl substituted by $C_{1-6}$alkoxy. In some embodiments is a compound of Formula (I), wherein $R^5$ is phenyl substituted by $C_{1-6}$haloalkyl. In some embodiments is a compound of Formula (I), wherein $R^5$ is phenyl substituted by $C_{1-6}$haloalkoxy. In some embodiments is a compound of Formula (I), wherein $R^5$ is phenyl substituted by —OH. In some embodiments is a compound of Formula (I), wherein $R^5$ is phenyl substituted by —$CH_2OH$. In some embodiments is a compound of Formula (I), wherein $R^5$ is phenyl substituted by —CN. In some embodiments is a compound of Formula (I), wherein $R^5$ is phenyl substituted by —$CO_2R^6$. In some embodiments is a compound of Formula (I), wherein $R^5$ is phenyl substituted by $C_{3-6}$cycloalkyl. In some embodiments is a compound of Formula (I), wherein $R^5$ is phenyl substituted by phenyl. In some embodiments is a compound of Formula (I), wherein X is —O—. In some embodiments is a compound of Formula (I), wherein X is —N(H)—. In some embodiments is a compound of Formula (I), wherein X is —$CH_2$—. In some embodiments is a compound of Formula (I), wherein $R^3$ is —$CH_2CH_3$. In some embodiments is a compound of Formula (I), wherein ═ is a single bond. In some embodiments is a compound of Formula (I), wherein ═ is a double bond.

In some embodiments provided herein, is a compound of Formula (Ia) having the structure:

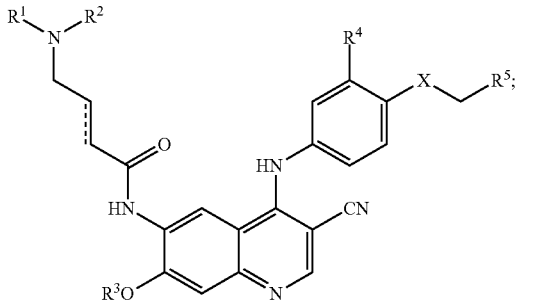

Formula (Ia)

wherein:
- ═══ is a single or double bond;
- X is —O—, —N(H)—, or —CH$_2$—;
- R$^1$ and R$^2$ are each independently C$_{1-6}$alkyl; or R$^1$ and R$^2$ together with the nitrogen to which they are attached are combined to form a heterocycloalkyl ring;
- R$^3$ is C$_{1-6}$alkyl;
- R$^4$ is halogen, C$_{1-6}$alkyl, C$_{1-6}$alkoxy, C$_{1-6}$haloalkyl, or —CN;
- R$^5$ is aryl or heteroaryl, wherein aryl and heteroaryl are unsubstituted or substituted by one or more substituents selected from halogen, C$_{1-6}$alkyl, C$_{1-6}$alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl; and
- R$^6$ is H or C$_{1-6}$alkyl;

or a pharmaceutically acceptable salt, solvate, or prodrug thereof.

In some embodiments is a compound of Formula (Ia), wherein R$^4$ is halogen. In some embodiments is a compound of Formula (Ia), wherein R$^4$ is —Cl. In some embodiments is a compound of Formula (Ia), wherein R$^4$ is —Br. In some embodiments is a compound of Formula (Ia), wherein R$^4$ is C$_{1-6}$alkyl. In some embodiments is a compound of Formula (Ia), wherein R$^4$ is —CH$_3$. In some embodiments is a compound of Formula (Ia), wherein R$^4$ is C$_{1-6}$alkoxy. In some embodiments is a compound of Formula (Ia), wherein R$^4$ is C$_{1-6}$haloalkyl. In some embodiments is a compound of Formula (Ia), wherein R$^4$ is —CN. In some embodiments is a compound of Formula (Ia), wherein R$^1$ and R$^2$ are each independently C$_{1-6}$alkyl. In some embodiments is a compound of Formula (Ia), wherein R$^1$ and R$^2$ are each —CH$_3$. In some embodiments is a compound of Formula (Ia), wherein R$^1$ and R$^2$ together with the nitrogen to which they are attached are combined to form a heterocycloalkyl ring. In some embodiments is a compound of Formula (Ia), wherein R$^1$ and R$^2$ together with the nitrogen to which they are attached are combined to form a piperidine ring. In some embodiments is a compound of Formula (Ia), wherein R$^1$ and R$^2$ together with the nitrogen to which they are attached are combined to form a piperazine ring. In some embodiments is a compound of Formula (Ia), wherein R$^1$ and R$^2$ together with the nitrogen to which they are attached are combined to form a morpholine ring. In some embodiments is a compound of Formula (Ia), wherein R$^5$ is heteroaryl and wherein heteroaryl is unsubstituted or substituted by one or more substituents selected from halogen, C$_{1-6}$alkyl, C$_{1-6}$alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl. In some embodiments is a compound of Formula (Ia), wherein R$^5$ is heteroaryl and wherein heteroaryl is substituted by one substituent selected from halogen, C$_{1-6}$alkyl, C$_{1-6}$alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl. In some embodiments is a compound of Formula (Ia), wherein R$^5$ is unsubstituted pyridyl. In some embodiments is a compound of Formula (Ia), wherein R$^5$ is pyridyl substituted by one or more substituents selected from halogen, C$_{1-6}$alkyl, C$_{1-6}$alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl. In some embodiments is a compound of Formula (Ia), wherein R$^5$ is pyridyl substituted by one substituent selected from halogen, C$_{1-6}$alkyl, C$_{1-6}$alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl. In some embodiments is a compound of Formula (Ia), wherein R$^5$ is pyridyl substituted by C$_{1-6}$alkyl. In some embodiments is a compound of Formula (Ia), wherein R$^5$ is pyridyl substituted by —CH$_3$. In some embodiments is a compound of Formula (Ia), wherein R$^5$ is pyridyl substituted by halogen. In some embodiments is a compound of Formula (Ia), wherein R$^5$ is pyridyl substituted by —Cl. In some embodiments is a compound of Formula (Ia), wherein R$^5$ is pyridyl substituted by —Br. In some embodiments is a compound of Formula (Ia), wherein R$^5$ is pyridyl substituted by C$_{1-6}$alkoxy. In some embodiments is a compound of Formula (Ia), wherein R$^5$ is pyridyl substituted by C$_{1-6}$haloalkyl. In some embodiments is a compound of Formula (Ia), wherein R$^5$ is pyridyl substituted by C$_{1-6}$haloalkoxy. In some embodiments is a compound of Formula (Ia), wherein R$^5$ is pyridyl substituted by —OH. In some embodiments is a compound of Formula (Ia), wherein R$^5$ is pyridyl substituted by —CH$_2$OH. In some embodiments is a compound of Formula (Ia), wherein R$^5$ is pyridyl substituted by —CN. In some embodiments is a compound of Formula (Ia), wherein R$^5$ is pyridyl substituted by —CO$_2$R$^6$. In some embodiments is a compound of Formula (Ia), wherein R$^5$ is pyridyl substituted by C$_{3-6}$cycloalkyl. In some embodiments is a compound of Formula (Ia), wherein R$^5$ is pyridyl substituted by phenyl. In some embodiments is a compound of Formula (Ia), wherein R$^5$ is aryl and wherein aryl is unsubstituted or substituted by one or more substituents selected from halogen, C$_{1-6}$alkyl, C$_{1-6}$alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl. In some embodiments is a compound of Formula (Ia), wherein R$^5$ is unsubstituted phenyl. In some embodiments is a compound of Formula (Ia), wherein R$^5$ is phenyl substituted by one or more substituents selected from halogen, C$_{1-6}$alkyl, C$_{1-6}$alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl. In some embodiments is a compound of Formula (Ia), wherein R$^5$ is phenyl substituted by one substituent selected from halogen, C$_{1-6}$ alkyl, C$_{1-6}$ alkoxy, C$_{1-6}$ haloalkyl, C$_{1-6}$haloalkoxy, —OH, —CH$_2$OH, —CN, —CO$_2$R$^6$, C$_{3-6}$cycloalkyl, and phenyl. In some embodiments is a compound of Formula (Ia), wherein R$^5$ is phenyl substituted by C$_{1-6}$alkyl. In some embodiments is a compound of Formula (Ia), wherein R$^5$ is phenyl substituted by —CH$_3$. In some embodiments is a compound of Formula (Ia), wherein R$^5$ is phenyl substituted by halogen. In some embodiments is a compound of Formula (Ia), wherein R$^5$ is phenyl substituted by —Cl. In some embodiments is a compound of Formula (Ia), wherein R$^5$ is phenyl substituted by —Br. In some embodiments is a compound of Formula (Ia), wherein R$^5$ is phenyl substituted by C$_{1-6}$alkoxy. In some embodiments is a compound of Formula (Ia), wherein R$^5$ is phenyl substituted by C$_{1-6}$haloalkyl. In some embodiments is a compound of Formula (Ia), wherein R$^5$ is phenyl substituted by C$_{1-6}$haloalkoxy. In some embodiments is a compound of Formula (Ia), wherein $R^5$ is phenyl substituted by —OH. In some embodiments is a compound of Formula (Ia), wherein $R^5$ is phenyl substituted by —CH$_2$OH. In some embodiments is a compound of Formula (Ia), wherein $R^5$ is phenyl substituted by —CN. In some embodiments is a compound of Formula (Ia), wherein $R^5$ is phenyl substituted by —CO$_2$R$^6$. In some embodiments is a compound of Formula (Ia), wherein $R^5$ is phenyl substituted by $C_{3-6}$cycloalkyl. In some embodiments is a compound of Formula (Ia), wherein $R^5$ is phenyl substituted by phenyl. In some embodiments is a compound of Formula (Ia), wherein X is —O—. In some embodiments is a compound of Formula (Ia), wherein X is —N(H)—. In some embodiments is a compound of Formula (Ia), wherein X is —CH$_2$—. In some embodiments is a compound of Formula (Ia), wherein $R^3$ is —CH$_2$CH$_3$. In some embodiments is a compound of Formula (Ia), wherein ═══ is a single bond. In some embodiments is a compound of Formula (Ia), wherein ═══ is a double bond.

In some embodiments provided herein, is a compound of Formula (Ib) having the structure:

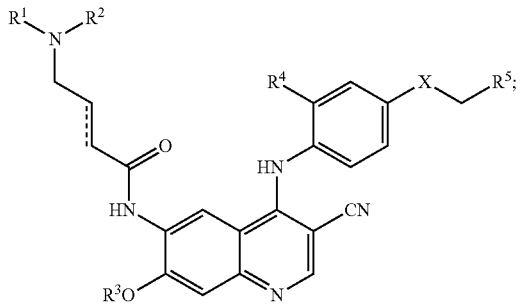

Formula (Ib)

wherein:
═══ is a single or double bond;
X is —O—, —N(H)—, or —CH$_2$—;
$R^1$ and $R^2$ are each independently $C_{1-6}$alkyl; or $R^1$ and $R^2$ together with the nitrogen to which they are attached are combined to form a heterocycloalkyl ring;
$R^3$ is $C_{1-6}$alkyl;
$R^4$ is halogen, $C_{1-6}$alkyl, $C_{1-6}$alkoxy, $C_{1-6}$haloalkyl, or —CN;
$R^5$ is aryl or heteroaryl, wherein aryl and heteroaryl are unsubstituted or substituted by one or more substituents selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl; and
$R^6$ is H or $C_{1-6}$alkyl;
or a pharmaceutically acceptable salt, solvate, or prodrug thereof.

In some embodiments is a compound of Formula (Ib), wherein $R^4$ is halogen. In some embodiments is a compound of Formula (Ib), wherein $R^4$ is —Cl. In some embodiments is a compound of Formula (Ib), wherein $R^4$ is —Br. In some embodiments is a compound of Formula (Ib), wherein $R^4$ is $C_{1-6}$alkyl. In some embodiments is a compound of Formula (Ib), wherein $R^4$ is —CH$_3$. In some embodiments is a compound of Formula (Ib), wherein $R^4$ is $C_{1-6}$alkoxy. In some embodiments is a compound of Formula (Ib), wherein $R^4$ is $C_{1-6}$haloalkyl. In some embodiments is a compound of Formula (Ib), wherein $R^4$ is —CN. In some embodiments is a compound of Formula (Ib), wherein $R^1$ and $R^2$ are each independently $C_{1-6}$alkyl. In some embodiments is a compound of Formula (Ib), wherein $R^1$ and $R^2$ are each —CH$_3$. In some embodiments is a compound of Formula (Ib), wherein $R^1$ and $R^2$ together with the nitrogen to which they are attached are combined to form a heterocycloalkyl ring. In some embodiments is a compound of Formula (Ib), wherein $R^1$ and $R^2$ together with the nitrogen to which they are attached are combined to form a piperidine ring. In some embodiments is a compound of Formula (Ib), wherein $R^1$ and $R^2$ together with the nitrogen to which they are attached are combined to form a piperazine ring. In some embodiments is a compound of Formula (Ib), wherein $R^1$ and $R^2$ together with the nitrogen to which they are attached are combined to form a morpholine ring. In some embodiments is a compound of Formula (Ib), wherein $R^5$ is heteroaryl and wherein heteroaryl is unsubstituted or substituted by one or more substituents selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments is a compound of Formula (Ib), wherein $R^5$ is heteroaryl and wherein heteroaryl is substituted by one substituent selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments is a compound of Formula (Ib), wherein $R^5$ is unsubstituted pyridyl. In some embodiments is a compound of Formula (Ib), wherein $R^5$ is pyridyl substituted by one or more substituents selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments is a compound of Formula (Ib), wherein $R^5$ is pyridyl substituted by one substituent selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments is a compound of Formula (Ib), wherein $R^5$ is pyridyl substituted by $C_{1-6}$alkyl. In some embodiments is a compound of Formula (Ib), wherein $R^5$ is pyridyl substituted by —CH$_3$. In some embodiments is a compound of Formula (Ib), wherein $R^5$ is pyridyl substituted by halogen. In some embodiments is a compound of Formula (Ib), wherein $R^5$ is pyridyl substituted by —Cl. In some embodiments is a compound of Formula (Ib), wherein $R^5$ is pyridyl substituted by —Br. In some embodiments is a compound of Formula (Ib), wherein $R^5$ is pyridyl substituted by $C_{1-6}$alkoxy. In some embodiments is a compound of Formula (Ib), wherein $R^5$ is pyridyl substituted by $C_{1-6}$haloalkyl. In some embodiments is a compound of Formula (Ib), wherein $R^5$ is pyridyl substituted by $C_{1-6}$haloalkoxy. In some embodiments is a compound of Formula (Ib), wherein $R^5$ is pyridyl substituted by —OH. In some embodiments is a compound of Formula (Ib), wherein $R^5$ is pyridyl substituted by —CH$_2$OH. In some embodiments is a compound of Formula (Ib), wherein $R^5$ is pyridyl substituted by —CN. In some embodiments is a compound of Formula (Ib), wherein $R^5$ is pyridyl substituted by —CO$_2$R$^6$. In some embodiments is a compound of Formula (Ib), wherein $R^5$ is pyridyl substituted by $C_{3-6}$cycloalkyl. In some embodiments is a compound of Formula (Ib), wherein $R^5$ is pyridyl substituted by phenyl. In some embodiments is a compound of Formula (Ib), wherein $R^5$ is aryl and wherein aryl is unsubstituted or substituted by one or more substituents selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments is a compound of Formula (Ib), wherein $R^5$ is unsubstituted phenyl. In some embodiments is a compound of Formula (Ib), wherein $R^5$ is phenyl substituted by one or more substituents selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments is a compound of Formula (Ib), wherein R$^5$ is phenyl substituted by one substituent selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments is a compound of Formula (Ib), wherein R$^5$ is phenyl substituted by $C_{1-6}$alkyl. In some embodiments is a compound of Formula (Ib), wherein R$^5$ is phenyl substituted by —CH$_3$. In some embodiments is a compound of Formula (Ib), wherein R$^5$ is phenyl substituted by halogen. In some embodiments is a compound of Formula (Ib), wherein R$^5$ is phenyl substituted by —Cl. In some embodiments is a compound of Formula (Ib), wherein R$^5$ is phenyl substituted by —Br. In some embodiments is a compound of Formula (Ib), wherein R$^5$ is phenyl substituted by $C_{1-6}$alkoxy. In some embodiments is a compound of Formula (Ib), wherein R$^5$ is phenyl substituted by $C_{1-6}$haloalkyl. In some embodiments is a compound of Formula (Ib), wherein R$^5$ is phenyl substituted by $C_{1-6}$haloalkoxy. In some embodiments is a compound of Formula (Ib), wherein R$^5$ is phenyl substituted by —OH. In some embodiments is a compound of Formula (Ib), wherein R$^5$ is phenyl substituted by —CH$_2$OH. In some embodiments is a compound of Formula (Ib), wherein R$^5$ is phenyl substituted by —CN. In some embodiments is a compound of Formula (Ib), wherein R$^5$ is phenyl substituted by —CO$_2$R$^6$. In some embodiments is a compound of Formula (Ib), wherein R$^5$ is phenyl substituted by $C_{3-6}$cycloalkyl. In some embodiments is a compound of Formula (Ib), wherein R$^5$ is phenyl substituted by phenyl. In some embodiments is a compound of Formula (Ib), wherein X is —O—. In some embodiments is a compound of Formula (Ib), wherein X is —N(H)—. In some embodiments is a compound of Formula (Ib), wherein X is —CH$_2$—. In some embodiments is a compound of Formula (Ib), wherein R$^3$ is —CH$_2$CH$_3$. In some embodiments is a compound of Formula (Ib), wherein ═ is a single bond. In some embodiments is a compound of Formula (Ib), wherein ═ is a double bond.

In some embodiments provided herein, is a compound of Formula (II) having the structure:

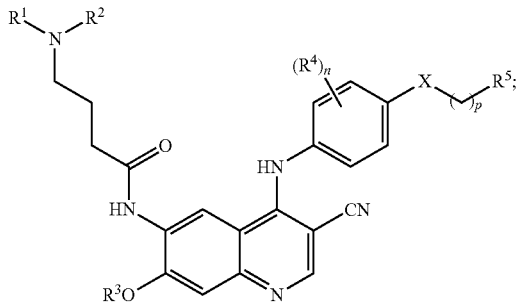

Formula (II)

wherein:
X is —O—, —N(H)—, or —CH$_2$—;
R$^1$ and R$^2$ are each independently $C_{1-6}$alkyl; or R$^1$ and R$^2$ together with the nitrogen to which they are attached are combined to form a heterocycloalkyl ring;
R$^3$ is $C_{1-6}$alkyl;
each R$^4$ is independently halogen, $C_{1-6}$alkyl, $C_{1-6}$alkoxy, $C_{1-6}$haloalkyl, or —CN;

R$^5$ is aryl or heteroaryl, wherein aryl and heteroaryl are unsubstituted or substituted with one or more substituents selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl;
R$^6$ is H or $C_{1-6}$alkyl;
n is 0, 1, 2, or 3; and
p is 1, 2, or 3;
or a pharmaceutically acceptable salt, solvate, or prodrug thereof.

In In some embodiments is a compound of Formula (II), wherein p is 1. In some embodiments is a compound of Formula (II), wherein p is 2. In some embodiments is a compound of Formula (II), wherein p is 3. In some embodiments is a compound of Formula (II), wherein n is 0. In some embodiments is a compound of Formula (II), wherein n is 1. In some embodiments is a compound of Formula (II), wherein n is 2. In some embodiments is a compound of Formula (II), wherein n is 1 or 2. In some embodiments is a compound of Formula (II), wherein n is 3. In some embodiments is a compound of Formula (II), wherein each R$^4$ is halogen. In some embodiments is a compound of Formula (II), wherein each R$^4$ is independently —Cl or —Br. In some embodiments is a compound of Formula (II), wherein each R$^4$ is —Cl. In some embodiments is a compound of Formula (II), wherein each R$^4$ is —Br. In some embodiments is a compound of Formula (II), wherein each R$^4$ is $C_{1-6}$alkyl. In some embodiments is a compound of Formula (II), wherein each R$^4$ is —CH$_3$. In some embodiments is a compound of Formula (II), wherein each R$^4$ is independently halogen or $C_{1-6}$alkyl. In some embodiments is a compound of Formula (II), wherein each R$^4$ is independently —Cl or —CH$_3$. In some embodiments is a compound of Formula (II), wherein each R$^4$ is $C_{1-6}$alkoxy. In some embodiments is a compound of Formula (II), wherein each R$^4$ is $C_{1-6}$haloalkyl. In some embodiments is a compound of Formula (II), wherein each R$^4$ is —CN. In some embodiments is a compound of Formula (II), wherein R$^1$ and R$^2$ are each independently $C_{1-6}$alkyl. In some embodiments is a compound of Formula (II), wherein R$^1$ and R$^2$ are each —CH$_3$. In some embodiments is a compound of Formula (II), wherein R$^1$ and R$^2$ together with the nitrogen to which they are attached are combined to form a heterocycloalkyl ring. In some embodiments is a compound of Formula (II), wherein R$^1$ and R$^2$ together with the nitrogen to which they are attached are combined to form a piperidine ring. In some embodiments is a compound of Formula (II), wherein R$^1$ and R$^2$ together with the nitrogen to which they are attached are combined to form a piperazine ring. In some embodiments is a compound of Formula (II), wherein R$^1$ and R$^2$ together with the nitrogen to which they are attached are combined to form a morpholine ring. In some embodiments is a compound of Formula (II), wherein R$^5$ is heteroaryl and wherein heteroaryl is unsubstituted or substituted by one or more substituents selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments is a compound of Formula (II), wherein R$^5$ is heteroaryl and wherein heteroaryl is substituted by one substituent selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments is a compound of Formula (II), wherein R$^5$ is unsubstituted pyridyl. In some embodiments is a compound of Formula (II), wherein R$^5$ is pyridyl substituted by one or more substituents selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, C$_{3-6}$cycloalkyl, and phenyl. In some embodiments is a compound of Formula (II), wherein R$^5$ is pyridyl substituted by one substituent selected from halogen, C$_{1-6}$alkyl, C$_{1-6}$ alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl. In some embodiments is a compound of Formula (II), wherein R$^5$ is pyridyl substituted by C$_{1-6}$alkyl. In some embodiments is a compound of Formula (II), wherein R$^5$ is pyridyl substituted by —CH$_3$. In some embodiments is a compound of Formula (II), wherein R$^5$ is pyridyl substituted by halogen. In some embodiments is a compound of Formula (II), wherein R$^5$ is pyridyl substituted by —Cl. In some embodiments is a compound of Formula (II), wherein R$^5$ is pyridyl substituted by —Br. In some embodiments is a compound of Formula (II), wherein R$^5$ is pyridyl substituted by C$_{1-6}$alkoxy. In some embodiments is a compound of Formula (II), wherein R$^5$ is pyridyl substituted by C$_{1-6}$haloalkyl. In some embodiments is a compound of Formula (II), wherein R$^5$ is pyridyl substituted by C$_{1-6}$haloalkoxy. In some embodiments is a compound of Formula (II), wherein R$^5$ is pyridyl substituted by —OH. In some embodiments is a compound of Formula (II), wherein R$^5$ is pyridyl substituted by —CH$_2$OH. In some embodiments is a compound of Formula (II), wherein R$^5$ is pyridyl substituted by —CN. In some embodiments is a compound of Formula (II), wherein R$^5$ is pyridyl substituted by —CO$_2$R$^6$. In some embodiments is a compound of Formula (II), wherein R$^5$ is pyridyl substituted by C$_{3-6}$cycloalkyl. In some embodiments is a compound of Formula (II), wherein R$^5$ is pyridyl substituted by phenyl. In some embodiments is a compound of Formula (II), wherein R$^5$ is aryl and wherein aryl is unsubstituted or substituted by one or more substituents selected from halogen, C$_{1-6}$alkyl, C$_{1-6}$alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl. In some embodiments is a compound of Formula (II), wherein R$^5$ is unsubstituted phenyl. In some embodiments is a compound of Formula (II), wherein R$^5$ is phenyl substituted by one or more substituents selected from halogen, C$_{1-6}$ alkyl, C$_{1-6}$ alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl. In some embodiments is a compound of Formula (II), wherein R$^5$ is phenyl substituted by one substituent selected from halogen, C$_{1-6}$alkyl, C$_{1-6}$alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl. In some embodiments is a compound of Formula (II), wherein R$^5$ is phenyl substituted by C$_{1-6}$alkyl. In some embodiments is a compound of Formula (II), wherein R$^5$ is phenyl substituted by —CH$_3$. In some embodiments is a compound of Formula (II), wherein R$^5$ is phenyl substituted by halogen. In some embodiments is a compound of Formula (II), wherein R$^5$ is phenyl substituted by —Cl. In some embodiments is a compound of Formula (II), wherein R$^5$ is phenyl substituted by —Br. In some embodiments is a compound of Formula (II), wherein R$^5$ is phenyl substituted by C$_{1-6}$alkoxy. In some embodiments is a compound of Formula (II), wherein R$^5$ is phenyl substituted by C$_{1-6}$haloalkyl. In some embodiments is a compound of Formula (II), wherein R$^5$ is phenyl substituted by C$_{1-6}$haloalkoxy. In some embodiments is a compound of Formula (II), wherein R$^5$ is phenyl substituted by —OH. In some embodiments is a compound of Formula (II), wherein R$^5$ is phenyl substituted by —CH$_2$OH. In some embodiments is a compound of Formula (II), wherein R$^5$ is phenyl substituted by —CN. In some embodiments is a compound of Formula (II), wherein R$^5$ is phenyl substituted by —CO$_2$R$^6$. In some embodiments is a compound of Formula (II), wherein R$^5$ is phenyl substituted by C$_{3-6}$cycloalkyl. In some embodiments is a compound of Formula (II), wherein R$^5$ is phenyl substituted by phenyl. In some embodiments is a compound of Formula (II), wherein X is —O—. In some embodiments is a compound of Formula (II), wherein X is —N(H)—. In some embodiments is a compound of Formula (II), wherein X is —CH$_2$—. In some embodiments is a compound of Formula (II), wherein R$^3$ is —CH$_2$CH$_3$.

In some embodiments provided herein, is a compound of Formula (IIa) having the structure:

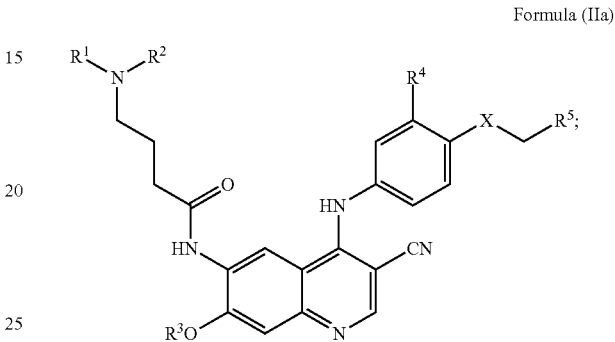

Formula (IIa)

wherein:
X is —O—, —N(H)—, or —CH$_2$—;
R$^1$ and R$^2$ are each independently C$_{1-6}$alkyl; or R$^1$ and R$^2$ together with the nitrogen to which they are attached are combined to form a heterocycloalkyl ring;
R$^3$ is C$_{1-6}$alkyl;
R$^4$ is halogen, C$_{1-6}$alkyl, C$_{1-6}$alkoxy, C$_{1-6}$haloalkyl, or —CN;
R$^5$ is aryl or heteroaryl, wherein aryl and heteroaryl are unsubstituted or substituted by one or more substituents selected from halogen, C$_{1-6}$alkyl, C$_{1-6}$alkoxy, C$_{1-6}$haloalkyl, C$_{1-6}$haloalkoxy, —OH, —CH$_2$OH, —CN, —CO$_2$R$^6$, C$_{3-6}$cycloalkyl, and phenyl; and
R$^6$ is H or C$_{1-6}$alkyl;
or a pharmaceutically acceptable salt, solvate, or prodrug thereof.

In some embodiments is a compound of Formula (IIa), wherein R$^4$ is halogen. In some embodiments is a compound of Formula (IIa), wherein R$^4$ is —Cl. In some embodiments is a compound of Formula (IIa), wherein R$^4$ is —Br. In some embodiments is a compound of Formula (IIa), wherein R$^4$ is C$_{1-6}$alkyl. In some embodiments is a compound of Formula (IIa), wherein R$^4$ is —CH$_3$. In some embodiments is a compound of Formula (IIa), wherein R$^4$ is C$_{1-6}$alkoxy. In some embodiments is a compound of Formula (IIa), wherein R$^4$ is C$_{1-6}$haloalkyl. In some embodiments is a compound of Formula (IIa), wherein R$^4$ is —CN. In some embodiments is a compound of Formula (IIa), wherein R$^1$ and R$^2$ are each independently C$_{1-6}$alkyl. In some embodiments is a compound of Formula (IIa), wherein R$^1$ and R$^2$ are each —CH$_3$. In some embodiments is a compound of Formula (IIa), wherein R$^1$ and R$^2$ together with the nitrogen to which they are attached are combined to form a heterocycloalkyl ring. In some embodiments is a compound of Formula (IIa), wherein R$^1$ and R$^2$ together with the nitrogen to which they are attached are combined to form a piperidine ring. In some embodiments is a compound of Formula (IIa), wherein R$^1$ and R$^2$ together with the nitrogen to which they are attached are combined to form a piperazine ring. In some embodiments is a compound of Formula (IIa), wherein R$^1$ and R$^2$ together with the nitrogen to which they are attached are combined to form a morpholine ring. In some embodiments is a compound of Formula (IIa), wherein $R^5$ is heteroaryl and wherein heteroaryl is unsubstituted or substituted by one or more substituents selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments is a compound of Formula (IIa), wherein $R^5$ is heteroaryl and wherein heteroaryl is substituted by one substituent selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments is a compound of Formula (IIa), wherein $R^5$ is unsubstituted pyridyl. In some embodiments is a compound of Formula (IIa), wherein $R^5$ is pyridyl substituted by one or more substituents selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments is a compound of Formula (IIa), wherein $R^5$ is pyridyl substituted by one substituent selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments is a compound of Formula (IIa), wherein $R^5$ is pyridyl substituted by $C_{1-6}$alkyl. In some embodiments is a compound of Formula (IIa), wherein $R^5$ is pyridyl substituted by —CH$_3$. In some embodiments is a compound of Formula (IIa), wherein $R^5$ is pyridyl substituted by halogen. In some embodiments is a compound of Formula (IIa), wherein $R^5$ is pyridyl substituted by —Cl. In some embodiments is a compound of Formula (IIa), wherein $R^5$ is pyridyl substituted by —Br. In some embodiments is a compound of Formula (IIa), wherein $R^5$ is pyridyl substituted by $C_{1-6}$alkoxy. In some embodiments is a compound of Formula (IIa), wherein $R^5$ is pyridyl substituted by $C_{1-6}$haloalkyl. In some embodiments is a compound of Formula (IIa), wherein $R^5$ is pyridyl substituted by $C_{1-6}$haloalkoxy. In some embodiments is a compound of Formula (IIa), wherein $R^5$ is pyridyl substituted by —OH. In some embodiments is a compound of Formula (IIa), wherein $R^5$ is pyridyl substituted by —CH$_2$OH. In some embodiments is a compound of Formula (IIa), wherein $R^5$ is pyridyl substituted by —CN. In some embodiments is a compound of Formula (IIa), wherein $R^5$ is pyridyl substituted by —CO$_2$R$^6$. In some embodiments is a compound of Formula (IIa), wherein $R^5$ is pyridyl substituted by $C_{3-6}$cycloalkyl. In some embodiments is a compound of Formula (IIa), wherein $R^5$ is pyridyl substituted by phenyl. In some embodiments is a compound of Formula (IIa), wherein $R^5$ is aryl and wherein aryl is unsubstituted or substituted by one or more substituents selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments is a compound of Formula (IIa), wherein $R^5$ is unsubstituted phenyl. In some embodiments is a compound of Formula (IIa), wherein $R^5$ is phenyl substituted by one or more substituents selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments is a compound of Formula (IIa), wherein $R^5$ is phenyl substituted by one substituent selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl. In some embodiments is a compound of Formula (IIa), wherein $R^5$ is phenyl substituted by $C_{1-6}$alkyl. In some embodiments is a compound of Formula (IIa), wherein $R^5$ is phenyl substituted by —CH$_3$. In some embodiments is a compound of Formula (IIa), wherein $R^5$ is phenyl substituted by halogen. In some embodiments is a compound of Formula (IIa), wherein $R^5$ is phenyl substituted by —Cl. In some embodiments is a compound of Formula (IIa), wherein $R^5$ is phenyl substituted by —Br. In some embodiments is a compound of Formula (IIa), wherein $R^5$ is phenyl substituted by $C_{1-6}$alkoxy. In some embodiments is a compound of Formula (IIa), wherein $R^5$ is phenyl substituted by $C_{1-6}$haloalkyl. In some embodiments is a compound of Formula (IIa), wherein $R^5$ is phenyl substituted by $C_{1-6}$haloalkoxy. In some embodiments is a compound of Formula (IIa), wherein $R^5$ is phenyl substituted by —OH. In some embodiments is a compound of Formula (IIa), wherein $R^5$ is phenyl substituted by —CH$_2$OH. In some embodiments is a compound of Formula (IIa), wherein $R^5$ is phenyl substituted by —CN. In some embodiments is a compound of Formula (IIa), wherein $R^5$ is phenyl substituted by —CO$_2$R$^6$. In some embodiments is a compound of Formula (IIa), wherein $R^5$ is phenyl substituted by $C_{3-6}$cycloalkyl. In some embodiments is a compound of Formula (IIa), wherein $R^5$ is phenyl substituted by phenyl. In some embodiments is a compound of Formula (IIa), wherein X is —O—. In some embodiments is a compound of Formula (IIa), wherein X is —N(H)—. In some embodiments is a compound of Formula (IIa), wherein X is —CH$_2$—. In some embodiments is a compound of Formula (IIa), wherein $R^3$ is —CH$_2$CH$_3$.

In some embodiments provided herein, is a compound of Formula (IIb) having the structure:

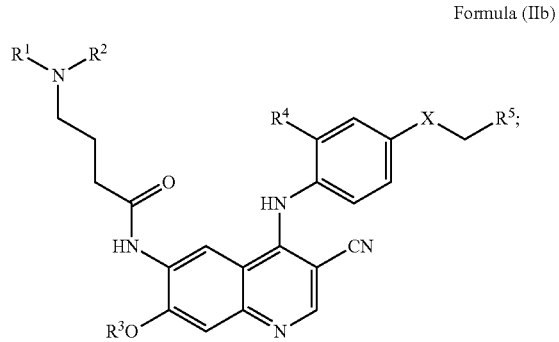

Formula (IIb)

wherein:

X is —O—, —N(H)—, or —CH$_2$—;

$R^1$ and $R^2$ are each independently $C_{1-6}$alkyl; or $R^1$ and $R^2$ together with the nitrogen to which they are attached are combined to form a heterocycloalkyl ring;

$R^3$ is $C_{1-6}$alkyl;

$R^4$ is halogen, $C_{1-6}$alkyl, $C_{1-6}$alkoxy, $C_{1-6}$haloalkyl, or —CN;

$R^5$ is aryl or heteroaryl, wherein aryl and heteroaryl are unsubstituted or substituted by one or more substituents selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl; and $R^6$ is H or $C_{1-6}$alkyl;

or a pharmaceutically acceptable salt, solvate, or prodrug thereof.

In some embodiments is a compound of Formula (IIb), wherein $R^4$ is halogen. In some embodiments is a compound of Formula (IIb), wherein $R^4$ is —Cl. In some embodiments is a compound of Formula (IIb), wherein $R^4$ is —Br. In some embodiments is a compound of Formula (IIb), wherein $R^4$ is $C_{1-6}$alkyl. In some embodiments is a compound of Formula (IIb), wherein $R^4$ is —$CH_3$. In some embodiments is a compound of Formula (IIb), wherein $R^4$ is $C_{1-6}$alkoxy. In some embodiments is a compound of Formula (IIb), wherein $R^4$ is $C_{1-6}$haloalkyl. In some embodiments is a compound of Formula (IIb), wherein $R^4$ is —CN. In some embodiments is a compound of Formula (IIb), wherein $R^1$ and $R^2$ are each independently $C_{1-6}$alkyl. In some embodiments is a compound of Formula (IIb), wherein $R^1$ and $R^2$ are each —$CH_3$. In some embodiments is a compound of Formula (IIb), wherein $R^1$ and $R^2$ together with the nitrogen to which they are attached are combined to form a heterocycloalkyl ring. In some embodiments is a compound of Formula (IIb), wherein $R^1$ and $R^2$ together with the nitrogen to which they are attached are combined to form a piperidine ring. In some embodiments is a compound of Formula (IIb), wherein $R^1$ and $R^2$ together with the nitrogen to which they are attached are combined to form a piperazine ring. In some embodiments is a compound of Formula (IIb), wherein $R^1$ and $R^2$ together with the nitrogen to which they are attached are combined to form a morpholine ring. In some embodiments is a compound of Formula (IIb), wherein $R^5$ is heteroaryl and wherein heteroaryl is unsubstituted or substituted by one or more substituents selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl. In some embodiments is a compound of Formula (IIb), wherein $R^5$ is heteroaryl and wherein heteroaryl is substituted by one substituent selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl. In some embodiments is a compound of Formula (IIb), wherein $R^5$ is unsubstituted pyridyl. In some embodiments is a compound of Formula (IIb), wherein $R^5$ is pyridyl substituted by one or more substituents selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl. In some embodiments is a compound of Formula (IIb), wherein $R^5$ is pyridyl substituted by one substituent selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl. In some embodiments is a compound of Formula (IIb), wherein $R^5$ is pyridyl substituted by $C_{1-6}$alkyl. In some embodiments is a compound of Formula (IIb), wherein $R^5$ is pyridyl substituted by —$CH_3$. In some embodiments is a compound of Formula (IIb), wherein $R^5$ is pyridyl substituted by halogen. In some embodiments is a compound of Formula (IIb), wherein $R^5$ is pyridyl substituted by —Cl. In some embodiments is a compound of Formula (IIb), wherein $R^5$ is pyridyl substituted by —Br. In some embodiments is a compound of Formula (IIb), wherein $R^5$ is pyridyl substituted by $C_{1-6}$alkoxy. In some embodiments is a compound of Formula (IIb), wherein $R^5$ is pyridyl substituted by $C_{1-6}$haloalkyl. In some embodiments is a compound of Formula (IIb), wherein $R^5$ is pyridyl substituted by $C_{1-6}$haloalkoxy. In some embodiments is a compound of Formula (IIb), wherein $R^5$ is pyridyl substituted by —OH. In some embodiments is a compound of Formula (IIb), wherein $R^5$ is pyridyl substituted by —$CH_2OH$. In some embodiments is a compound of Formula (IIb), wherein $R^5$ is pyridyl substituted by —CN. In some embodiments is a compound of Formula (IIb), wherein $R^5$ is pyridyl substituted by —$CO_2R^6$. In some embodiments is a compound of Formula (IIb), wherein $R^5$ is pyridyl substituted by $C_{3-6}$cycloalkyl. In some embodiments is a compound of Formula (IIb), wherein $R^5$ is pyridyl substituted by phenyl. In some embodiments is a compound of Formula (IIb), wherein $R^5$ is aryl and wherein aryl is unsubstituted or substituted by one or more substituents selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl. In some embodiments is a compound of Formula (IIb), wherein $R^5$ is unsubstituted phenyl. In some embodiments is a compound of Formula (IIb), wherein $R^5$ is phenyl substituted by one or more substituents selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl. In some embodiments is a compound of Formula (IIb), wherein $R^5$ is phenyl substituted by one substituent selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl. In some embodiments is a compound of Formula (IIb), wherein $R^5$ is phenyl substituted by $C_{1-6}$alkyl. In some embodiments is a compound of Formula (IIb), wherein $R^5$ is phenyl substituted by —$CH_3$. In some embodiments is a compound of Formula (IIb), wherein $R^5$ is phenyl substituted by halogen. In some embodiments is a compound of Formula (IIb), wherein $R^5$ is phenyl substituted by —Cl. In some embodiments is a compound of Formula (IIb), wherein $R^5$ is phenyl substituted by —Br. In some embodiments is a compound of Formula (IIb), wherein $R^5$ is phenyl substituted by $C_{1-6}$alkoxy. In some embodiments is a compound of Formula (IIb), wherein $R^5$ is phenyl substituted by $C_{1-6}$haloalkyl. In some embodiments is a compound of Formula (IIb), wherein $R^5$ is phenyl substituted by $C_{1-6}$haloalkoxy. In some embodiments is a compound of Formula (IIb), wherein $R^5$ is phenyl substituted by —OH. In some embodiments is a compound of Formula (IIb), wherein $R^5$ is phenyl substituted by —$CH_2OH$. In some embodiments is a compound of Formula (IIb), wherein $R^5$ is phenyl substituted by —CN. In some embodiments is a compound of Formula (IIb), wherein $R^5$ is phenyl substituted by —$CO_2R^6$. In some embodiments is a compound of Formula (IIb), wherein $R^5$ is phenyl substituted by $C_{3-6}$cycloalkyl. In some embodiments is a compound of Formula (IIb), wherein $R^5$ is phenyl substituted by phenyl. In some embodiments is a compound of Formula (IIb), wherein X is —O—. In some embodiments is a compound of Formula (IIb), wherein X is —N(H)—. In some embodiments is a compound of Formula (IIb), wherein X is —$CH_2$—. In some embodiments is a compound of Formula (IIb), wherein $R^3$ is —$CH_2CH_3$.

In some embodiments is a compound, or a pharmaceutically acceptable salt, solvate, or prodrug thereof, having the structure selected from:

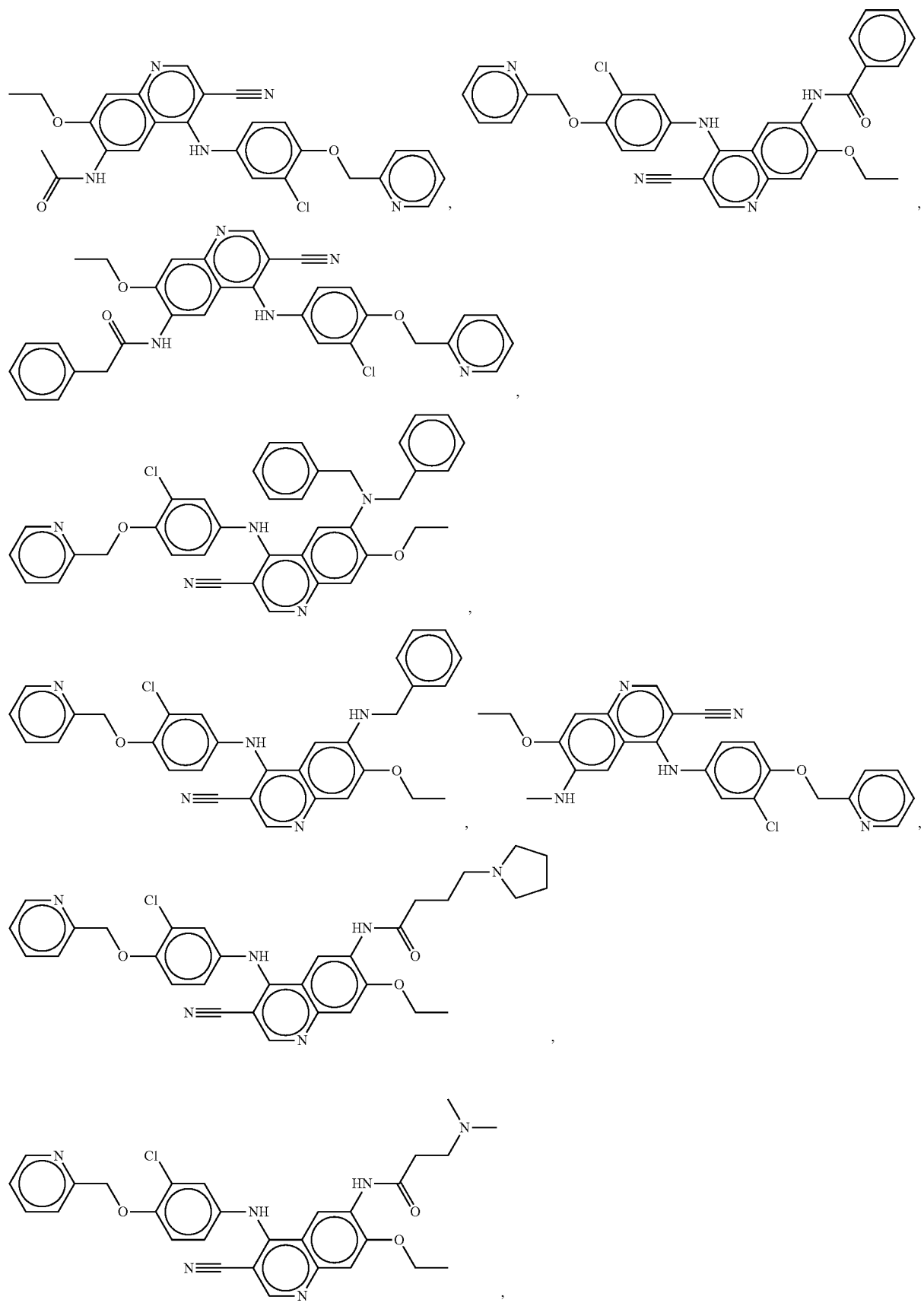

-continued
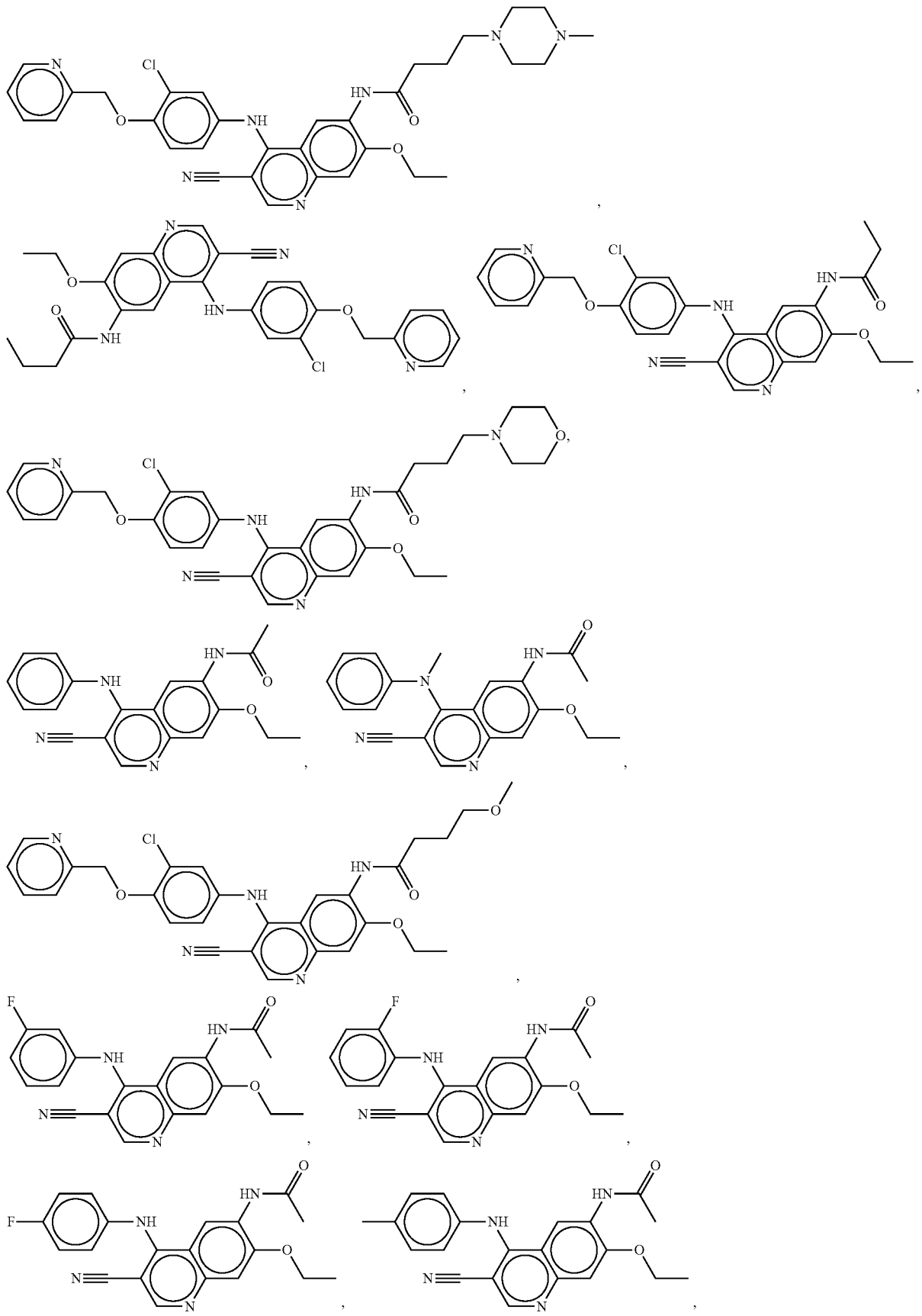

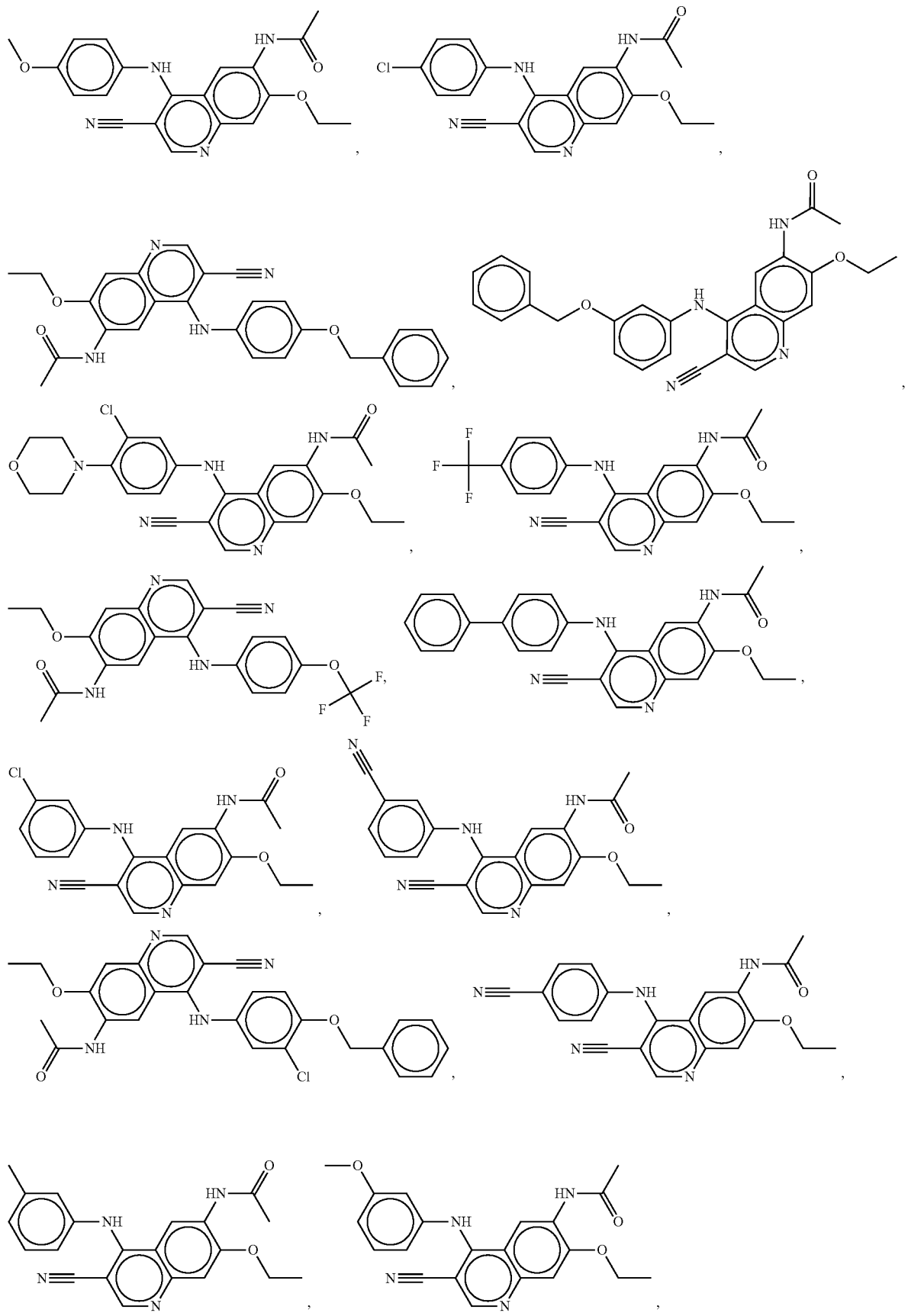
-continued

-continued
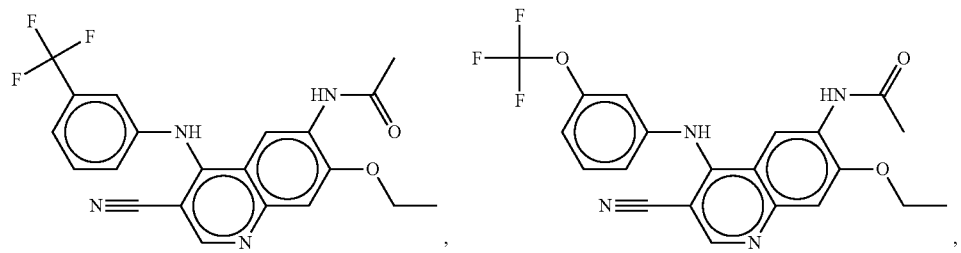
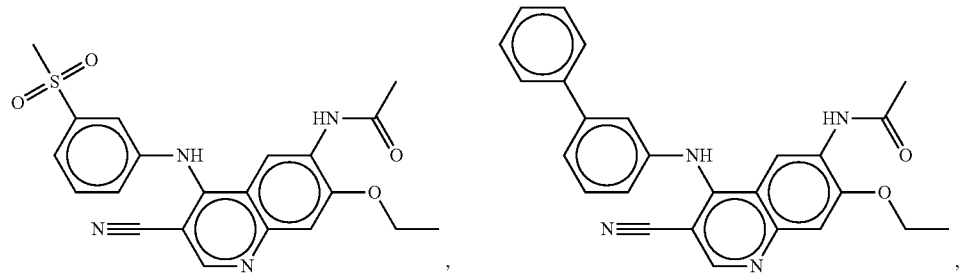
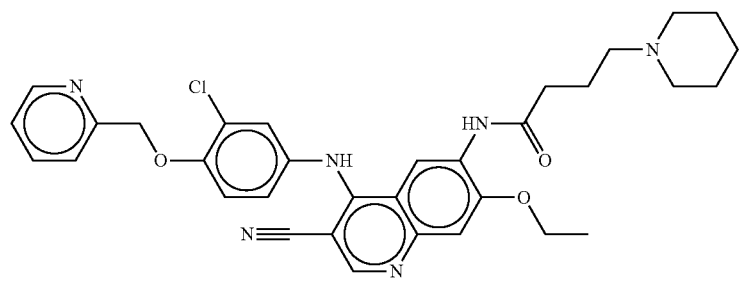
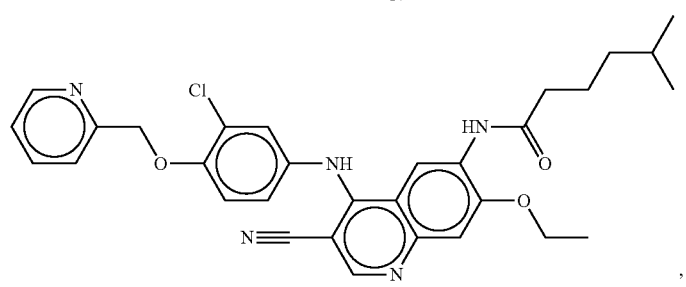
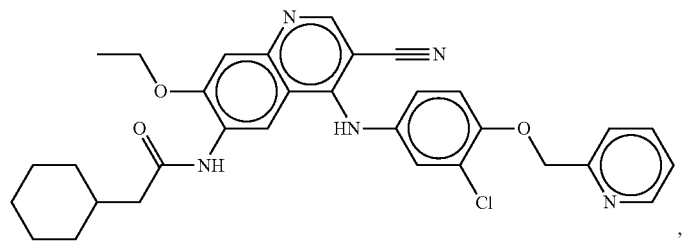
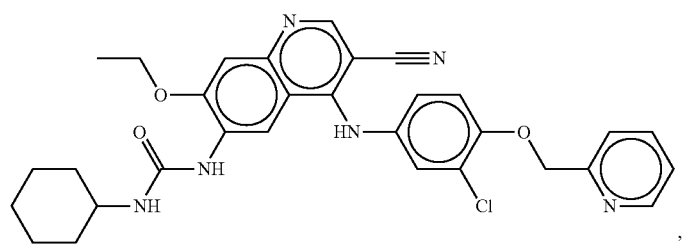

-continued
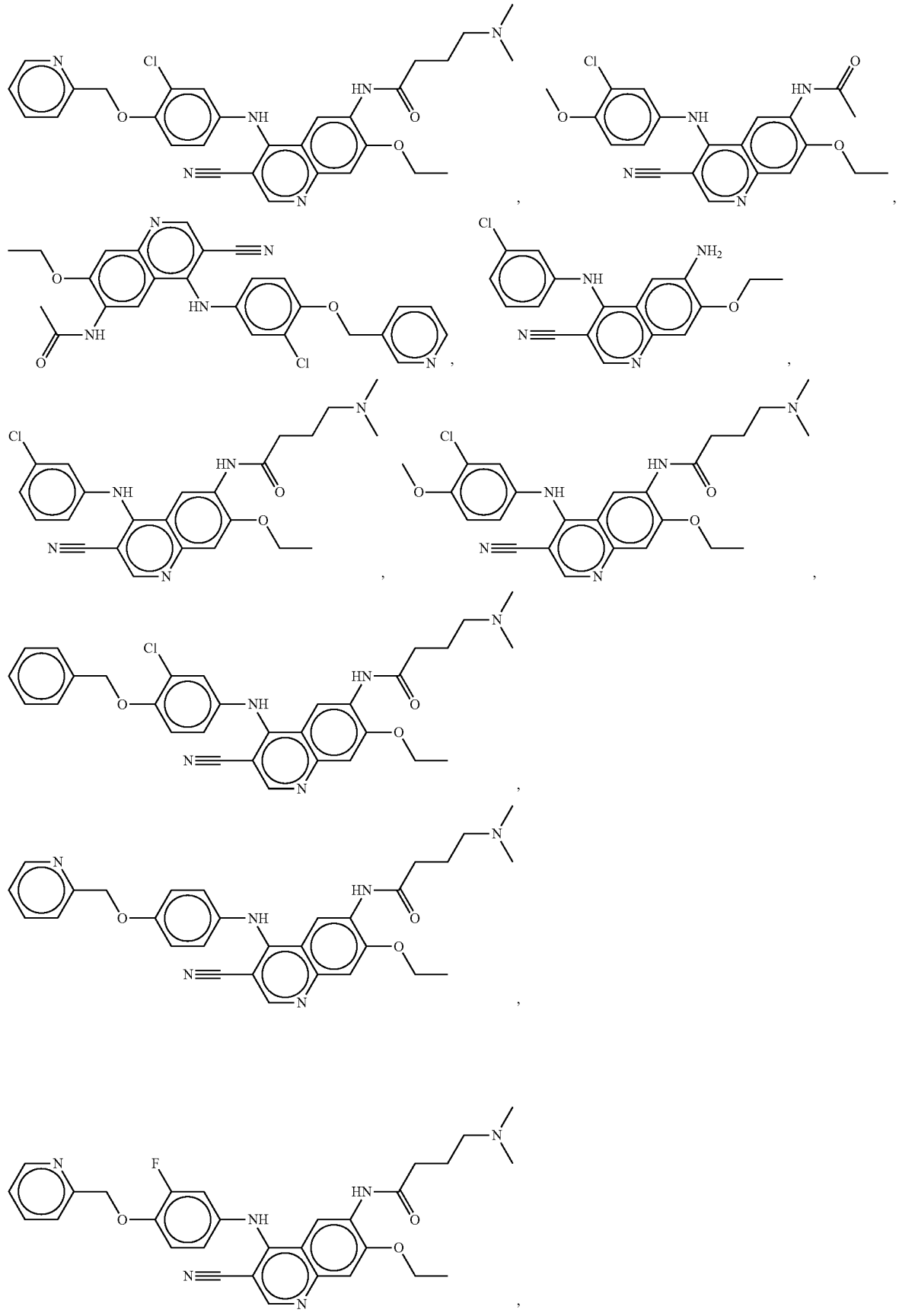

-continued
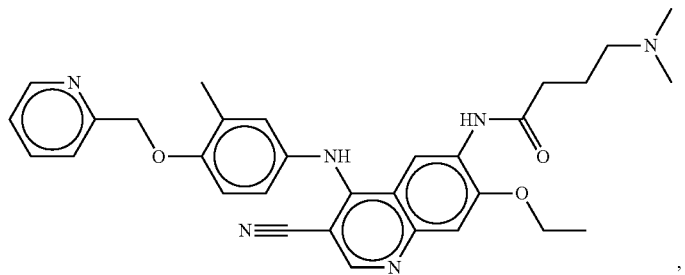

-continued
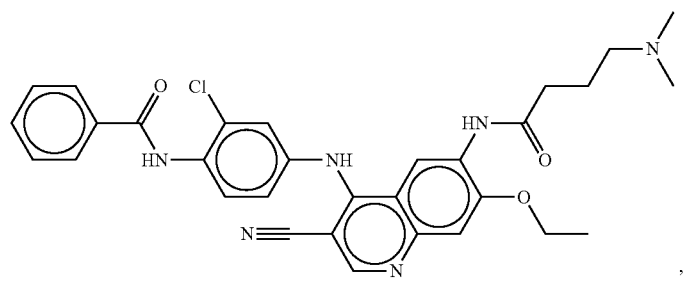
,
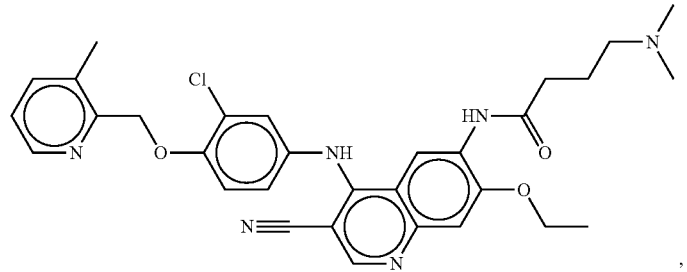
,
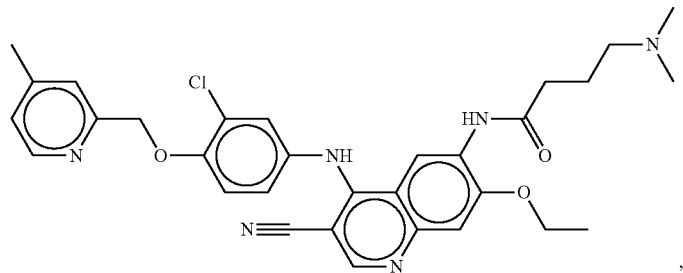
,
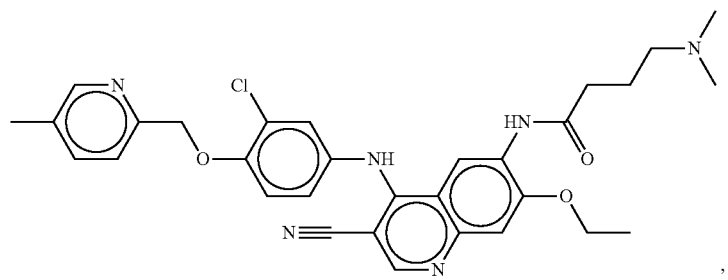
,
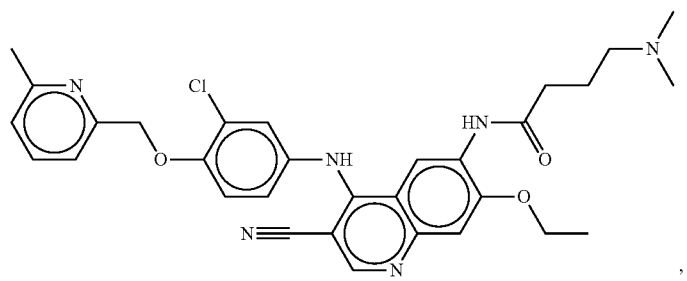
,
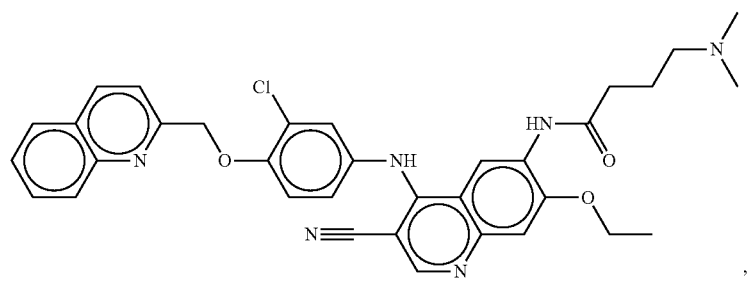
,

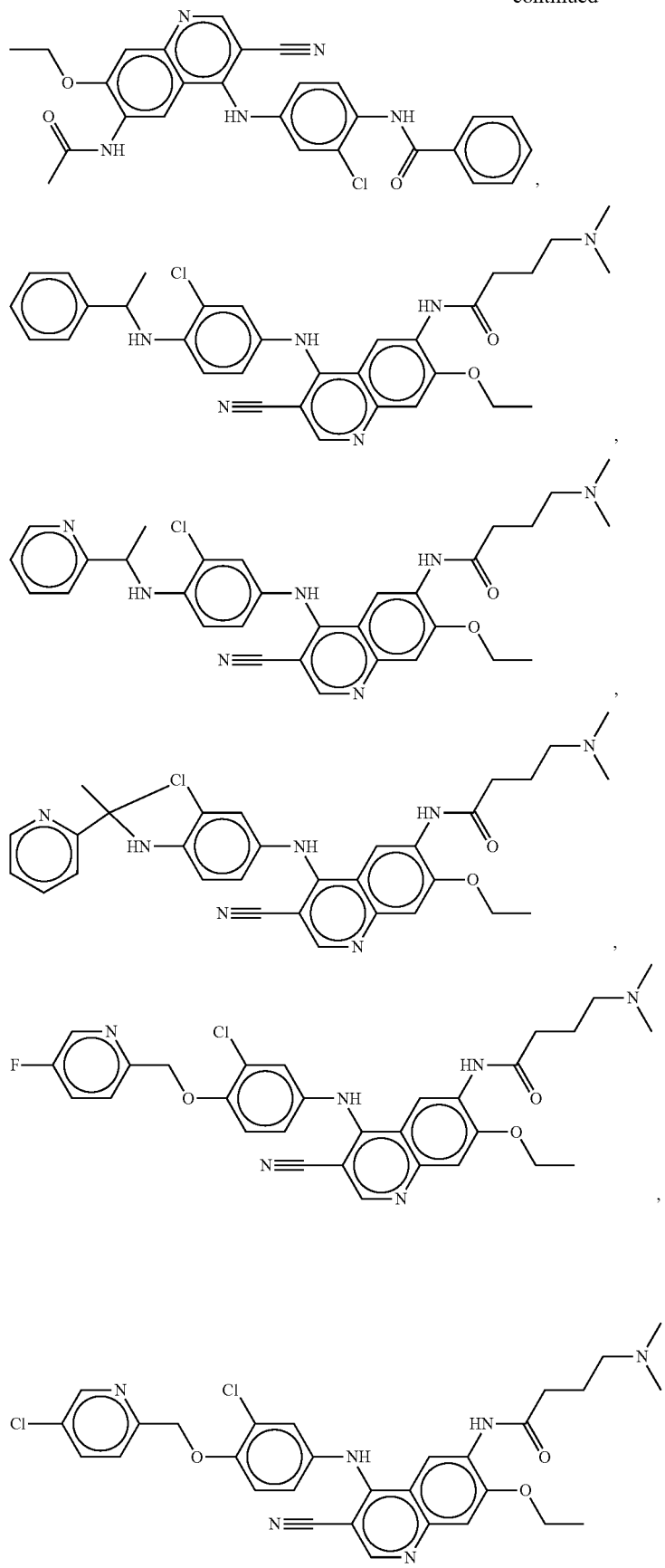

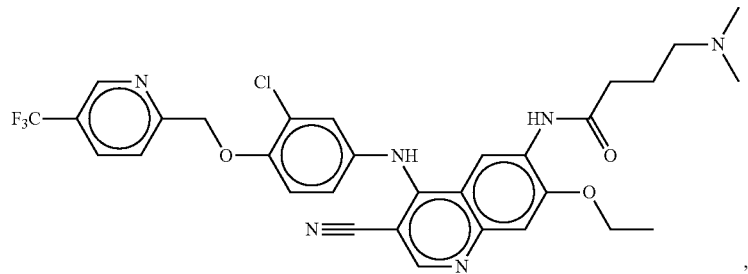
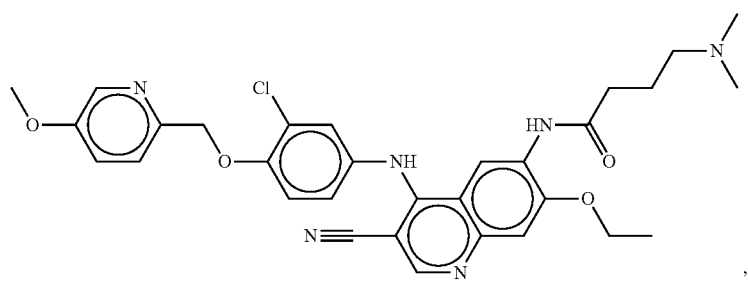
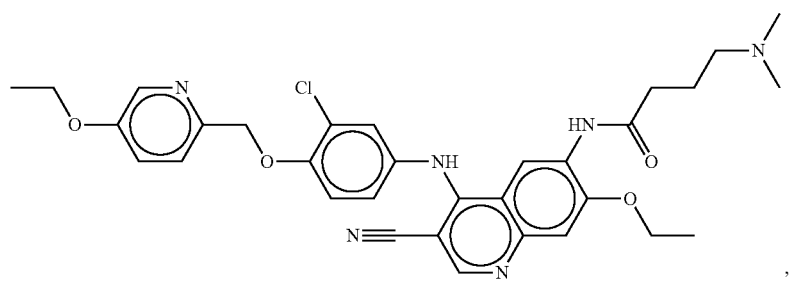
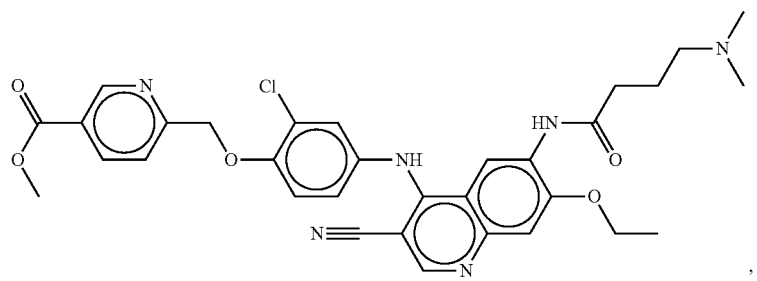
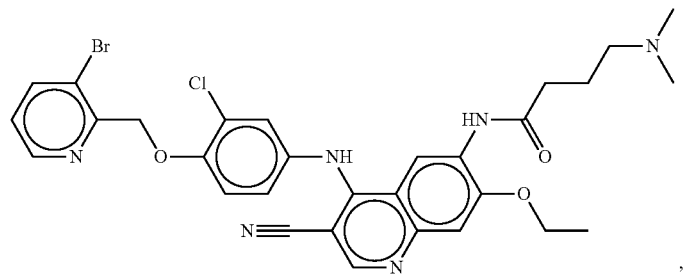
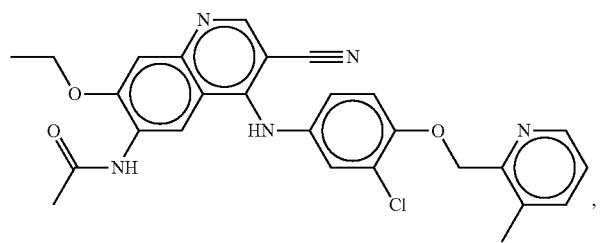

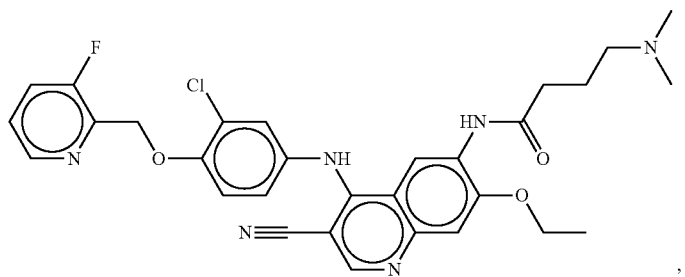
,
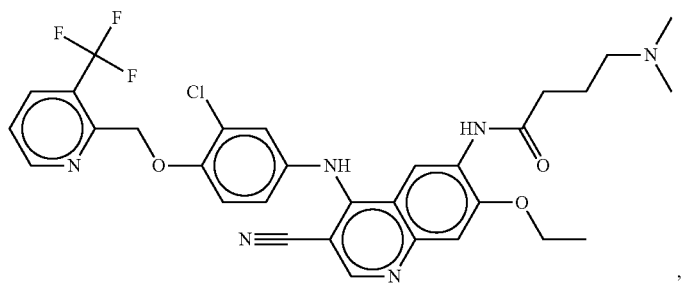
,
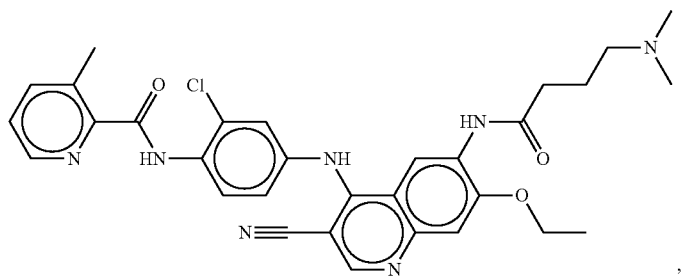
,
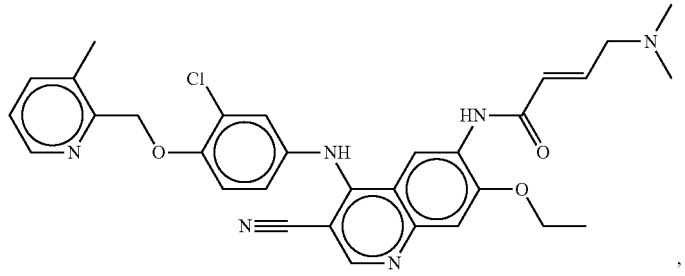
,
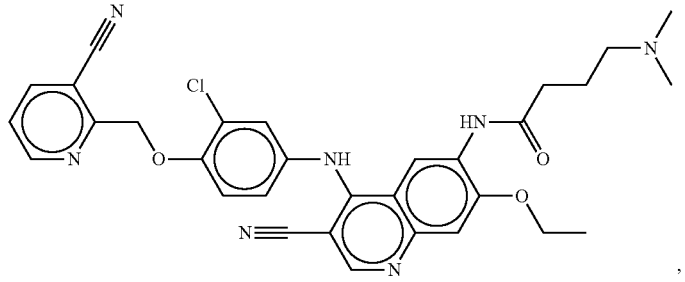
,
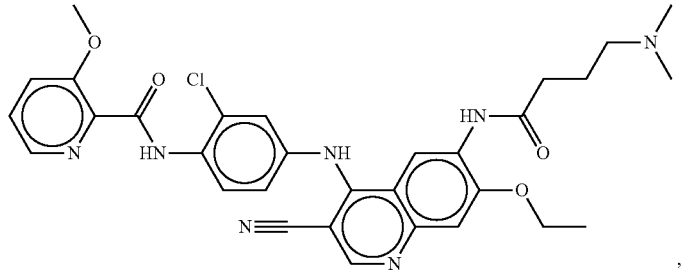
,

-continued
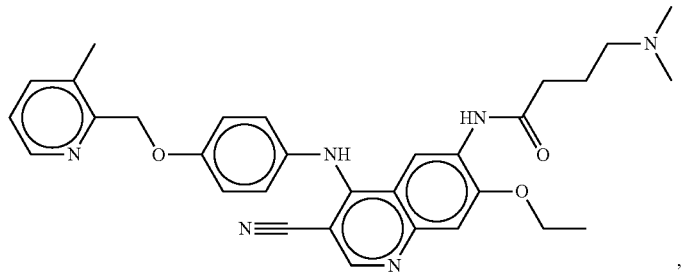
,
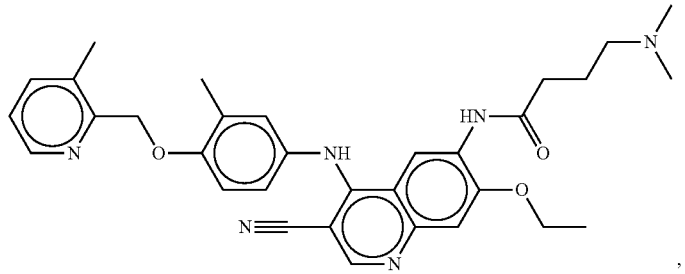
,
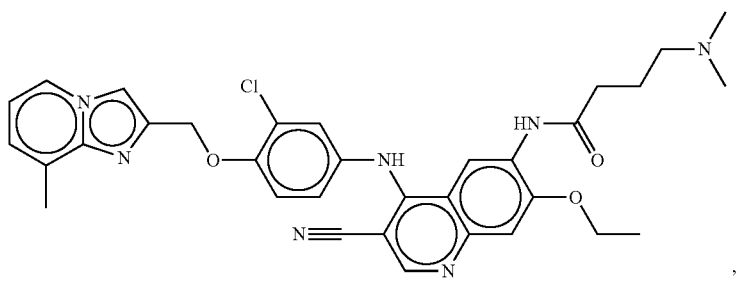
,
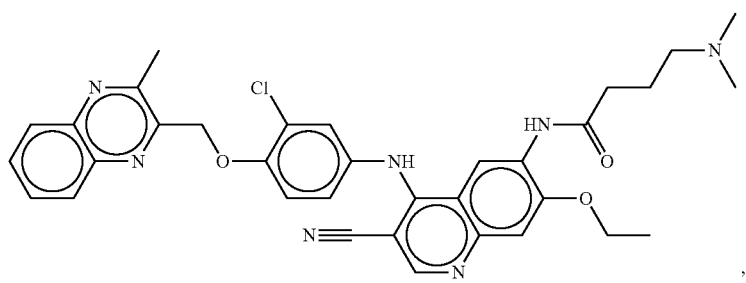
,
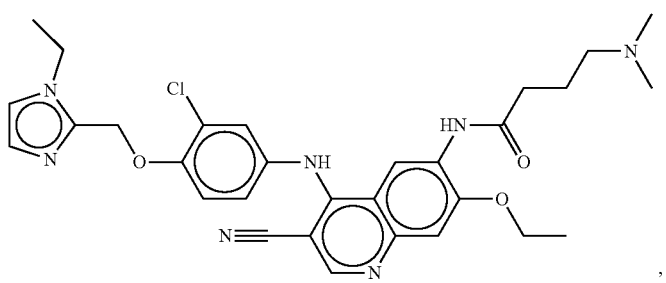
,
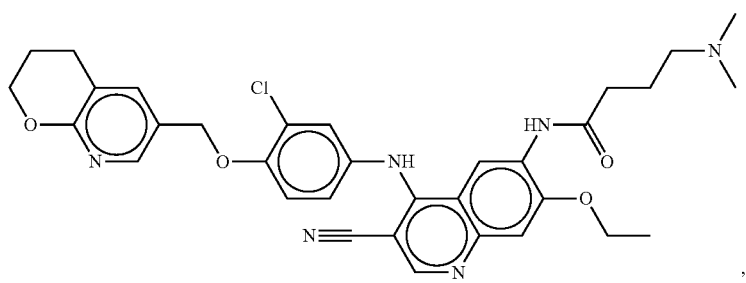
, -continued
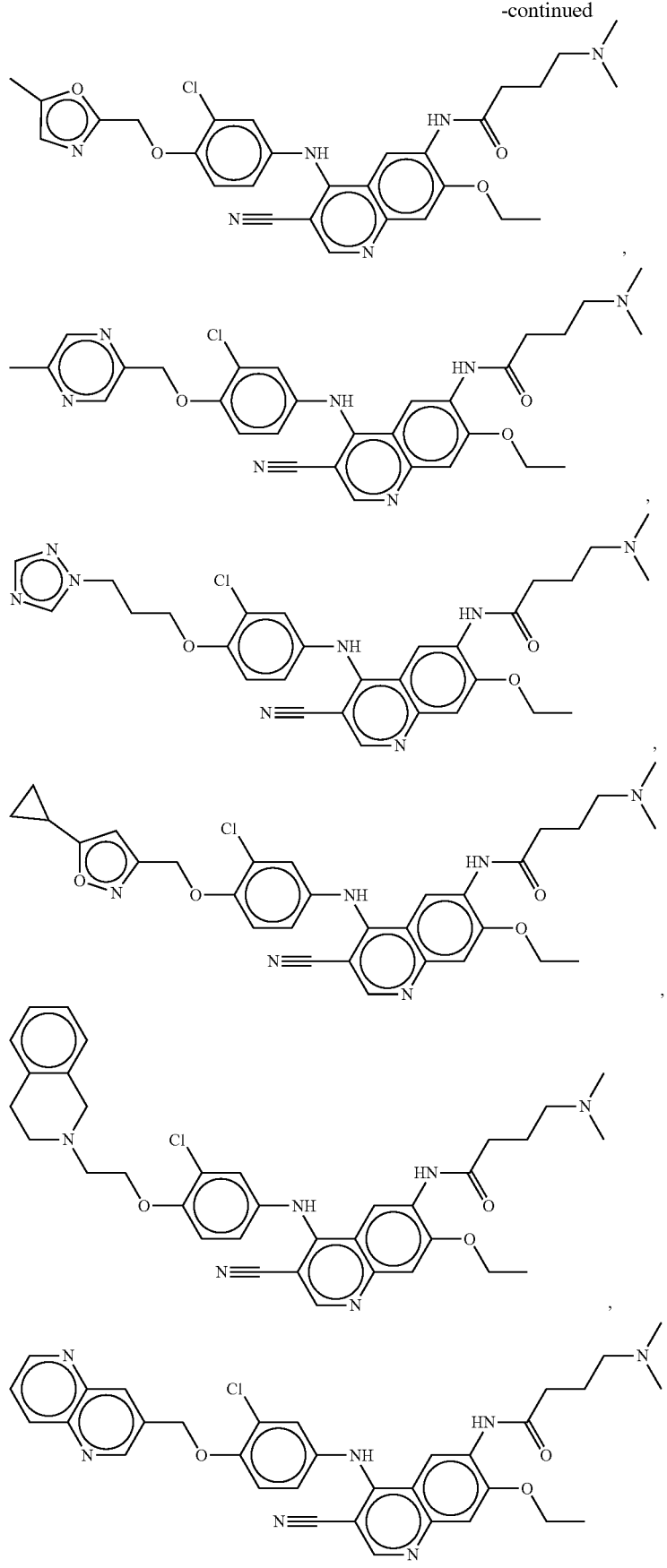

-continued
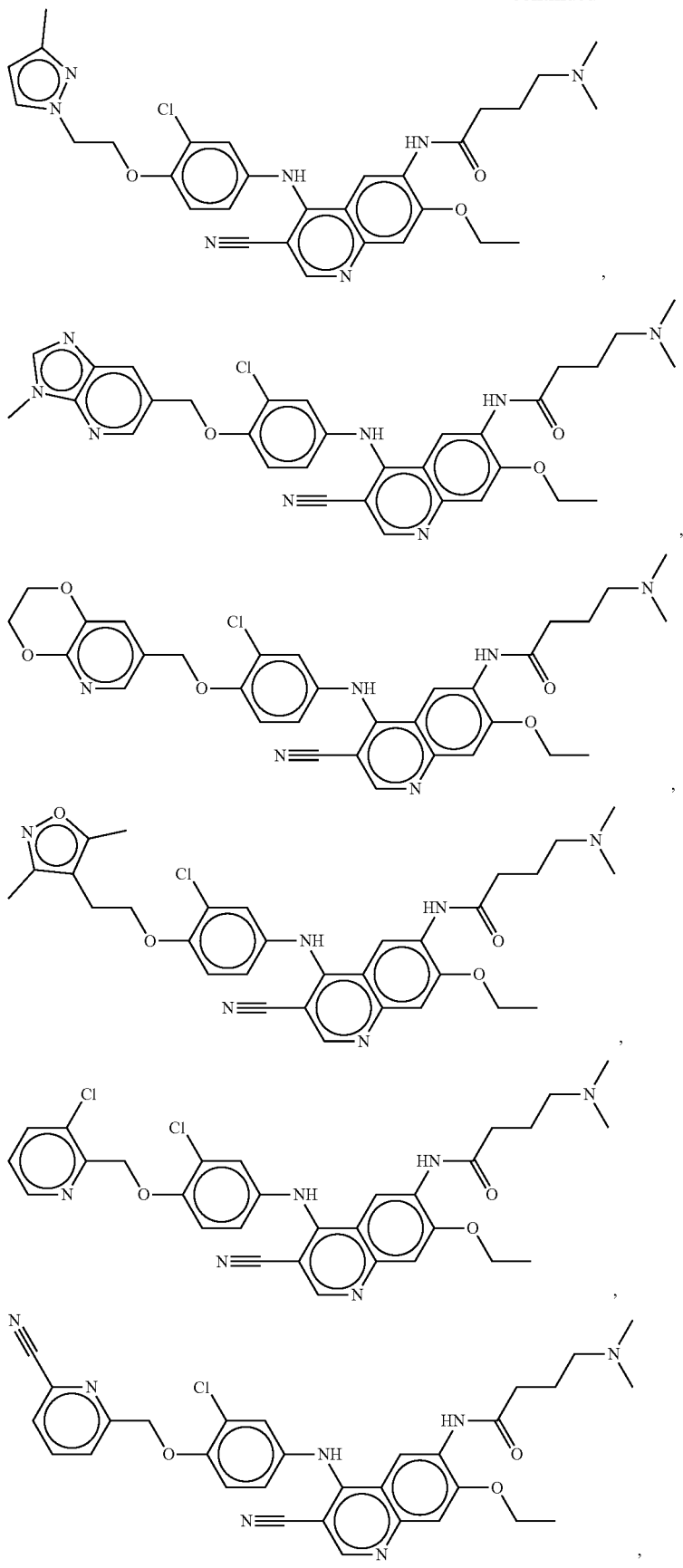

-continued
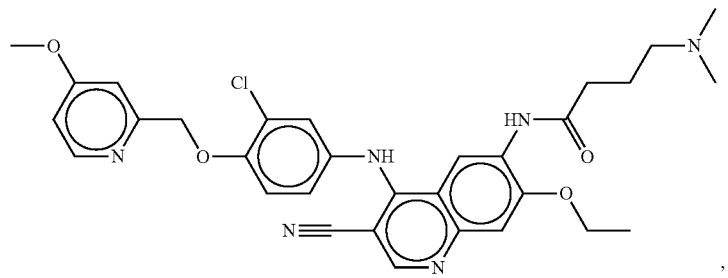,
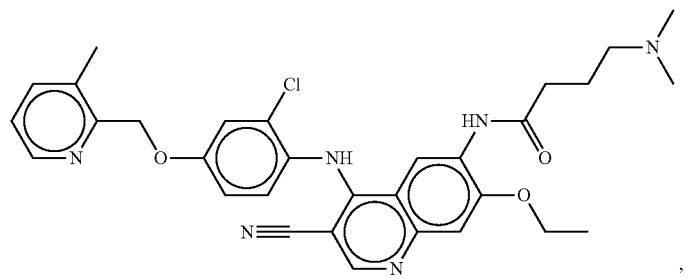,
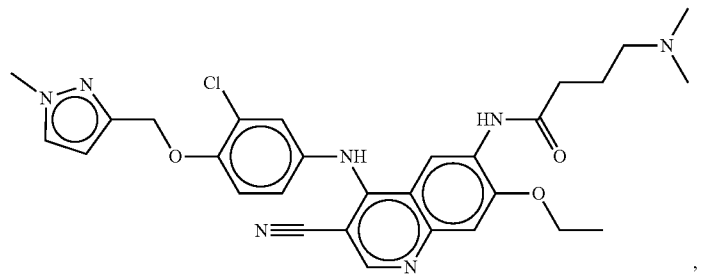,
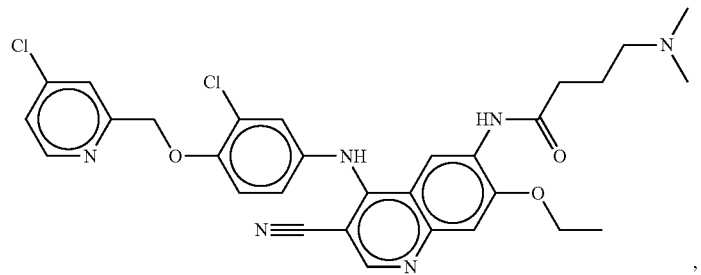,
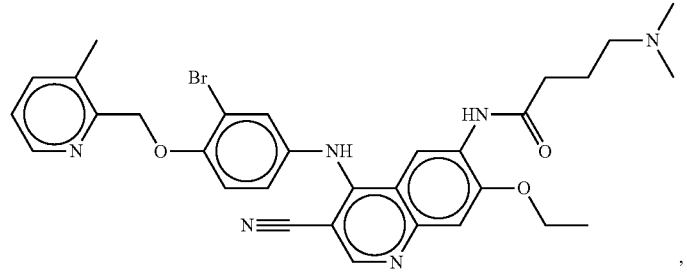,
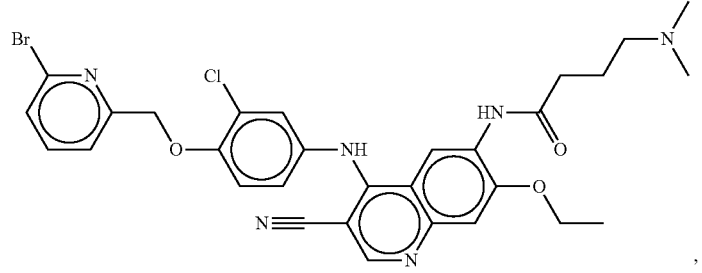, -continued
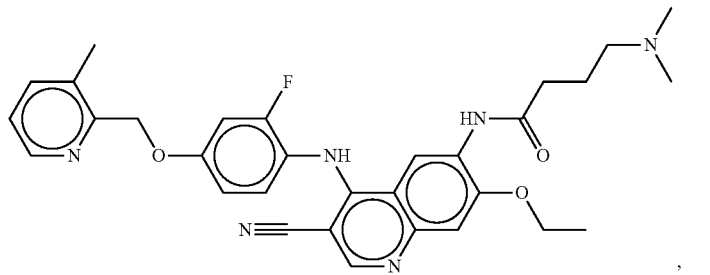
,
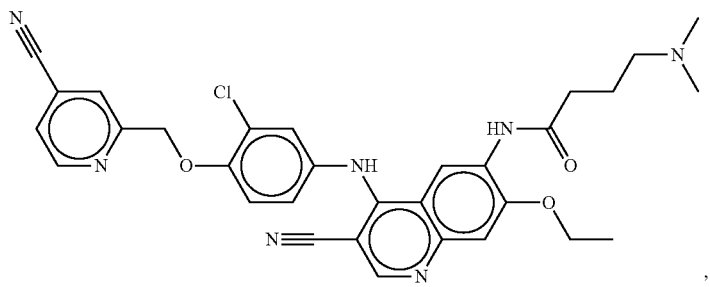
,
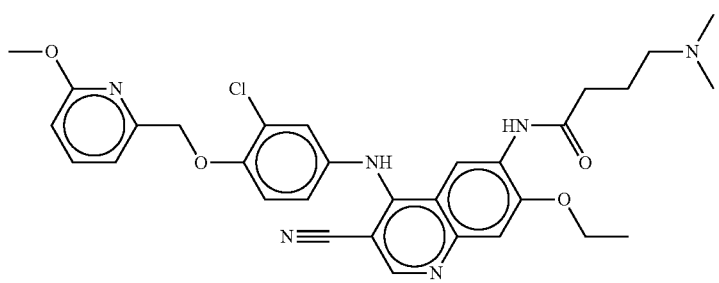
,
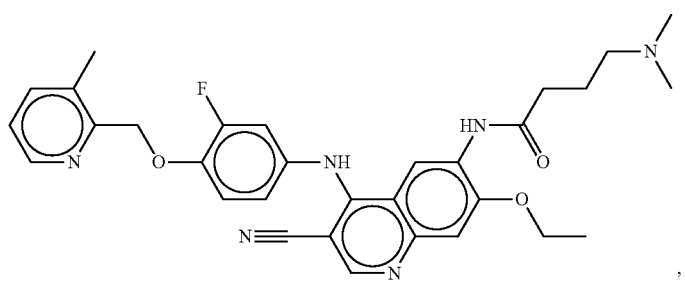
,
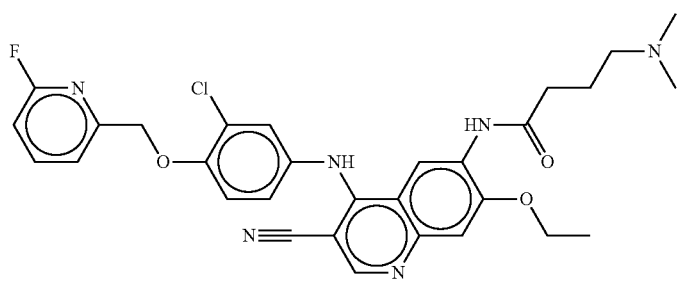
,
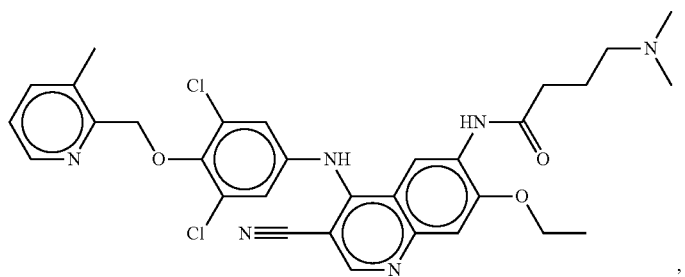
, -continued
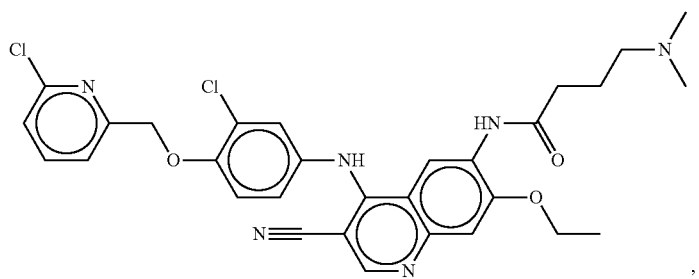,
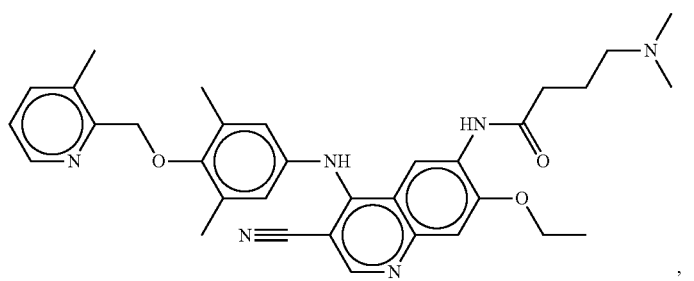,
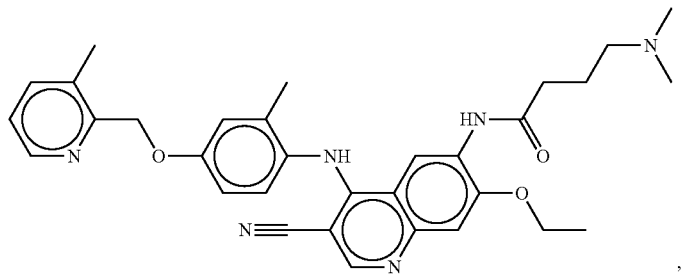,
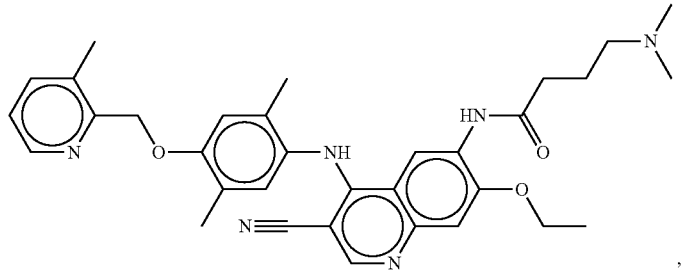,
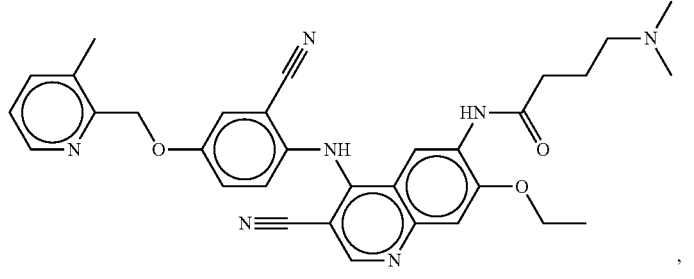,
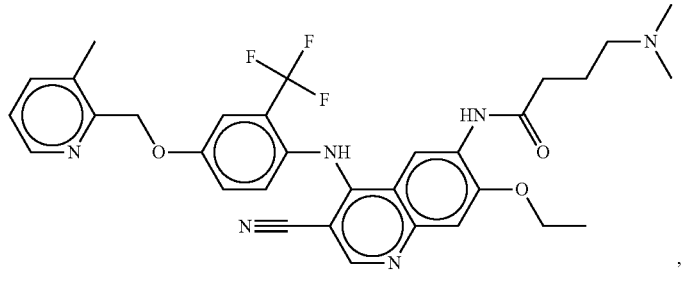, -continued
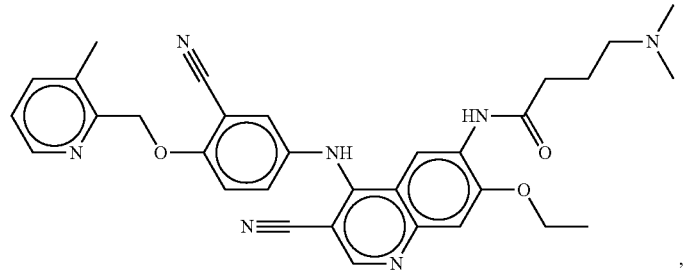
,
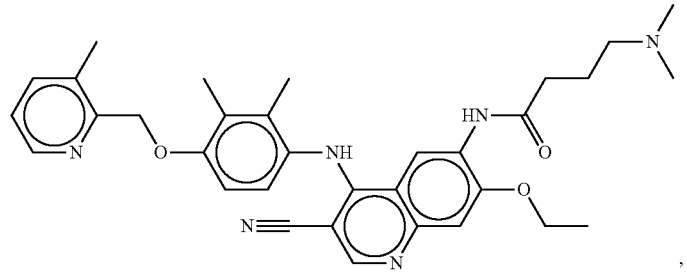
,
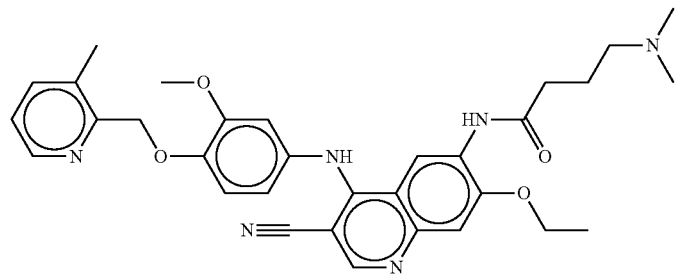
,
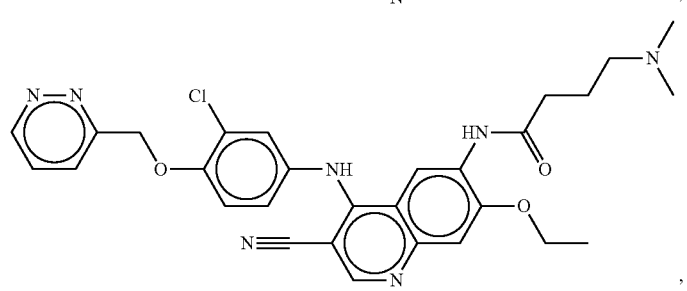
,
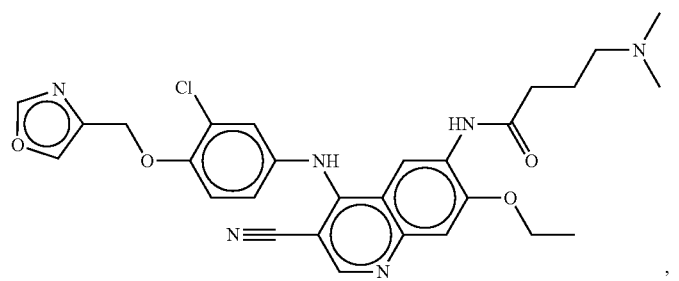
,
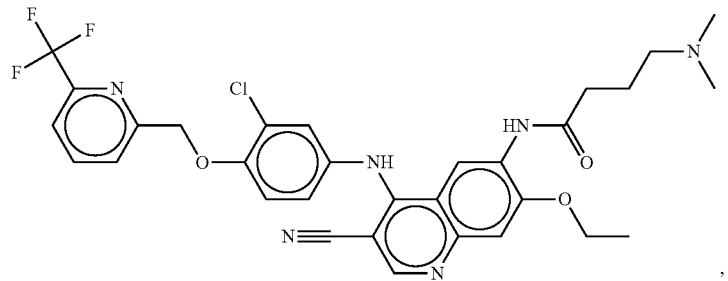
, -continued
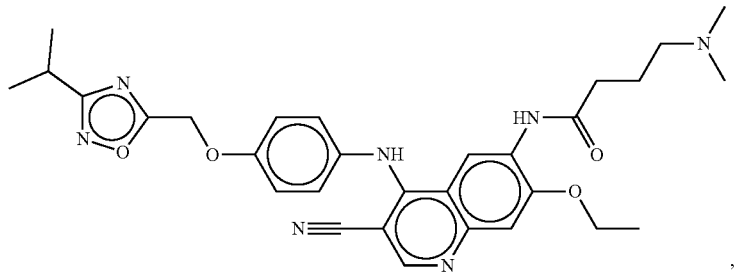
,
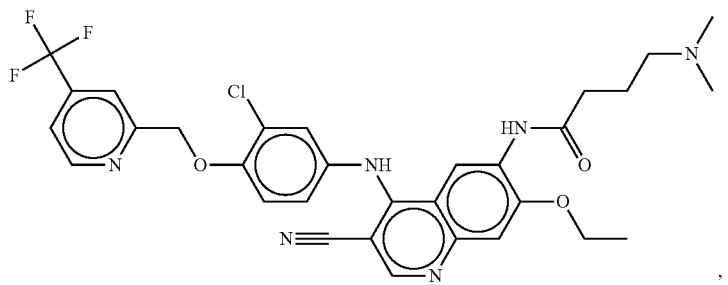
,
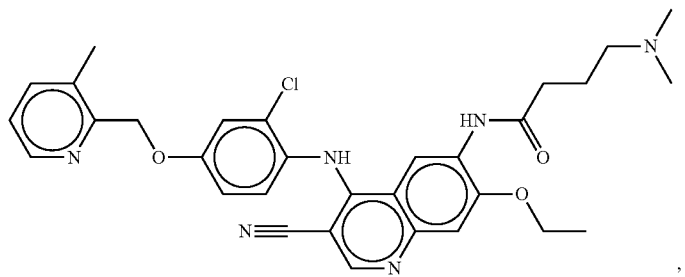
,
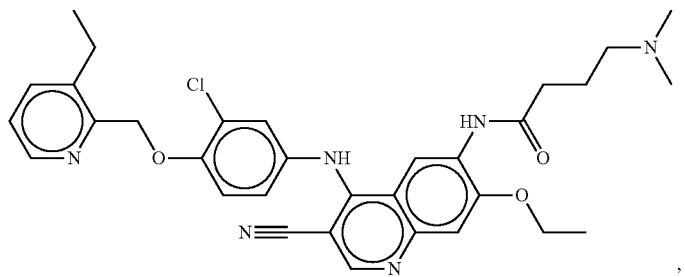
,
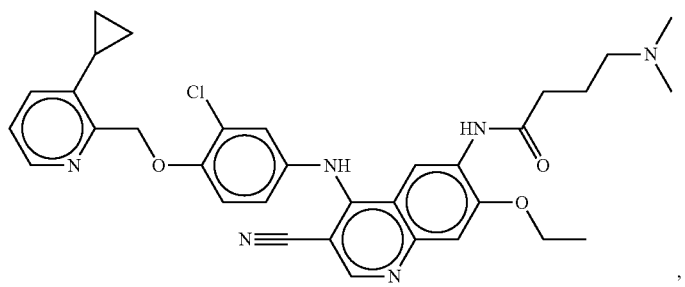
,
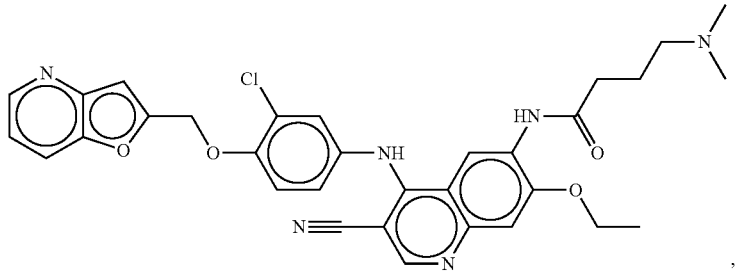
,

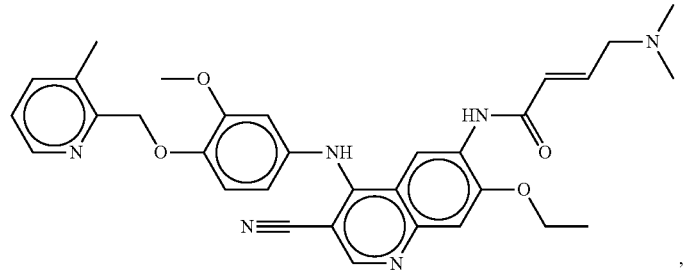,
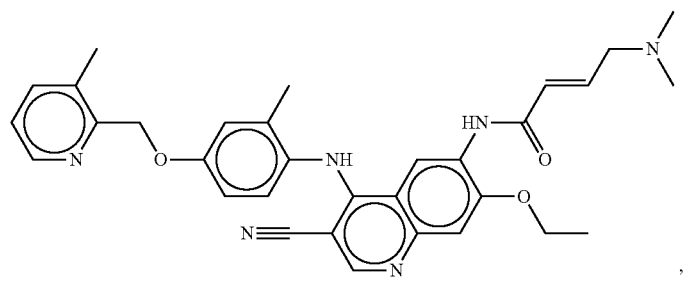,
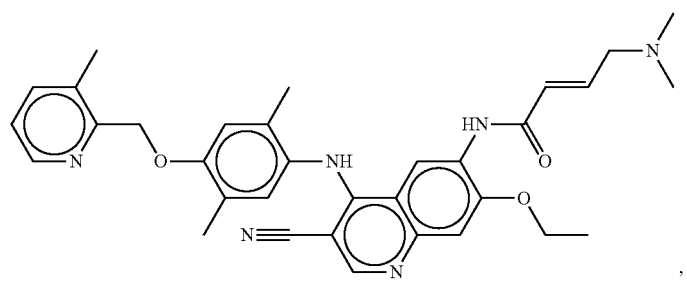,
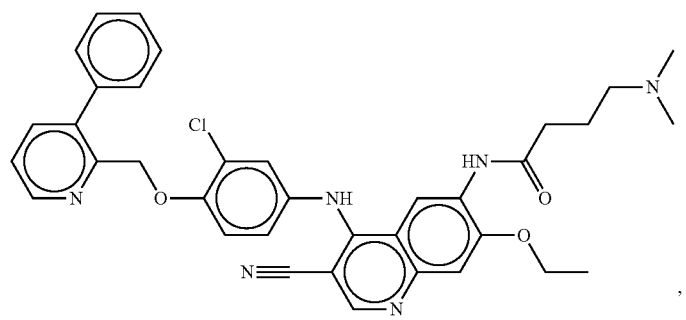,
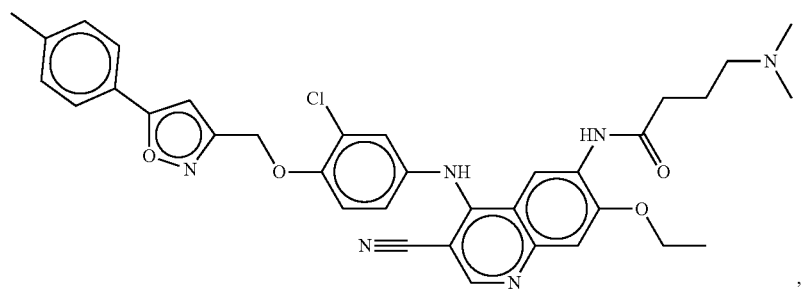,
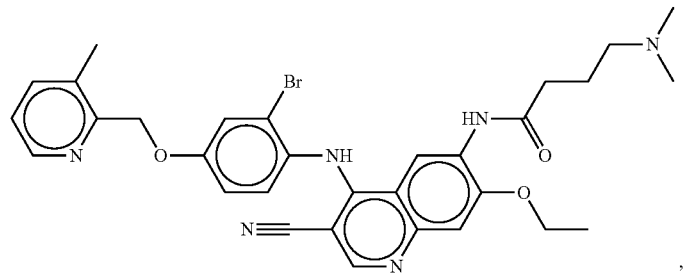,

-continued
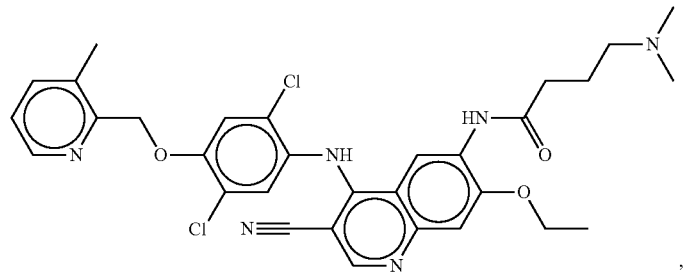
,
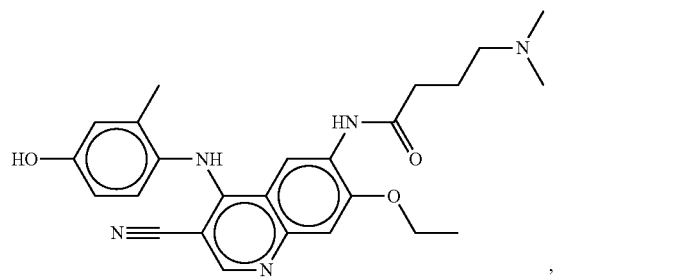
,
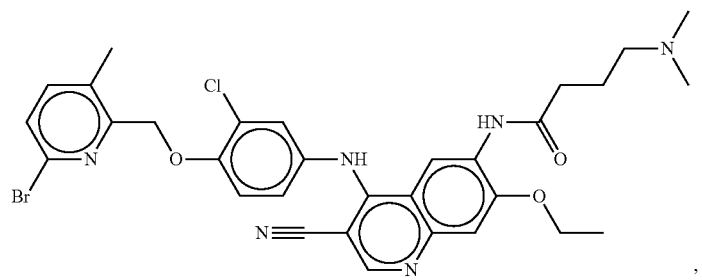
,
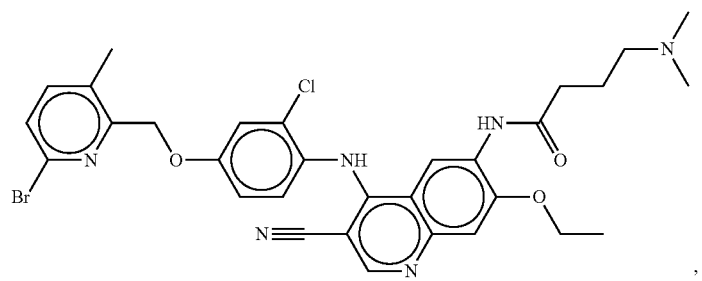
,
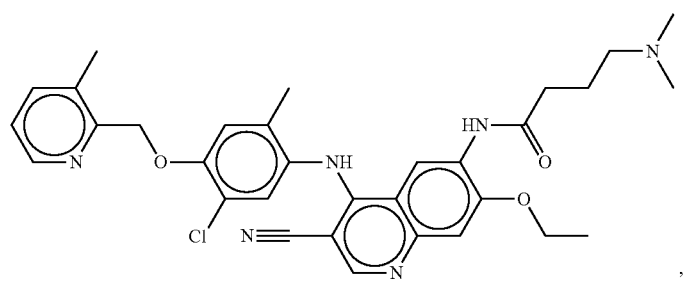
,
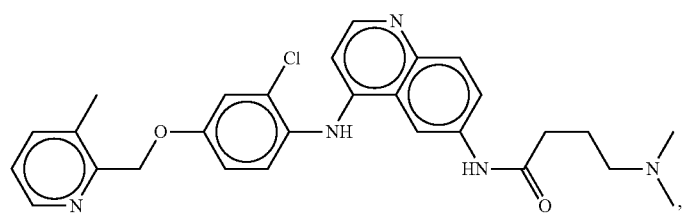
, -continued
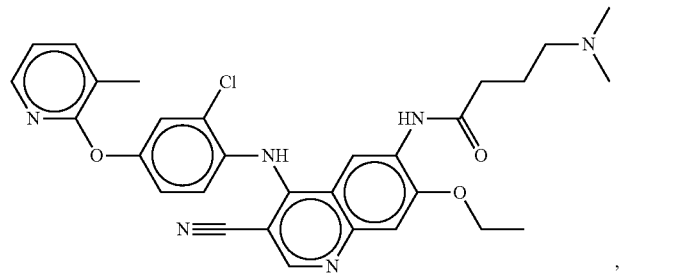
,
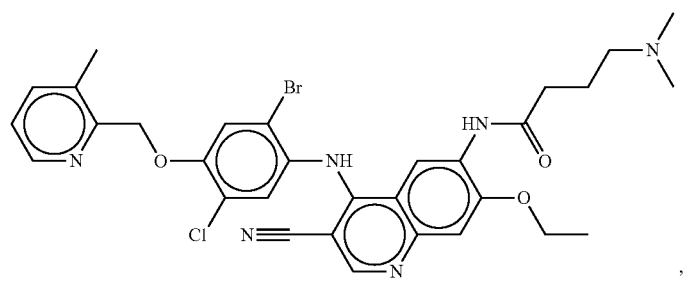
,
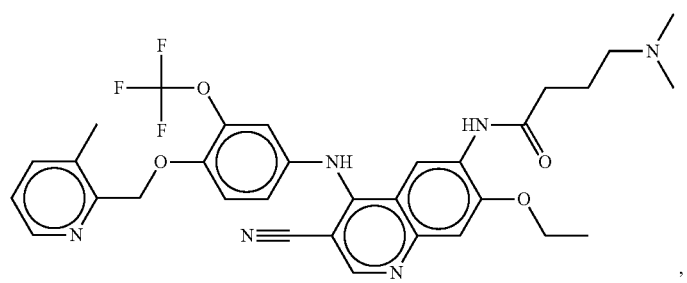
,
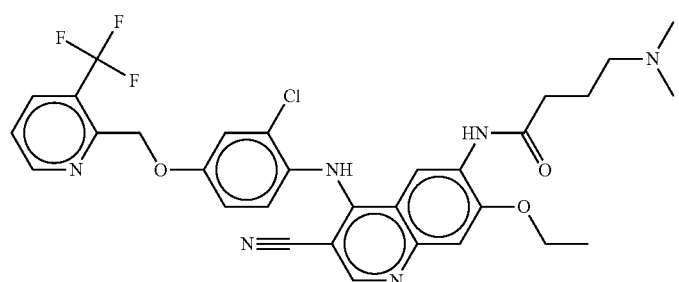
,
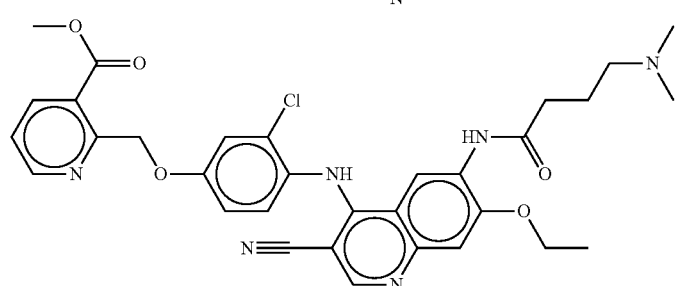
,
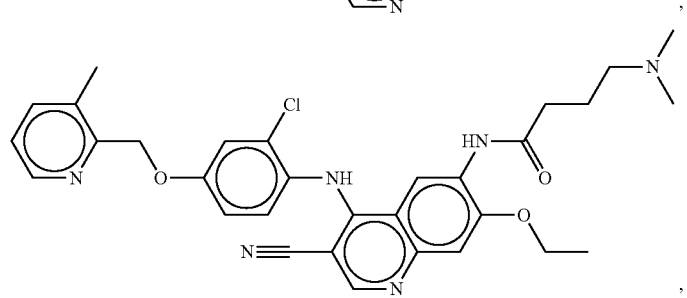
,

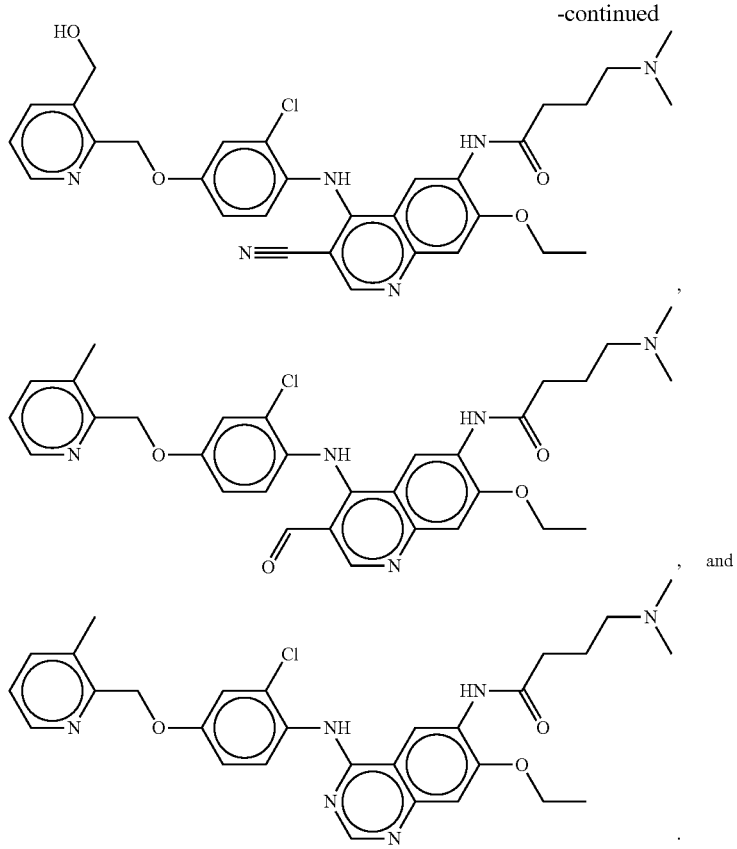

Preparation of Compounds

Compounds of Formula (I), (Ia), (Ib), (II), (IIa), or (IIb) may be synthesized using standard synthetic reactions known to those of skill in the art or using methods known in the art. The reactions can be employed in a linear sequence to provide the compounds or they may be used to synthesize fragments which are subsequently joined by the methods known in the art. Also described herein are pharmaceutically acceptable salts, pharmaceutically acceptable solvates, and pharmaceutically acceptable prodrugs of such compounds. Pharmaceutical compositions comprising at least one such compound or a pharmaceutically acceptable salt, pharmaceutically acceptable solvate, pharmaceutically active metabolite or pharmaceutically acceptable prodrug of such compound, and a pharmaceutically acceptable excipient are also provided.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents can be synthesized using techniques and materials known to those of skill in the art, such as described, for example, in March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001); Green and Wuts, PROTECTIVE GROUPS IN ORGANIC SYNTHESIS 3rd Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989); (all of which are incorporated by reference in their entirety). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared as a single isomer or a mixture of isomers.

The starting materials and intermediates for the compounds of this invention may be prepared by the application or adaptation of the methods described herein, their obvious chemical equivalents, or, for example, as described in literature such as The Science of Synthesis, Volumes 1-8. Editors E. M. Carreira et al. Thieme publishers (2001-2008).

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In certain embodiments, the compounds described herein exist as partially or fully deuterated forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^2H$, $^3H$, $^{13}C$, $^{14}C$, $^{15}N$, $^{18}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i. e., $^3H$ and carbon-14, i.e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfate, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of the invention and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\text{ alkyl})_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Methods

Disclosed herein is a compound of Formula (I), (Ia), (Ib), (II), (IIa), or (IIb) that modulates an activity of a mammalian sterile 20-like kinase 1 (MST1), a cleaved product thereof, or a homolog thereof. Further disclosed herein is a method of treating a metabolic condition in a subject comprising administering to the subject a compound of Formula (I), (Ia), (Ib), (II), (IIa), or (IIb). In some embodiments is a method of treating a metabolic condition in a subject comprising administering to the subject a compound of Formula (I), (Ia), (Ib), (II), (IIa), or (IIb), wherein the metabolic condition is diabetes mellitus. In some embodiments is a method of treating a metabolic condition in a subject comprising administering to the subject a compound of Formula (I), (Ia), (Ib), (II), (IIa), or (IIb), wherein the metabolic condition is type 1 diabetes mellitus. In some embodiments is a method of treating a metabolic condition in a subject comprising administering to the subject a compound of Formula (I), (Ia), (Ib), (II), (IIa), or (IIb), wherein the metabolic condition is type 2 diabetes mellitus.

In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits the activity of the mammalian sterile 20-like kinase 1 (MST1), the cleaved product thereof, or the homolog thereof. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits the activity of the mammalian sterile 20-like kinase 1 (MST1), the cleaved product thereof, or the homolog thereof, and the activity is selected from a phosphorylation activity, an inflammatory activity, a cleavage activity, an apoptotic activity, a ubiquitinating activity, a mitochondrial activity, and combinations thereof. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits the activity of the mammalian sterile 20-like kinase 1 (MST1), the cleaved product thereof, or the homolog thereof, and the activity is phosphorylation activity. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits the activity of the mammalian sterile 20-like kinase 1 (MST1), the cleaved product thereof, or the homolog thereof, and the activity is an inflammatory activity. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits the activity of the mammalian sterile 20-like kinase 1 (MST1), the cleaved product thereof, or the homolog thereof, and the activity is a cleavage activity. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits the activity of the mammalian sterile 20-like kinase 1 (MST1), the cleaved product thereof, or the homolog thereof, and the activity is an apoptotic activity. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits the activity of the mammalian sterile 20-like kinase 1 (MST1), the cleaved product thereof, or the homolog thereof, and the activity is a ubiquitinating activity. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits the activity of the mammalian sterile 20-like kinase 1 (MST1), the cleaved product thereof, or the homolog thereof, and the activity is a mitochondrial activity.

In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits phosphorylation of a protein downstream of the activity of the mammalian sterile 20-like kinase 1, the cleaved product thereof, or the homolog thereof. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits phosphorylation of a protein downstream of the activity of the mammalian sterile 20-like kinase 1, the cleaved product thereof, or the homolog thereof, and the protein downstream is selected from a transcription factor, a kinase, and a histone. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits phosphorylation of a protein downstream of the activity of the mammalian sterile 20-like kinase 1, the cleaved product thereof, or the homolog thereof, and the protein downstream is a transcription factor. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits phosphorylation of a protein downstream of the activity of the mammalian sterile 20-like kinase 1, the cleaved product thereof, or the homolog thereof, and the protein downstream is a transcription factor and the transcription factor is pancreatic and duodenal homeobox 1 (PDX-1) or a homolog thereof. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits phosphorylation of a protein downstream of the activity of the mammalian sterile 20-like kinase 1, the cleaved product thereof, or the homolog thereof, and the protein downstream is a kinase. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits phosphorylation of a protein downstream of the activity of the mammalian sterile 20-like kinase 1, the cleaved product thereof, or the homolog thereof, and the protein downstream is Janus kinase. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits phosphorylation of a protein downstream of the activity of the mammalian sterile 20-like kinase 1, the cleaved product thereof, or the homolog thereof, and the protein downstream is a histone. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits phosphorylation of a protein downstream of the activity of the mammalian sterile 20-like kinase 1, the cleaved product thereof, or the homolog thereof, and the protein downstream is a histone and the histone is histone 2B.

In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits cleavage of a protein downstream of the activity of the mammalian sterile 20-like kinase 1, the cleaved product thereof, or the homolog thereof. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits cleavage of a protein downstream of the activity of the mammalian sterile 20-like kinase 1, the cleaved product thereof, or the homolog thereof, and the protein downstream is caspase. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits cleavage of a protein downstream of the activity of the mammalian sterile 20-like kinase 1, the cleaved product thereof, or the homolog thereof, and the protein downstream is selected from caspase 9, caspase 3, and MST1. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits cleavage of a protein downstream of the activity of the mammalian sterile 20-like kinase 1, the cleaved product thereof, or the homolog thereof, and the protein downstream is caspase 9. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits cleavage of a protein downstream of the activity of the mammalian sterile 20-like kinase 1, the cleaved product thereof, or the homolog thereof, and the protein downstream is caspase 3. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits cleavage of a protein downstream of the activity of the mammalian sterile 20-like kinase 1, the cleaved product thereof, or the homolog thereof, and the protein downstream is MST1.

In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits apoptotic activity of a protein downstream of the activity of the mammalian sterile 20-like kinase 1, the cleaved product thereof, or the homolog thereof. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits apoptotic activity of a protein downstream of the activity of the mammalian sterile 20-like kinase 1, the cleaved product thereof, or the homolog thereof, and the protein downstream is selected from JNK, Bim, Bax, Bcl-2, homologs thereof, and combinations thereof. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits apoptotic activity of a protein downstream of the activity of the mammalian sterile 20-like kinase 1, the cleaved product thereof, or the homolog thereof, and the protein downstream is JNK. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits apoptotic activity of a protein downstream of the activity of the mammalian sterile 20-like kinase 1, the cleaved product thereof, or the homolog thereof, and the protein downstream is Bim. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits apoptotic activity of a protein downstream of the activity of the mammalian sterile 20-like kinase 1, the cleaved product thereof, or the homolog thereof, and the protein downstream is Bax. In some embodiments is a method of treating a metabolic condition in a subject comprising administering to the subject a compound of Formula (I), (Ia), (Ib), (II), (IIa), or (IIb), wherein the compound of Formula (I), (Ia), (Ib), (II), (IIa), or (IIb) inhibits apoptotic activity of a protein downstream of the activity of the mammalian sterile 20-like kinase 1, the cleaved product thereof, or the homolog thereof, and the protein downstream is Bcl-2.

Also disclosed herein in some embodiments is a method of treating an inflammatory condition in a subject comprising administering to the subject a compound of Formula (I), (Ia), (Ib), (II), (IIa), or (IIb).

Also disclosed herein in some embodiments is a method of treating an autoimmune disorder in a subject comprising administering to the subject a compound of Formula (I), (Ia), (Ib), (II), (IIa), or (IIb).

Also disclosed herein is a method of treating cancer in a subject comprising administering to the subject a compound of Formula (I), (Ia), (Ib), (II), (IIa), or (IIb), or a pharmaceutically acceptable salt, solvate, or prodrug thereof, and a pharmaceutically acceptable excipient. Further disclosed herein is a method of treating cancer in a subject comprising administering to the subject a compound of Formula (II), (IIa), or (IIb), or a pharmaceutically acceptable salt, solvate, or prodrug thereof, and a pharmaceutically acceptable excipient.

In some embodiments of the methods described herein the compound is neratinib.

In some embodiments of the methods described herein the compound has the structure:

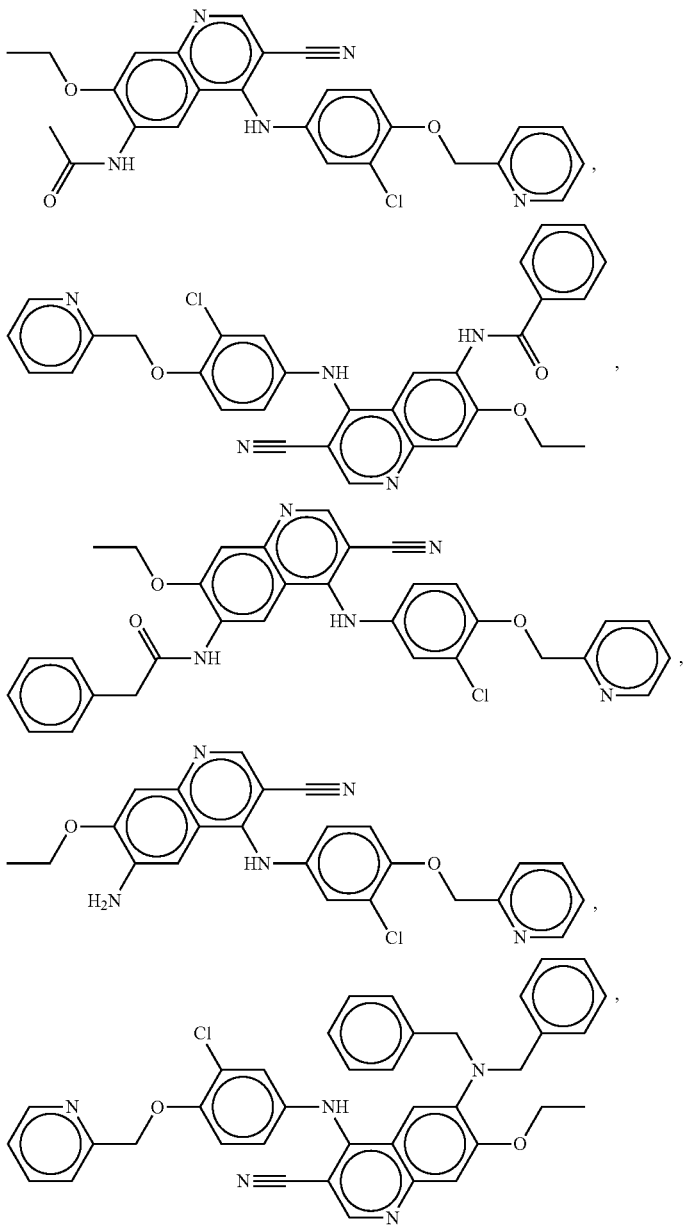

-continued
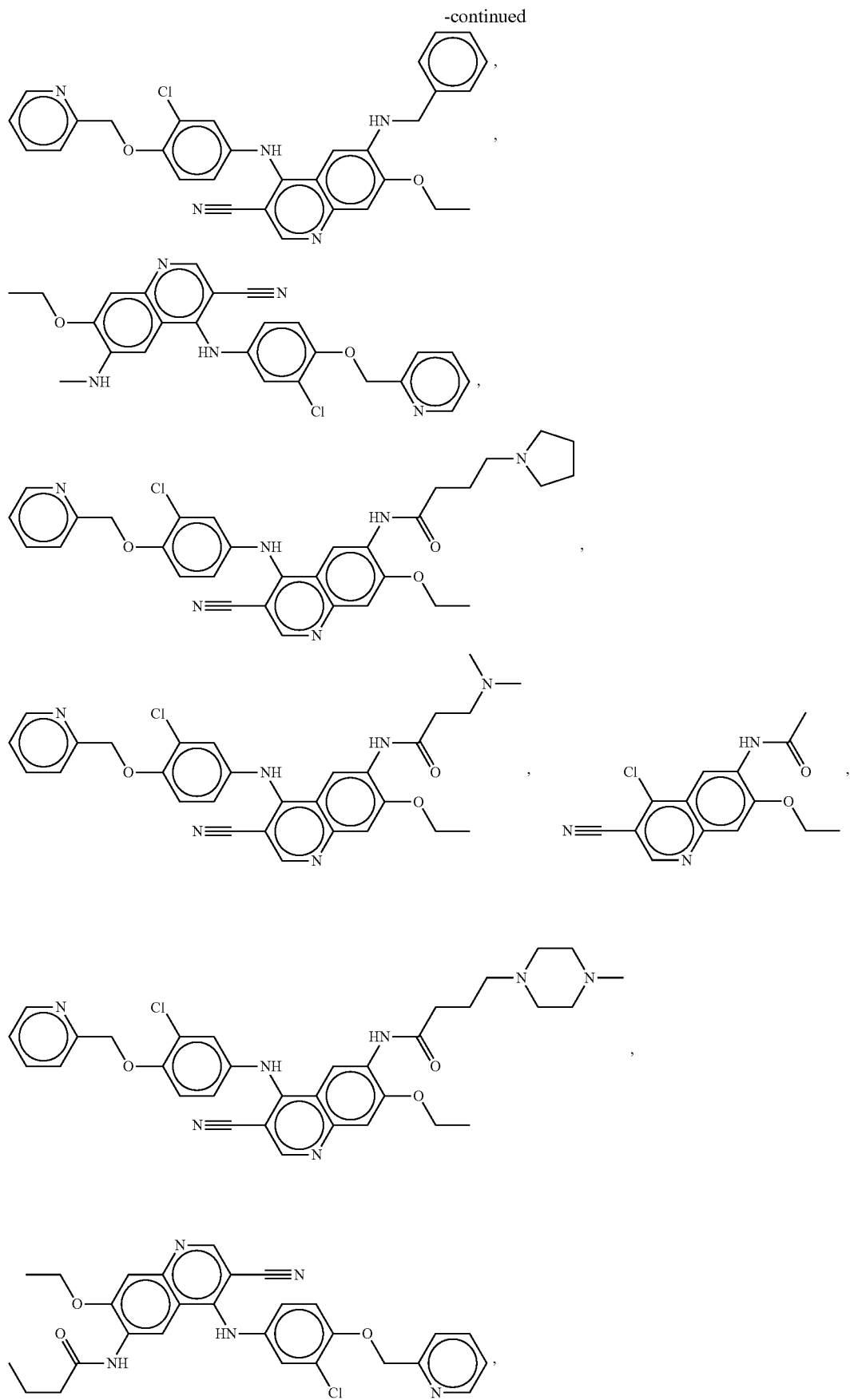

-continued
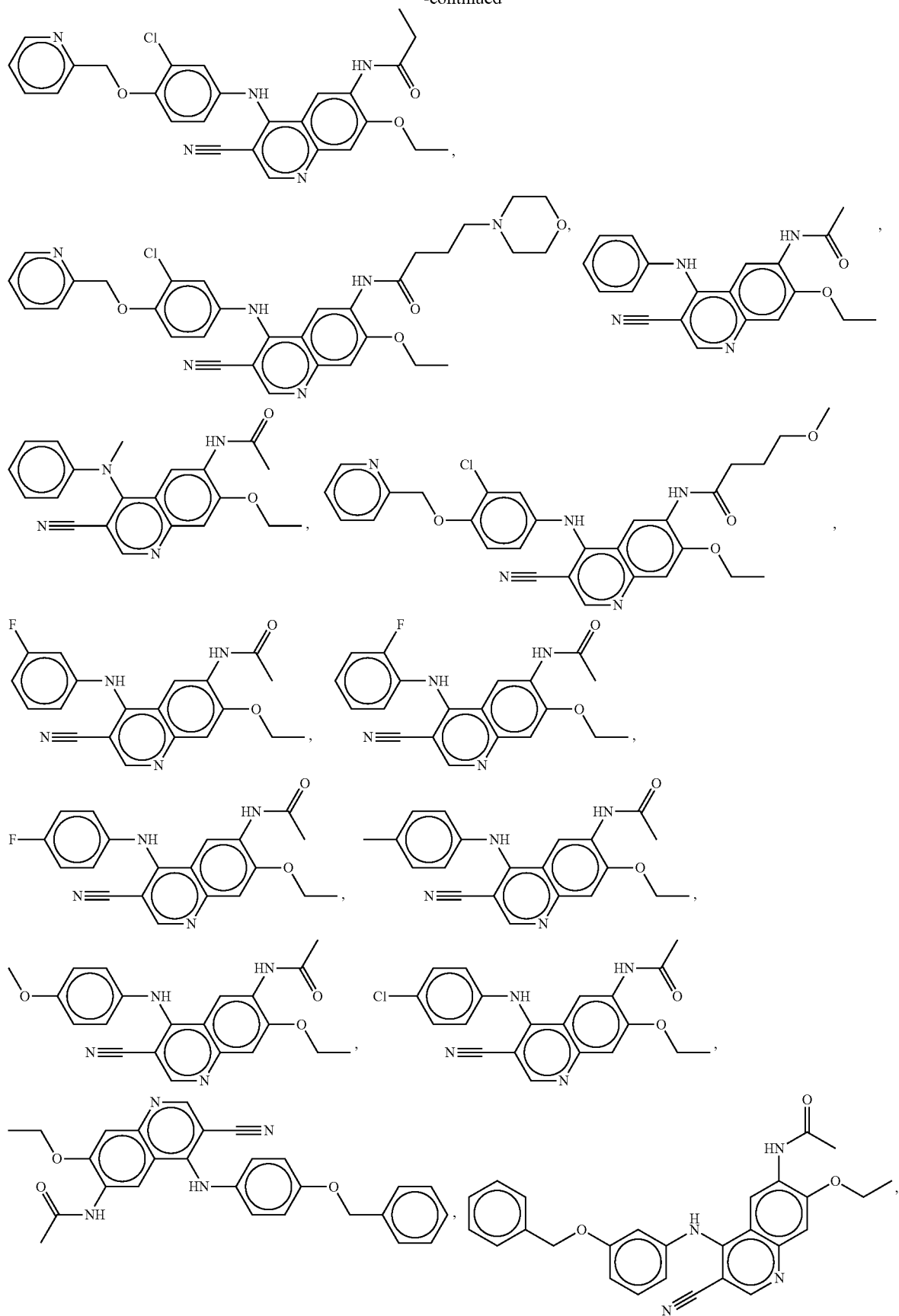

-continued
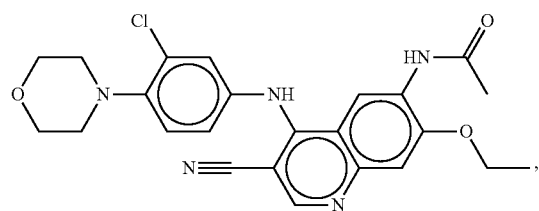
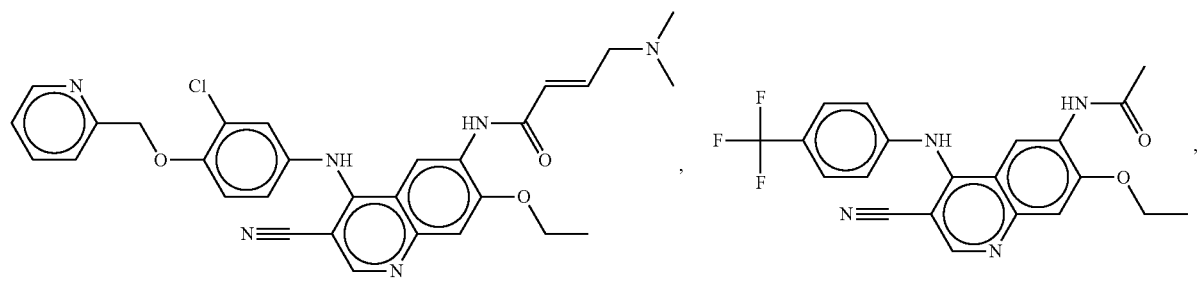
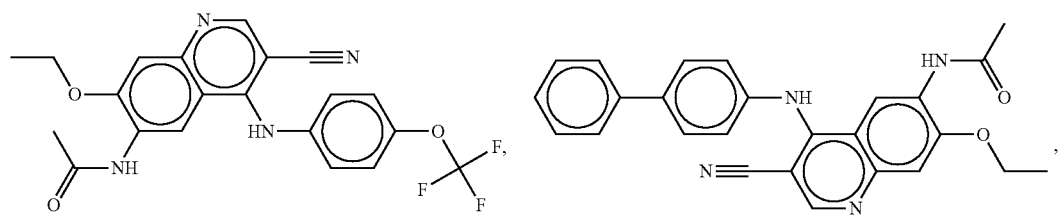
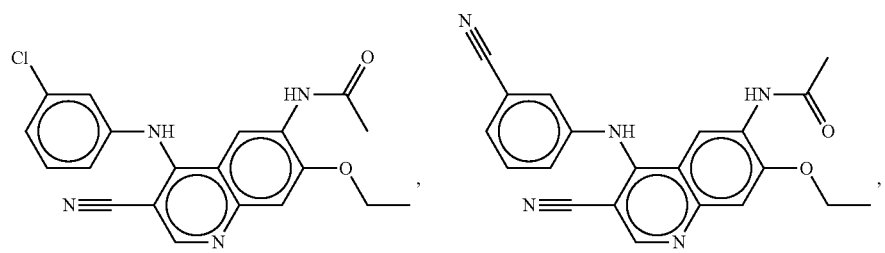
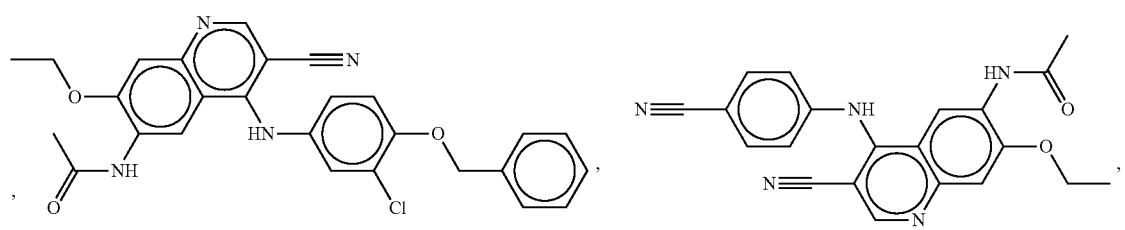
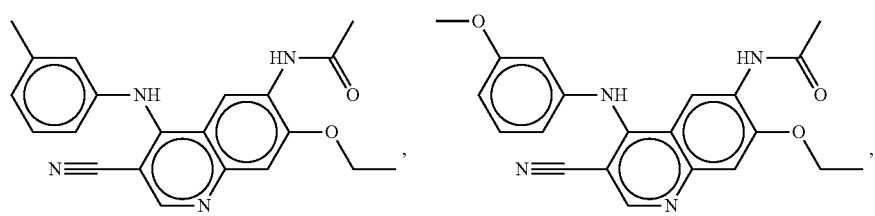
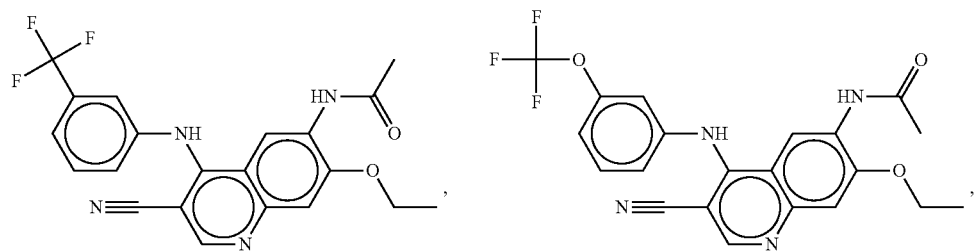

-continued
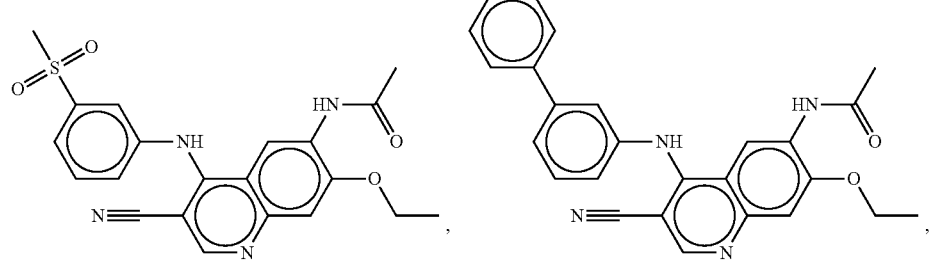
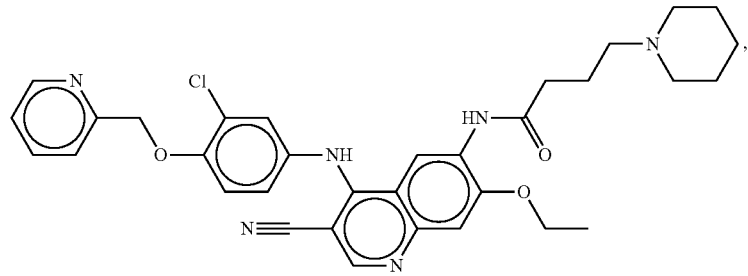
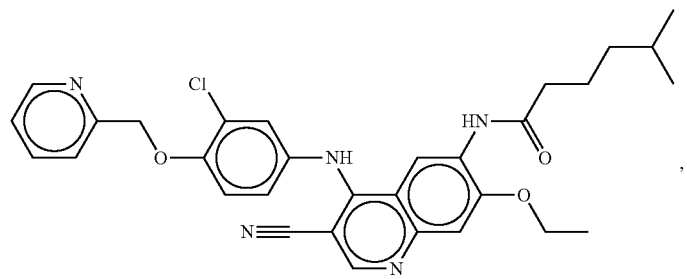
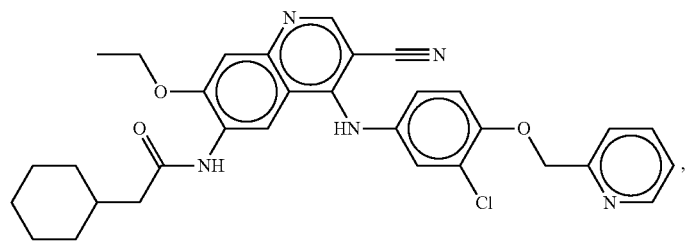
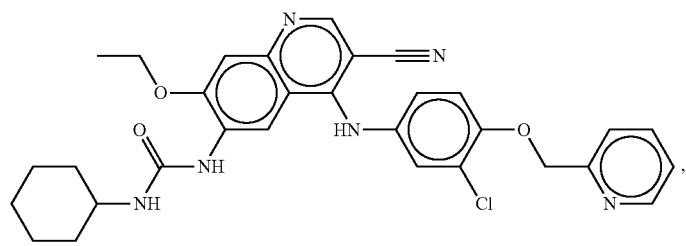
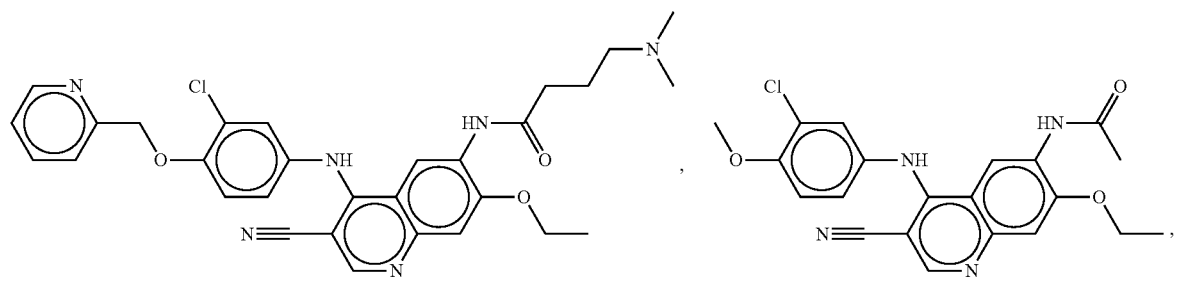

-continued
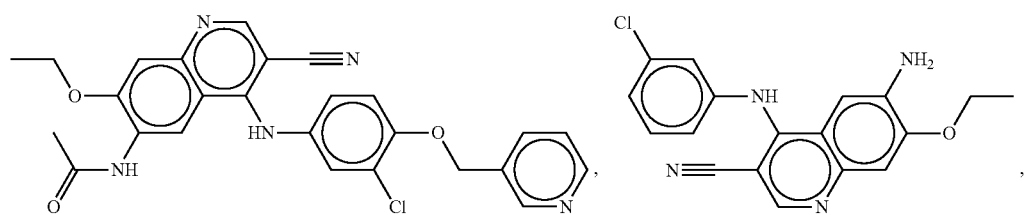
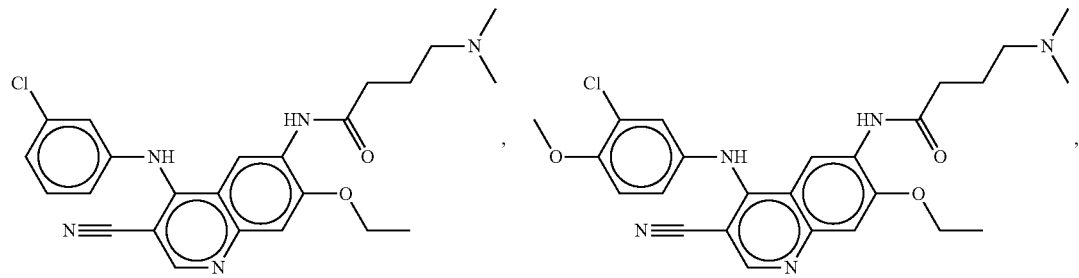
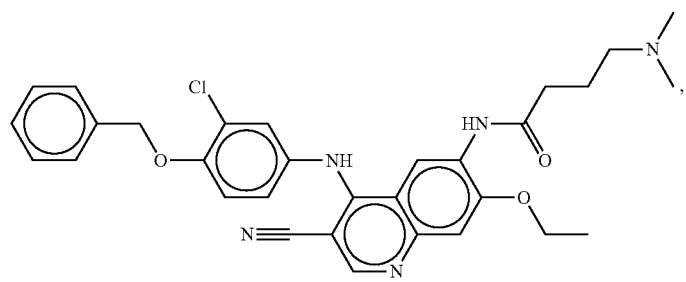
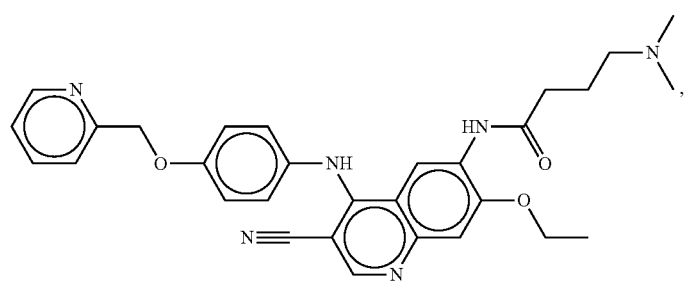
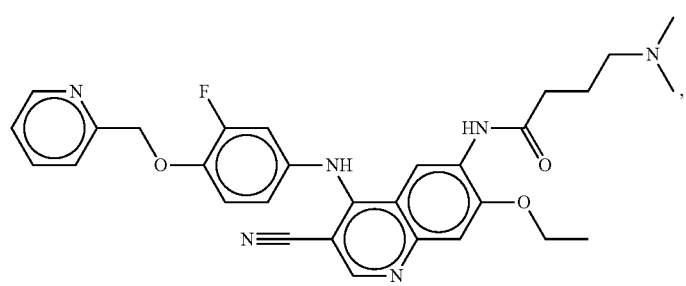
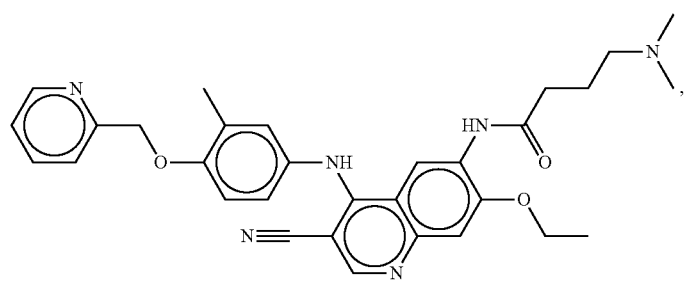

-continued
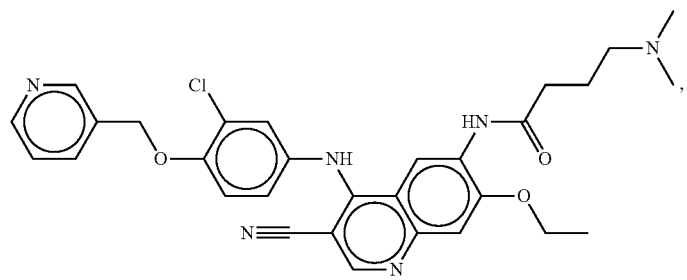
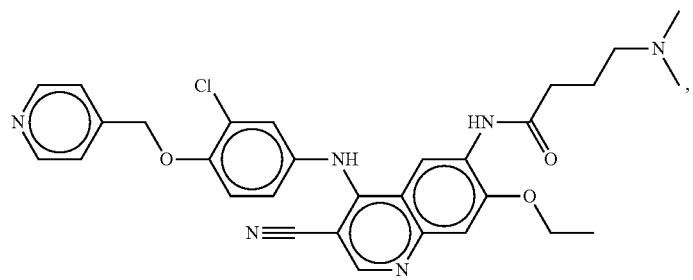
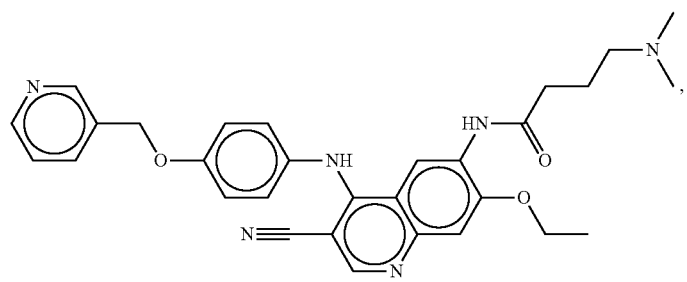
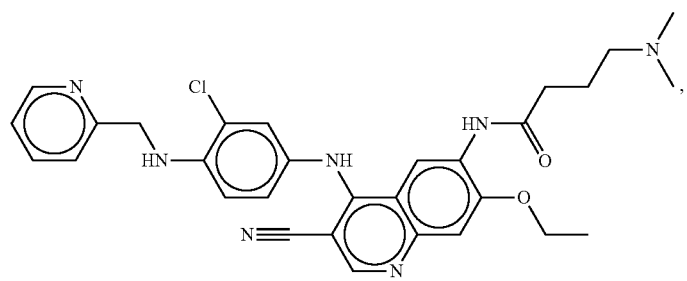
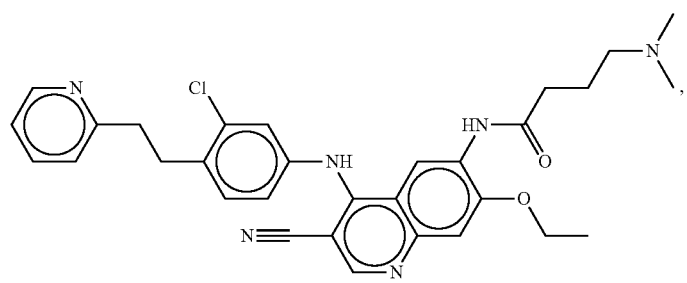
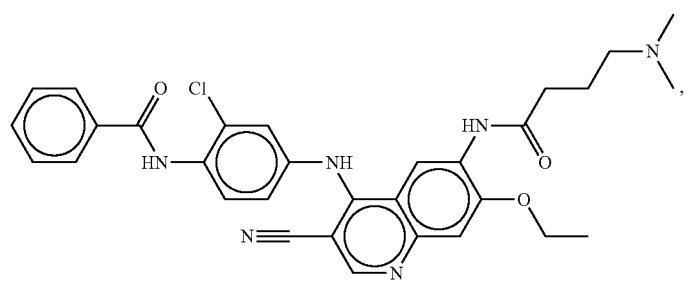

-continued
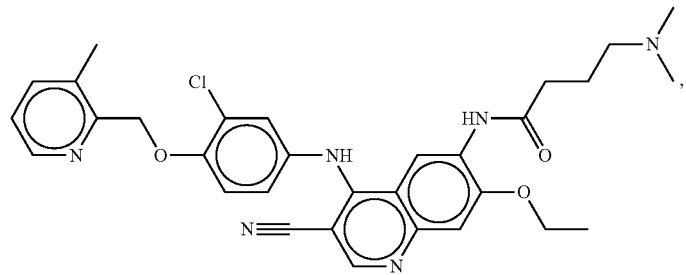
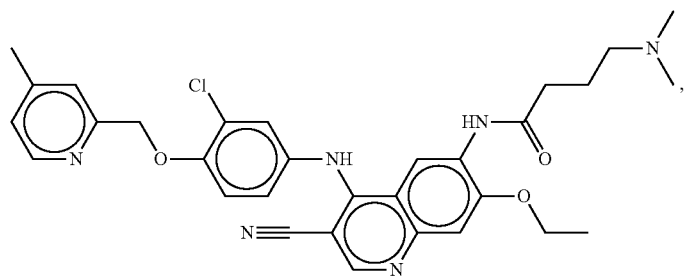
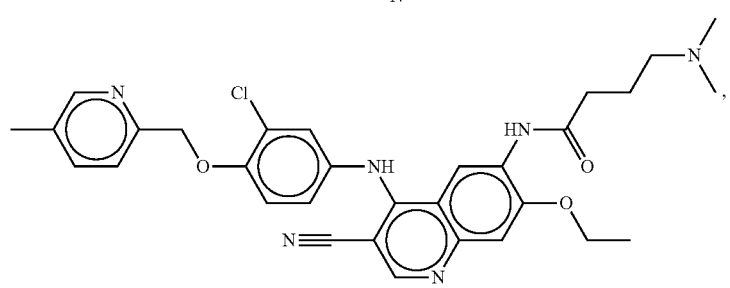
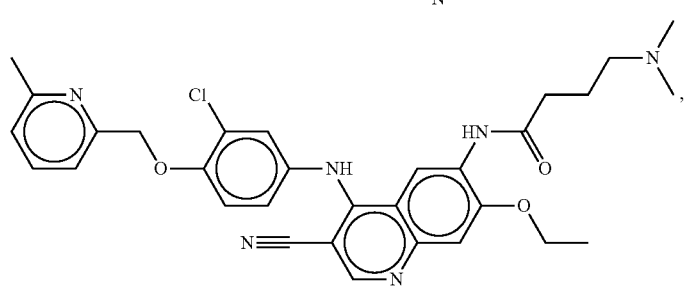
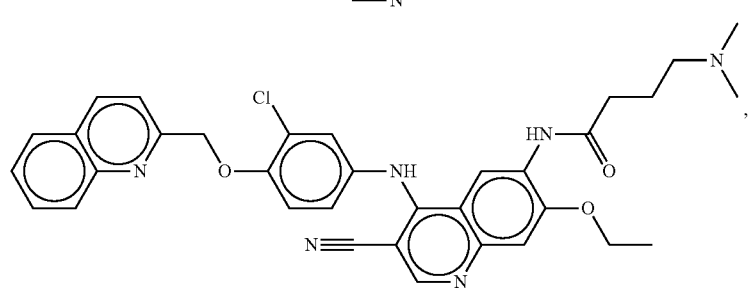
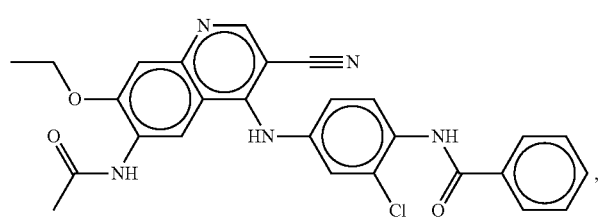

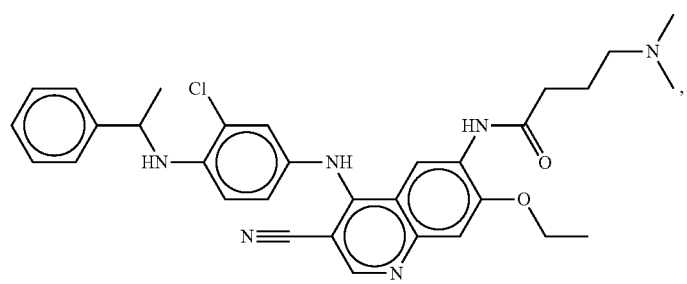
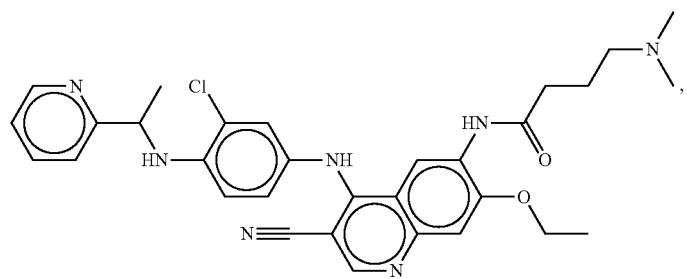
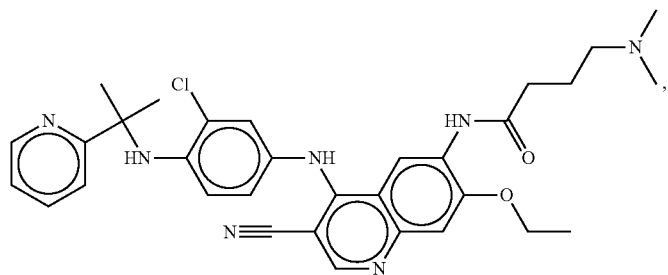
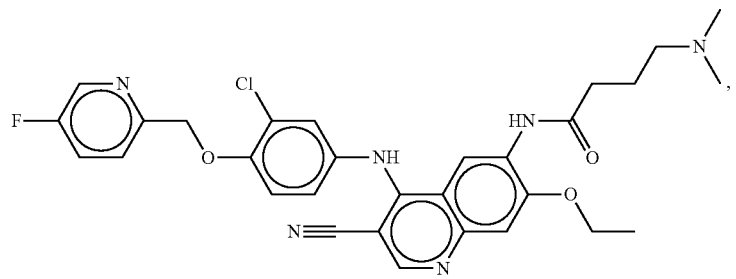
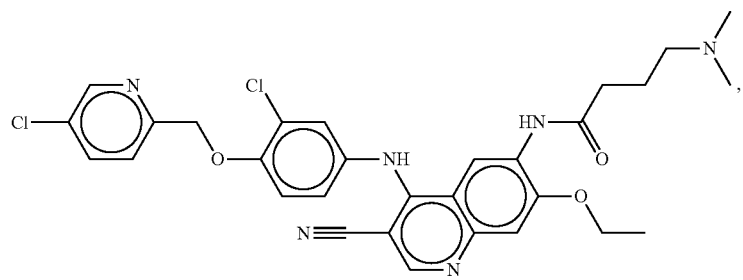
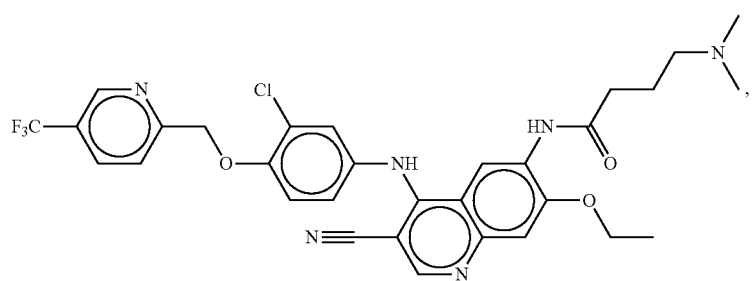

-continued
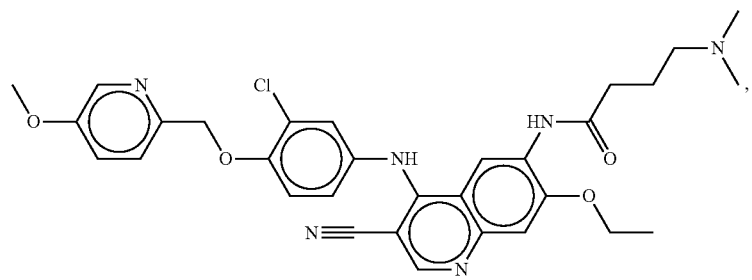
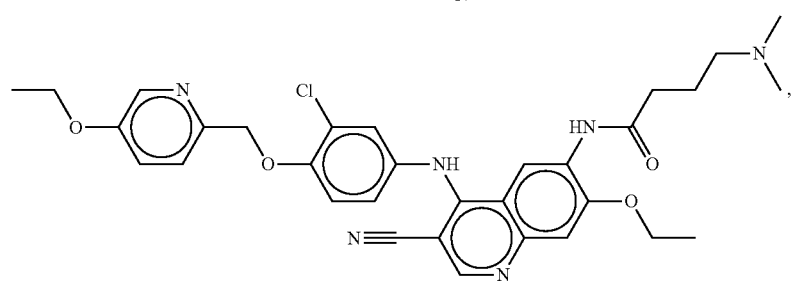
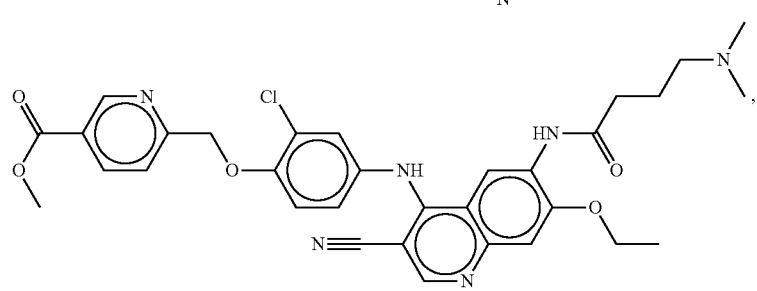
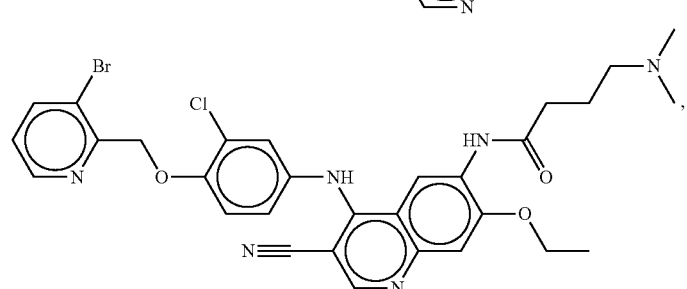
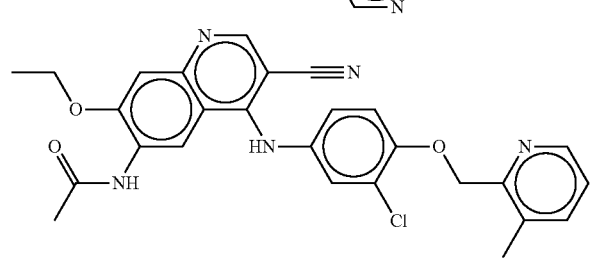
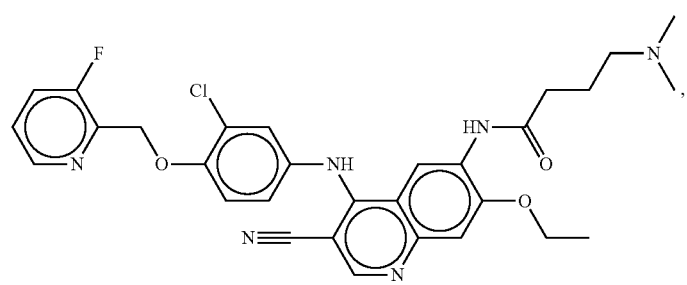

-continued
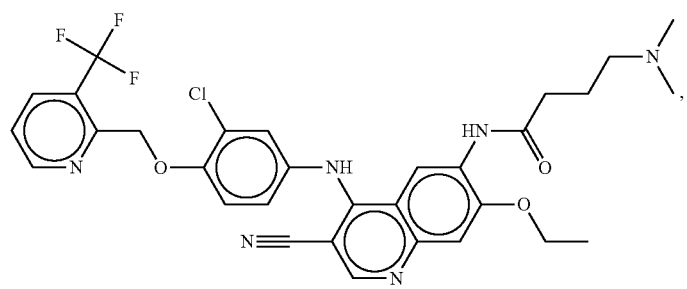
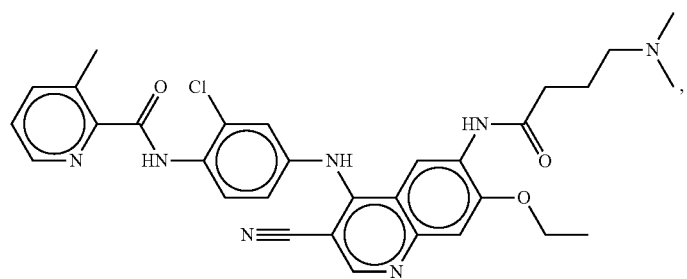
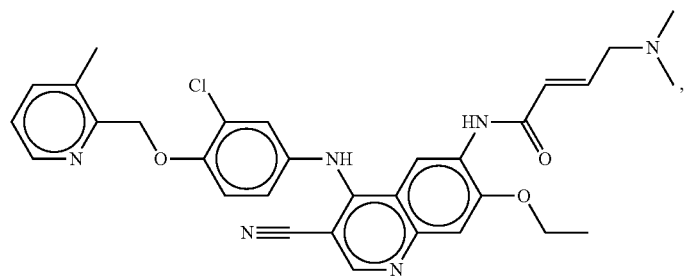
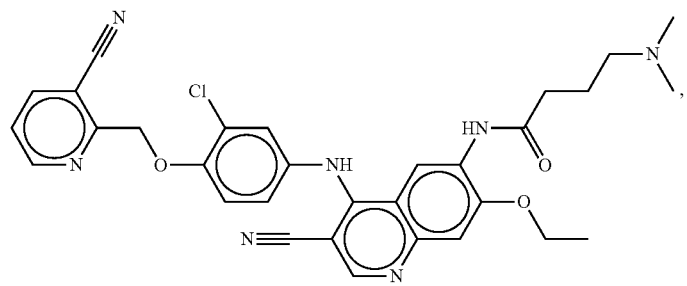
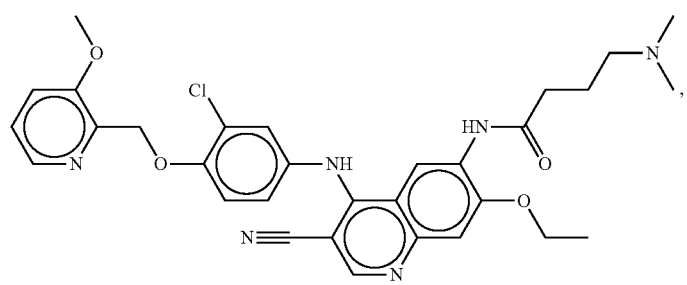
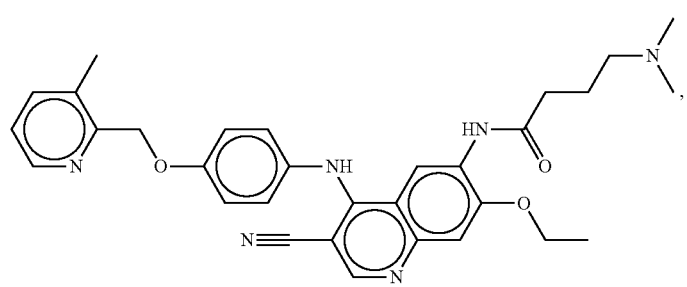

-continued
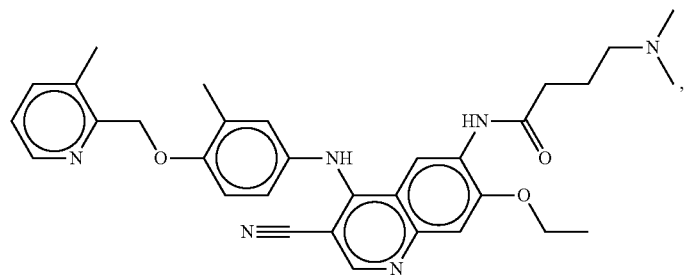
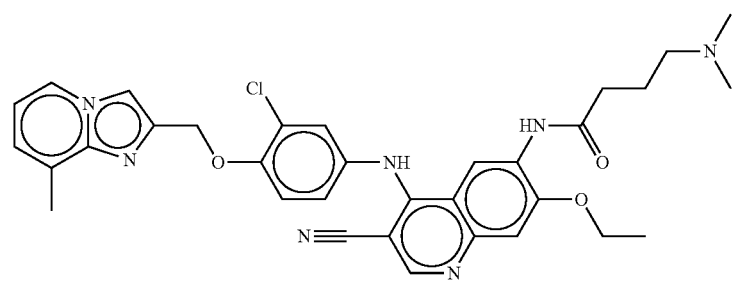
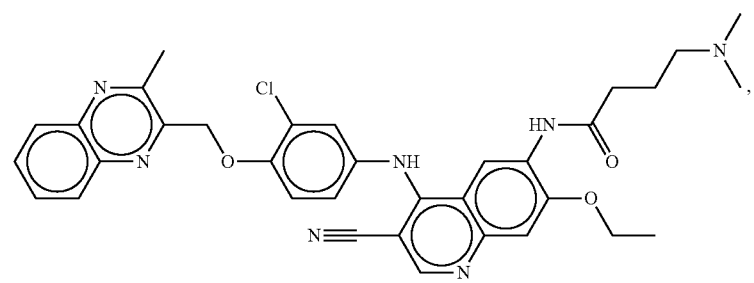
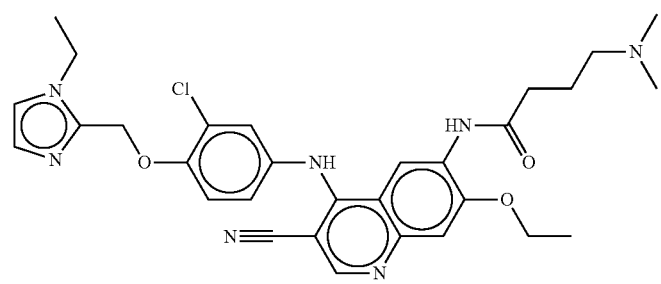
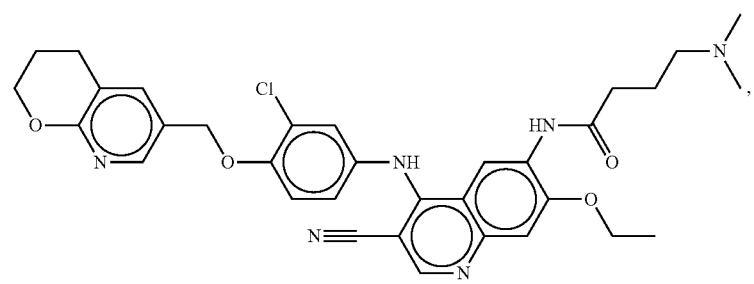
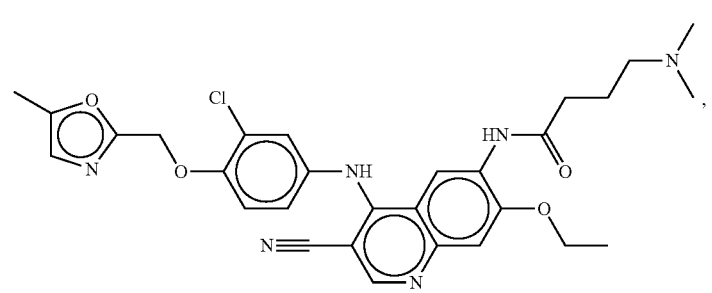

-continued
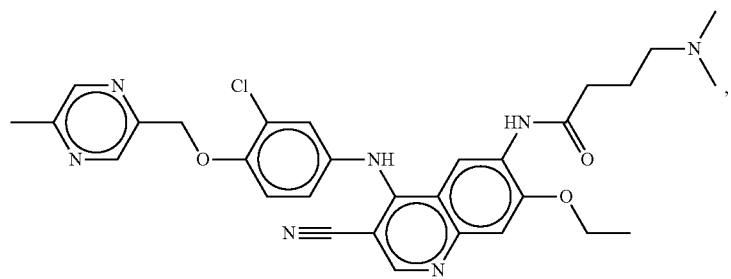
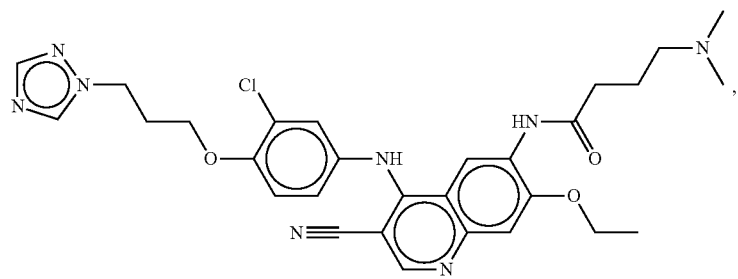
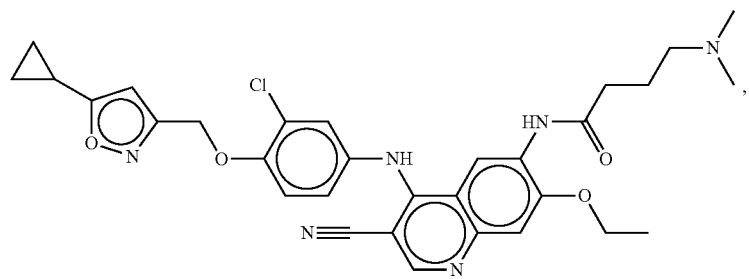
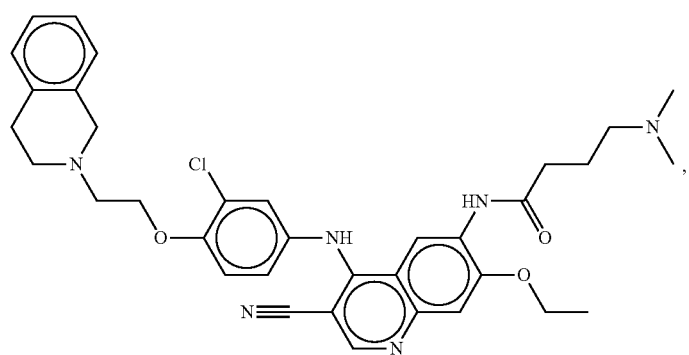
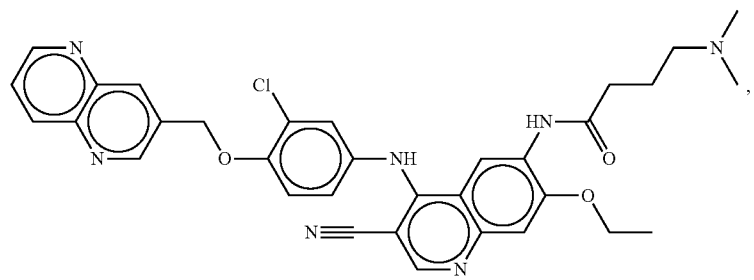

-continued
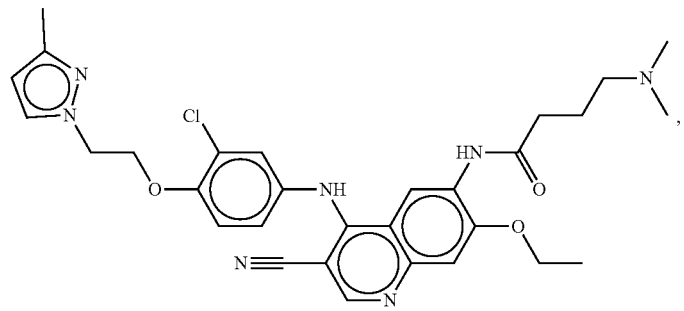
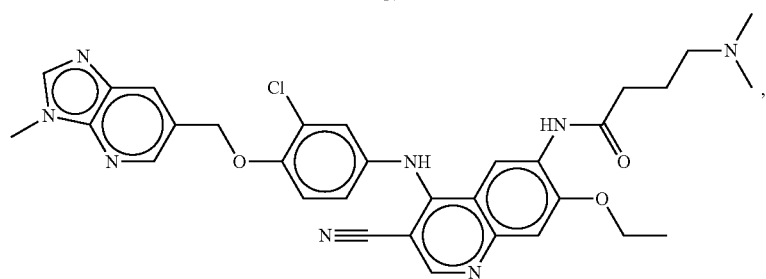
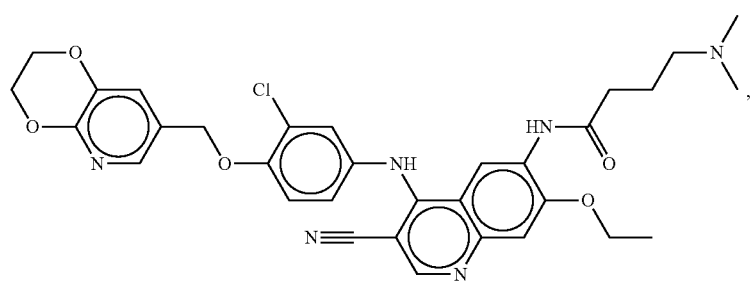
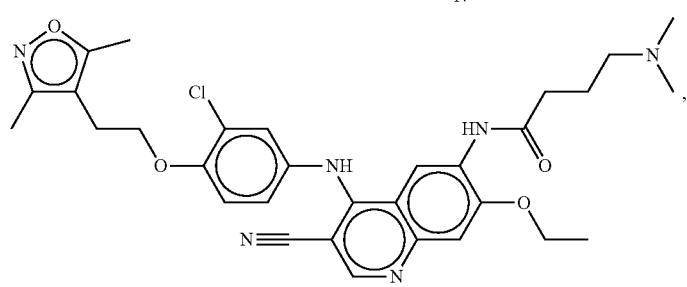
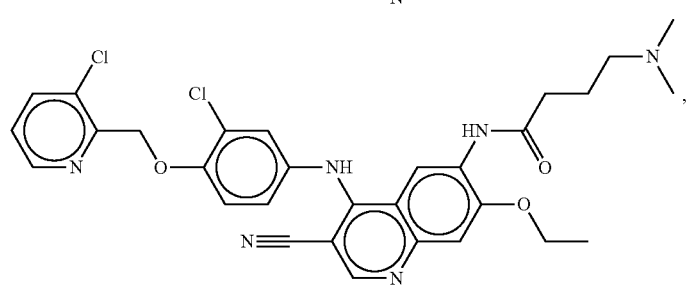
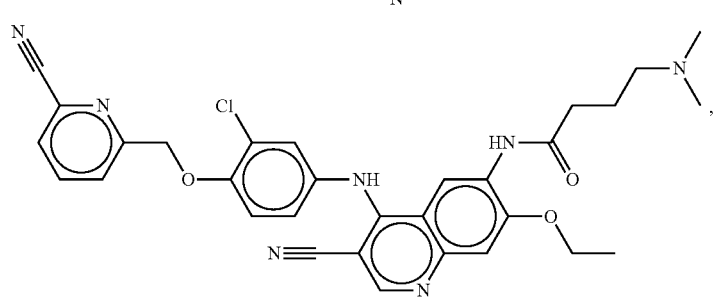

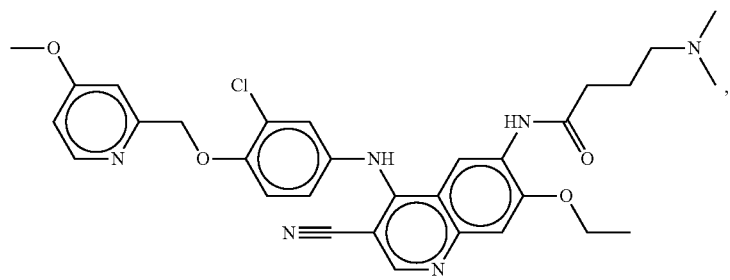
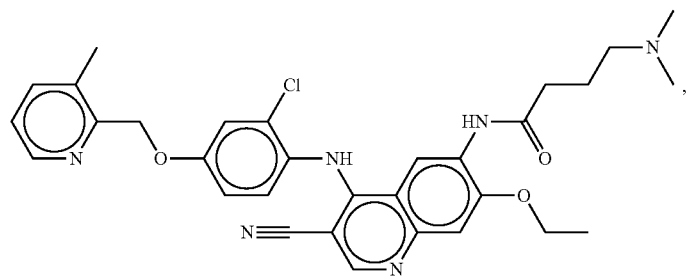
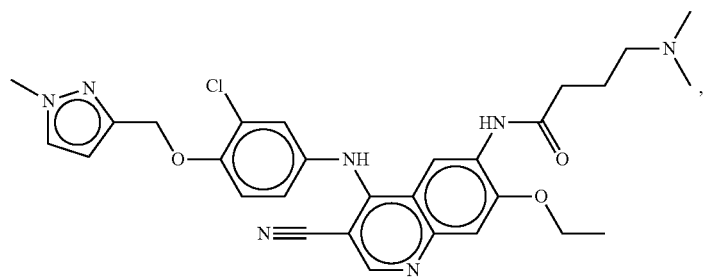
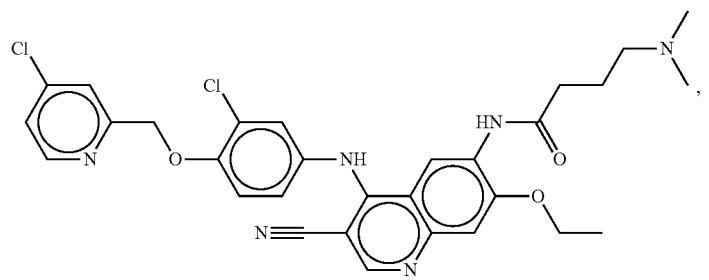
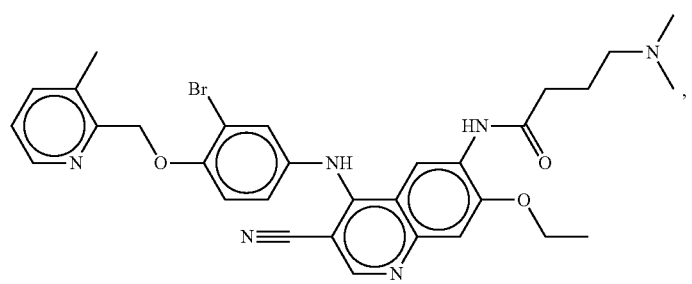
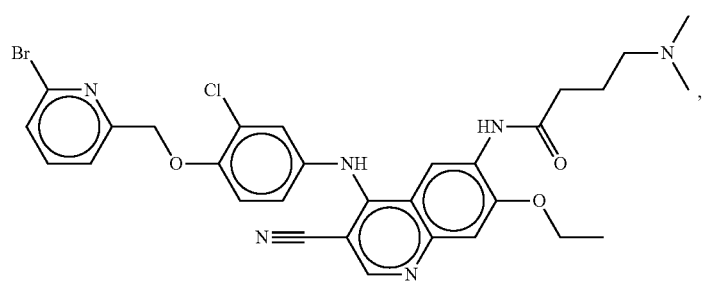

-continued
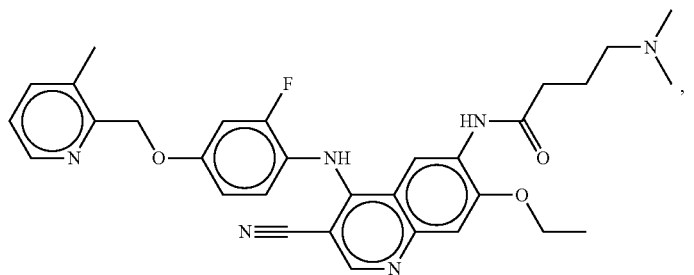
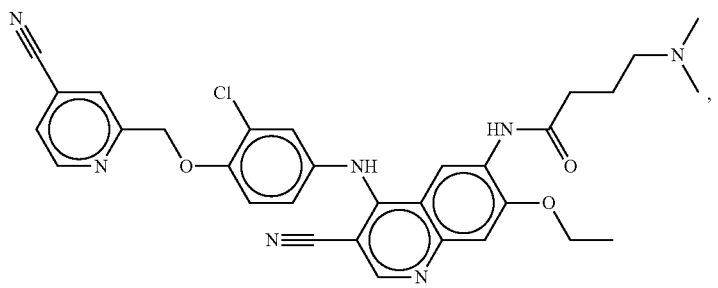
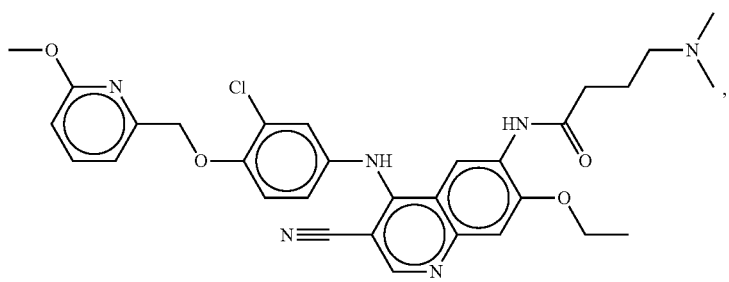
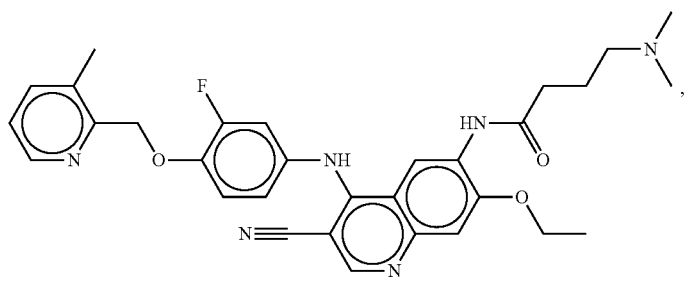
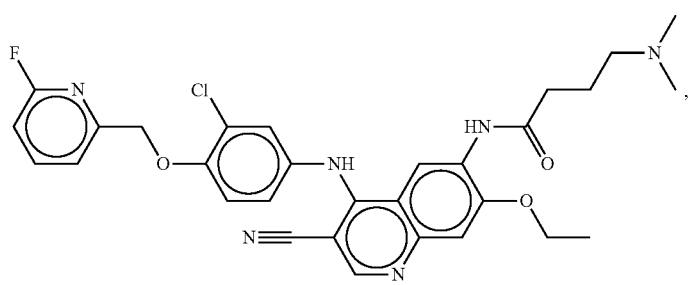
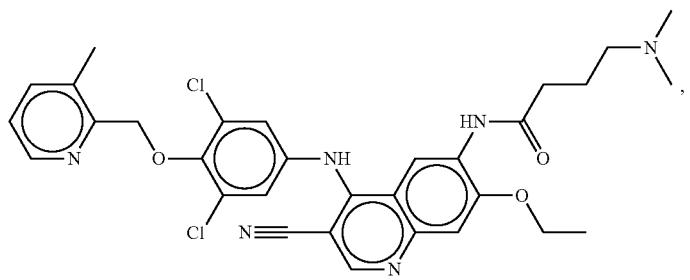

-continued
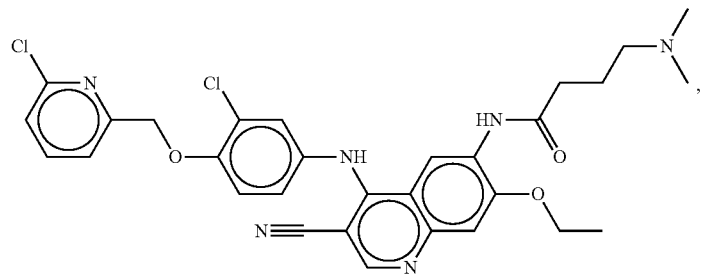
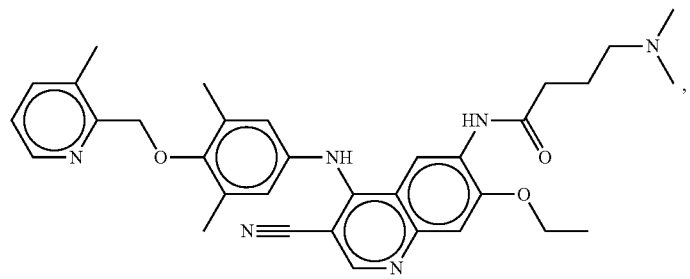
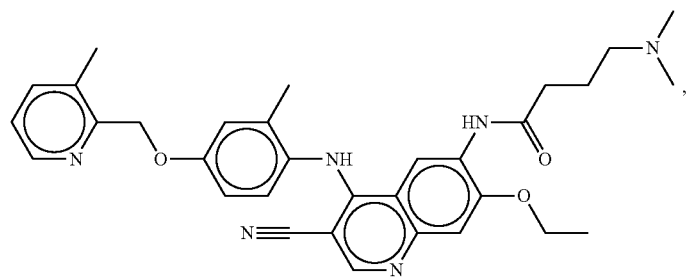
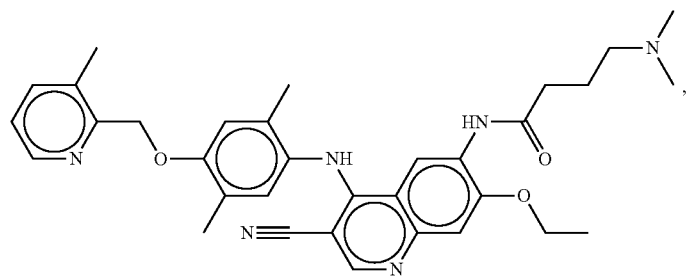
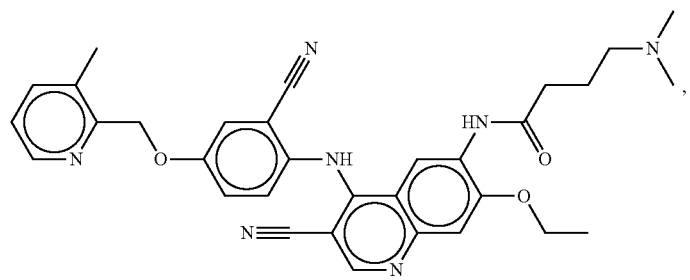
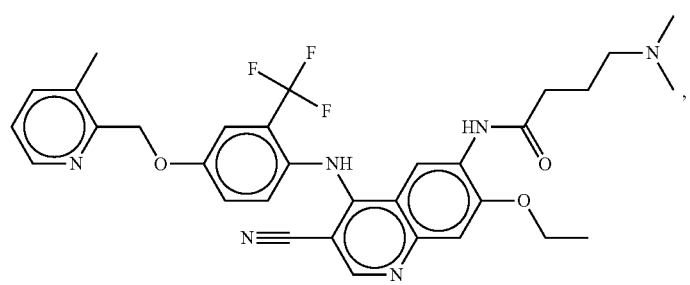

-continued
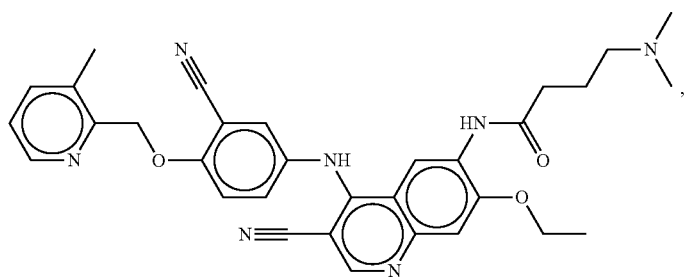
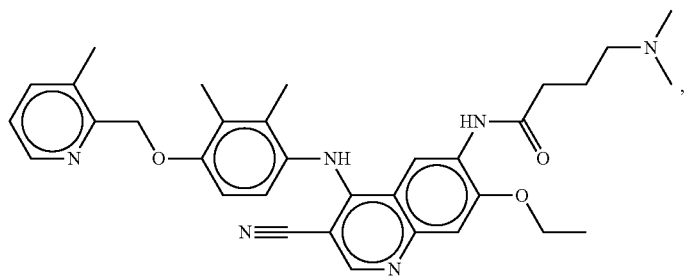
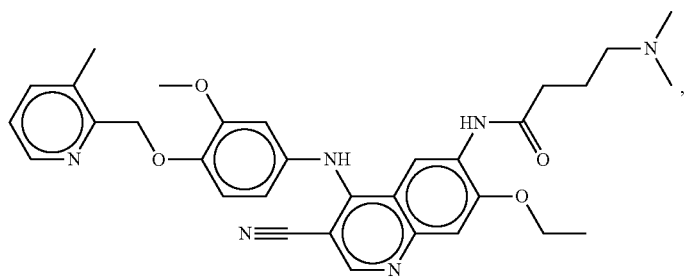
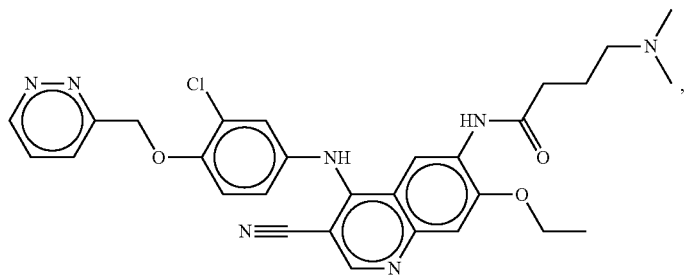
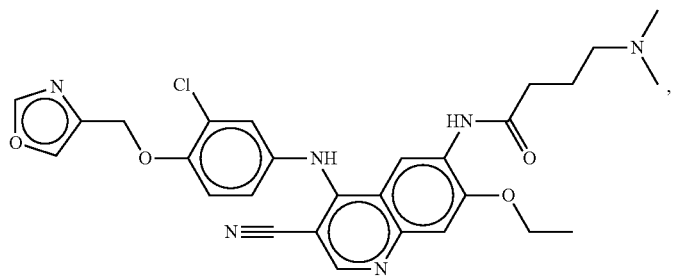
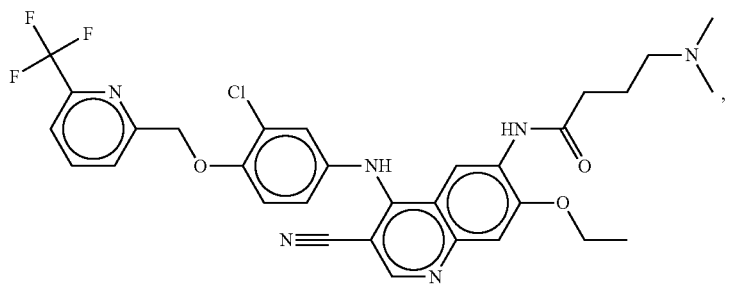

-continued
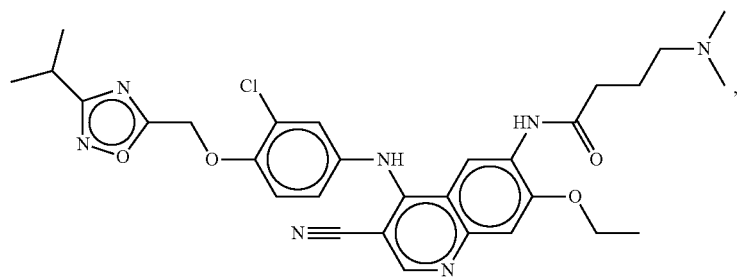
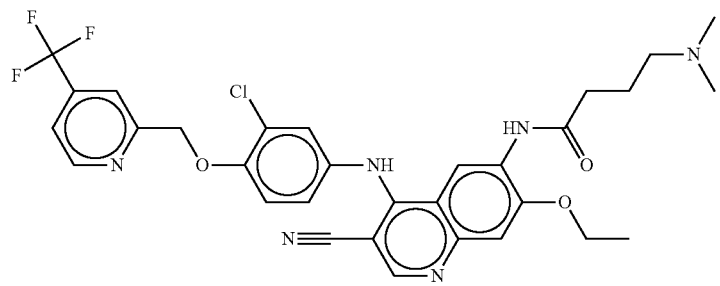
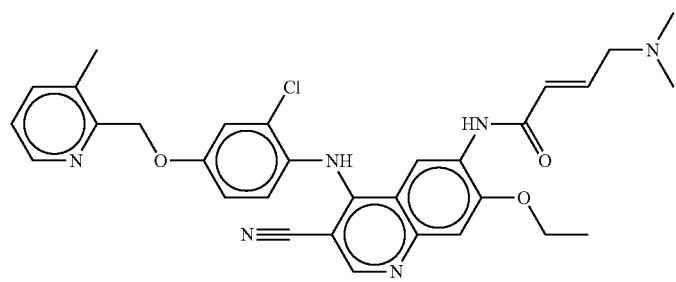
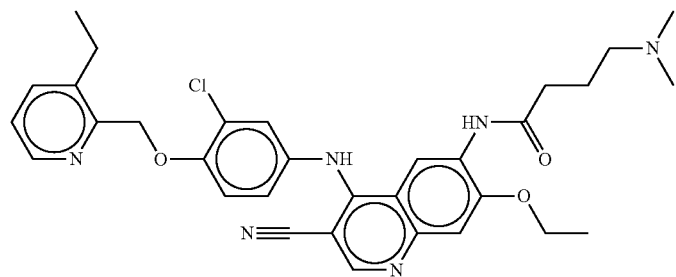
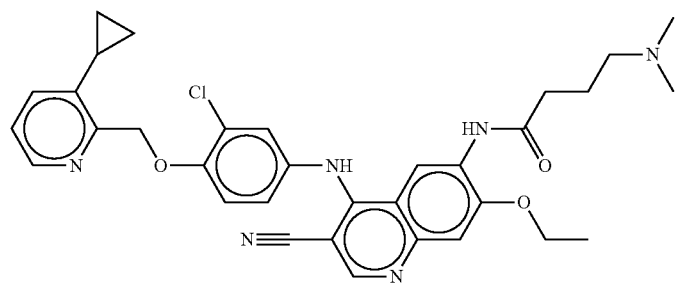
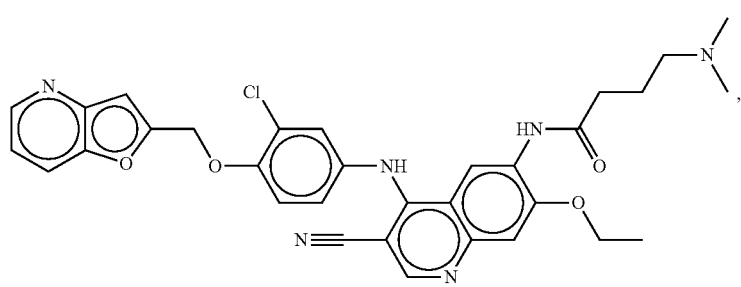

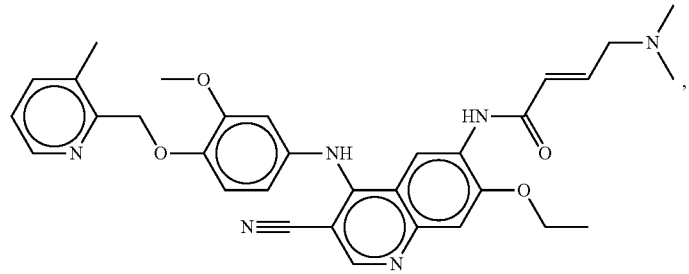
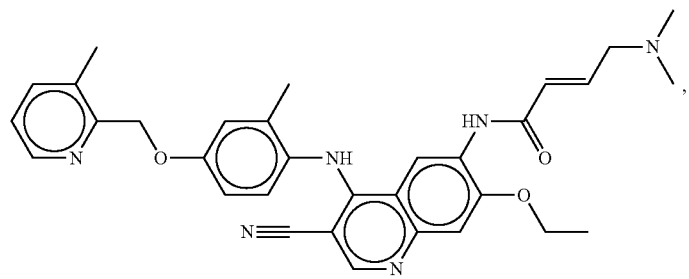
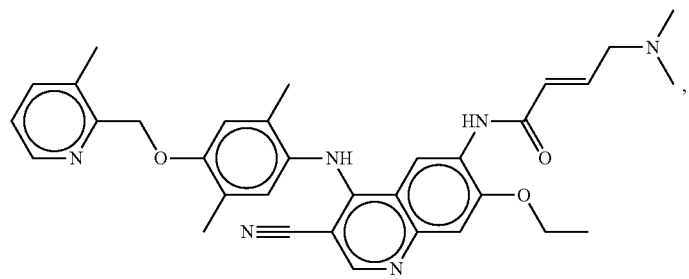
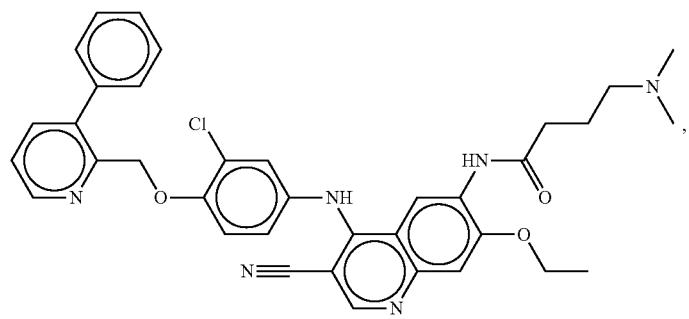
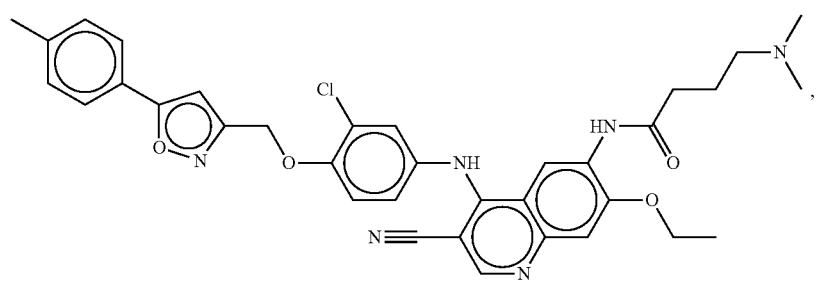
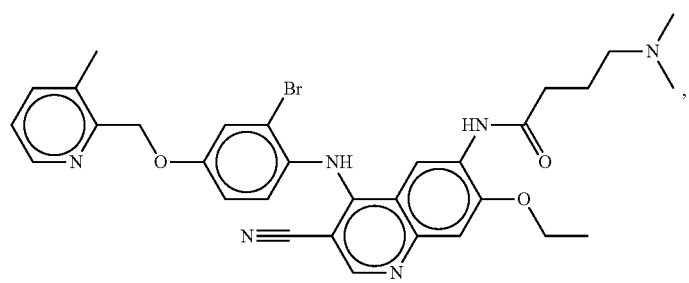

-continued
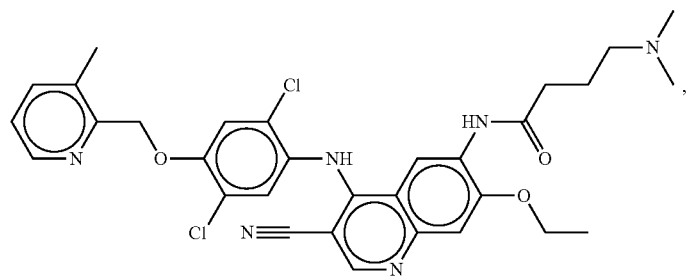
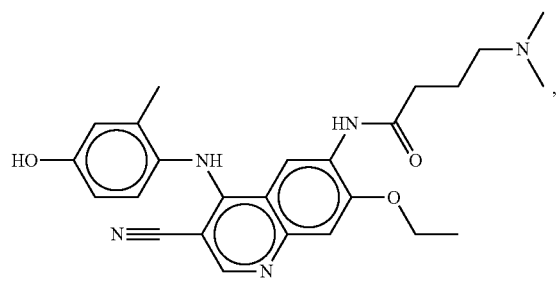
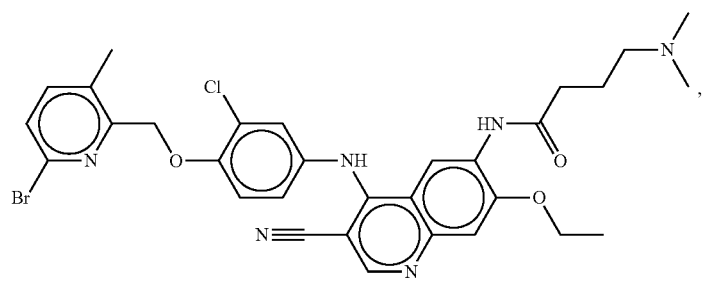
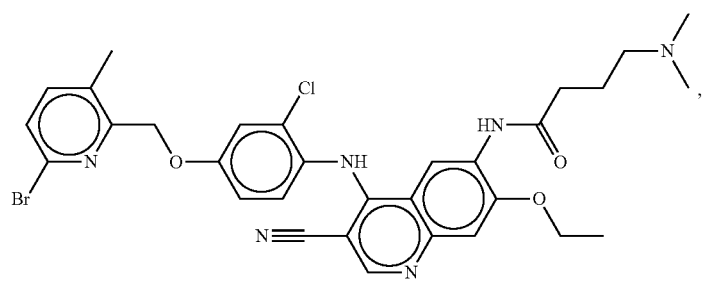
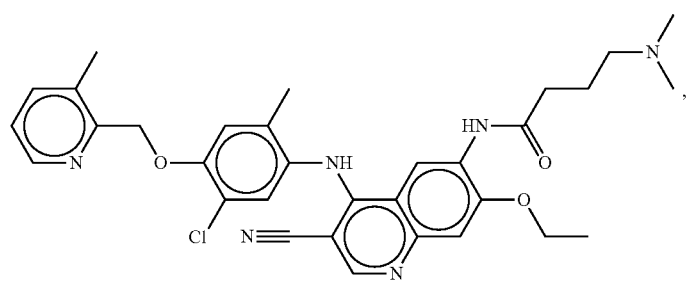
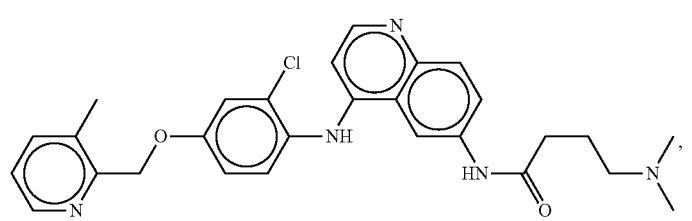

-continued
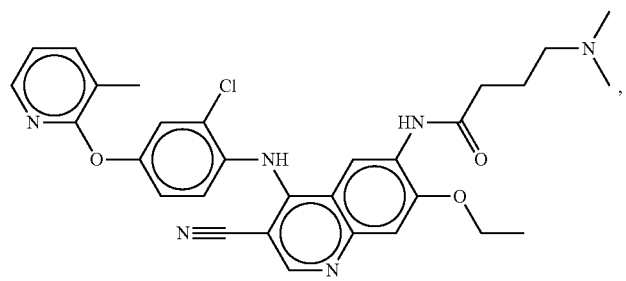
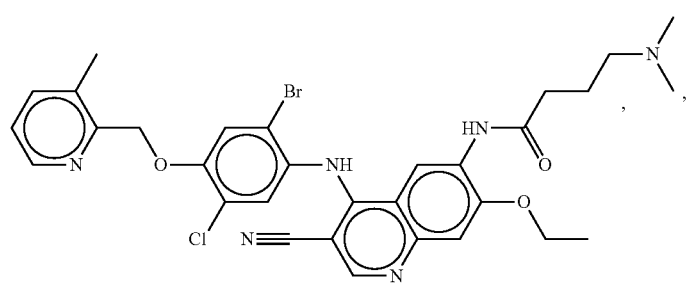
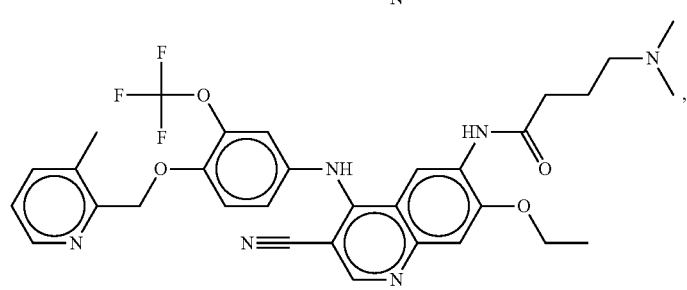
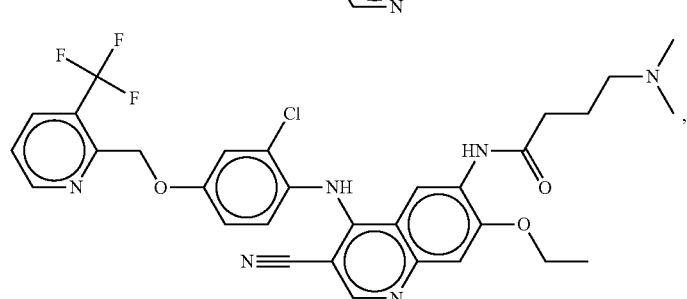
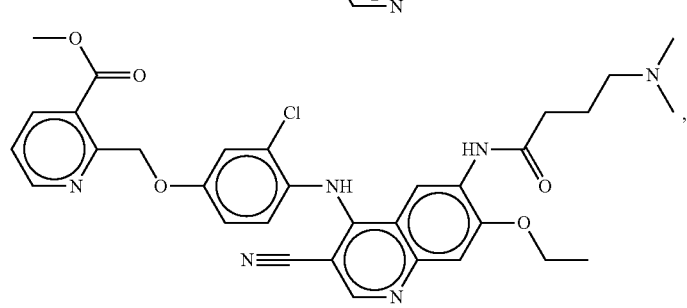
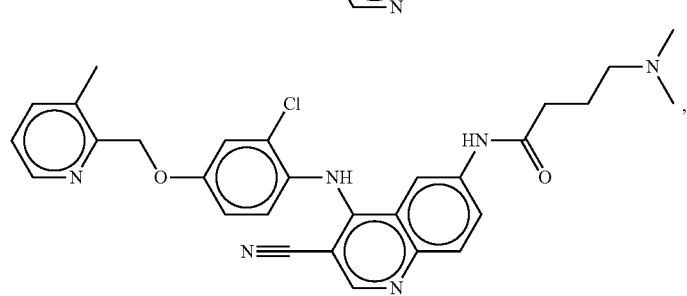

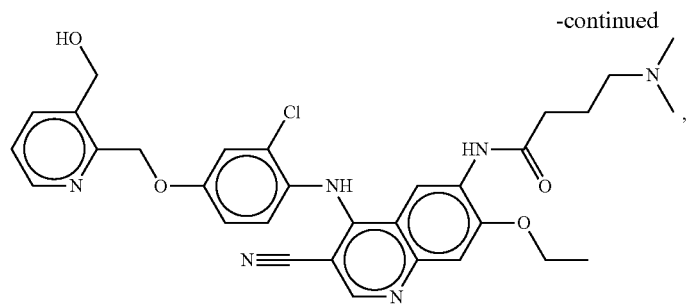

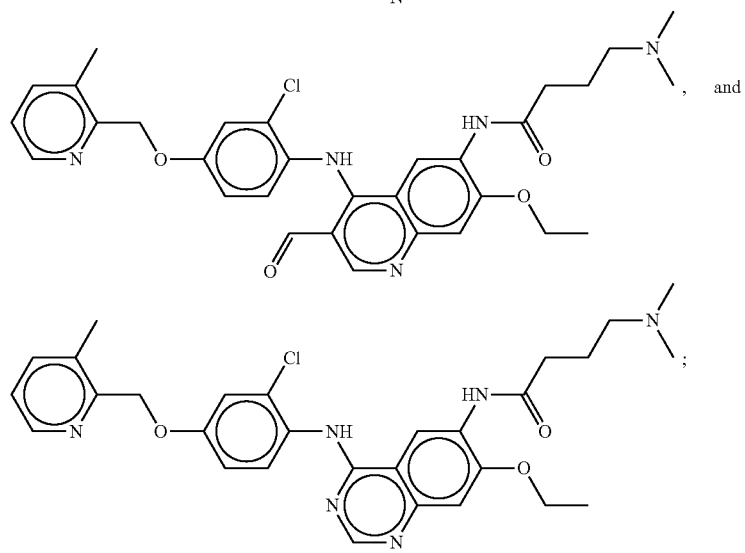

or a pharmaceutically acceptable salt, solvate, or prodrug thereof.

In some embodiments, the compounds of Formula (I), (Ia), (Ib), (II), (IIa), or (IIb) described herein inhibit the activity of the MST1 directly or indirectly. In some embodiments, the compounds of Formula (I), (Ia), (Ib), (II), (IIa), or (IIb) described herein inhibit a protein upstream of MST1. As used herein, the term "upstream" indicates a protein that has activity that effects MST1 expression or activity. In some embodiments, the compounds of Formula (I), (Ia), (Ib), (II), (IIa), or (IIb) described herein inhibit a protein downstream of MST1. As used herein, the term "downstream" indicates a protein that has activity that is affected by MST1 expression or activity. In some embodiments, the protein upstream or the protein downstream is a component of a Hippo signaling pathway.

In some embodiments, provided herein is a compound, or pharmaceutically acceptable salt, solvate, or prodrug thereof, selected from:

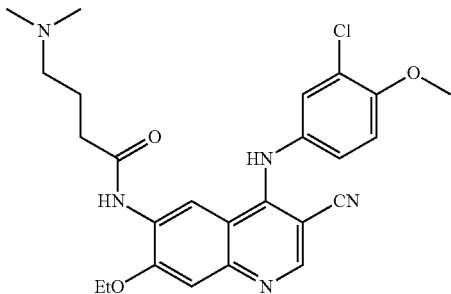

-continued

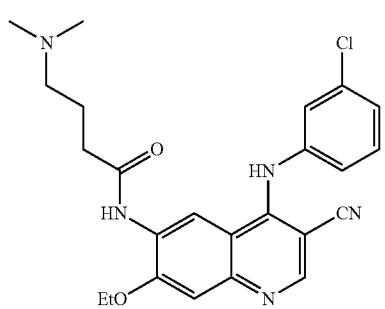

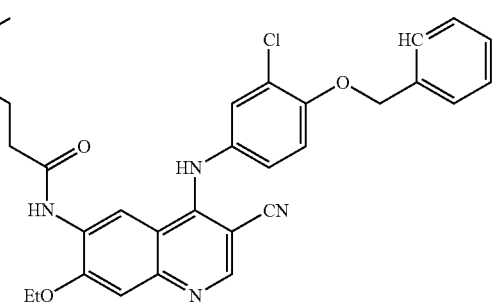

125
-continued
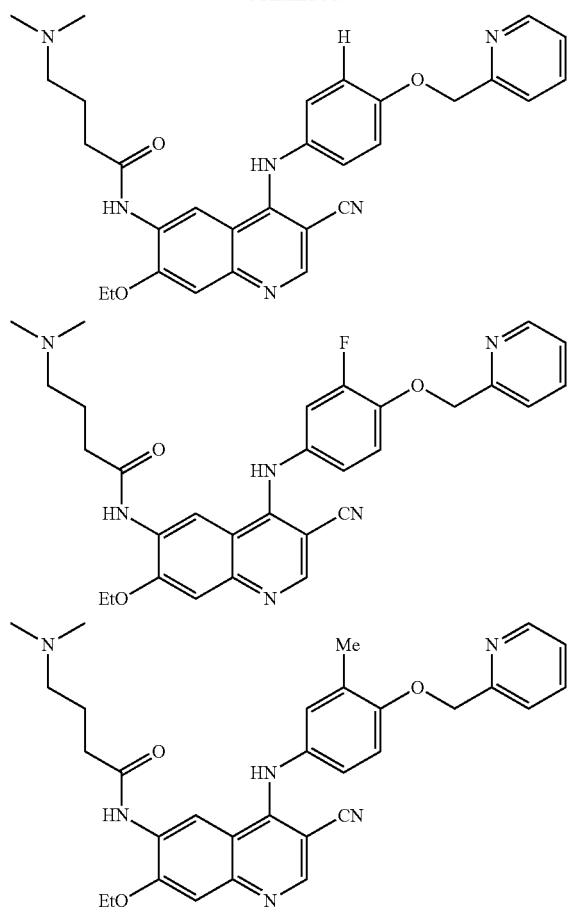
126
-continued
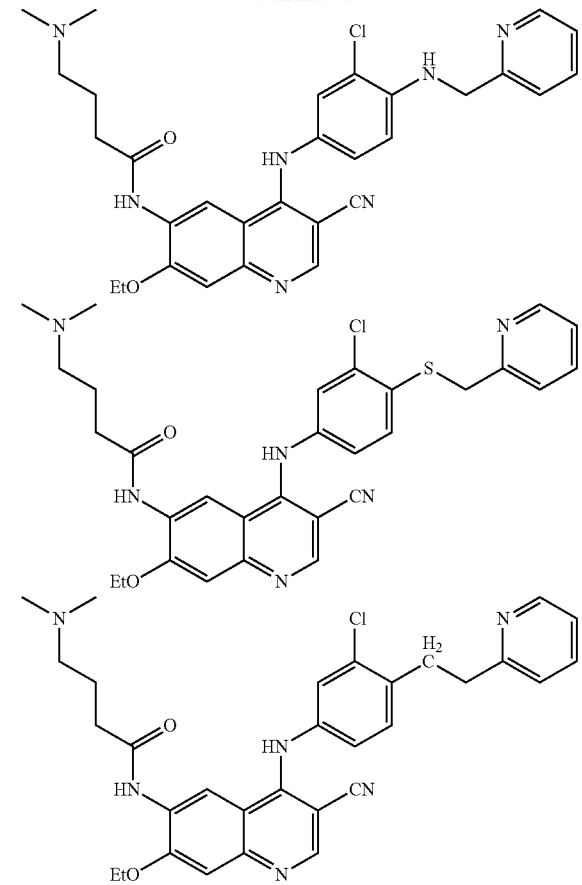
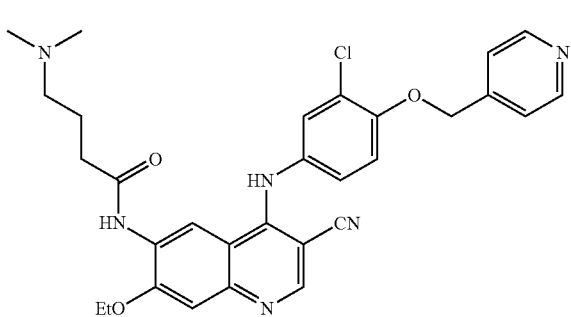
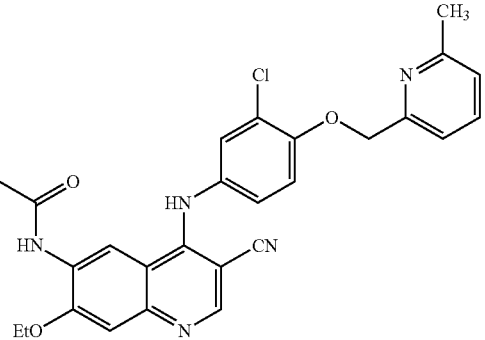

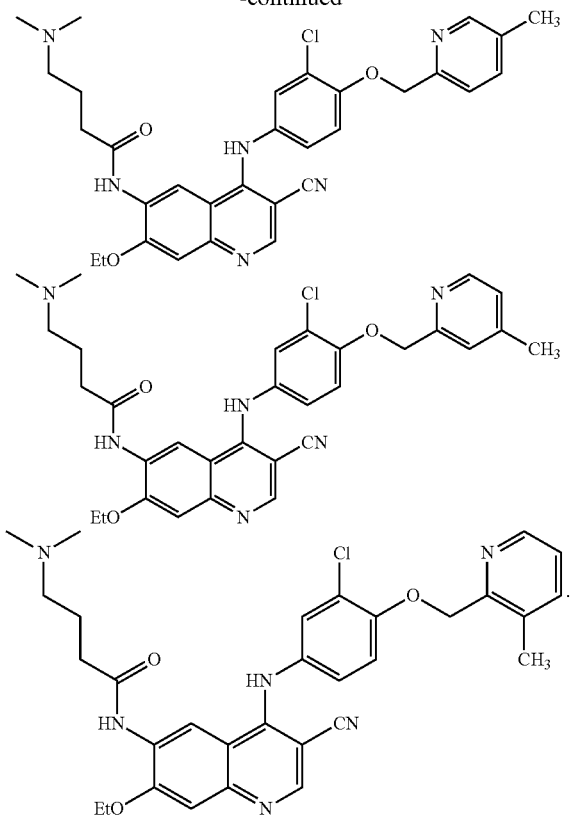

In some embodiments, the compounds described herein may inhibit an activity of MST1. The activity may be selected from a phosphorylation activity, an inflammatory activity, a cleavage activity, an apoptotic activity, a ubiquinating activity, a mitochondrial activity, and combinations thereof. The activity may be an activity directed toward MST1. The activity may be directed toward a non-MST1 protein or substrate. The activity may be selected from auto-phosphorylation.

In some embodiments, the compounds described herein may inhibit phosphorylation of a protein downstream of the activity of MST1. The compounds described herein may inhibit phosphorylation of a protein upstream of the activity of MST1. The protein downstream may be selected from a transcription factor, a kinase, a histone. The transcription factor may be pancreatic and duodenal homeobox 1 (PDX-1) or a homolog thereof. The histone may be histone 2B (H2B). The kinase may be a Janus kinase (JNK). The compounds described herein may inhibit cleavage of a protein downstream of the activity of the MST1. The protein downstream may be an apoptotic protein. The protein downstream may be a caspase. The caspase may be an initiator caspase. The caspase may be an effector caspase. The caspase may be selected from caspase 9, caspase 3 and MST1. The compounds described herein may inhibit apoptotic activity of a protein downstream of the activity of the MST1. The protein downstream may be selected from INK, Bim, Bax, Bcl-2, homologs thereof, and combinations thereof.

Further disclosed herein are methods of treating a metabolic condition in a subject comprising administering a compound described herein, or a pharmaceutically acceptable salt, solvate, or prodrug thereof, to the subject. Disclosed herein are methods of treating diabetes mellitus in a subject comprising administering a compound described herein, or a pharmaceutically acceptable salt, solvate, or prodrug thereof, to the subject.

Further disclosed herein are methods of treating a metabolic condition in a subject comprising administering neratinib to the subject. Disclosed herein are methods of treating diabetes mellitus in a subject comprising administering neratinib to the subject.

The metabolic condition may be a metabolic disease, a metabolic disorder or a symptom thereof. The metabolic condition may acute. The metabolic condition may be chronic. The metabolic condition may be a risk for a metabolic disease. The metabolic condition may be a pre-metabolic condition. For example, the subject may be insulin insensitive or have high glucose levels, but not diagnosed with diabetes mellitus.

The metabolic condition may be diabetes mellitus. The method of claim 1, wherein the metabolic condition is selected from type 1 diabetes mellitus and type 2 diabetes mellitus. Diabetes mellitus may include, type I diabetes, type 2 diabetes, gestational diabetes, and prediabetes. The diabetes mellitus may be caused by a disease of the pancreas, a surgery or a medication.

In some embodiments, the metabolic condition may be one or more symptoms and/or conditions of a metabolic disease/disorder. Examples of diabetes/metabolic related conditions include, but are not limited to, diabetic retinopathy, diabetic nephropathy, diabetic heart disease, diabetic foot disorders, diabetic neuropathy, macrovascular disease, diabetic cardiomyopathy, infection and diabetic ketoacidosis. Diabetic neuropathy may include, but is not limited to symmetric polyneuropathy, autonomic neuropathy, radiculopathy, cranial neuropathy, and mononeuropathy.

Further disclosed herein are methods of treating an inflammatory condition in a subject comprising administering to the subject a compound described herein, or a pharmaceutically acceptable salt, solvate, or prodrug thereof, that inhibits an activity of a mammalian sterile 20-like kinase 1 (MST1), a cleaved product thereof, or a homolog thereof. In some embodiments are methods of treating an inflammatory condition in a subject comprising administering to the subject a compound described herein, or a pharmaceutically acceptable salt, solvate, or prodrug thereof, that inhibits an activity of a mammalian sterile 20-like kinase 1 (MST1), a cleaved product thereof, or a homolog thereof, wherein the compound is neratinib. In some embodiments, the inflammatory condition is selected from, but not limited to, Alzheimer's, arthritis (osteoarthritis, rheumatoid arthritis (RA), psoriatic arthritis), asthma, atherosclerosis, Crohn's disease, colitis, dermatitis, fibromyalgia, hepatitis, irritable bowel syndrome (IBS), Parkinson's disease, celiac disease, lupus, chronic obstructive pulmonary disease, and psoriasis.

In some embodiments, the method further comprises treating the subject with an additional therapy. In some embodiments, the additional therapy is a therapy for the treatment of diabetes mellitus. In some embodiments, the additional therapy is a sulfonylurea. In some embodiments, the additional therapy is a thiazolidine. In some embodiments, the additional therapy is a dipeptidyl peptidase-4 (DPP-4) inhibitor. In some embodiments, the additional therapy is selected from metformin, sitagliptin, exenatide, colesevelam, sitagliptin, metformin, glipizide, glimepiride, canagliflozin, insulin, rosiglitazone, saxagliptin, alogliptin, chlorpropamide, glibenclaimide, gliclazide, glucomannan, miglitol, pioglitazone, repaglinide, simvastatin, tolazamide, tolbutamide, vildagliptin, and combinations thereof.

Disclosed herein are methods of treating an autoimmune disorder in a subject comprising administering to the subject a compound described herein, or a pharmaceutically acceptable salt, solvate, or prodrug thereof, that inhibits an activity of a mammalian sterile 20-like kinase 1 (MST1), a cleaved product thereof, or a homolog thereof. In some embodiments is a method of treating an autoimmune disorder in a subject comprising administering to the subject a compound described herein, or a pharmaceutically acceptable salt, solvate, or prodrug thereof, that inhibits an activity of a mammalian sterile 20-like kinase 1 (MST1), a cleaved product thereof, or a homolog thereof, wherein the compound is neratinib. In some embodiments, the autoimmune disorder is selected from, but are not limited to, acute disseminated encephalomyelitis, alopecia areata, antiphospholipid syndrome, autoimmune cardiomyopathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendrocrine syndrome, autoimmune progesterone dermatitis, autoimmune thrombocytopenic purpura, autoimmune urticaria, autoimmune uveitis, Behcet's disease, Celiac disease, cold agglutinin disease, Crohn's disease, dermatomyositis, diabetes mellitus type 1, eosinophilic fasciitis, gastrointestinal pemphigoid, Goodpasture's syndrome, Grave's disease, Guillain-Barre syndrome, Hashimoto's encephalopathy, Hashimoto's thyroiditis, idiopathic thrombocytopenic purpura, lupus erythematosus, Miller-Fisher syndrome, mixed connective tissue disease, multiple sclerosis, myasthenia gravis, narcolepsy, pemphigus vulgaris, pernicious anemia, polymyositis, primary biliary cirrhosis, psoriasis, psoriatic arthritis, relapsing polychondritis, rheumatoid arthritis, rheumatic fever, Sjogren's syndrome, temporal arteritis, transverse myelitis, ulcerative colitis, undifferentiated connective tissue disease, vasculitis, and Wegener's granulomatosis.

In some embodiments, the compounds described herein may inhibit an activity of MST1. In some embodiments, the compounds described herein may inhibit an activity of MST2. In some embodiments, the compounds described herein may inhibit an activity of MST1 and MST2. The activity may be selected from a phosphorylation activity, an inflammatory activity, a cleavage activity, an apoptotic activity, a ubiquinating activity, a mitochondrial activity, and combinations thereof. The activity may be an activity directed toward MST1. The activity may be directed toward a non-MST1 protein or substrate. The activity may be selected from auto-phosphorylation.

Pharmaceutical Compositions/Formulations

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999), herein incorporated by reference for such disclosure.

Provided herein are pharmaceutical compositions that include a compound of Formula (I), (Ia), (Ib), (II), (IIa), or (IIb) and at least one pharmaceutically acceptable inactive ingredient. In some embodiments, the compounds described herein are administered as pharmaceutical compositions in which a compound of Formula (I), (Ia), (Ib), (II), (IIa), or (IIb) is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula (I), (Ia), (Ib), (II), (IIa), or (IIb) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound of Formula (I), (Ia), (Ib), (II), (IIa), or (IIb) are manufactured in a conventional manner, such as, by way of example only, by means of conventional mixing, dissolving, granulating, dragee-making, levigating, emulsifying, encapsulating, entrapping or compression processes.

Routes of Administration

Suitable routes of administration include, but are not limited to, oral, intravenous, aerosol, parenteral, ophthalmic, pulmonary, transmucosal, transdermal, nasal, and topical administration. In addition, by way of example only, parenteral delivery includes intramuscular, subcutaneous, intravenous, intramedullary injections, as well as intrathecal, direct intraventricular, intraperitoneal, intralymphatic, and/or intranasal injections.

In certain embodiments, a compound of Formula (I), (Ia), (Ib), (II), (IIa), or (IIb) is administered in a local rather than systemic manner, for example, via topical application of the compound directly on to skin, or intravenously, or subcutaneously, often in a depot preparation or sustained release formulation. In specific embodiments, long acting formulations are administered by implantation (for example subcutaneously or intramuscularly) or by intramuscular injection. In yet other embodiments, the compound as described herein is provided in the form of a rapid release formulation, in the form of an extended release formulation, or in the form of an intermediate release formulation. In yet other embodiments, the compound described herein is administered topically (e.g., as a patch, an ointment, or in combination with a wound dressing, or as a wash or a spray). In alternative embodiments, a formulation is administered systemically (e.g., by injection, or as a pill).

Methods of Dosing

For certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), (Ia), (Ib), (II), (IIa), or (IIb) in order to prevent a return of the symptoms of the disease or condition.

In certain embodiments wherein the patient's condition does not improve, upon the doctor's discretion the administration of the compound of Formula (I), (Ia), (Ib), (II), (IIa), or (IIb) is administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

In certain embodiments the dose of drug being administered may be temporarily reduced or temporarily suspended for a certain length of time (i.e., a "drug diversion"). In specific embodiments, the length of the drug diversion is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug diversion is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. After a suitable length of time, the normal dosing schedule is optionally reinstated.

In some embodiments, once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated. In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously (or over a short period of time) or at appropriate intervals, for example as two, three, four or more sub-doses per day.

In some embodiments, as a patient is started on a regimen of an antiviral compound, the patient is also weaned off (e.g., step-wise decrease in dose) a second treatment regimen.

In one embodiment, the daily dosages appropriate for a compound of Formula (I), (Ia), (Ib), (II), (IIa), or (IIb) described herein are from about 0.01 to about 10 mg/kg per body weight. In specific embodiments, an indicated daily dosage in a large mammal, including, but not limited to, humans, is in the range from about 0.5 mg to about 1000 mg, conveniently administered in divided doses, including, but not limited to, up to four times a day. In one embodiment, the daily dosage is administered in extended release form. In certain embodiments, suitable unit dosage forms for oral administration comprise from about 1 to 500 mg active ingredient. In other embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

EXAMPLES

These examples are provided for illustrative purposes only and not to limit the scope of the claims provided herein. The starting materials and reagents used for the synthesis of the compounds described herein may be synthesized or can be obtained from commercial sources, such as, but not limited to, Sigma-Aldrich, Acros Organics, Fluka, and Fischer Scientific.

Example 1

Synthesis of N-(4-chloro-3-cyano-7-ethoxyquinolin-6-yl)-4-(dimethylamino)butanamide (5)

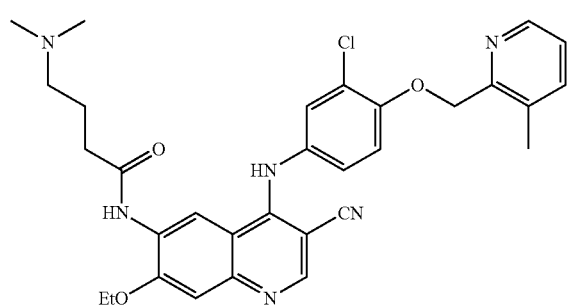

5

Step 1:
6-Amino-4-chloro-7-ethoxyquinoline-3-carbonitrile (2)

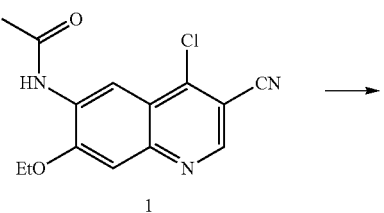

1

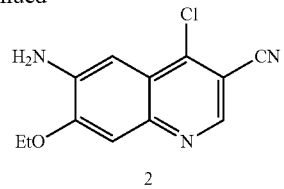

2

N-(4-Chloro-3-cyano-7-ethoxyquinolin-6-yl)acetamide (1) (1.53 g, 5.27 mmol) was suspended and stirred in 10 mL of water and the reaction flask was placed in a 0° C. ice-water bath. Concentrated HCl (15 mL) was added dropwise with stirring over 10 mins. The reaction flask was placed in a 50° C. oil bath and reaction progress was monitored by LCMS until ~90% conversion, at which point competing byproducts began to appear as observed by LCMS. The reaction was stirred in a 0° C. ice-water bath and was quenched with saturated $NaHCO_3$. The product was extracted into EtOAc and evaporated to dryness. The crude product (1.2 g of ~85:15 product:starting material, ~4.85 mmol) was taken on to the next step without further purification.

Step 2: N-(4-chloro-3-cyano-7-ethoxyquinolin-6-yl)-4-(dimethylamino)butanamide (3)

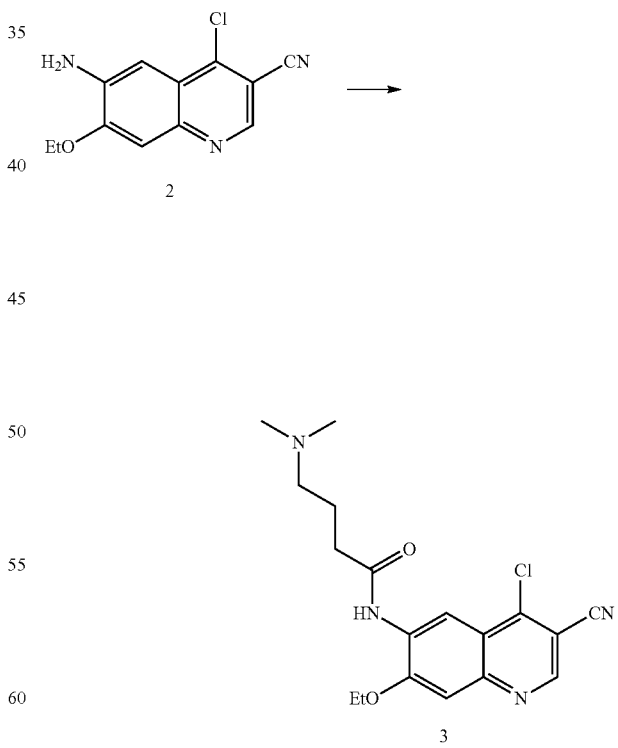

4-(Dimethylamino)butanoic acid hydrochloride (1.95 g, 11.6 mmol) was suspended in EtOAc (20 mL) and DMF (0.08 mL, 1.0 mmol) under argon in a 0° C. ice-water bath. Oxalyl chloride (0.870 mL, 10.2 mmol) was added dropwise over 5 minutes and the suspension was stirred in the ice-water bath for 20 minutes. The bath was removed and the reaction was allowed to stir at ambient temperature for 2 h then was placed into a 0° C. ice-water bath. A solution of 2 (1.20 g, 4.85 mmol) in NMP was then added and the reaction was allowed to stir in the ice-water bath for 90 minutes. The reaction was quenched by the addition of water (40 mL), washed with EtOAc (50 mL) and the organic layer was extracted with 1 N HCl (30 mL). The combined aqueous layers were basified to pH 11 with 10 N NaOH to precipitate the product. The product (1.118 g) was collected via filtration as a yellow solid and was used in the next step without purification. NMR shows >90% purity. $^1$H NMR (400 MHz, Methanol-d$_4$) δ 9.16 (s, 1H), 8.83 (s, 1H), 7.49 (s, 1H), 4.39 (q, J=6.9 Hz, 2H), 2.61 (t, J=7.3 Hz, 2H), 2.52-2.43 (m, 2H), 2.32 (s, 6H), 1.95 (p, J=7.5 Hz, 2H), 1.58 (t, J=7.0 Hz, 3H). MS-ESI (m/z) calcd for $[C_{18}H_{21}ClN_4O_2+H]^+$ 361.14; found: 361.15.

Step 3: 3-chloro-4-((3-methylpyridin-2-yl)methoxy)aniline (4)

4-Amino-2-chlorophenol (72 mg, 0.50 mmol), 2-(chloromethyl)-3-methylpyridine (100 mg, 0.56 mmol) and cesium carbonate (0.82 g, 2.5 mmol) were stirred in acetonitrile (2.5 mmol) at ambient temperature overnight. [Note: when chloromethyl-substituted heterocycles were not available, the chloride was formed from the alcohol and SOCl$_2$]. The suspension was filtered and evaporated to dryness before being purified by gradient flash chromatography (0 to 100% EtOAc in hexanes with 0.1% trimethylamine). The major peak by UV was collected and its identity was checked on LCMS to ensure it was the desired product; m/z of 249.1 (M+1$^+$) was observed. This product was taken to the next step without further characterization.

Step 4: N-(4-chloro-3-cyano-7-ethoxyquinolin-6-yl)-4-(dimethylamino)butanamide (5)

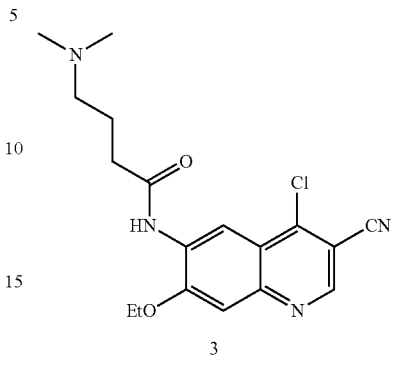

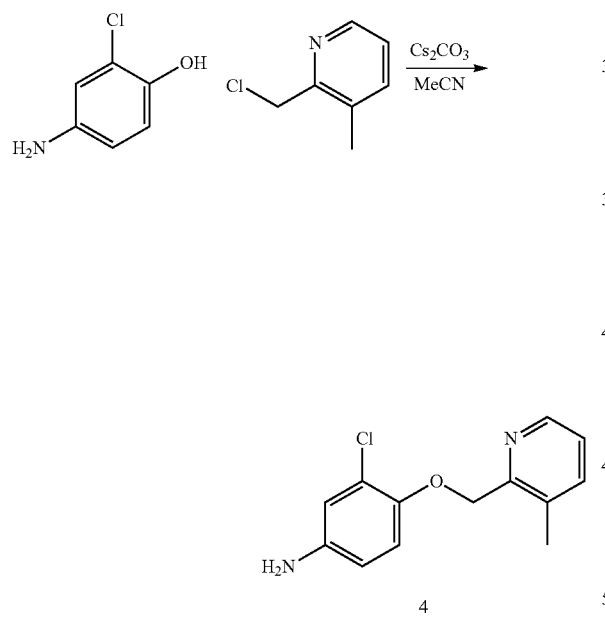

Compound 3 (18 mg, 0.05 mmol), pyridine-hydrochloride (6 mg, 0.05 mmol) and Compound 4 (12.5 mg, 0.05 mmol) were stirred in isopropanol (0.5 mL) in a heating block at 75° C. for 16 h. After cooling to ambient temperature, the reaction mixture was diluted with MeOH to dissolve all components and purified by preparative HPLC to yield the product (5, 7.23 mg) as the bis-TFA salt. $^1$H NMR (400 MHz, Methanol-d4) δ 9.09 (s, 1H), 8.77 (s, 1H), 8.49 (d, J=5.2 Hz, 1H), 7.98 (d, J=7.9 Hz, 1H), 7.59-7.53 (m, 2H), 7.44-7.34 (m, 3H), 5.44 (s, 2H), 4.40 (q, J=7.0 Hz, 2H), 3.29-3.20 (m, 2H), 2.93 (s, 6H), 2.74 (t, J=6.9 Hz, 2H), 2.55 (s, 3H), 2.12 (dt, J=15.2, 7.1 Hz, 2H), 1.59 (t, J=7.0 Hz, 3H); MS-ESI (m/z) calcd for $[C_{31}H_{33}ClN_6O_3+H]^+$ 573.24; found: 573.24.

Examples 2-83 were prepared according to a similar procedure as described for Example 1:

| Ex. | Structure | Analytical Data |
|---|---|---|
| 2 | 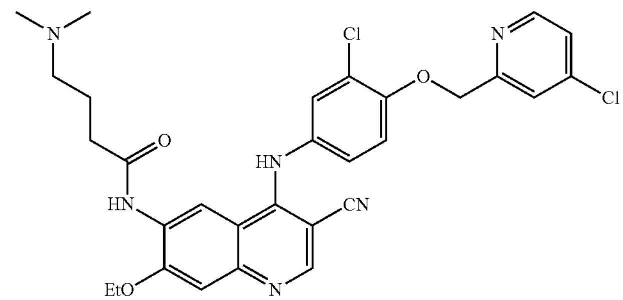 [SMILES: CCOc1cc2ncc(C#N)c(Nc3ccc(OCc4cc(Cl)ccn4)c(Cl)c3)c2cc1NC(=O)CCCN(C)C] | $^1$H NMR (400 MHz, Methanol-d$_4$) δ 9.03 (s, 1H), 8.65 (s, 1H), 8.54 (d, J = 6.9 Hz, 1H), 7.77 (s, 1H), 7.55 (d, J = 8.19 Hz, 1H), 7.36 (d, J = 9.4 Hz, 1H), 7.36-7.27(m, 3H), 5.28 (s, 2H), 4.40 (q, J = 6.9 Hz, 2H), 3.40-3.26 (m, 2H), 2.94 (s, 6H), 2.75 (t, J = 6.8 Hz, 2H), 2.32-2.1 (m, 2H), 1.58 (t, J = 7.0 Hz, 3H); MS-ESI (m/z) calcd for [C$_{30}$H$_{30}$Cl$_2$N$_6$O$_3$ + H]$^+$ 593.18; found: 593.20. |
| 3 | 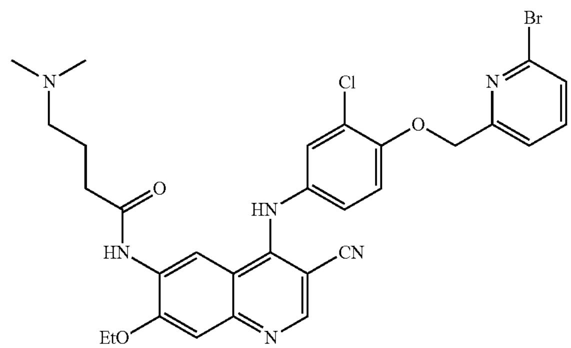 | $^1$H NMR (400 MHz, Methanol-d$_4$) δ 9.03 (s, 1H), 8.68 (s, 1H), 7.78 (t, J = 7.7 Hz, 1H), 7.68 (d, J = 7.6 Hz, 1H), 7.57-7.40 (m, 2H), 7.37 (d, J = 6.19 Hz, 1H), 7.36-7.27(m, 2H), 5.25 (s, 2H), 4.40 (q, J = 6.9 Hz, 2H), 3.40-3.25 (m, 2H), 2.94 (s, 6H), 2.75 (t, J = 6.4 Hz, 2H), 2.30-2.13 (m, 2H), 1.59 (t, J = 7.0 Hz, 3H); MS-ESI (m/z) calcd for [C$_{30}$H$_{30}$BrClN$_6$O$_3$ + H]$^+$ 637.13; found: 637.20. |
| 4 | 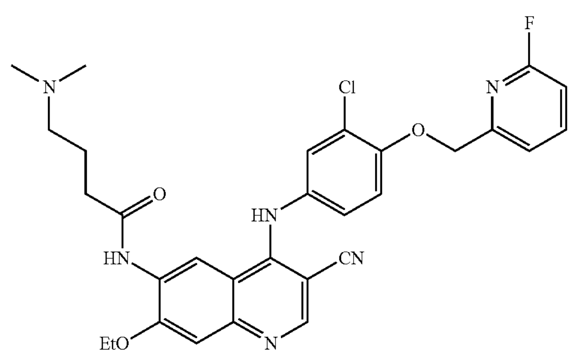 | $^1$H NMR (400 MHz, Methanol-d$_4$ δ 9.05 (s, 1H), 8.71 (s, 1H), 8.01 (q, J = 7.9 Hz, 1H), 7.60-7.50 (m, 2H), 7.48-7.36 (m, 2H), 7.26 (d, J = 6.2 Hz, 1H), 7.05(dd, J = 8.3, 2.2 Hz, 1H), 5.26 (s, 2H), 4.40 (q, J = 6.9 Hz, 2H), 3.40-3.26 (m, 2H), 2.94 (s, 6H), 2.74 (t, J = 6.8 Hz, 2H), 2.30-2.13 (m, 2H), 1.59 (t, J = 6.8 Hz, 3H); MS-ESI (m/z) calcd for [C$_{30}$H$_{30}$ClFN$_6$O$_3$ + H]$^+$ 577.20; found: 577.20. |
| 5 | 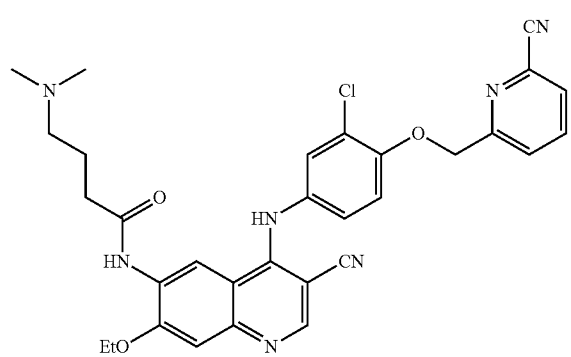 | $^1$H NMR (400 MHz, Methanol-d$_4$) δ 9.05 (s, 1H), 8.71 (s, 1H), 8.09 (t, J = 7.8 Hz, 1H), 7.98-7.70 (m, 1H), 7.65 (d, J = 7.6 Hz, 1H), 7.56 (d, J = 6.2 Hz, 1H), 7.48-7.37 (m, 2H), 7.28 (d, J = 8.8, 1H), 5.24 (s, 2H), 4.40 (q, J = 6.4 Hz, 2H), 3.40-3.26 (m, 2H), 2.94 (s, 6H), 2.75 (t, J = 6.9 Hz, 2H), 2.28-2.13 (m, 2H), 1.59 (t, J = 6.9 Hz, 3H); MS-ESI (m/z) calcd for [C$_{31}$H$_{30}$ClN$_7$O$_3$ + H]$^+$ 585.08; found: 585.20. |

-continued

| Ex. | Structure | Analytical Data |
|---|---|---|
| 6 | 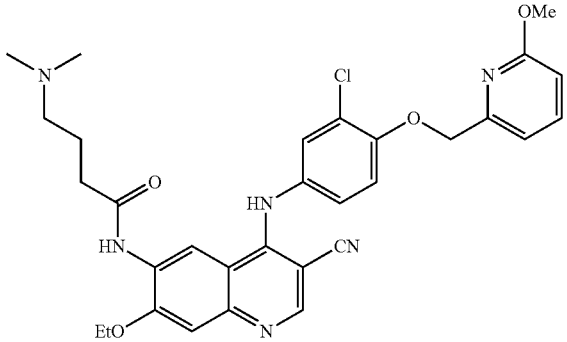 [SMILES: CCOc1cc2ncc(C#N)c(Nc3ccc(OCc4cccc(OC)n4)c(Cl)c3)c2cc1NC(=O)CCCN(C)C] | $^1$H NMR (400 MHz, Methanol-$d_4$) δ 9.08 (s, 1H), 8.75 (s, 1H), 7.98-7.71 (m, 1H), 7.57 (s, 1H), 7.65-7.37 (m, 2H), 7.27 (d, J = 8.8 Hz, 1H), 7.20 (d, J = 7.34, 1H), 6.75 (d, J = 8.3 Hz, 1H), 5.24 (s, 2H), 4.41 (q, J = 6.9 Hz, 2H), 3.94 (s, 3H), 3.40-3.26 (m, 2H), 2.94 (s, 6H), 2.75 (t, J = 6.9 Hz, 2H), 2.28-2.12 (m, 2H), 1.60 (t, J = 6.9 Hz, 3H); MS-ESI (m/z) calcd for $[C_{31}H_{33}ClN_6O_4$+ H]$^+$ 589.23; found: 589.20. |
| 7 | 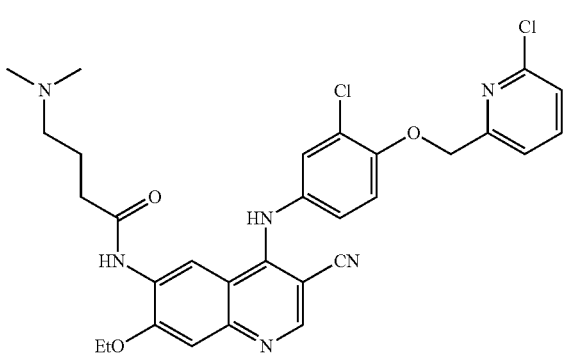 [SMILES: CCOc1cc2ncc(C#N)c(Nc3ccc(OCc4cccc(Cl)n4)c(Cl)c3)c2cc1NC(=O)CCCN(C)C] | $^1$H NMR (400 MHz, Methanol-$d_4$) δ 9.04 (s, 1H), 8.69 (s, 1H), 7.89 (t, J = 7.8 Hz, 1H), 7.66 (s, 1H), 7.55 (d, J = 8.1 Hz, 1H), 7.44 (d, J = 7.9 Hz, 1H), 7.36-7.30(m, 2H), 7.26 (s, 1H), 5.26 (s, 2H), 4.40 (q, J = 6.9 Hz, 2H), 3.40-3.26 (m, 2H), 2.94 (s, 6H), 2.75 (t, J = 6.8 Hz, 2H), 2.32-2.14 (m, 2H), 1.58 (t, J = 6.9 Hz, 3H); MS-ESI (m/z) calcd for $[C_{30}H_{30}Cl_2N_6O_3$ + H]$^+$ 593.18; found: 593.20. |
| 8 | 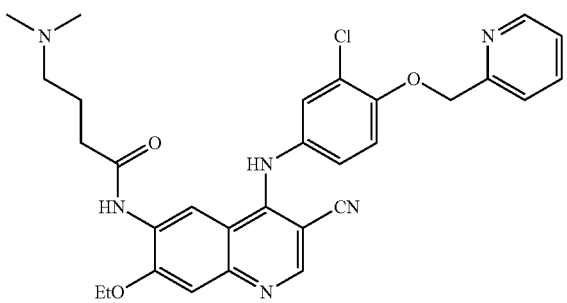 [SMILES: CCOc1cc2ncc(C#N)c(Nc3ccc(OCc4ccccn4)c(Cl)c3)c2cc1NC(=O)CCCN(C)C] | $^1$H NMR (400 MHz, Methanol-$d_4$) δ 9.13 (s, 1H), 8.81 (s, 1H), 8.66 (d, J = 5.3 Hz, 1H), 8.10 (td, J = 7.8, 1.7 Hz, 1H), 7.84 (d, J = 7.9 Hz, 1H), 7.62 (d, J = 2.5 Hz, 1H), 7.60-7.53 (m, 1H), 7.44-7.39 (m, 2H), 7.31 (d, J = 8.8 Hz, 1H), 5.42 (s, 2H), 4.41 (q, J = 7.0 Hz, 2H), 3.34-3.29 (m, 6H), 3.29-3.19 (m, 2H), 2.74 (t, J = 6.9 Hz, 2H), 2.12 (dt, J = 14.9, 7.1 Hz, 2H), 1.59 (t, J = 7.0 Hz, 3H); MS-ESI (m/z) calcd for $[C_{30}H_{31}ClN_6O_3$ + H]$^+$ 559.22; found: 280.26 (z = 2). |
| 9 | 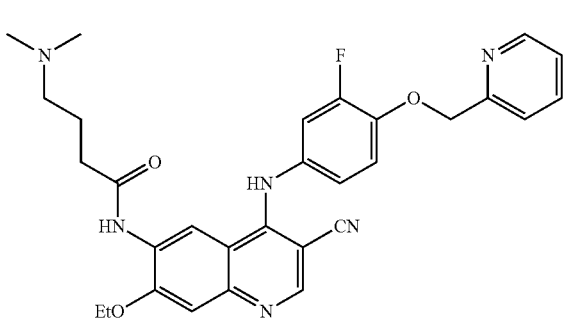 | $^1$H NMR (400 MHz, Methanol-$d_4$) δ 9.11 (s, 1H), 8.80 (s, 1H), 8.66-8.59 (m, 1H), 8.03 (td, J = 7.8. 1.8 Hz, 1H), 7.76 (d, J = 7.9 Hz, 1H), 7.52 (dd, J = 7.6, 1.2 Hz, 1H), 7.40-7.28 (m, 3H), 7.25 (dd, J = 8.6, 1.1 Hz, 1H), 5.38 (s, 2H), 4.41 (q, J = 7.0 Hz, 2H), 3.28-3.18 (m, 2H), 2.93 (s, 6H), 2.73 (t, J = 6.9 Hz, 2H), 2.16-2.08 (m, J = 14.8, 7.1 Hz, 2H), 1.59 (t, J = 7.0 Hz, 3H); $^{19}$F NMR (376 MHz, Methanol-$d_4$) δ -132.89; MS-ESI (m/z) calcd for $[C_{30}H_{31}FN_6O_3$ + H]$^+$ 543.25; found: 272.22 (z = 2). |

| Ex. | Structure | Analytical Data |
|---|---|---|
| 10 | 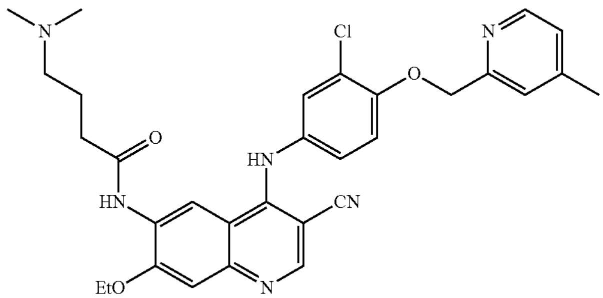 | $^1$H NMR (400 MHz, Methanol-d$_4$) δ 9.12 (s, 1H), 8.78 (s, 1H), 8.55 (d, J = 5.5 Hz, 1H), 7.74 (s, 1H), 7.61 (d, J = 2.5 Hz, 1H), 7.54 (d, J = 5.5 Hz, 1H), 7.44-7.37 (m, 2H), 7.30 (d, J = 8.8 Hz, 1H), 5.43 (s, 2H), 4.41 (q, J = 7.0 Hz, 2H), 3.28-3.20 (m, 2H), 2.93 (s, 6H), 2.74 (t, J = 6.9 Hz, 2H), 2.55 (s, 3H), 2.12 (dt, J = 14.9, 7.0 Hz, 2H), 1.59 (t, J = 7.0 Hz, 3H); MS-ESI (m/z) calcd for [C$_{31}$H$_{33}$ClN$_6$O$_3$ + H]$^+$ 573.24; found: 573.28. |
| 11 | 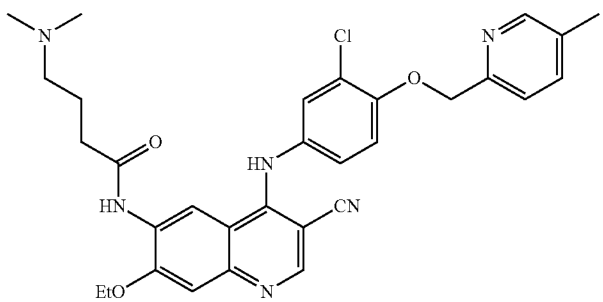 | $^1$H NMR (400 MHz, Methannol-d$_4$) δ 9.08 (s, 1H), 8.76 (s, 1H), 8.47 (s, 1H), 7.86 (d, J = 7.9 Hz, 1H), 7.68 (d, J = 8.1 Hz, 1H), 7.57 (d, J = 2.3 Hz, 1H), 7.40-7.34 (m, 2H), 7.28 (d, J = 8.8 Hz, 1H), 5.34 (s, 2H), 4.40 (q, J = 6.9 Hz, 2H), 3.27-3.21 (m, 2H), 2.93 (s, 6H), 2.73 (t, J = 6.8 Hz, 2H), 2.43 (s, 3H), 2.12 (p, J = 7.1 Hz, 2H), 1.58 (t, J = 7.0 Hz, 3H); MS-ESI (m/z) calcd for [C$_{31}$H$_{33}$ClN$_6$O$_3$ + H]$^+$ 573.24; found: 573.33. |
| 12 | 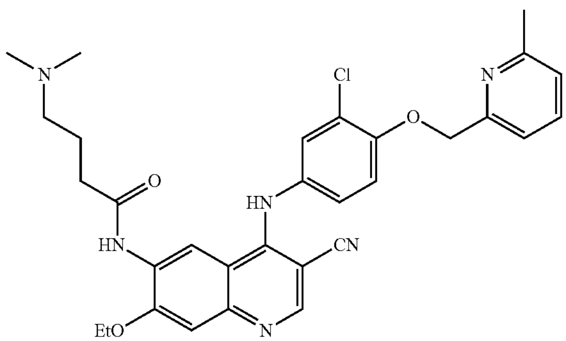 [SMILES: CCOc1cc2ncc(C#N)c(Nc3ccc(OCc4cccc(C)n4)c(Cl)c3)c2cc1NC(=O)CCCN(C)C] | $^1$H NMR (400 MHz, Methanol-d$_4$) δ 9.11 (s, 1H), 8.77 (s, 1H), 8.03 (t, J = 7.8 Hz, 1H), 7.69 (d, J = 7.8 Hz, 1H), 7.59 (d, J = 2.5 Hz, 1H), 7.49 (d, J = 7.8 Hz, 1H), 7.43-7.36 (m, 2H), 7.30 (d, J = 8.8 Hz, 1H), 5.38 (s, 2H), 4.41 (q, J = 7.0 Hz, 2H), 3.29-3.21 (m, 2H), 2.93 (s, 6H), 2.74 (t, J = 6.9 Hz, 2H), 2.67 (s, 3H), 2.12 (dt, J = 14.8, 6.9 Hz, 2H), 1.59 (t, J = 7.0 Hz, 3H); MS-ESI (m/z) calcd for [C$_{31}$H$_{33}$ClN$_6$O$_3$ + H]$^+$ 573.24; found: 573.26. |
| 13 | 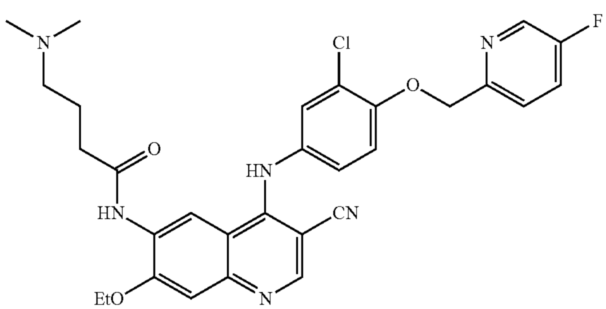 [SMILES: CCOc1cc2ncc(C#N)c(Nc3ccc(OCc4ccc(F)cn4)c(Cl)c3)c2cc1NC(=O)CCCN(C)C] | $^1$H NMR (400 MHz, Methanol-d$_4$) δ 9.08 (s, 1H), 8.75 (s, 1H), 8.49 (d, J = 2.7 Hz, 1H), 7.77-7.64 (m, 3H), 7.57 (d, J = 2.5 Hz, 1H), 7.40-7.34 (m, 2H), 7.27 (d, J = 8.8 Hz, 1H), 5.33 (s, 2H), 4.40 (q, J = 7.0 Hz, 2H), 3.25 (dd, J = 9.0, 7.0 Hz, 2H), 2.93 (s, 6H), 2.73 (t, J = 6.9 Hz, 2H), 2.18-2.06 (m, 2H), 1.58 (t, J = 7.0 Hz, 3H); $^{19}$F NMR (376 MHz, Methanol-d$_4$) δ −131.24; MS-ESI (m/z) calcd for [C$_{30}$H$_{30}$ClFN$_6$O$_3$ + H]$^+$ 577.21; found: 577.22. |
| 14 | 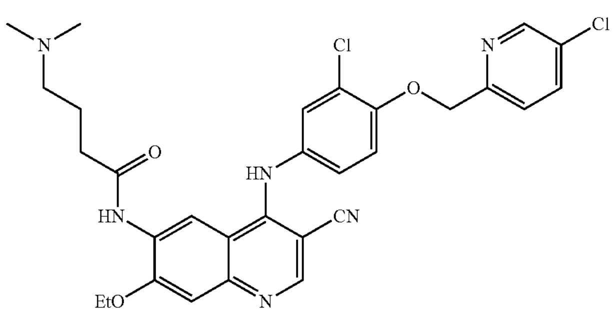 [SMILES: CCOc1cc2ncc(C#N)c(Nc3ccc(OCc4ccc(Cl)cn4)c(Cl)c3)c2cc1NC(=O)CCCN(C)C] | $^1$H NMR (400 MHz, Methanol-d$_4$) δ 9.06 (s, 1H). 8.72 (s, 1H), 8.58 (d, J = 2.3 Hz, 1H), 7.93 (dd, J = 8.4, 2.4 Hz, 1H), 7.69 (d, J = 8.5 Hz, 1H), 7.55 (d, J = 2.5 Hz, 1H), 7.38-7.31 (m, 2H), 7.25 (d, J = 8.8 Hz, 1H), 5.33 (s, 2H), 4.39 (q, J = 6.8 Hz, 2H), 3.28-3.21 (m, 2H), 2.93 (s, 6H), 2.73 (t, J = 6.9 Hz, 2H), 2.12 (dt, J = 15.0, 7.0 Hz, 2H), 1.58 (t, J = 7.0 Hz, 3H); MS-ESI (m/z) calcd for [C$_{30}$H$_{30}$Cl$_2$N$_6$O$_3$ + H]$^+$ 593.18; found: 593.14. |

| Ex. | Structure | Analytical Data |
|---|---|---|
| 15 | 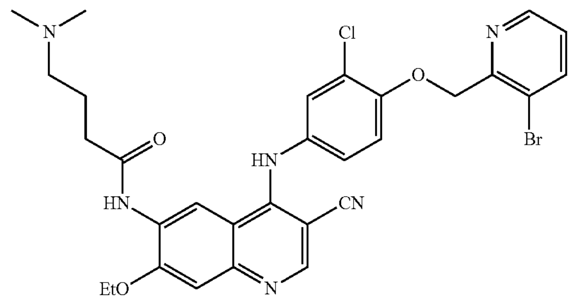 | $^1$H NMR (400 MHz, Methanol-$d_4$) δ 9.08 (d, J = 1.2 Hz, 1H), 8.76 (d, J = 1.3 Hz, 1H), 8.62-8.55 (m, 1H), 8.20-8.13 (m, 1H), 7.54 (s, 1H), 7.44-7.33 (m, 4H), 5.45 (d, J = 1.3 Hz, 2H), 4.42 (q, J = 6.9 Hz, 2H), 3.30-3.23 (m, 2H), 2.95 (s, 6H), 2.80-2.68 (m, 2H), 2.14 (dt, J = 14.9, 7.5 Hz, 2H), 1.60 (t, J = 6.7, 3H); MS-ESI (m/z) calcd for [$C_{30}H_{30}BrClN_6O_3$ + H]$^+$ 637.13; found: 320.08 (z = 2). |
| 16 | 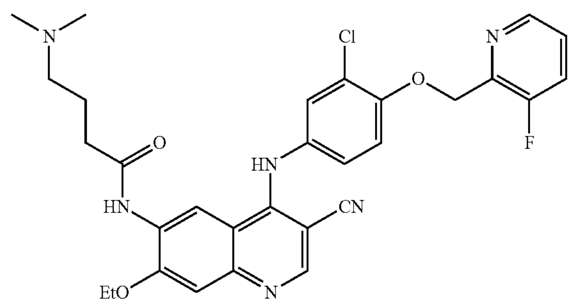 [SMILES: CCOc1cc2ncc(C#N)c(Nc3ccc(OCc4ncccc4F)c(Cl)c3)c2cc1NC(=O)CCCN(C)C] | $^1$H NMR (400 MHz, Methanol-$d_4$) δ 9.07 (d, J = 1.3 Hz, 1H), 8.76 (d, J = 1.4 Hz, 1H), 8.52-8.42 (m, 1H), 7.74 (t, J = 9.1 Hz, 1H), 7.60-7.50 (m, 2H), 7.44-7.35 (m, 2H), 5.40 (t, J = 1.7 Hz, 2H), 4.46-4.37 (m, 2H), 3.31-3.22 (m, 2H), 2.95 (d, J = 1.5 Hz, 6H), 2.75 (td, J = 7.1, 1.5 Hz, 2H), 2.22-2.05 (m, 2H), 1.60 (td, J = 7.1, 1.6 Hz, 3H); $^{19}$F NMR (376 MHz, Methanol-$d_4$) δ -125.66; MS-ESI (m/z) calcd for [$C_{30}H_{30}ClFN_6O_3$ + H]$^+$ 577.21; found: 289.3 (z = 2). |
| 17 | 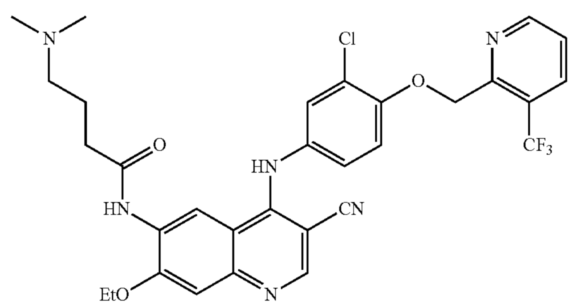 | $^1$H NMR (400 MHz, Methanol-$d_4$) δ 9.07 (s, 1H), 8.86 (d, J = 5.1 Hz, 1H), 8.76 (s, 1H), 8.28 (d, J = 7.8 Hz, 1H), 7.72-7.63 (m, 1H), 7.53 (d, J = 2.4 Hz, 1H), 7.41-7.31 (m, 3H), 5.48 (s, 2H), 4.42 (q, J = 7.0 Hz, 2H), 3.29-3.23 (m, 2H), 2.95 (s, 6H), 2.75 (t, J = 6.8 Hz, 2H), 2.14 (dt, J = 14.3, 7.6 Hz, 2H), 1.60 (t, J = 7.0 Hz, 3H); $^{19}$F NMR (376 MHz, Methanol-$d_4$) δ -61.50; MS-ESI (m/z) calcd for [$C_{31}H_{30}ClF_3N_6O_3$ + H]$^+$ 627.21; found: 627.15. |
| 18 | 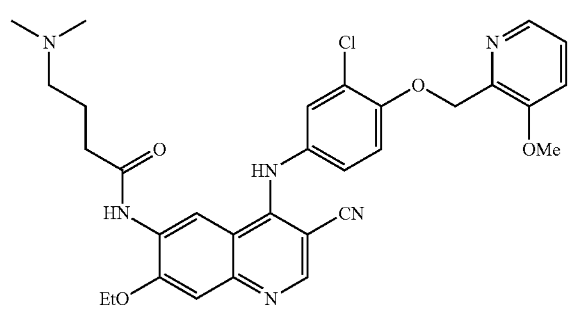 [SMILES: CCOc1cc2ncc(C#N)c(Nc3ccc(OCc4ncccc4OC)c(Cl)c3)c2cc1NC(=O)CCCN(C)C] | $^1$H NMR (400 MHz, Methanol-$d_4$) δ 9.10 (s, 1H), 8.79 (s, 1H), 8.21 (d, J = 4.4 Hz, 1H), 7.72 (d, J = 8.6 Hz, 1H), 7.62-7.52 (m, 2H), 7.43-7.31 (m, 3H), 5.38 (s, 2H), 4.40 (q, J = 6.6 Hz, 2H), 3.98 (s, 3H), 3.28-3.22 (m, 2H), 2.93 (s, 6H), 2.80-2.69 (m, 2H), 2.22-2.05 (m, 2H), 1.58 (t, J = 7.0 Hz, 3H); MS-ESI (m/z) calcd for [$C_{31}H_{33}ClN_6O_4$ + H]$^+$ 589.23; found: 295.31 (z = 2). |
| 19 | 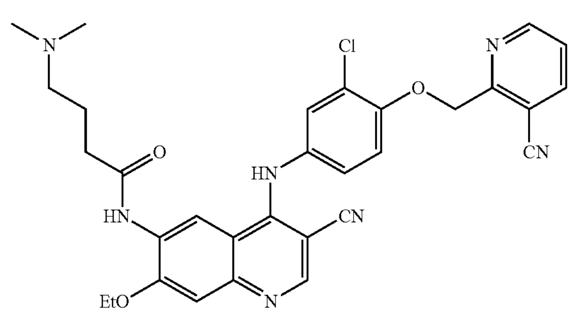 [SMILES: CCOc1cc2ncc(C#N)c(Nc3ccc(OCc4ncccc4C#N)c(Cl)c3)c2cc1NC(=O)CCCN(C)C] | $^1$H NMR (400 MHz, Methanol-$d_4$) δ 9.03 (s, 1H), 8.86 (s, 1H), 8.77-8.69 (m, 1H), 8.35-8.26 (m, 1H), 7.69-7.60 (m, 1H), 7.57-7.48 (m, 1H), 7.45-7.31 (m, 3H), 5.50 (s, 2H), 4.41 (q, J = 8.9 Hz, 2H), 3.31-3.21 (m, 2H), 2.95 (s, 2H), 2.80-2.68 (m, 6H), 2.20-2.06 (m, 2H), 1.60 (t, J = 9.0 Hz, 3H); MS-ESI (m/z) calcd for [$C_{31}H_{30}ClN_7O_3$ + H]$^+$ 584.22; found: 292.81 (z = 2). |

| Ex. | Structure | Analytical Data |
|---|---|---|
| 20 | 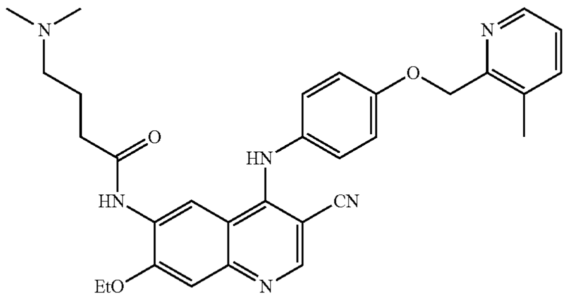 [SMILES: CCOc1cc2ncc(C#N)c(Nc3ccc(OCc4ncccc4C)cc3)c2cc1NC(=O)CCCN(C)C] | $^1$H NMR (400 MHz, Methanol-$d_4$) δ 9.13 (s, 1H), 8.75 (s, 1H), 8.55 (d, J = 5.5 Hz, 1H), 8.12 (d, J = 7.1 Hz, 1H), 7.71-7.64 (m, 1H), 7.46 (d, J = 9.0 Hz, 1H), 7.38 (s, 1H), 7.29 (d, J = 8.8 Hz, 2H), 5.46 (s, 2H), 4.42 (q, J = 7.2 Hz, 2H), 3.31-3.22 (m, 2H), 2.95 (s, 6H), 2.76 (t, J = 6.1 Hz, 2H), 2.55 (s, 3H), 2.20-2.09 (m, 2H), 1.61 (t, J = 6.9 Hz, 3H); MS-ESI (m/z) calcd for [$C_{31}H_{34}N_6O_3$ + H]$^+$ 539.28; found: 270.4 (z = 2). |
| 21 | 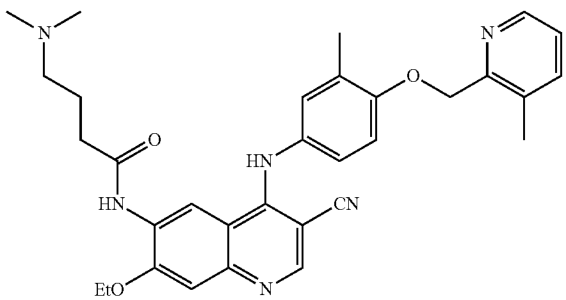 [SMILES: CCOc1cc2ncc(C#N)c(Nc3ccc(OCc4ncccc4C)c(C)c3)c2cc1NC(=O)CCCN(C)C] | $^1$H NMR (400 MHz, Methanol-$d_4$) δ 9.12 (s, 1H), 8.76 (s, 1H), 8.58-8.49 (m, 1H), 8.13-8.03 (m, 1H), 7.69-7.60 (m, 1H), 7.42-7.19 (m, 4H), 5.44 (s, 2H), 4.51-4.34 (m, 2H), 3.29-3.21 (m, 2H), 2.95 (s, 6H), 2.80-2.70 (m, 2H), 2.56 (s, 3H), 2.32 (s, 3H), 2.21-2.10 (m, 2H), 1.66-1.55 (m, 3H); MS-ESI (m/z) calcd for [$C_{32}H_{36}N_6O_3$ + H]$^+$ 553.29; found: 553.27. |
| 22 | 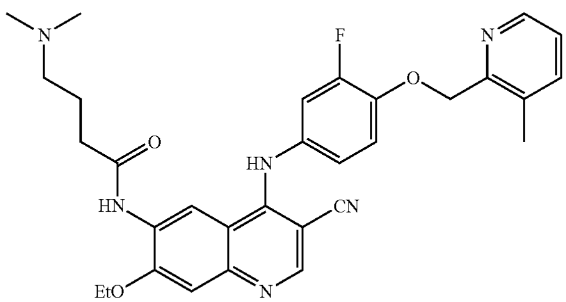 [SMILES: CCOc1cc2ncc(C#N)c(Nc3ccc(OCc4ncccc4C)c(F)c3)c2cc1NC(=O)CCCN(C)C] | $^1$H NMR (400 MHz, Methanol-$d_4$) δ 9.12 (s, 1H), 8.79 (s, 1H), 8.59-8.51 (m, 1H), 8.12 (d, J = 8.2 Hz, 1H), 7.72-7.64 (m, 1H), 7.51-7.24 (m, 4H), 5.51 (s, 2H), 4.43 (q, J = 6.5 Hz, 2H), 3.30-3.21 (m, 2H), 2.94 (s, 6H), 2.80-2.69 (m, 2H), 2.56 (s, 3H), 2.21-2.07 (m, 2H), 1.60 (t, J = 6.9 Hz, 3H); $^{19}$F NMR (376 MHz, Methanol-$d_4$) δ -132.47; MS-ESI (m/z) calcd for [$C_{31}H_{33}FN_6O_3$ + H]$^+$ 557.27; found: 279.36 (z = 2). |
| 23 | 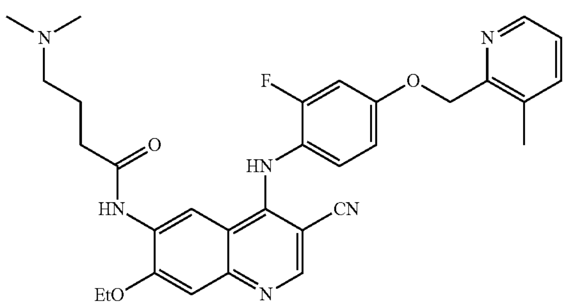 | $^1$H NMR (400 MHz, Methanol-$d_4$) δ 9.16 (s, 1H), 8.78 (s, 1H), 8.55 (d, J = 5.2 Hz, 1H), 8.10 (d, J = 8.0 Hz, 1H), 7.66 (dd, J = 7.8, 5.1 Hz, 1H), 7.52 (t, J = 8.9 Hz, 1H), 7.41 (s, 1H), 7.22-7.09 (m, 2H), 5.46 (s, 2H), 4.43 (q, J = 7.0 Hz, 2H), 3.31-3.23 (m, 2H), 2.95 (s, 6H), 2.77 (t, J = 6.9 Hz, 2H), 2.55 (s, 3H), 2.15 (dt, J = 15.2, 7.0 Hz, 2H), 1.61 (t, J = 7.0 Hz, 3H); $^{19}$F NMR (376 MHz, Methanol-$d_4$) δ -120.09; MS-ESI (m/z) calcd for [$C_{31}H_{33}FN_6O_3$ + H]$^+$ 557.27; found: 279.36 (z = 2). |
| 24 | 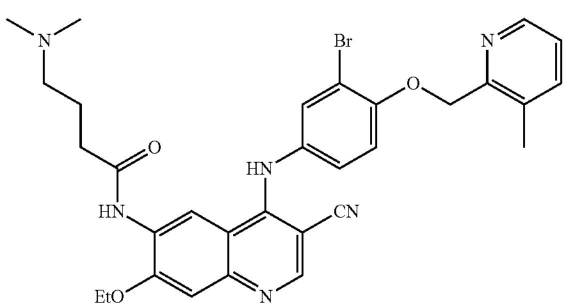 | $^1$H NMR (400 MHz, Methanol-$d_4$) δ 9.12 (s, 1H), 8.80 (s, 1H), 8.52 (d, J = 5.6 Hz, 1H), 8.06-7.97 (m, 1H), 7.77-7.69 (m, 1H), 7.61 (d, J = 10.5, 5.0 Hz, 1H), 7.51-7.43 (m, 1H), 7.42-7.32 (m, 2H), 5.47 (s, 2H), 4.43 (q, J = 7.0 Hz, 4H), 3.28-3.20 (m, 2H), 2.95 (s, 6H), 2.80-2.68 (m, 2H), 2.58 (s, 3H), 2.19-2.05 (m, 2H), 1.61 (t, J = 7.1 Hz, 3H); MS-ESI (m/z) calcd for [$C_{31}H_{33}BrN_6O_3$ + H]$^+$ 617.19; found: 310.08 (z = 2). |

| Ex. | Structure | Analytical Data |
|---|---|---|
| 25 | 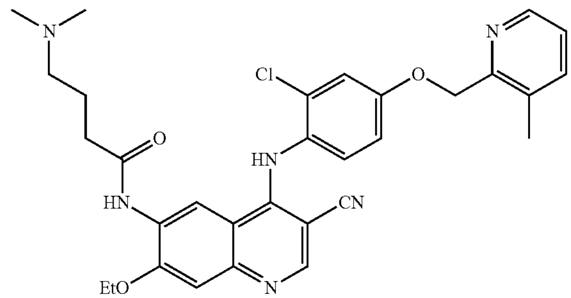 [SMILES: CCOc1cc2ncc(C#N)c(Nc3ccc(OCc4ncccc4C)cc3Cl)c2cc1NC(=O)CCCN(C)C] | ¹H NMR (400 MHz, Methanol-d₄) δ 9.19 (s, 1H), 8.80 (s, 1H), 8.57 (d, J = 5.2 Hz, 1H), 8.15 (d, J = 7.8 Hz, 1H), 7.75-7.67 (m, 1H), 7.59 (d, J = 8.9 Hz, 1H), 7.48-7.44 (m, 1H), 7.43 (s, 1H), 7.28 (d, J = 8.8 Hz, 1H), 5.50 (s, 2H), 4.44 (q, J = 7.0 Hz, 2H), 3.31-3.22 (m, 2H), 2.95 (s, 6H), 2.77 (t, J = 6.8 Hz, 2H), 2.56 (s, 3H), 2.15 (dt, J = 14.2, 6.8 Hz, 2H), 1.61 (t, J = 7.1 Hz, 3H); MS-ESI (m/z) calcd for $[C_{31}H_{33}ClN_6O_3 + H]^+$ 573.24; found: 573.13. |
| 26 | 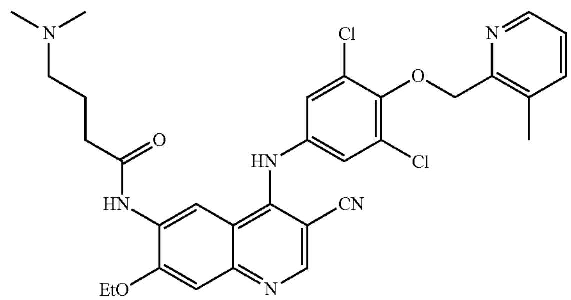 | ¹H NMR (400 MHz, Methanol-d₄) δ 9.00 (s, 1H), 8.71 (s, 1H), 8.53-8.48 (m, 1H), 8.09-8.02 (m, 1H), 7.67-7.60 (m, 1H), 7.46-7.39 (m, 3H), 5.43 (s, 2H), 4.41 (q, J = 6.6 Hz, 2H), 3.31-3.20 (m, 2H), 2.95 (s, 6H), 2.79-2.69 (m, 2H), 2.60 (s, 3H), 2.20-2.07 (m, 2H), 1.60 (t, J = 8.1 Hz, 3H); MS-ESI (m/z) calcd for $[C_{31}H_{32}Cl_2N_6O_3 + H]^+$ 607.20; found: 304.33 (z = 2). |
| 27 | 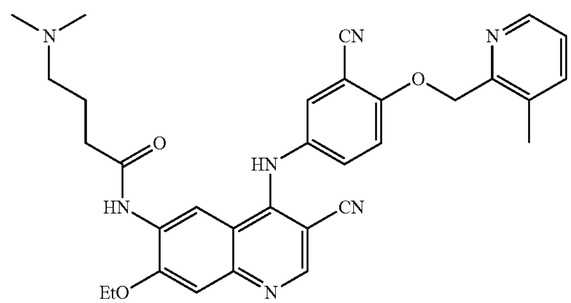 [SMILES: CCOc1cc2ncc(C#N)c(Nc3ccc(OCc4ncccc4C)c(C#N)c3)c2cc1NC(=O)CCCN(C)C] | ¹H NMR (400 MHz, Methanol-d₄) δ 9.08 (s, 1H), 8.77 (s, 1H), 8.51-8.44 (m, 1H), 7.89 (d, J = 5.3 Hz, 1H), 7.80 (s, 1H), 7.76-7.68 (m, 1H), 7.56-7.46 (m, 2H), 7.40 (s, 1H), 5.51 (s, 2H), 4.48-4.36 (m, 2H), 3.29-3.21 (m, 2H), 2.94 (s, 6H), 2.82-2.69 (m, 2H), 2.56 (s, 3H), 2.19-2.06 (m, 2H), 1.65-1.54 (m, 3H); MS-ESI (m/z) calcd for $[C_{32}H_{33}N_7O_3 + H]^+$ 564.27; found: 564.41. |
| 28 | 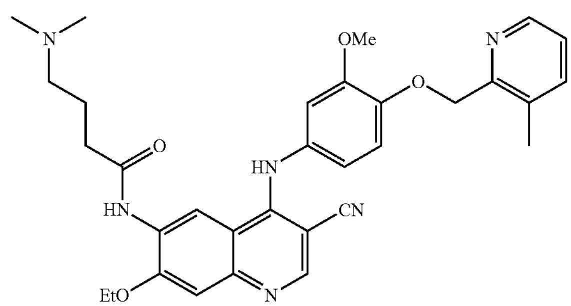 [SMILES: CCOc1cc2ncc(C#N)c(Nc3ccc(OCc4ncccc4C)c(OC)c3)c2cc1NC(=O)CCCN(C)C] | ¹H NMR (400 MHz, Methanol-d₄) δ 9.10 (s, 1H), 8.76 (s, 1H), 8.60-8.53 (m, 1H), 8.22-8.14 (m, 1H), 7.77-7.68 (m, 1H), 7.39 (s, 1H), 7.28 (d, J = 8.6 Hz, 1H), 7.18 (s, 1H), 7.05 (d, J = 9.2 Hz, 1H), 5.45 (s, 2H), 4.42 (q, J = 7.1 Hz, 2H), 3.88 (s, 3H), 3.32-3.22 (m, 2H), 2.95 (s, 6H), 2.80-2.71 (m, 2H), 2.55 (s, 3H), 2.20-2.08 (m, 2H), 1.60 (t, J = 6.9 Hz, 3H); MS-ESI (m/z) calcd for $[C_{32}H_{36}N_6O_4 + H]^+$ 569.29; found: 569.36. |
| 29 | 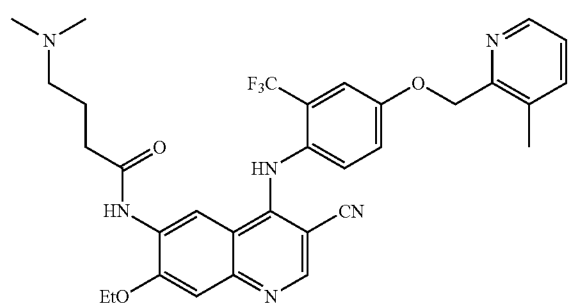 [SMILES: CCOc1cc2ncc(C#N)c(Nc3ccc(OCc4ncccc4C)cc3C(F)(F)F)c2cc1NC(=O)CCCN(C)C] | ¹H NMR (400 MHz, Methanol-d₄) δ 9.20-9.08 (m, 1H), 8.81-8.69 (m, 1H), 8.59-8.47 (m, 1H), 8.12-7.94 (m, 1H), 7.75-7.34 (m, 5H), 5.58-5.43 (m, 2H), 4.50-4.36 (m, 2H), 3.20-3.09 (m, 2H), 3.03-2.86 (m, 6H), 2.83-2.68 (m, 2H), 2.62-2.47 (m, 3H), 2.22-2.08 (m, 2H), 1.69-1.51 (m, 3H); ¹⁹F NMR (376 MHz, Methanol-d₄) δ -62.53; MS-ESI (m/z) calcd for $[C_{32}H_{33}F_3N_6O_3 + H]^+$ 607.26; found: 607.34. |

| Ex. | Structure | Analytical Data |
|---|---|---|
| 30 | 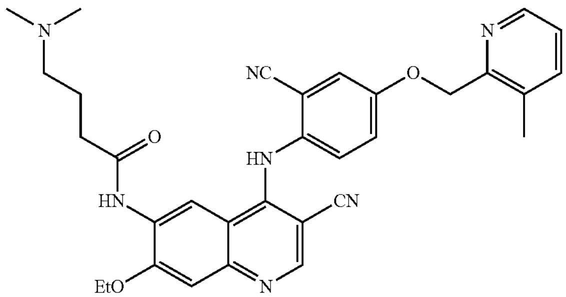 [SMILES: CCOc1cc2ncc(C#N)c(Nc3ccc(OCc4ncccc4C)cc3C#N)c2cc1NC(=O)CCCN(C)C] | MS-ESI (m/z) calcd for [C₃₂H₃₃N₇O₃ + H]⁺ 564.27; found: 564.34. |
| 31 | 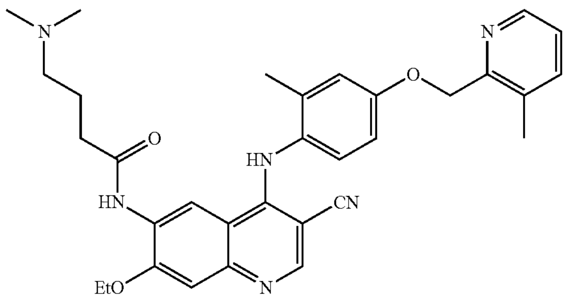 [SMILES: CCOc1cc2ncc(C#N)c(Nc3ccc(OCc4ncccc4C)cc3C)c2cc1NC(=O)CCCN(C)C] | ¹H NMR (400 MHz, Methanol-d₄) δ 9.16 (s, 1H), 8.74 (s, 1H), 8.61-8.52 (m, 1H), 8.15 (d, J = 11.0 Hz, 1H), 7.74-7.66 (m, 1H), 7.44-7.34 (m, 2H), 7.19 (s, 1H), 7.13 (d, J = 2.1 Hz, 1H), 5.46 (s, 2H), 4.43 (q, J = 6.2 Hz, 4H), 3.31-3.21 (m, 2H), 2.95 (s, 6H), 2.83-2.72 (m, 2H), 2.56 (s, 3H), 2.34 (s, 2H), 2.21-2.09 (m, 2H), 1.66-1.56 (m, 3H); MS-ESI (m/z) calcd for [C₃₂H₃₆N₆O₃ + H]⁺ 553.29; found: 553.38. |
| 32 | 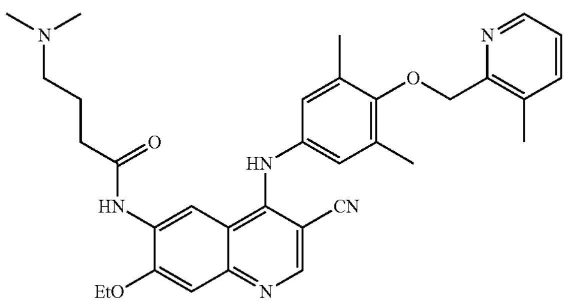 [SMILES: CCOc1cc2ncc(C#N)c(Nc3cc(C)c(OCc4ncccc4C)c(C)c3)c2cc1NC(=O)CCCN(C)C] | ¹H NMR (400 MHz, Methanol-d₄) δ 9.14 (s, 1H), 8.79 (s, 1H), 8.67-8.57 (m, 1H), 8.39-8.27 (m, 1H), 7.92-7.81 (m, 1H), 7.42 (s, 1H), 7.24 (s, 2H), 5.35 (s, 2H), 4.47-4.34 (m, 2H), 3.31-2.25 (m, 2H), 2.97 (s, 6H), 2.82-2.67 (m, 2H), 2.55 (s, 3H), 2.39 (s, 6H), 2.24-2.07 (m, 2H), 1.67-1.53 (m, 3H); MS-ESI (m/z) calcd for [C₃₃H₃₈N₆O₃ + H]⁺ 567.31; found: 567.38. |
| 33 | 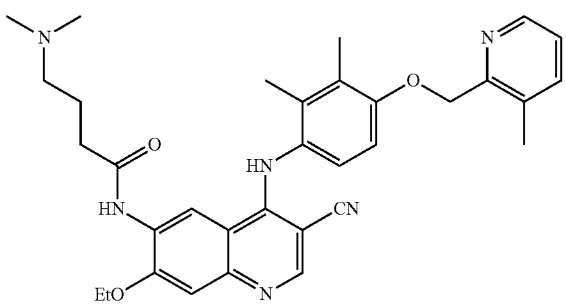 [SMILES: CCOc1cc2ncc(C#N)c(Nc3ccc(OCc4ncccc4C)c(C)c3C)c2cc1NC(=O)CCCN(C)C] | ¹H NMR (400 MHz, Methanol-d₄) δ 9.17 (s, 1H), 8.75 (s, 1H), 8.56 (d, J = 5.1 Hz, 1H), 8.16 (d, J = 8.0 Hz, 1H), 7.71 (t, J = 6.3 Hz, 1H), 7.39 (s, 1H), 7.27 (d, J = 8.6 Hz, 1H), 7.12 (d, J = 8.7 Hz, 1H), 5.45 (s, 2H), 4.43 (q, J = 6.9 Hz, 2H), 3.27 (dd, J = 9.8, 6.9 Hz, 2H), 2.95 (s, 6H), 2.76 (t, J = 6.9 Hz, 2H), 2.57 (s, 3H), 2.31 (s, 3H), 2.27 (s, 3H), 2.21-2.10 (m, 2H), 1.61 (t, J = 6.8 Hz, 3H); MS-ESI (m/z) calcd for [C₃₃H₃₈N₆O₃ + H]⁺ 567.31; found: 567.58. |
| 34 | 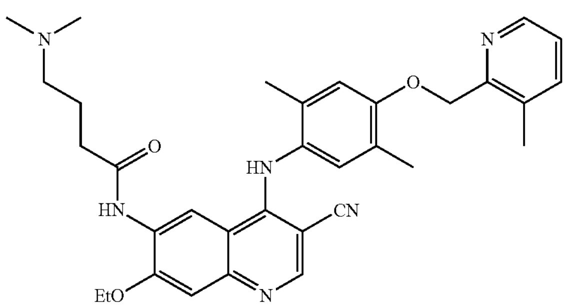 [SMILES: CCOc1cc2ncc(C#N)c(Nc3cc(C)c(OCc4ncccc4C)cc3C)c2cc1NC(=O)CCCN(C)C] | ¹H NMR (400 MHz, Methanol-d₄) δ 9.15 (s, 1H), 8.75 (s, 1H), 8.54 (d, J = 5.4 Hz, 1H), 8.13-8.04 (m, 1H), 7.69-7.59 (m, 1H), 7.38 (s, 1H), 7.21 (s, 1H), 7.14 (s, 1H), 5.42 (s, 2H), 4.43 (q, J = 6.4, 5.9 Hz, 2H), 3.32-3.22 (m, 2H), 2.95 (s, 6H), 2.81-2.71 (m, 2H), 2.56 (s, 3H), 2.31 (s, 3H), 2.26 (s, 3H), 2.16 (d, J = 7.8 Hz, 2H), 1.61 (t, J = 6.9 Hz, 3H); MS-ESI (m/z) calcd for [C₃₃H₃₈N₆O₃ + H]⁺ 567.31; found: 567.32. |

| Ex. | Structure | Analytical Data |
|---|---|---|
| 35 | 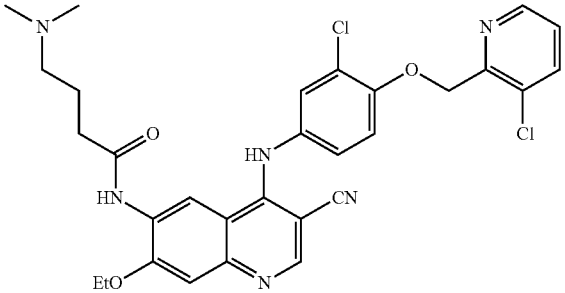 | $^1$H NMR (400 MHz, Methanol-$d_4$) δ 9.06 (s, 1H), 8.74 (s, 1H), 7.55 (d, J = 6.78 Hz, 1H), 7.53 (t, J = 6.2 Hz, 1H), 7.55 (d, J = 8.1 Hz, 1H), 7.44 (d, J = 7.9 Hz, 1H), 7.36-7.30(m, 2H), 7.26 (s, 1H), 5.44 (s, 2H), 4.41 (q, J = 6.9 Hz, 2H), 3.40-3.26 (m, 2H), 2.94 (s, 6H), 2.75 (t, J = 6.4 Hz, 2H), 2.32-2.13 (m, 2H), 1.59 (t, J = 6.9 Hz, 3H); MS-ESI (m/z) calcd for $[C_{30}H_{30}Cl_2N_6O_3 + H]^+$ 593.15; found: 593.15. |
| 36 | 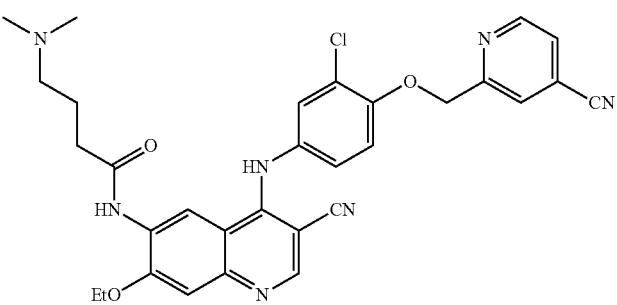 [SMILES: CCOc1cc2ncc(C#N)c(Nc3ccc(OCc4cc(C#N)ccn4)c(Cl)c3)c2cc1NC(=O)CCCN(C)C] | $^1$H NMR (400 MHz, Methanol-$d_4$) δ 9.08 (s, 1H), 8.83 (d, J = 6.2 Hz, 1H), 8.73 (d, J = 7.8 Hz, 1H), 7.95 (s, 1H), 7.72 (d, J = 7.2 Hz, 1H), 7.59 (t, J = 6.2 Hz, 1H), 7.48-7.37 (m, 2H), 7.29 (d, J = 8.3 Hz, 1H), 5.46 (s, 2H), 4.40 (q, J = 6.3 Hz, 2H), 3.40-3.26 (m, 2H), 2.94 (s, 6H), 2.75 (t, J = 6.9 Hz, 2H), 2.28-2.14 (m, 2H), 1.60 (t, J = 6.1 Hz, 3H); MS-ESI (m/z) calcd for $[C_{31}H_{30}ClN_7O_3 + H]^+$ 584.21; found: 584.2. |
| 37 | 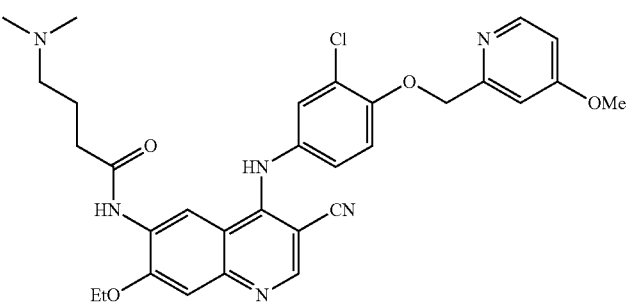 [SMILES: CCOc1cc2ncc(C#N)c(Nc3ccc(OCc4cc(OC)ccn4)c(Cl)c3)c2cc1NC(=O)CCCN(C)C] | $^1$H NMR (400 MHz, Methanol-$d_4$) δ 9.05 (s, 1H), 8.74 (s, 1H), 8.60 (d, J = 6.2 Hz, 1H), 7.60 (dd, J = 6.4, 2.60 Hz, 2H), 7.50-7.30 (m, 4H), 5.49 (s, 2H), 4.41 (q, J = 6.9 Hz, 2H), 4.12 (s, 3H), 3.40-3.26 (m, 2H), 2.94 (s, 6H), 2.75 (t, J = 6.4 Hz, 2H), 2.28-2.15 (m, 2H), 1.60 (t, J = 6.9 Hz, 3H); MS-ESI (m/z) calcd for $[C_{31}H_{33}ClN_6O_4 + H]^+$ 589.23; found: 589.20. |
| 38 | 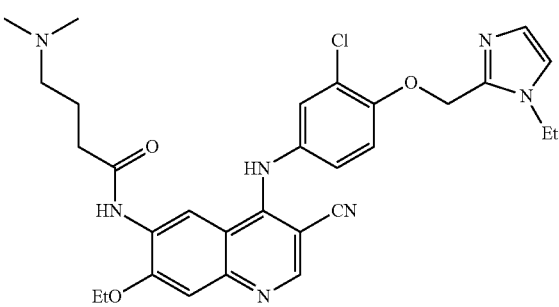 [SMILES: CCOc1cc2ncc(C#N)c(Nc3ccc(OCc4nccn4CC)c(Cl)c3)c2cc1NC(=O)CCCN(C)C] | $^1$H NMR (400 MHz, Methanol-$d_4$) δ 9.09 (s, 1H), 8.77 (s, 1H), 7.64 (d, J = 6.2 Hz, 1H), 7.60 (d, J = 6.4 Hz, 2H), 7.50-7.40 (m, 3H), 5.59 (s, 2H), 4.41 (q, J = 6.9 Hz, 4H), 3.40-3.26 (m, 2H), 2.95 (s, 6H), 2.75 (t, J = 6.2 Hz, 2H), 2.28-2.15 (m, 2H), 1.70-1.59 (m, 6H); MS-ESI (m/z) calcd for $[C_{30}H_{34}ClN_7O_3 + H]^+$ 576.24; found; 576.34. |
| 39 | 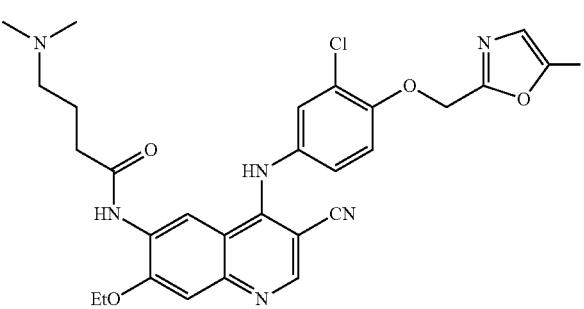 | $^1$H NMR (400 MHz, Methanol-$d_4$) δ 9.08 (s, 1H), 8.75 (s, 1H), 7.53 (d, J = 6.8 Hz, 1H), 7.39 (d, J = 6.4 Hz, 1H), 7.50-7.40 (m, 3H), 5.13 (s, 2H), 4.41 (q, J = 6.8 Hz, 2H), 3.40-3.26 (m, 2H), 2.94 (s, 6H), 2.75 (t, J = 6.4 Hz, 2H), 2.50 (s, 3H), 2.28-2.13 (m, 2H), 1.59 (t, J = 6.9 Hz, 3H); MS-ESI (m/z) calcd for $[C_{29}H_{31}ClN_6O_4 + H]^+$ 563.21; found: 563.25. |

| Ex. | Structure | Analytical Data |
|---|---|---|
| 40 | 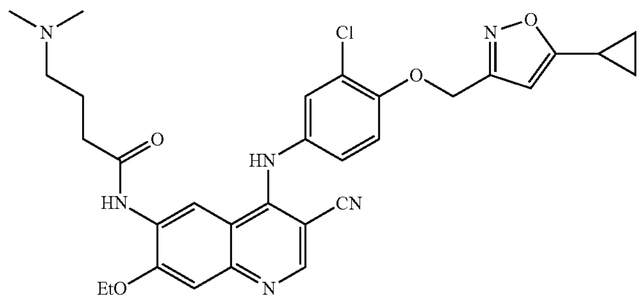 [SMILES: CCOc1cc2ncc(C#N)c(Nc3ccc(OCc4cc(C5CC5)on4)c(Cl)c3)c2cc1NC(=O)CCCN(C)C] | ¹H NMR (400 MHz, Methanol-d₄) δ 9.05 (s, 1H), 8.73 (s, 1H), 7.52 (d, J = 6.4 Hz, 1H), 7.52 (d, J = 6.9 Hz, 1H), 7.50-7.34 (m, 3H), 5.25 (s, 2H), 4.38 (q, J = 6.1 Hz, 2H), 3.40-3.25 (m, 2H), 2.91 (s, 6H), 2.71 (t, J = 4.67 Hz, 2H), 2.28-2.13 (m, 3H), 1.56 (t, J = 6.9 Hz, 3H), 1.08-0.95 (m, 4H); MS-ESI (m/z) calcd for [$C_{31}H_{33}ClN_6O_4$ + H]⁺ 589.23; found: 589.23. |
| 41 | 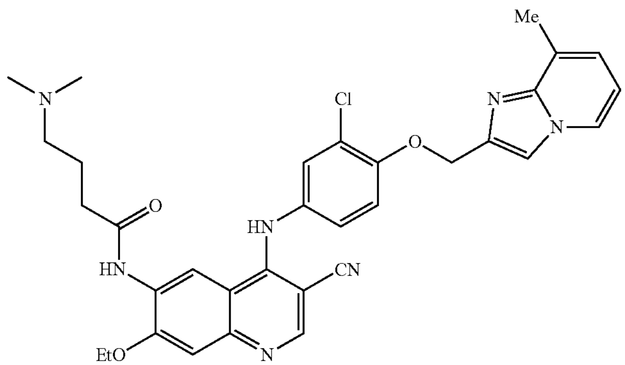 [SMILES: CCOc1cc2ncc(C#N)c(Nc3ccc(OCc4cn5cccc(C)c5n4)c(Cl)c3)c2cc1NC(=O)CCCN(C)C] | ¹H NMR (400 MHz, Methanol-d₄) δ 9.08 (s, 1H), 8.69 (s, 1H), 8.58 (d, J = 6.7 Hz, 1H), 8.27 (s, 1H), 7.90-7.75 (m, 1H), 7.55 (s, 1H), 7.41 (d, J = 7.2 Hz, 1H), 7.48-7.37 (m, 3H), 5.50 (s, 2H), 4.38 (q, J = 6.9 Hz, 2H), 3.40-3.26 (m, 2H), 2.91 (s, 6H), 2.72 (t, J = 6.9 Hz, 2H), 2.64 (s, 3H), 2.28-2.14 (m, 2H), 1.60 (t, J = 6.1 Hz, 3H); MS-ESI (m/z) calcd for [$C_{33}H_{34}ClN_7O_3$ + H]⁺ 612.24; found: 612.3. |
| 42 | 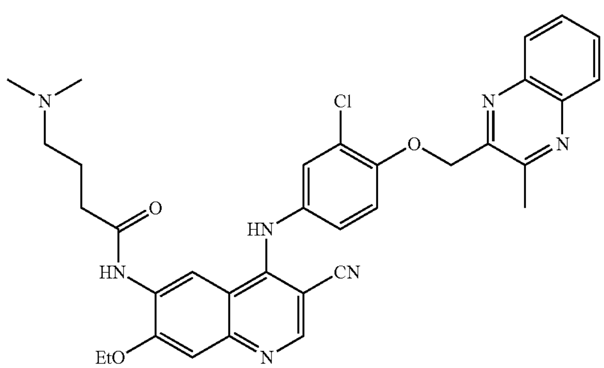 [SMILES: CCOc1cc2ncc(C#N)c(Nc3ccc(OCc4nc5ccccc5nc4C)c(Cl)c3)c2cc1NC(=O)CCCN(C)C] | ¹H NMR (400 MHz, Methanol-d₄) δ 9.11 (s, 1H), 8.75 (s, 1H), 8.18 (dd, J = 6.7, 6.1 Hz, 2H), 8.27 (s, 1H), 7.90-7.80 (m, 2H), 7.60 (d, J = 6.4 Hz, 1H), 7.48-7.37 (m, 3H), 5.60 (s, 2H), 4.48 (q, J = 6.2 Hz, 2H), 3.40-3.26 (m, 2H), 2.93 (s, 9H), 2.72 (t, J = 6.2 Hz, 2H), 2.28-2.14 (m, 2H), 1.60 (t, J = 6.4 Hz, 3H); MS-ESI (m/z) calcd for [$C_{34}H_{34}ClN_7O_3$ + H]⁺ 624.24; found: 624.19. |
| 43 | 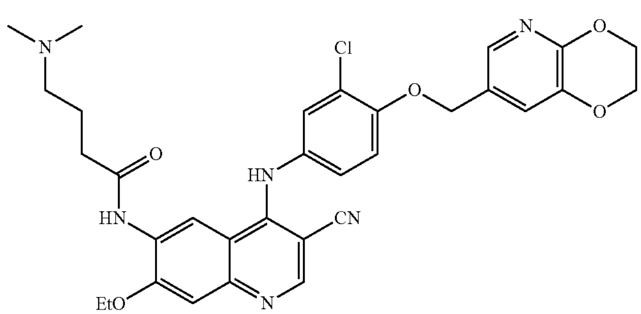 [SMILES: CCOc1cc2ncc(C#N)c(Nc3ccc(OCc4cnc5c(c4)OCCO5)c(Cl)c3)c2cc1NC(=O)CCCN(C)C] | ¹H NMR (400 MHz, Methanol-d₄) δ 9.08 (s, 1H), 8.74 (s, 1H), 7.87 (d, J = 6.8 Hz, 1H), 7.54 (d, J = 6.2 Hz, 1H), 7.40-7.34 (m, 3H), 7.30 (d, J = 8.4 Hz, 1H), 5.20 (s, 2H), 4.41 (q, J = 6.9 Hz, 2H), 4.49-4.32 (m, 4H), 3.42-3.26 (m, 2H), 2.94 (s, 6H), 2.75 (t, J = 6.4 Hz, 2H), 2.28-2.13 (m, 2H), 1.60 (t, J = 6.2 Hz, 3H); MS-ESI (m/z) calcd for [$C_{32}H_{33}ClN_6O_5$ + H]⁺ 617.22; found: 617.10. |

| Ex. | Structure | Analytical Data |
|---|---|---|
| 44 | 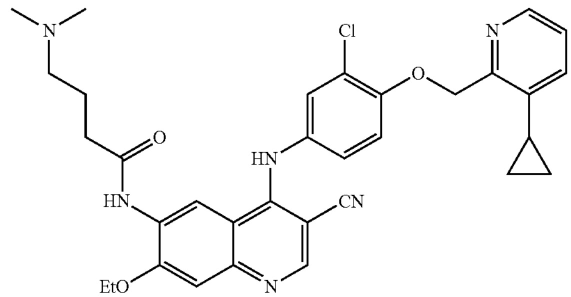 [SMILES: CCOc1cc2ncc(C#N)c(Nc3ccc(OCc4ncccc4C4CC4)c(Cl)c3)c2cc1NC(=O)CCCN(C)C] | ¹H NMR (400 MHz, Methanol-d₄) δ 9.09 (s, 1H), 8.75 (s, 1H), 8.45 (s, 1H), 7.73 (d, J = 8.04 Hz, 2H), 7.55 (s, 1H), 7.50-7.40 (m, 3H), 5.56 (s, 2H), 4.41 (q, J = 6.1 Hz, 2H), 3.40-3.26 (m, 2H), 2.94 (s, 6H), 2.75 (t, J = 6.9 Hz, 2H), 2.28-2.13 (m, 3H), 1.60 (t, J = 6.9 Hz, 3H), 1.08-0.95 (m, 4H); MS-ESI (m/z) calcd for [C₃₃H₃₅ClN₆O₃ + H]⁺ 599.25; found: 599.20. |
| 45 | 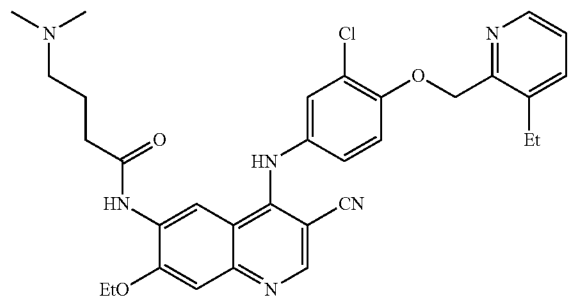 [SMILES: CCOc1cc2ncc(C#N)c(Nc3ccc(OCc4ncccc4CC)c(Cl)c3)c2cc1NC(=O)CCCN(C)C] | ¹H NMR (400 MHz, Methanol-d₄) δ 9.15 (s, 1H), 8.81 (s, 1H), 8.45 (s, 1H), 8.59 (dd, J = 8.04, 5.53 Hz, 1H), 8.21 (d, J = 7.86 Hz, 1H), 7.80-7.61 (m, 1H), 7.50-7.45 (m, 3H), 5.52 (s, 2H), 4.42 (q, J = 6.95 Hz, 2H), 3.40-3.26 (m, 2H), 3.00-2.95 (m, 8H), 2.75 (t, J = 6.4 Hz, 2H), 2.28-2.15 (m, 2H), 1.60 (t, J = 6.4 Hz, 3H), 1.36 (t, J = 7.54 Hz, 3H); MS-ESI (m/z) calcd for [C₃₂H₃₅ClN₆O₃ + H]⁺ 587.25; found: 587.20. |
| 46 | 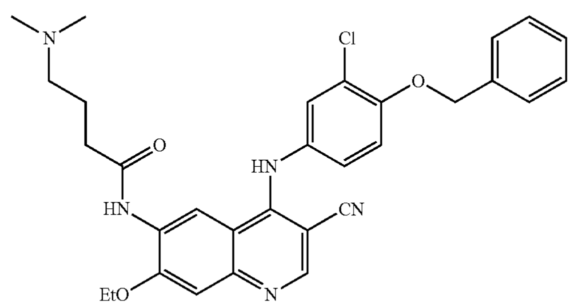 [SMILES: CCOc1cc2ncc(C#N)c(Nc3ccc(OCc4ccccc4)c(Cl)c3)c2cc1NC(=O)CCCN(C)C] | ¹H NMR (400 MHz, Methanol-d₄) δ 9.04 (s, 1H), 8.72 (s, 1H), 7.64-7.14 (m, 9H), 5.25 (s, 2H), 4.50-4.24 (m, 2H), 2.92 (s, 6H), 2.82-2.61 (m, 2H), 2.26-1.93 (m, 2H), 1.70-1.44 (m, 3H). |
| 47 | 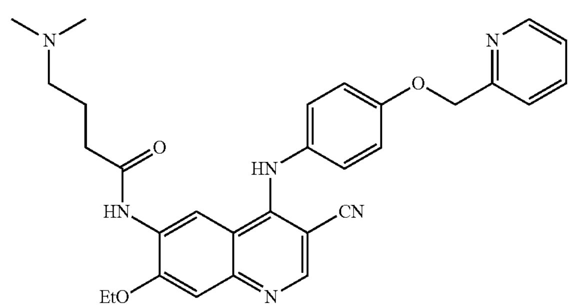 [SMILES: CCOc1cc2ncc(C#N)c(Nc3ccc(OCc4ccccn4)cc3)c2cc1NC(=O)CCCN(C)C] | ¹H NMR (400 MHz, Methanol-d₄) δ 9.14 (s, 1H), 8.76 (s, 1H), 8.71-8.65 (m, 1H), 8.17 (td, J = 7.8, 1.7 Hz, 1H), 7.85 (d, J = 7.9 Hz, 1H), 7.64 (dd, J = 7.6, 5.3 Hz, 1H), 7.44 (d, J = 9.0 Hz, 2H), 7.39 (s, 1H), 7.21 (d, J = 9.0 Hz, 2H), 5.40 (s, 2H), 4.42 (t, J = 7.0 Hz, 2H), 3.28-3.19 (m, 2H), 2.92 (s, 6H), 2.74 (s, 2H), 2.21-2.04 (m, 2H), 1.59 (t, J = 7.0 Hz, 3H); MS-ESI (m/z) calcd for [C₃₀H₃₂N₆O₃ + H]⁺ 525.26; found: 263.25 (z = 2). |
| 48 | 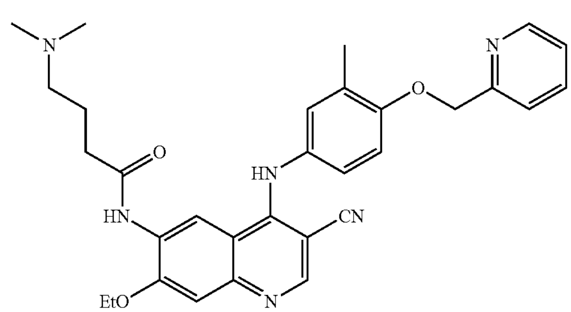 [SMILES: CCOc1cc2ncc(C#N)c(Nc3ccc(OCc4ccccn4)c(C)c3)c2cc1NC(=O)CCCN(C)C] | ¹H NMR (400 MHz, Methanol-d₄) δ 9.12 (s, 1H), 8.76 (s, 1H), 8.64 (d, J = 5.2 Hz, 1H), 8.12-8.00 (m, 1H), 7.79 (d, J = 7.9 Hz, 1H), 7.61-7.51 (m, 1H), 7.37 (s, 1H), 7.33-7.23 (m, 2H), 7.10 (dd, J = 8.7, 1.8 Hz, 1H), 5.35 (s, 2H), 4.40 (t, J = 7.1 Hz, 2H), 3.24 (ddd, J = 10.2, 5.5, 1.8 Hz, 2H), 2.93 (s, 6H), 2.74 (t, J = 6.9 Hz, 2H), 2.37 (s, 2H), 2.12 (p, J = 7.0, 6.3 Hz, 2H), 1.59 (t, J = 7.0 Hz, 3H); MS-ESI (m/z) calcd for [C₃₁H₃₄N₆O₃ + H]⁺ 539.28; found: 270.27 (z = 2). |

| Ex. | Structure | Analytical Data |
|---|---|---|
| 49 | 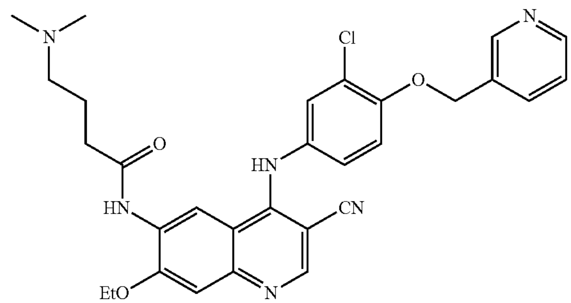 [SMILES: CCOc1cc2ncc(C#N)c(Nc3ccc(OCc4cccnc4)c(Cl)c3)c2cc1NC(=O)CCCN(C)C] | $^1$H NMR (400 MHz, Methanol-d$_4$) δ 9.13 (s, 1H), 8.89-8.85 (m, 1H), 8.78 (s, 1H), 8.72 (dd, J = 5.4, 1.5 Hz, 1H), 8.41 (dt, J = 8.1, 1.7 Hz, 1H), 7.84 (ddd, J = 8.1, 5.4, 0.9 Hz, 1H), 7.60 (d, J = 2.5 Hz, 1H), 7.43 (dd, J = 8.7, 2.5 Hz, 1H), 7.39 (s, 1H), 7.35 (d, J = 8.8 Hz, 1H), 5.45 (s, 2H), 4.41 (q, J = 7.0 Hz, 2H), 3.29-3.19 (m, 2H), 2.93 (s, 6H), 2.74 (t, J = 7.0 Hz, 2H), 2.17-2.07 (m, 2H), 1.59 (t, J = 7.0 Hz, 3H); MS-ESI (m/z) calcd for [C$_{30}$H$_{31}$ClN$_6$O$_3$ + H]$^+$ 559.22; found: 280.26 (z = 2). |
| 50 | 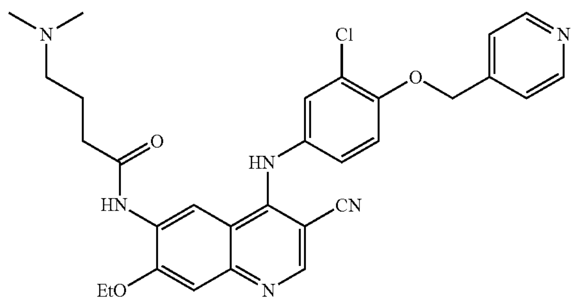 [SMILES: CCOc1cc2ncc(C#N)c(Nc3ccc(OCc4ccncc4)c(Cl)c3)c2cc1NC(=O)CCCN(C)C] | $^1$H NMR (400 MHz, Methanol-d$_4$) δ 9.12 (s, 1H), 8.83-8.74 (m, 3H), 8.06-8.00 (m, 2H), 7.63 (d, J = 2.3 Hz, 1H), 7.45-7.37 (m, 2H), 7.31 (dd, J = 8.9, 1.2 Hz, 1H), 5.56 (s, 2H), 4.41 (q, J = 6.9 Hz, 2H), 3.28-3.20 (m, 2H), 2.93 (s, 6H), 2.74 (t, J = 7.0 Hz, 2H), 2.18-2.04 (m, 2H), 1.59 (t, J = 7.0 Hz, 3H); MS-ESI (m/z) calcd for [C$_{30}$H$_{31}$ClN$_6$O$_3$ + H]$^+$ 559.22; found: 280.26 (z = 2). |
| 51 | 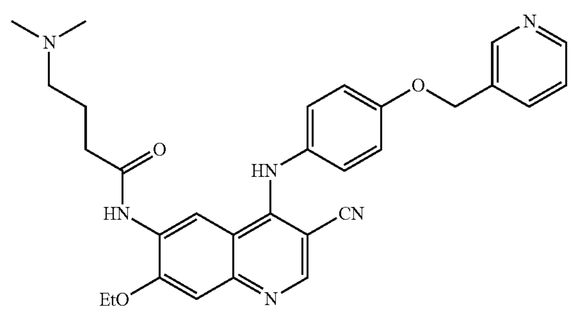 [SMILES: CCOc1cc2ncc(C#N)c(Nc3ccc(OCc4cccnc4)cc3)c2cc1NC(=O)CCCN(C)C] | $^1$H NMR (400 MHz, Methanol-d$_4$) δ 9.14 (s, 1H), 8.86 (s, 1H), 8.76 (s, 1H), 8.72 (dd, J = 5.5, 1.5 Hz, 1H), 8.42 (d, J = 8.2 Hz, 1H), 7.89-7.82 (m, 1H), 7.44 (d, J = 8.9 Hz, 2H), 7.38 (s, 1H), 7.21 (d, J = 8.8 Hz, 2H), 5.38 (s, 2H), 4.41 (q, J = 7.0 Hz, 2H), 3.29-3.21 (m, 2H), 2.93 (s, 6H), 2.74 (t, J = 7.0 Hz, 2H), 2.18-2.05 (m, 2H), 1.59 (t, J = 7.0 Hz, 3H); MS-ESI (m/z) calcd for [C$_{30}$H$_{32}$N$_6$O$_3$ + H]$^+$ 525.26; found: 263.25 (z = 2). |
| 52 | 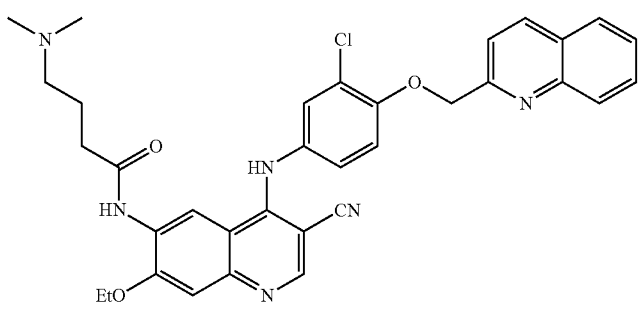 [SMILES: CCOc1cc2ncc(C#N)c(Nc3ccc(OCc4ccc5ccccc5n4)c(Cl)c3)c2cc1NC(=O)CCCN(C)C] | $^1$H NMR (400 MHz, Methanol-d$_4$) δ 9.08 (s, 1H), 8.76 (d, J = 1.8 Hz, 1H), 8.46 (d, J = 8.6 Hz, 1H), 8.07 (d, J = 8.8 Hz, 1H), 8.02-7.95 (m, 1H), 7.88-7.80 (m, 2H), 7.68-7.63 (m, 1H), 7.59 (d, J = 2.4 Hz, 1H), 7.41-7.28 (m, 3H), 5.54 (s, 2H), 4.40 (q, J = 7.0 Hz, 2H), 3.27-3.19 (m, 2H), 2.92 (d, J = 1.8 Hz, 6H), 2.73 (t, J = 6.9 Hz, 2H), 2.18-2.03 (m, 2H), 1.58 (t, J = 7.0 Hz, 3H); MS-ESI (m/z) calcd for [C$_{34}$H$_{33}$ClN$_6$O$_3$ + H]$^+$ 609.24; found: 609.26. |
| 53 | 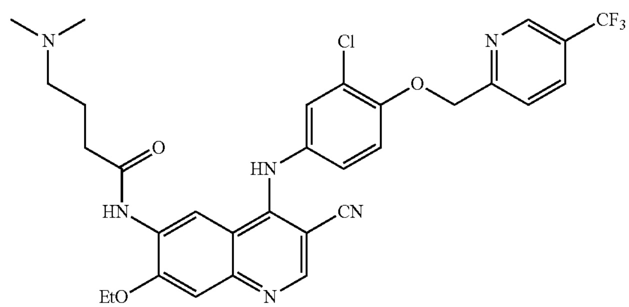 [SMILES: CCOc1cc2ncc(C#N)c(Nc3ccc(OCc4ccc(C(F)(F)F)cn4)c(Cl)c3)c2cc1NC(=O)CCCN(C)C] | MS-ESI (m/z) calcd for [C$_{31}$H$_{30}$ClF$_3$N$_6$O$_3$ + H]$^+$ 627.21; found: 627.09. |

| Ex. | Structure | Analytical Data |
| --- | --- | --- |
| 54 | 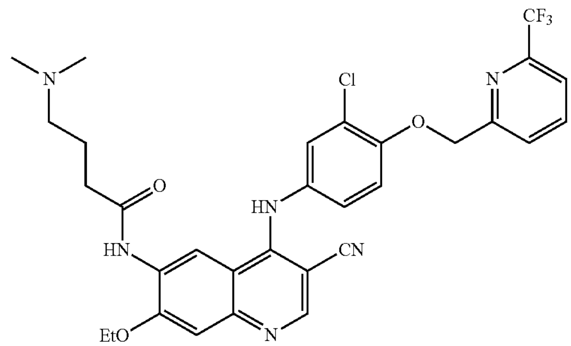 [SMILES: CCOc1cc2ncc(C#N)c(Nc3ccc(OCc4cccc(C(F)(F)F)n4)c(Cl)c3)c2cc1NC(=O)CCCN(C)C] | $^1$H NMR (400 MHz, Methanol-d$_4$) δ 8.10 (t, J = 7.6 Hz, 2H), 7.93 (t, J = 9.1 Hz, 2H), 7.77 (d, J = 7.8 Hz, 2H), 7.39-7.24 (m, 1H), 7.24-7.13 (m, 3H), 7.03 (dd, J = 9.0, 2.6 Hz, 1H), 5.41 (s, 1H), 5.30 (s, 3H), 4.39 (q, J = 7.2 Hz, 1H), 3.35 (s, 2H), 3.28-3.19 (m, 1H), 2.92 (s, 2H), 2.73 (t, J = 6.9 Hz, 1H), 2.12 (s, 0H), 1.58 (t, J = 6.9 Hz, 1H); MS-ESI (m/z) calcd for [C$_{31}$H$_{30}$ClF$_3$N$_6$O$_3$ + H]$^+$ 627.21; found: 627.10. |
| 55 | 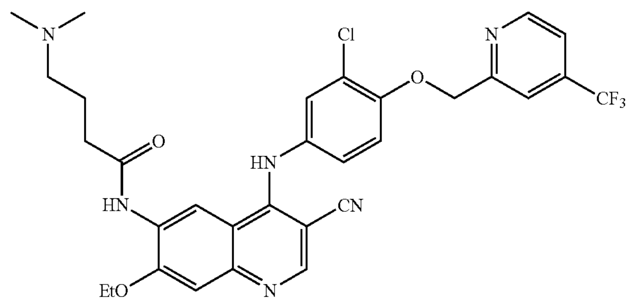 [SMILES: CCOc1cc2ncc(C#N)c(Nc3ccc(OCc4cc(C(F)(F)F)ccn4)c(Cl)c3)c2cc1NC(=O)CCCN(C)C] | $^1$H NMR (400 MHz, Methanol-d$_4$) δ 9.03 (s, 1H), 8.86 (s, 2H), 8.67 (s, 1H), 7.98 (d, J = 16.8 Hz, 1H), 7.71 (s, 1H), 7.56 (s, 1H), 7.41-7.28 (m, 3H), 5.45 (s, 2H), 4.41 (d, J = 7.1 Hz, 2H), 3.37 (d, J = 2.0 Hz, 1H), 3.25 (d, J = 7.9 Hz, 2H), 2.95 (d, J = 2.2 Hz, 6H), 2.75 (s, 2H), 2.14 (s, 2H), 1.60 (d, J = 14.4 Hz, 1H), 1.60 (s, 2H), 1.31 (s, 1H); MS-ESI (m/z) calcd for [C$_{31}$H$_{30}$ClF$_3$N$_6$O$_3$ + H]$^+$ 627.21; found: 627.09. |
| 56 | 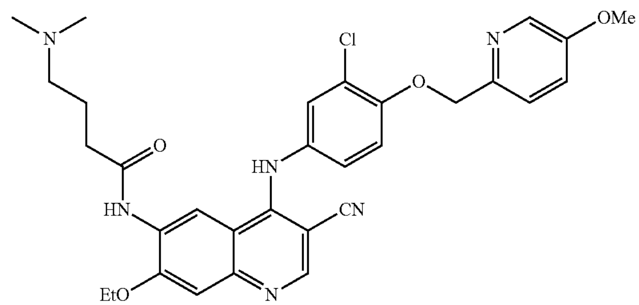 [SMILES: CCOc1cc2ncc(C#N)c(Nc3ccc(OCc4ccc(OC)cn4)c(Cl)c3)c2cc1NC(=O)CCCN(C)C] | $^1$H NMR (400 MHz, Methanol-d$_4$) δ 9.08 (d, J = 1.7 Hz, 1H), 8.76 (d, J = 1.6 Hz, 1H), 8.27 (d, J = 2.8 Hz, 1H), 7.65 (d, J = 8.6 Hz, 1H), 7.55 (d, J = 2.5 Hz, 1H), 7.51 (dd, J = 8.7, 2.8 Hz, 1H), 7.39-7.34 (m, 2H), 7.28 (d, J = 8.8 Hz, 1H), 5.27 (s, 2H), 4.40 (q, J = 7.0 Hz, 2H), 3.92 (d, J = 1.7 Hz, 3H), 3.28-3.18 (m, 2H), 2.93 (d, J = 1.7 Hz, 6H), 2.73 (dd, J = 7.8, 6.2 Hz, 2H), 2.12 (p, J = 7.2 Hz, 2H), 1.58 (t, J = 7.0 Hz, 3H); MS-ESI (m/z) calcd for [C$_{31}$H$_{33}$ClN$_6$O$_4$ + H]$^+$ 589.23: found: 589.18. |
| 57 | 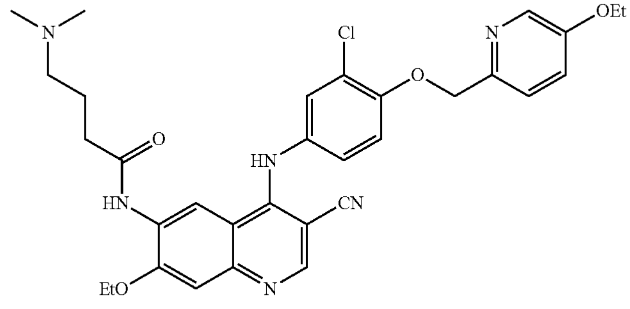 [SMILES: CCOc1ccc(COc2ccc(Nc3c(C#N)cnc4cc(OCC)c(NC(=O)CCCN(C)C)cc34)cc2Cl)nc1] | $^1$H NMR (400 MHz, Methanol-d$_4$) δ 9.08 (d, J = 1.9 Hz, 1H), 8.75 (d, J = 2.0 Hz, 1H), 8.25 (d, J = 2.7 Hz, 1H), 7.63 (d, J = 8.8 Hz, 1H), 7.55 (d, J = 2.4 Hz, 1H), 7.49 (dd, J = 8.7, 2.8 Hz, 1H), 7.39-7.33 (m, 2H), 7.30-7.24 (m, 1H), 5.26 (d, J = 2.0 Hz, 2H), 4.40 (q, J = 7.0 Hz, 2H), 4.16 (qd, J = 6.9, 2.0 Hz, 2H), 3.25 (ddd, J = 8.0, 6.5, 2.1 Hz, 2H), 2.93 (d, J = 1.9 Hz, 6H), 2.73 (t, J = 6.9 Hz, 2H), 2.12 (p, J = 7.1 Hz, 2H), 1.58 (t, J = 7.0 Hz, 3H), 1.44 (t, J = 7.0 Hz, 3H); MS-ESI (m/z) calcd for [C$_{32}$H$_{35}$ClN$_6$O$_4$ + H]$^+$ 603.25; found: 603.18. |

-continued

| Ex. | Structure | Analytical Data |
|---|---|---|
| 58 | 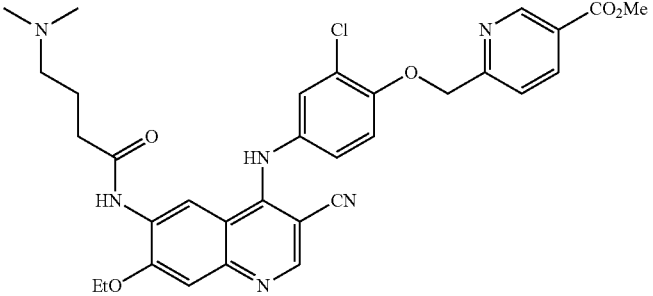 [SMILES: CCOc1cc2ncc(C#N)c(Nc3ccc(OCc4ccc(C(=O)OC)cn4)c(Cl)c3)c2cc1NC(=O)CCCN(C)C] | ¹H NMR (400 MHz, Methanol-$d_4$) δ 9.14 (dd, J = 2.2, 1.0 Hz, 1H), 9.07 (s, 1H), 8.74 (s, 1H), 8.44 (dd, J = 8.2, 2.0 Hz, 1H), 7.85-7.80 (m, 1H), 7.58 (d, J = 2.4 Hz, 1H), 7.40-7.33 (m, 2H), 7.26 (d, J = 8.8 Hz, 1H), 5.42 (s, 2H), 4.40 (q, J = 7.0 Hz, 2H), 3.97 (d, J = 1.5 Hz, 3H), 3.28-3.20 (m, 2H), 2.93 (s, 6H), 2.73 (t, J = 6.9 Hz, 2H), 2.18-2.06 (m, 2H), 1.58 (t, J = 7.0 Hz, 3H); MS-ESI (m/z) calcd for $[C_{32}H_{33}ClN_6O_5 + H]^+$ 617.23; found: 617.12. |
| 59 | 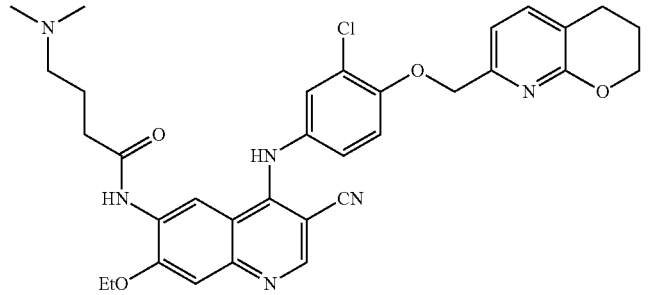 [SMILES: CCOc1cc2ncc(C#N)c(Nc3ccc(OCc4ccc5c(n4)OCCC5)c(Cl)c3)c2cc1NC(=O)CCCN(C)C] | ¹H NMR (400 MHz, Methanol-$d_4$) δ 8.71 (s, 1H), 8.40 (s, 1H), 8.13 (s, 2H), 7.83 (d, J = 7.0 Hz, 2H), 7.57-7.47 (m, 3H), 7.43-7.24 (m, 4H), 5.22 (d, J = 5.2 Hz, 4H), 4.48-4.34 (m, 9H), 3.97 (t, J = 7.3 Hz, 3H), 2.93 (d, J = 6.0 Hz, 11H), 2.74 (d, J = 6.8 Hz, 1H), 2.22 (t, J = 7.7 Hz, 2H), 2.08 (t, J = 5.8 Hz, 4H), 1.61-1.48 (m, 5H); MS-ESI (m/z) calcd for $[C_{33}H_{35}ClN_6O_4 + H]^+$ 615.24; found: 615.28. |
| 60 | 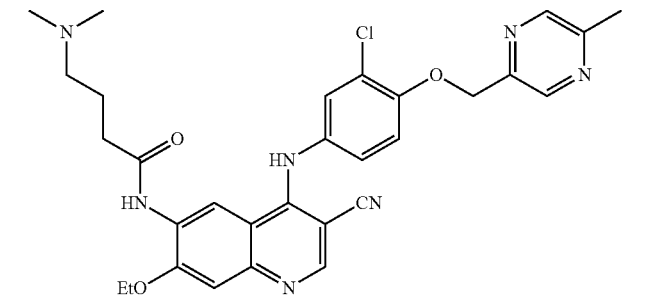 | ¹H NMR (400 MHz, Methanol-$d_4$) δ 9.03 (s, 1H), 8.74 (d, J = 1.4 Hz, 1H), 8.68 (s, 1H), 8.56 (s, 1H), 7.53 (d, J = 2.5 Hz, 1H), 7.39-7.27 (m, 3H), 5.36 (s, 2H), 4.88 (d, J = 15.5 Hz, 17H), 4.38 (q, J = 7.0 Hz, 2H), 3.34-3.19 (m, 11H), 2.92 (s, 7H), 2.73 (t, J = 6.9 Hz, 2H), 2.59 (s, 3H), 2.11 (p, J = 7.1 Hz, 2H), 1.57 (t, J = 7.0 Hz, 3H); MS-ESI (m/z) calcd for $[C_{30}H_{32}ClN_7O_3 + H]^+$ 574.23; found: 574.10 |
| 61 | 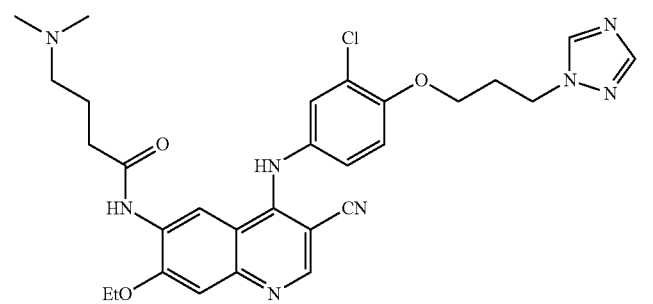 [SMILES: CCOc1cc2ncc(C#N)c(Nc3ccc(OCCCn4cncn4)c(Cl)c3)c2cc1NC(=O)CCCN(C)C] | ¹H NMR (400 MHz, Methanol-$d_4$) δ 9.11 (s, 1H), 8.78 (s, 1H), 8.48 (s, 1H), 8.02 (s, 1H), 7.55 (d, J = 2.6 Hz, 1H), 7.41-7.33 (m, 2H), 7.17 (d, J = 8.8 Hz, 1H), 4.53 (t, J = 6.7 Hz, 2H), 4.41 (q, J = 6.9 Hz, 2H), 4.16 (t, J = 5.8 Hz, 2H), 3.29-3.20 (m, 2H), 2.93 (s, 6H), 2.74 (t, J = 6.9 Hz, 2H), 2.44 (p, J = 6.3 Hz, 2H), 2.12 (dt, J = 14.8, 7.1 Hz, 2H), 1.59 (t, J = 7.0 Hz, 3H); MS-ESI (m/z) calcd for $[C_{29}H_{33}ClN_8O_3 + H]^+$ 577.24; found: 577.15. |
| 62 | 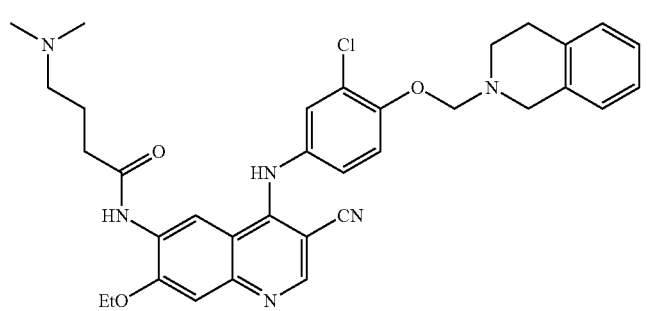 | ¹H NMR (400 MHz, Methanol-$d_4$) δ 9.10 (s, 1H), 8.72 (s, 1H), 7.61 (d, J = 2.5 Hz, 1H), 7.48-7.38 (m, 2H), 7.39-7.26 (m, 4H), 7.23 (d, J = 7.4 Hz, 1H), 4.88 (s, 1H), 4.73 (s, 2H), 4.68-4.61 (m, 2H), 4.40 (q, J = 6.9 Hz, 2H), 3.87 (dd, J = 5.5, 3.9 Hz, 2H), 3.32-3.20 (m, 6H), 2.93 (s, 5H), 2.74 (t, J = 6.9 Hz, 2H), 2.13 (p, J = 7.1 Hz, 2H), 1.58 (t, J = 7.0 Hz, 3H) ); MS-ESI (m/z) calcd for $[C_{35}H_{39}ClN_6O_3 + H]^+$ 627.28; found: 627.13. |

-continued

| Ex. | Structure | Analytical Data |
|---|---|---|
| 63 | 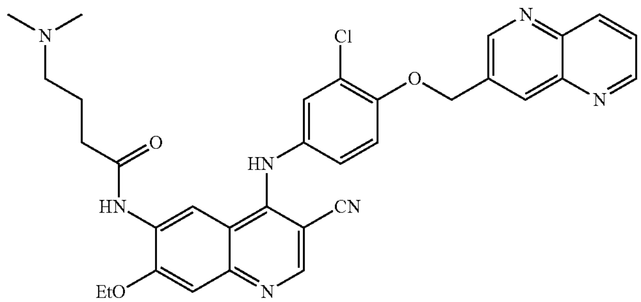 [SMILES: CCOc1cc2ncc(C#N)c(Nc3ccc(OCc4cnc5cccnc5c4)c(Cl)c3)c2cc1NC(=O)CCCN(C)C] | $^1$H NMR (400 MHz, Methanol-d$_4$) δ 9.16 (d, J = 2.1 Hz, 1H), 9.10-8.99 (m, 2H), 8.73 (s, 1H), 8.62 (s, 1H), 8.56-8.49 (m, 1H), 7.85 (dd, J = 8.6, 4.3 Hz, 1H), 7.58 (t, J = 1.4 Hz, 1H), 7.43-7.35 (m, 3H), 5.62-5.57 (m, 2H), 4.86 (t, J = 5.7 Hz, 21H), 4.40 (q, J = 6.8 Hz, 2H), 3.29-3.20 (m, 2H), 2.92 (s, 5H), 2.74 (t, J = 6.9 Hz, 2H), 2.17-2.08 (m, 3H), 1.58 (t, J = 7.0 Hz, 3H) ); MS-ESI (m/z) calcd for [C$_{33}$H$_{32}$ClN$_7$O$_3$ + H]$^+$ 610.23; found: 610.13. |
| 64 | 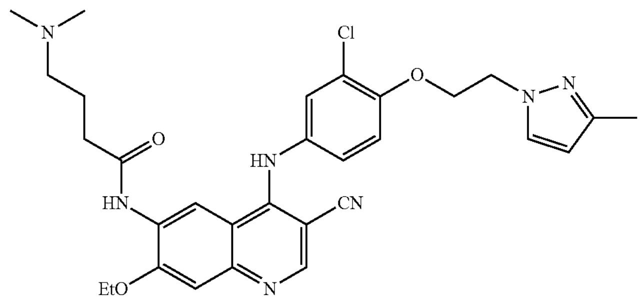 | $^1$H NMR (400 MHz, Methanol-d$_4$) δ 9.08 (s, 1H), 8.74 (s, 1H), 7.63 (d, J = 2.3 Hz, 1H), 7.50 (d, J = 2.6 Hz, 1H), 7.40-7.28 (m, 2H), 7.15 (d, J = 8.8 Hz, 1H), 6.08 (d, J = 2.2 Hz, 1H), 4.55-4.33 (m, 6H), 3.29-3.19 (m, 2H), 2.92 (s, 4H), 2.73 (t, J = 6.9 Hz, 2H), 2.25 (s, 3H), 2.11 (q, J = 1.1 Hz, 2H), 1.62-1.48 (m, 3H) ); MS-ESI (m/z) calcd for [C$_{30}$H$_{34}$ClN$_7$O$_3$ + H]$^+$ 576.24; found: 576.15. |
| 65 | 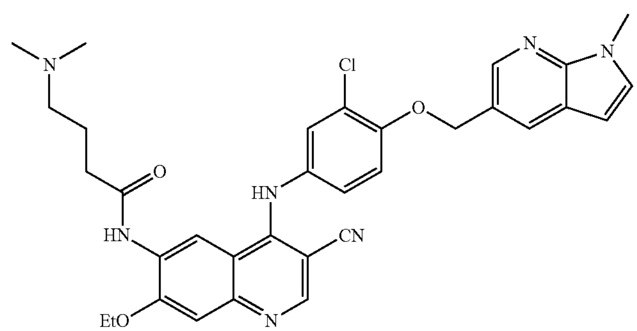 | $^1$H NMR (400 MHz, Methanol-d$_4$) δ 9.09 (s, 1H), 8.75 (s, 1H), 8.64 (d, J = 1.8 Hz, 1H), 8.56 (s, 1H), 8.28 (d, J = 1.9 Hz, 1H), 7.56 (d, J = 2.3 Hz, 1H), 7.44-7.33 (m, 3H), 5.45 (s, 2H), 4.87 (s, 7H), 4.40 (q, J = 7.0 Hz, 2H), 3.99 (s, 3H), 3.29-3.20 (m, 2H), 2.92 (s, 5H), 2.73 (t, J = 6.9 Hz, 2H), 2.12 (dt, J = 14.6, 7.0 Hz, 2H), 1.58 (t, J = 6.9 Hz, 3H) ); MS-ESI (m/z) calcd for [C$_{30}$H$_{30}$ClN$_6$O$_3$ + H]$^+$ 637.13; found: 637.10. |
| 66 | 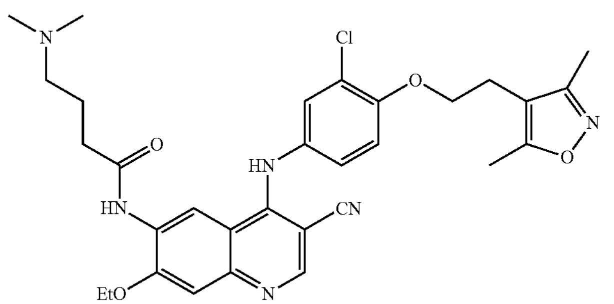 [SMILES: CCOc1cc2ncc(C#N)c(Nc3ccc(OCCc4c(C)noc4C)c(Cl)c3)c2cc1NC(=O)CCCN(C)C] | $^1$H NMR (400 MHz, Methanol-d$_4$) δ 9.04 (s, 1H), 8.68 (s, 1H), 7.48 (d, J = 2.6 Hz, 1H), 7.39-7.29 (m, 2H), 7.17 (d, J = 8.8 Hz, 1H), 5.49 (s, 2H), 4.86 (s, 6H), 4.39 (q, J = 6.9 Hz, 2H), 4.22 (t, J = 5.9 Hz, 2H), 3.35 (s, 1H), 3.32-3.20 (m, 3H), 2.92 (s, 9H), 2.73 (t, J = 6.9 Hz, 2H), 2.42 (s, 3H), 2.31 (s, 3H), 2.12 (dt, J = 14.7, 7.0 Hz, 2H), 1.58 (t, J = 7.0 Hz, 3H) ); MS-ESI (m/z) calcd for [C$_{31}$H$_{35}$ClN$_6$O$_4$ + H]$^+$ 591.24; found: 591.12. |
| 67 | 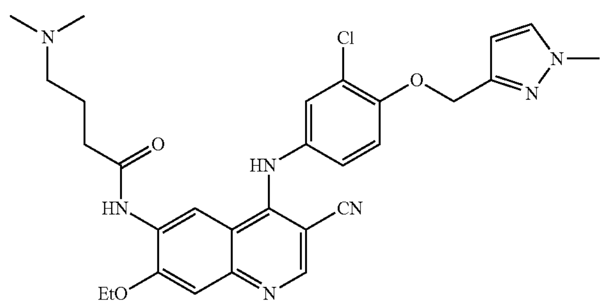 | $^1$H NMR (400 MHz, Methanol-d$_4$) δ 9.06 (s, 1H), 8.75 (s, 1H), 7.59 (d, J = 2.2 Hz, 1H), 7.51 (d, J = 2.3 Hz, 1H), 7.40-7.30 (m, 3H), 6.43 (d, J = 2.3 Hz, 1H), 5.19 (s, 2H), 4.40 (q, J = 7.0 Hz, 2H), 3.91 (s, 3H), 3.27-3.18 (m, 2H), 2.93 (s, 5H), 2.73 (t, J = 6.8 Hz, 2H), 2.12 (p, J = 7.2 Hz, 2H), 1.59 (t, J = 7.0 Hz, 3H); MS-ESI (m/z) calcd for [C$_{29}$H$_{32}$ClN$_7$O$_3$ + H]$^+$ 562.23; found: 562.10. |

| Ex. | Structure | Analytical Data |
|---|---|---|
| 68 | 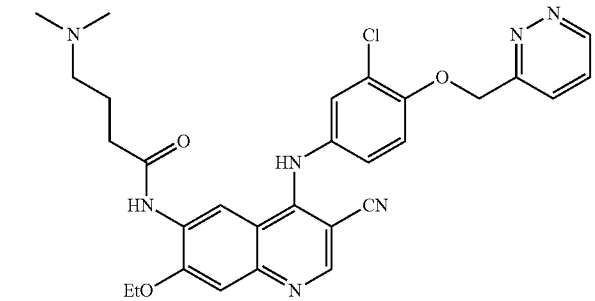 [SMILES: CCOc1cc2ncc(C#N)c(Nc3ccc(OCc4cccnn4)c(Cl)c3)c2cc1NC(=O)CCCN(C)C] | $^1$H NMR (400 MHz, Methanol-$d_4$) δ 9.20 (s, 1H), 9.01 (s, 1H), 8.67 (s, 1H), 8.02 (d, J = 8.4 Hz, 1H), 7.87-7.79 (m, 1H), 7.53 (d, J = 2.0 Hz, 1H), 7.35 (d, J = 7.3 Hz, 3H), 5.57 (s, 2H), 4.39 (d, J = 7.3 Hz, 2H), 3.35 (d, J = 2.0 Hz, 2H), 3.24 (t, J = 7.9 Hz, 2H), 2.93 (d, J = 2.2 Hz, 5H), 2.73 (t, J = 6.9 Hz, 2H), 2.12 (s, 2H), 1.58 (t, J = 7.1 Hz, 3H); MS-ESI (m/z) calcd for [$C_{29}H_{30}ClN_7O_3$ + H]$^+$ 560.21; found: 560.15. |
| 69 | 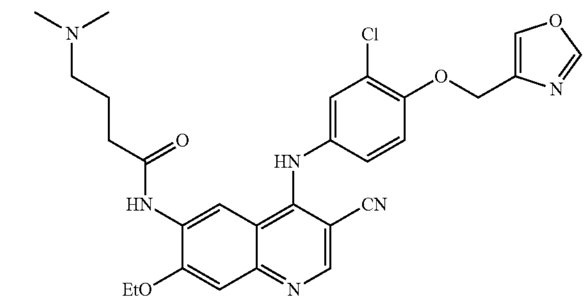 [SMILES: CCOc1cc2ncc(C#N)c(Nc3ccc(OCc4cocn4)c(Cl)c3)c2cc1NC(=O)CCCN(C)C] | $^1$H NMR (400 MHz, Methanol-$d_4$) δ 9.03 (s, 1H), 8.69 (s, 1H), 8.27 (s, 1H), 8.06 (s, 1H), 7.51 (d, J = 2.1 Hz, 1H), 7.39-7.28 (m, 3H), 5.19 (s, 2H), 4.39 (q, J = 7.0 Hz, 2H), 3.35 (d, J = 1.3 Hz, 1H), 3.29-3.20 (m, 2H), 2.93 (s, 6H), 2.73 (t, J = 6.9 Hz, 2H), 2.12 (p, J = 7.0 Hz, 2H), 1.58 (t, J = 7.0 Hz, 3H); MS-ESI (m/z) calcd for [$C_{28}H_{29}ClN_6O_4$ + H]$^+$ 549.19; found: 549.15. |
| 70 | 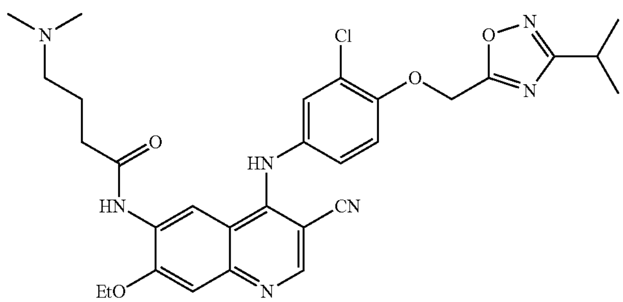 [SMILES: CCOc1cc2ncc(C#N)c(Nc3ccc(OCc4nc(C(C)C)no4)c(Cl)c3)c2cc1NC(=O)CCCN(C)C] | $^1$H NMR (400 MHz, Methanol-$d_4$) δ 9.03 (s, 1H), 8.69 (s, 1H), 8.27 (s, 1H), 8.06 (s, 1H), 7.51 (d, J = 2.1 Hz, 1H), 7.39-7.28 (m, 3H), 5.19 (s, 2H), 4.39 (q, J = 7.0 Hz, 2H), 3.35 (d, J = 1.3 Hz, 1H), 3.29-3.20 (m, 2H), 2.93 (s, 6H), 2.73 (t, J = 6.9 Hz, 2H), 2.12 (p, J = 7.0 Hz, 2H), 1.58 (t, J = 7.0 Hz, 3H); MS-ESI (m/z) calcd for [$C_{30}H_{34}ClN_7O_4$ + H]$^+$ 592.24; found: 592.20. |
| 71 | 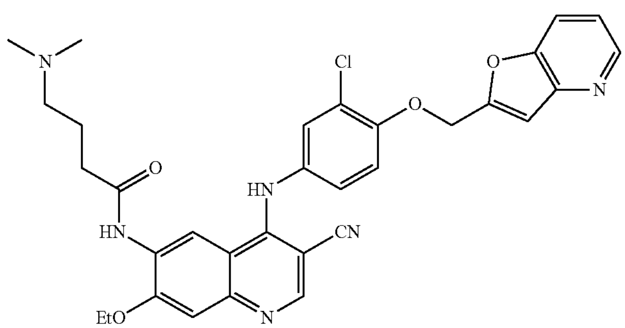 [SMILES: CCOc1cc2ncc(C#N)c(Nc3ccc(OCc4cc5ncccc5o4)c(Cl)c3)c2cc1NC(=O)CCCN(C)C] | $^1$H NMR (400 MHz, Methanol-$d_4$) δ 9.10 (d, J = 2.0 Hz, 1H), 8.81-8.75 (m, 1H), 8.53 (d, J = 4.8 Hz, 1H), 8.08 (d, J = 8.5 Hz, 1H), 7.57 (s, 1H), 7.50-7.35 (m, 4H), 7.16 (d, J = 2.0 Hz, 1H), 5.49 (d, J = 1.7 Hz, 2H), 4.45-4.35 (m, 2H), 3.75-3.60 (m, 2H), 3.34-3.19 (m, 3H), 2.95-2.89 (m, 6H), 2.73 (td, J = 6.9, 1.7 Hz, 2H), 2.12 (q, J = 7.6 Hz, 2H), 1.58 (ddd, J = 8.1, 6.9, 1.9 Hz, 3H); ); MS-ESI (m/z) calcd for $C_{32}H_{31}ClN_6O_4$ + H]$^+$ 599.24; found: 599.10. |
| 72 | 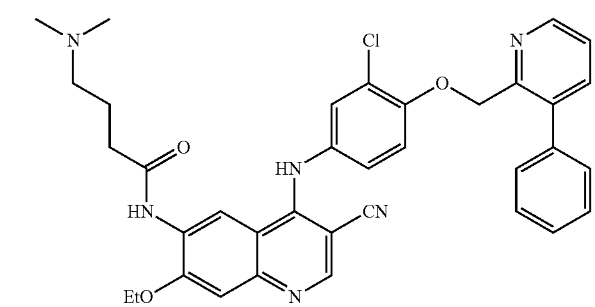 [SMILES: CCOc1cc2ncc(C#N)c(Nc3ccc(OCc4ncccc4-c4ccccc4)c(Cl)c3)c2cc1NC(=O)CCCN(C)C] | $^1$H NMR (400 MHz, Methanol-$d_4$) δ 9.11 (d, J = 4.5 Hz, 1H), 8.81-8.75 (m, 6H), 8.50 (d, J = 4.9 Hz, 1H), 8.08 (d, J = 8.5 Hz, 1H), 7.55 (s, 1H), 7.48-7.32 (m, 4H), 7.15 (d, J = 2.0 Hz, 1H), 5.45 (d, J = 1.7 Hz, 2H), 4.42-4.35 (m, 2H), 3.72-3.60 (m, 2H), 3.35-3.15 (m, 3H), 2.95-2.80 (m, 6H), 2.72 (td, J = 6.6, 1.7 Hz, 2H), 2.10 (q, J = 7.4 Hz, 2H), 1.56 (ddd, J = 8.1, 6.4, 1.8 Hz, 3H); ); MS-ESI (m/z) calcd for $C_{36}H_{35}ClN_6O_3$ + H]$^+$ 635.25; found: 635.20. |

| Ex. | Structure | Analytical Data |
|---|---|---|
| 73 | 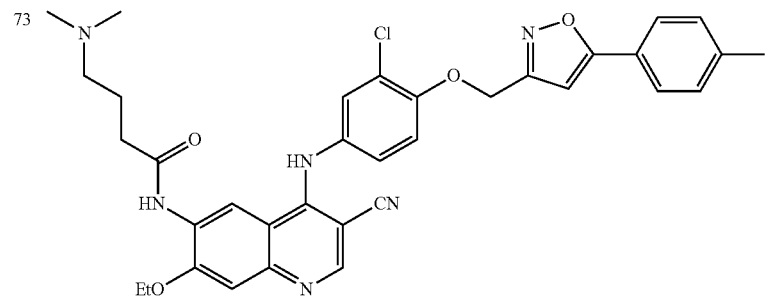 | $^1$H NMR (400 MHz, Methanol-d$_4$) δ 9.02 (d, J = 3.6 Hz, 1H), 8.70 (s, 1H), 7.78-7.70 (m, 2H), 7.53 (s, 1H), 7.38-7.30 (m, 5H), 6.86 (d, J = 3.4 Hz, 1H), 5.38 (d, J = 3.4 Hz, 2H), 4.39 (s, 2H), 3.31 (d, J = 9.7 Hz, 6H), 3.24 (s, 1H), 2.93 (d, J = 3.2 Hz, 5H), 2.73 (s, 2H), 2.41 (d, J = 3.5 Hz, 3H), 2.11 (s, 2H), 1.58 (q, J = 6.0 Hz, 3H) ); MS-ESI (m/z) calcd for [C$_{35}$H$_{35}$ClN$_6$O$_4$ + H]$^+$ 639.24; found: 639.15. |
| 74 | 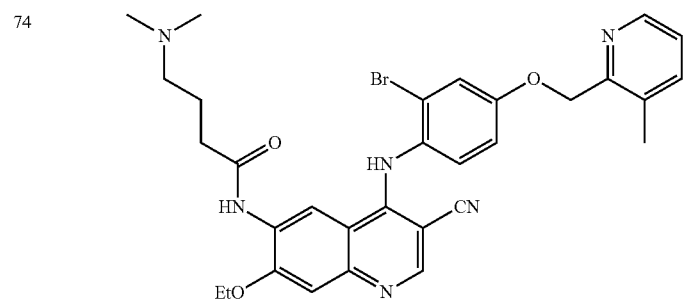 | $^1$H NMR (400 MHz, Methanol-d$_4$) δ 9.16-9.11 (m, 1H), 8.74 (d, J = 1.4 Hz, 1H), 8.50 (d, J = 5.3 Hz, 1H), 8.01 (d, J = 7.7 Hz, 1H), 7.63-7.51 (m, 3H), 7.38 (d, J = 1.2 Hz, 1H), 7.26 (d, J = 9.3 Hz, 1H), 5.42 (s, 2H), 4.41 (q, J = 6.9 Hz, 2H), 3.32 (s, 2H), 3.30-3.21 (m, 1H), 2.93 (s, 5H), 2.75 (t, J = 6.9 Hz, 2H), 2.52 (s, 3H), 2.14 (q, J = 7.8 Hz, 2H), 1.59 (t, J = 7.0 Hz, 3H); MS-ESI (m/z) calcd for [C$_{31}$H$_{33}$BrN$_6$O$_3$ + H]$^+$ 617.18; found: 617.15. |
| 75 | 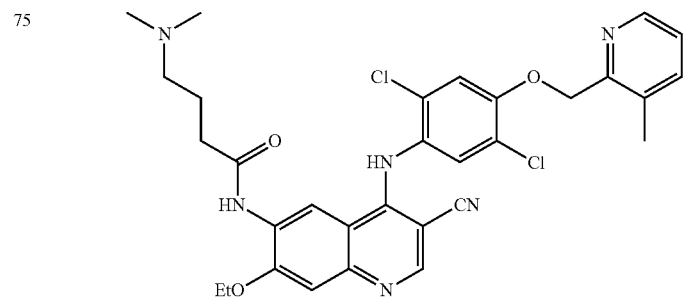 | $^1$H NMR (400 MHz, Methanol-d$_4$) δ 9.15-9.10 (m, 1H), 8.77 (s, 1H), 8.47 (d, J = 4.9 Hz, 1H), 7.91 (d, J = 7.9 Hz, 1H), 7.69 (s, 1H), 7.58 (s, 1H), 7.51 (t, J = 6.6 Hz, 1H), 7.40 (s, 1H), 5.46-5.41 (m, 2H), 4.86 (d, J = 4.7 Hz, 5H), 4.46-4.36 (m, 2H), 3.34-3.21 (m, 5H), 2.93 (d, J = 1.9 Hz, 5H), 2.74 (t, J = 7.0 Hz, 2H), 2.53 (s, 3H), 2.14 (q, J = 7.8 Hz, 2H), 1.63-1.54 (m, 3H); MS-ESI (m/z) calcd for [C$_{31}$H$_{32}$Cl$_2$N$_6$O$_3$ + H]$^+$ 607.19; found: 607.15. |
| 76 | 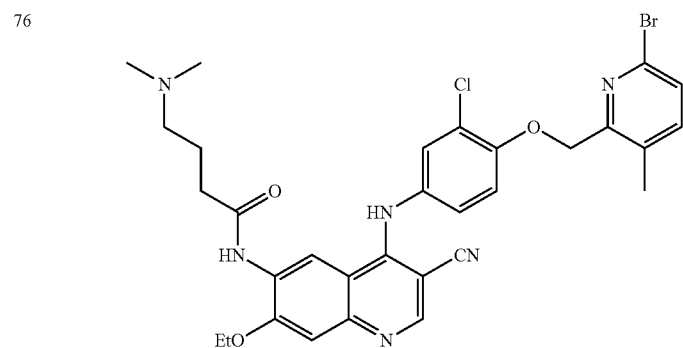 | $^1$H NMR (400 MHz, Methanol-d$_4$) δ 9.02 (s, 1H), 8.69 (s, 1H), 7.60 (d, J = 8.5 Hz, 1H), 7.55-7.46 (m, 2H), 7.35 (d, J = 6.2 Hz, 3H), 5.31 (s, 2H), 4.39 (d, J = 7.4 Hz, 2H), 3.34-3.20 (m, 4H), 2.92 (t, J = 2.0 Hz, 6H), 2.73 (t, J = 7.0 Hz, 2H), 2.45 (d, J = 2.1 Hz, 3H), 2.11 (d, J = 9.5 Hz, 2H), 1.58 (t, J = 7.1 Hz, 3H); MS-ESI (m/z) calcd for [C$_{31}$H$_{32}$BrClN$_6$O$_3$ + H]$^+$ 651.14; found: 327.04 (z = 2). |

| Ex. | Structure | Analytical Data |
|---|---|---|
| 77 | 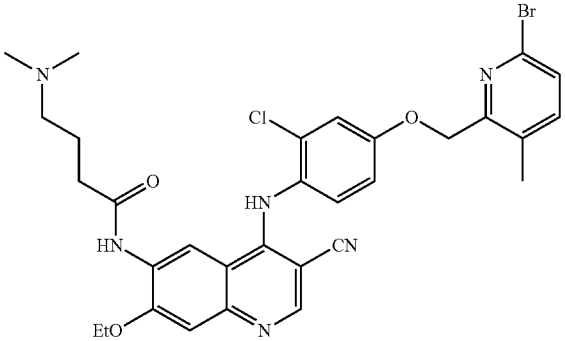 [SMILES: CCOc1cc2ncc(C#N)c(Nc3ccc(OCc4nc(Br)ccc4C)cc3Cl)c2cc1NC(=O)CCCN(C)C] | $^1$H NMR (400 MHz, Methanol-$d_4$) δ 9.09 (s, 1H), 8.70 (s, 1H), 7.59 (d, J = 8.3 Hz, 1H), 7.55-7.45 (m, 2H), 7.37 (s, 1H), 7.32 (s, 1H), 7.15 (s, 1H), 5.25 (d, J = 2.1 Hz, 2H), 4.40 (d, J = 7.5 Hz, 2H), 3.31 (d, J = 9.8 Hz, 3H), 2.94 (d, J = 1.6 Hz, 5H), 2.75 (s, 3H), 2.42 (d, J = 1.8 Hz, 3H), 2.13 (s, 2H), 1.58 (t, J = 6.9 Hz, 3H); MS-ESI (m/z) calcd for $[C_{31}H_{32}Cl_2N_6O_3 + H]^+$ 651.14; found: 327.04 (z = 2). |
| 78 | 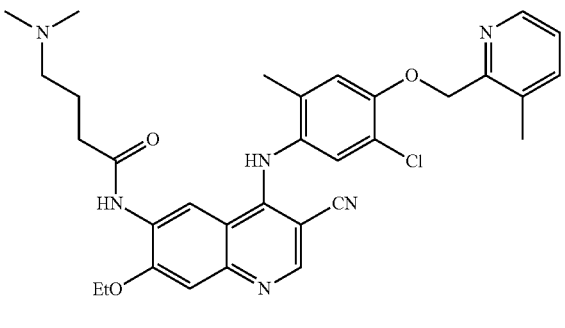 [SMILES: CCOc1cc2ncc(C#N)c(Nc3cc(Cl)c(OCc4ncccc4C)cc3C)c2cc1NC(=O)CCCN(C)C] | $^1$H NMR (400 MHz, Methanol-$d_4$) δ 9.16 (s, 1H), 8.79 (s, 1H), 8.59 (d, J = 5.5 Hz, 1H), 8.23 (dd, J = 8.0, 1.5 Hz, 1H), 7.76 (dd, J = 7.9, 5.4 Hz, 1H), 7.53 (s, 1H), 7.41 (s, 1H), 7.35 (s, 1H), 5.53 (s, 2H), 4.41 (q, J = 6.9 Hz, 3H), 3.27-3.21 (m, 3H), 2.92 (s, 7H), 2.74 (t, J = 7.0 Hz, 2H), 2.58 (s, 3H), 2.33 (s, 3H), 2.16-2.07 (m, 3H), 1.58 (t, J = 7.0 Hz, 4H); MS-ESI (m/z) calcd for $[C_{31}H_{32}ClN_6O_3 + H]^+$ 587.25; found: 294.37 (z = 2). |
| 79 | 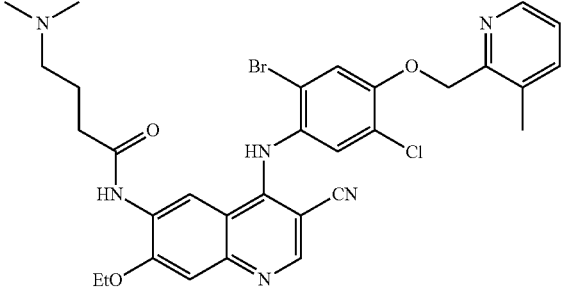 [SMILES: CCOc1cc2ncc(C#N)c(Nc3cc(Cl)c(OCc4ncccc4C)cc3Br)c2cc1NC(=O)CCCN(C)C] | $^1$H NMR (400 MHz, Methanol-$d_4$) δ 9.14 (s, 1H), 8.79 (s, 1H), 8.52-8.45 (m, 1H), 7.92 (d, J = 7.8 Hz, 1H), 7.72 (d, J = 9.7 Hz, 2H), 7.53 (dd, J = 7.8, 5.1 Hz, 1H), 7.40 (s, 1H), 2.57-2.50 (m, 4H), 5.45 (s, 2H), 2.14 (dt, J = 14.9, 7.1 Hz, 2H), 4.47-4.36 (m, 3H), 1.64-1.56 (m, 4H), 2.94 (s, 6H), 2.75 (t, J = 6.9 Hz, 2H); MS-ESI (m/z) calcd for $[C_{31}H_{32}BrClN_6O_3 + H]^+$ 651.14; found: 326.97 (z = 2). |
| 80 | 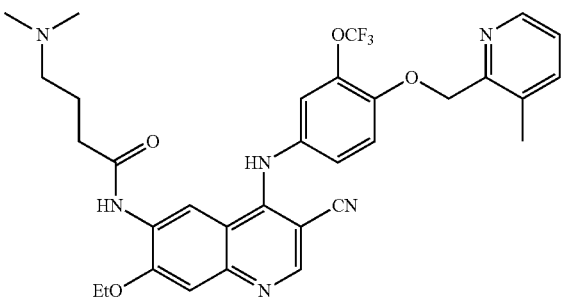 [SMILES: CCOc1cc2ncc(C#N)c(Nc3ccc(OCc4ncccc4C)c(OC(F)(F)F)c3)c2cc1NC(=O)CCCN(C)C] | $^1$H NMR (400 MHz, Methanol-$d_4$) δ 9.14 (s, 1H), 8.81 (s, 1H), 8.53 (ddd, J = 5.3, 1.5, 0.7 Hz, 1H), 8.08 (ddd, J = 7.9, 1.6, 0.8 Hz, 1H), 7.64 (dd, J = 7.8, 5.2 Hz, 1H), 7.57-7.46 (m, 3H), 7.41 (s, 1H), 5.49 (s, 2H), 4.90 (s, 25H), 4.41 (q, J = 7.0 Hz, 2H), 3.35-3.21 (m, 13H), 2.93 (s, 6H), 2.74 (t, J = 6.9 Hz, 2H), 2.55 (s, 3H), 2.19-2.07 (m, 2H), 1.61 (s, 1H); ); MS-ESI (m/z) calcd for $[C_{32}H_{33}F_3N_6O_4 + H]^+$ 623.25; found: 312.32 (z = 2). |
| 81 | 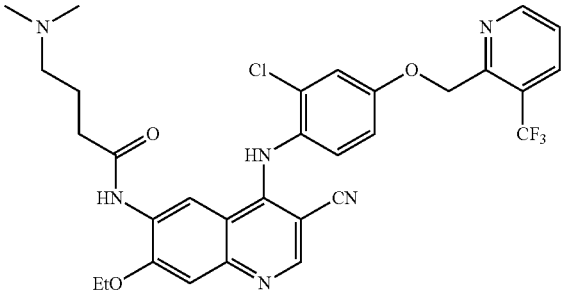 [SMILES: CCOc1cc2ncc(C#N)c(Nc3ccc(OCc4ncccc4C(F)(F)F)cc3Cl)c2cc1NC(=O)CCCN(C)C] | $^1$H NMR (400 MHz, Methanol-$d_4$) δ 9.11 (s, 1H), 8.85-8.79 (m, 1H), 8.74 (s, 1H), 8.24 (d, J = 8.0 Hz, 1H), 7.63 (dd, J = 8.0, 4.9 Hz, 1H), 7.49 (d, J = 8.8 Hz, 1H), 7.36 (s, 1H), 7.28 (d, J = 2.8 Hz, 1H), 7.12 (dd, J = 8.8, 2.8 Hz, 1H), 5.41 (s, 2H), 4.39 (q, J = 7.0 Hz, 2H), 3.28-3.20 (m, 3H), 2.92 (s, 7H), 2.73 (t, J = 6.9 Hz, 2H), 2.11 (dt, J = 15.0, 7.1 Hz, 2H), 1.58 (t, J = 7.0 Hz, 3H); MS-ESI (m/z) calcd for $[C_{31}H_{30}ClF_3N_6O_3 + H]^+$ 627.20; found: 314.35 (z = 2). |

| Ex. | Structure | Analytical Data |
|---|---|---|
| 82 | 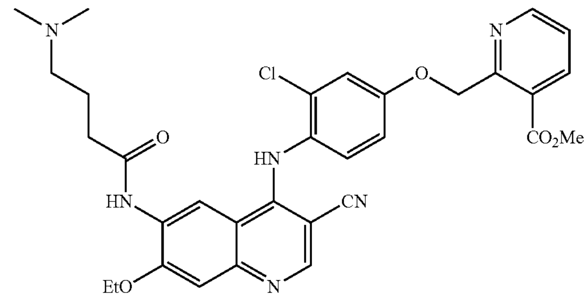 [SMILES: CCOc1cc2ncc(C#N)c(Nc3ccc(OCc4ncccc4C(=O)OC)cc3Cl)c2cc1NC(=O)CCCN(C)C] | $^1$H NMR (400 MHz, Methanol-d$_4$) δ 9.12 (s, 1H), 8.77-8.68 (m, 2H), 8.36 (dd, J = 7.9, 1.7 Hz, 1H), 7.59-7.45 (m, 2H), 7.37 (s, 1H), 7.26 (d, J = 2.8 Hz, 1H), 7.09 (dd, J = 8.8, 2.8 Hz, 1H), 5.58 (s, 2H), 4.97-4.78 (m, 3H), 4.39 (q, J = 7.0 Hz, 2H), 3.89 (s, 3H), 3.29-3.19 (m, 3H), 2.92 (s, 6H), 2.73 (t, J = 6.9 Hz, 2H), 2.11 (dt, J = 14.4, 7.0 Hz, 2H), 1.57 (t, J = 7.0 Hz, 3H); MS-ESI (m/z) calcd for [C$_{32}$H$_{33}$ClN$_6$O$_5$ + H]$^+$ 617.22; found: 617.24. |
| 83 | 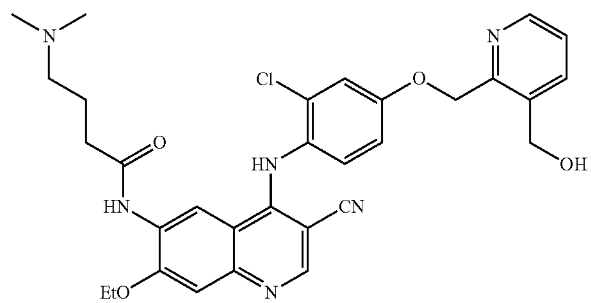 [SMILES: CCOc1cc2ncc(C#N)c(Nc3ccc(OCc4ncccc4CO)cc3Cl)c2cc1NC(=O)CCCN(C)C] | $^1$H NMR (400 MHz, Methanol-d$_4$) δ 9.16 (s, 1H), 8.80 (s, 1H), 8.60 (s, 1H), 8.28 (d, J = 7.8 Hz, 1H), 7.74-7.66 (m, 1H), 7.54 (d, J = 8.8 Hz, 1H), 7.39 (d, J = 2.9 Hz, 2H), 7.21 (dd, J = 8.9, 2.7 Hz, 1H), 5.46 (s, 2H), 4.96-4.86 (m, 1H), 4.83 (s, 2H), 4.40 (q, J = 7.0 Hz, 2H), 3.29-3.18 (m, 2H), 2.91 (s, 6H), 2.72 (t, J = 6.9 Hz, 2H), 2.11 (dt, J = 14.8, 7.0 Hz, 2H), 1.57 (t, J = 6.9 Hz, 3H), 1.37-1.24 (m, 2H), 0.88 (t, J = 7.1 Hz, 1H); MS-ESI (m/z) calcd for [C$_{31}$H$_{33}$ClN$_6$O$_4$ + H]$^+$ 589.23; found: 589.7. |

Example 84

Synthesis of N-(4-(3-chloro-4-((3-methylpyridin-2-yl)methoxy)phenylamino)-3-cyano-7-ethoxyquinolin-6-yl)acetamide

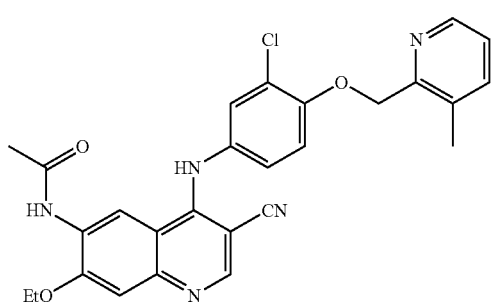 [SMILES: CCOc1cc2ncc(C#N)c(Nc3ccc(OCc4ncccc4C)c(Cl)c3)c2cc1NC(C)=O]

N-(4-(3-chloro-4-((3-methylpyridin-2-yl)methoxy)phenylamino)-3-cyano-7-ethoxyquinolin-6-yl)acetamide was prepared by a similar procedure to that described for example 1 by coupling Compound 1 with Compound 4. $^1$H NMR (400 MHz, Methanol-d$_4$) δ 9.09 (s, 1H), 8.78 (d, J=1.2 Hz, 1H), 8.51 (d, J=5.2 Hz, 1H), 8.00 (d, J=7.8 Hz, 1H), 7.58 (d, J=7.8 Hz, 2H), 7.42 (d, J=1.4 Hz, 2H), 7.37 (d, J=1.1 Hz, 1H), 5.47 (s, 2H), 4.42 (q, J=7.3 Hz, 2H), 2.56 (s, 3H), 2.30 (d, J=1.3 Hz, 3H), 1.61 (t, J=6.9 Hz, 3H); MS-ESI (m/z) calcd for [C$_{27}$H$_{24}$ClN$_5$O$_3$+H]$^+$ 502.16; found: 502.18.

Examples 85-89 were prepared according to a similar procedure as described for Example 84:

| Ex. | Structure | Analytical Data |
| --- | --- | --- |
| 85 | 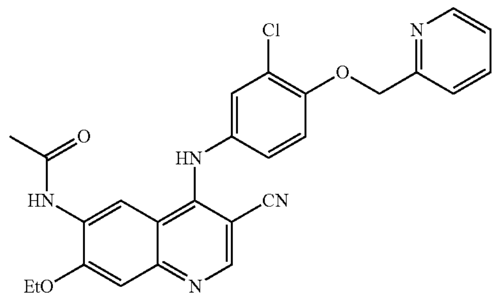 [SMILES: CCOc1cc2ncc(C#N)c(Nc3ccc(OCc4ccccn4)c(Cl)c3)c2cc1NC(C)=O] | ¹H NMR (400 MHz, Methanol-d₄) δ 9.06 (s, 1H), 8.73 (s, 1H), 8.60 (d, J = 4.9 Hz, 1H), 7.96 (td, J = 7.8, 1.8 Hz, 1H), 7.75 (d, J = 7.9 Hz, 1H), 7.58 (d, J = 2.6 Hz, 1H), 7.45 (dd, J = 7.3, 5.0 Hz, 1H), 7.38 (dd, J = 8.7, 2.6 Hz, 1H), 7.35 (s, 1H), 7.28 (d, J = 8.8 Hz, 1H), 5.36 (s, 2H), 4.41 (q, J = 7.0 Hz, 2H), 2.30 (s, 3H), 1.61 (t, J = 7.0 Hz, 3H); MS-ESI (m/z) calcd for [C$_{26}$H$_{22}$ClN$_5$O$_3$ + H]⁺ 488.15; found: 488.19. |
| 86 | 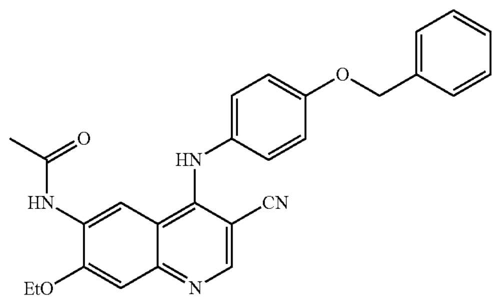 [SMILES: CCOc1cc2ncc(C#N)c(Nc3ccc(OCc4ccccc4)cc3)c2cc1NC(C)=O] | ¹H NMR (400 MHz, Methanol-d₄) δ 9.07 (s, 1H), 8.74 (s, 1H), 7.47 (d, J = 6.9 Hz, 2H), 7.42-7.36 (m, 4H), 7.35-7.30 (m, 2H), 7.13 (d, J = 9.0 Hz, 2H), 5.16 (s, 2H), 4.40 (q, J = 7.0 Hz, 2H), 2.28 (s, 3H), 1.59 (t, J = 7.0 Hz, 3H); MS-ESI (m/z) calcd for [C$_{27}$H$_{24}$N$_4$O$_3$ + H]⁺ 453.19; found: 453.21. |
| 87 | 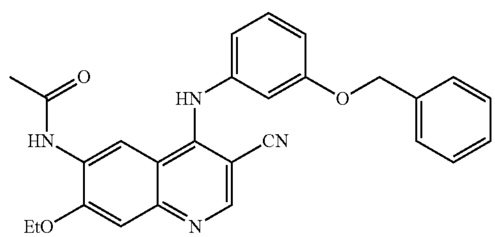 [SMILES: CCOc1cc2ncc(C#N)c(Nc3cccc(OCc4ccccc4)c3)c2cc1NC(C)=O] | ¹H NMR (400 MHz, Methanol-d₄) δ 9.08 (s, 1H), 8.77 (s, 1H), 7.49-7.28 (m, 7H), 7.13 (ddd, J = 8.4, 2.5, 0.9 Hz, 1H), 7.08 (t, J = 2.2 Hz, 1H), 7.04 (ddd, J = 7.8, 2.0, 0.9 Hz, 1H), 5.14 (s, 2H), 4.40 (q, J = 7.0 Hz, 2H), 2.28 (s, 3H), 1.59 (t, J = 7.0 Hz, 3H); MS-ESI (m/z) calcd for [C$_{27}$H$_{24}$N$_4$O$_3$ + H]⁺ 453.19; found: 453.21. |
| 88 | 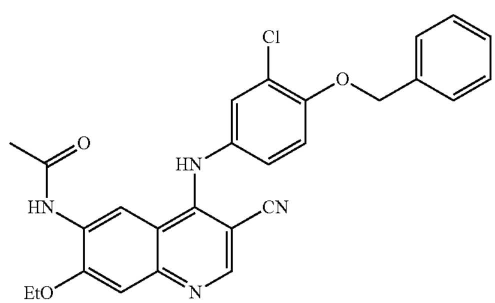 [SMILES: CCOc1cc2ncc(C#N)c(Nc3ccc(OCc4ccccc4)c(Cl)c3)c2cc1NC(C)=O] | ¹H NMR (400 MHz, Methanol-d₄) δ 9.08 (s, 1H), 8.78 (s, 1H), 7.55 (d, J = 2.6 Hz, 1H), 7.52-7.48 (m, 2H), 7.44-7.32 (m, 5H), 7.26 (d, J = 8.8 Hz, 1H), 5.25 (s, 2H), 4.40 (q, J = 7.0 Hz, 2H), 2.28 (s, 3H), 1.59 (t, J = 7.0 Hz, 3H); MS-ESI (m/z) calcd for [C$_{27}$H$_{23}$ClN$_4$O$_3$ + H]⁺ 487.15; found: 487.17. |
| 89 | 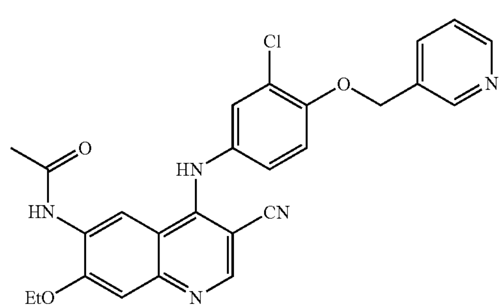 [SMILES: CCOc1cc2ncc(C#N)c(Nc3ccc(OCc4cccnc4)c(Cl)c3)c2cc1NC(C)=O] | ¹H NMR (400 MHz, Methanol-d4) δ 9.09 (s, 1H), 8.86 (s, 1H), 8.78 (s, 1H), 8.70 (d, J = 4.4 Hz, 1H), 8.38 (d, J = 8.0 Hz, 1H), 7.82 (dd, J = 8.0, 5.3 Hz, 1H), 7.61 (d, J = 2.5 Hz, 1H), 7.44 (dd, J = 8.7, 2.6 Hz, 1H), 7.35 (t, J = 4.4 Hz, 2H), 5.44 (s, 2H), 4.41 (q, J = 7.0 Hz, 2H), 2.29 (s, 3H), 1.60 (t, J = 7.0 Hz, 3H); MS-ESI (m/z) calcd for [C$_{26}$H$_{22}$ClN$_5$O$_3$ + H]⁺ 488.15; found: 488.15. |

Example 90

Synthesis of (E)-N-(4-(3-chloro-4-((3-methylpyridin-2-yl)methoxy)phenylamino)-3-cyano-7-ethoxyquinolin-6-yl)-4-(dimethylamino)but-2-enamide (7)

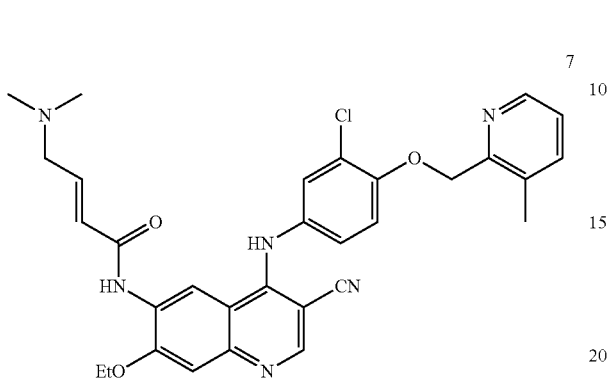

Step 1: (E)-N-(4-chloro-3-cyano-7-ethoxyquinolin-6-yl)-4-(dimethylamino)but-2-enamide (6)

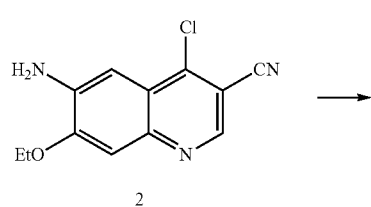

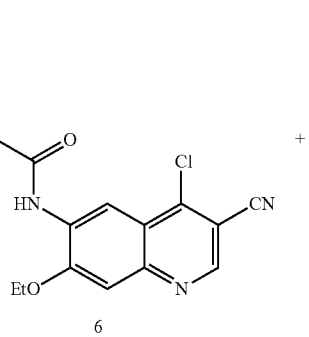

Step 2: (E)-N-(4-(3-chloro-4-((3-methylpyridin-2-yl)methoxy)phenylamino)-3-cyano-7-ethoxyquinolin-6-yl)-4-(dimethylamino)but-2-enamide (7)

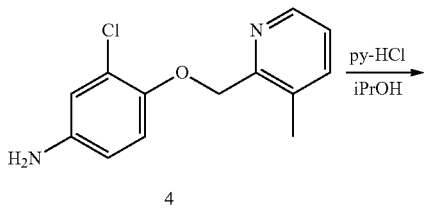

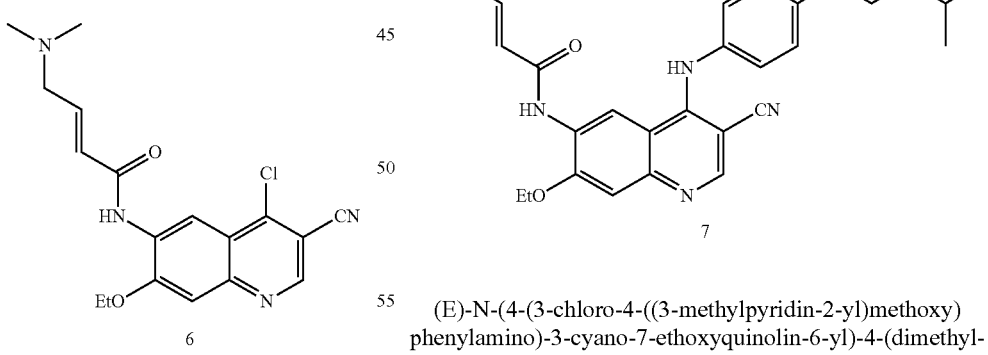

(E)-N-(4-chloro-3-cyano-7-ethoxyquinolin-6-yl)-4-(dimethylamino)but-2-enamide (6) was prepared following the procedure of Example 1, Step 2, starting with (2E)-4-(dimethylamino)but-2-enoic acid hydrochloride. $^1$H NMR (400 MHz, Methanol-$d_4$) δ 9.29 (s, 1H), 8.87 (s, 1H), 7.54 (s, 1H), 7.09-6.96 (m, 1H), 6.57 (d, J=15.6 Hz, 1H), 4.42 (q, J=7.3, 6.9 Hz, 2H), 3.23 (d, J=6.5 Hz, 2H), 2.32 (s, 6H), 1.60 (t, J=7.0 Hz, 3H). MS-ESI (m/z) calcd for [C$_{18}$H$_{19}$ClN$_4$O$_2$+H]$^+$ 359.13; found: 359.14.

(E)-N-(4-(3-chloro-4-((3-methylpyridin-2-yl)methoxy)phenylamino)-3-cyano-7-ethoxyquinolin-6-yl)-4-(dimethylamino)but-2-enamide (7) was prepared by a similar procedure to that described for example 1 by coupling Compound 6 with Compound 4. $^1$H NMR (400 MHz, Methanol-$d_4$) δ 9.23 (s, 1H), 8.81 (s, 1H), 8.58 (d, J=4.7 Hz, 1H), 8.17 (d, J=7.7 Hz, 1H), 7.72 (dd, J=7.8, 5.4 Hz, 1H), 7.63 (d, J=2.2 Hz, 1H), 7.51-7.41 (m, 3H), 7.01 (dt, J=14.5, 7.1 Hz, 1H), 6.86 (d, J=15.3 Hz, 1H), 5.53 (s, 2H), 4.44 (q, J=7.0 Hz, 2H), 4.05 (d, J=7.0 Hz, 2H), 2.96 (s, 6H), 2.59 (s, 3H), 1.61 (t, J=7.0 Hz, 3H); MS-ESI (m/z) calcd for [C$_{31}$H$_{31}$ClN$_6$O$_3$+H]$^+$ 571.22; found: 571.28.

Example 91

Synthesis of (E)-N-(4-(2-chloro-4-((3-methylpyridin-2-yl)methoxy)phenylamino)-3-cyano-7-ethoxyquinolin-6-yl)-4-(dimethylamino)but-2-enamide (9)

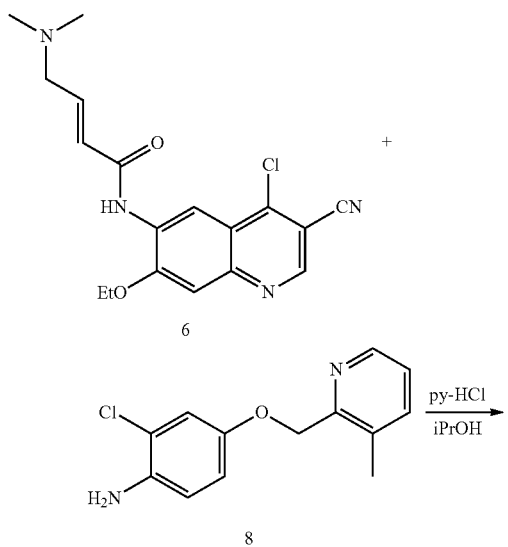

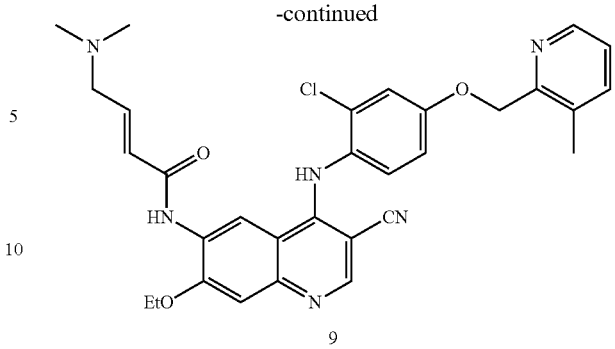

(E)-N-(4-(2-chloro-4-((3-methylpyridin-2-yl)methoxy)phenylamino)-3-cyano-7-ethoxyquinolin-6-yl)-4-(dimethylamino)but-2-enamide was prepared by a similar procedure to that described for example 90 by coupling Compound 6 with Compound 8. Compound 8 was prepared in a similar manner as outlined in example 1, step 3. $^1$H NMR (400 MHz, Methanol-d4) δ 9.09 (s, 1H), 8.78 (d, J=1.2 Hz, 1H), 8.51 (d, J=5.2 Hz, 1H), 8.00 (d, J=7.8 Hz, 1H), 7.58 (d, J=7.8 Hz, 2H), 7.42 (d, J=1.4 Hz, 2H), 7.37 (d, J=1.1 Hz, 1H), 5.47 (s, 2H), 4.42 (q, J=7.3 Hz, 2H), 2.56 (s, 3H), 2.30 (d, J=1.3 Hz, 3H), 1.61 (t, J=6.9 Hz, 3H); MS-ESI (m/z) calcd for [$C_{27}H_{24}ClN_5O_3$+H]$^+$ 502.16; found: 502.18.

Examples 92-94 were prepared according to a similar procedure as described for examples 90 and 91:

| Ex. | Structure | Analytical Data |
|---|---|---|
| 92 | 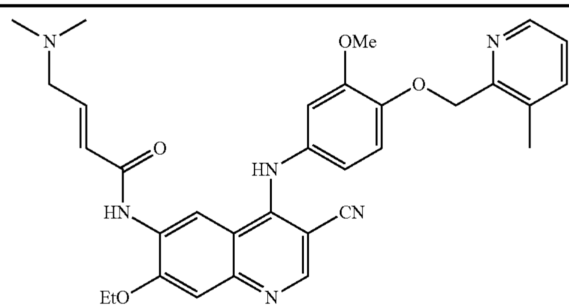 | $^1$H NMR (400 MHz, Methanol-d$_4$) δ 9.17 (s, 1H), 8.72 (s, 1H), 8.52 (d, J = 5.5 Hz, 1H), 8.13 (d, J = 7.8 Hz, 1H), 7.68 (s, 1H), 7.38 (s, 1H), 7.25 (d, J = 8.6 Hz, 1H), 7.15 (s, 1H), 7.06-6.98 (m, 1H), 6.83 (d, J = 15.3 Hz, 1H), 5.42 (s, 2H), 4.87 (s, 4H), 4.41 (d, J = 7.1 Hz, 2H), 4.02 (d, J = 7.2 Hz, 2H), 3.85 (s, 3H), 3.33 (s, 9H), 2.94 (s, 6H), 2.53 (s, 3H), 1.58 (t, J = 7.0 Hz, 3H); MS-ESI (m/z) calcd for [$C_{32}H_{34}N_6O_4$ + H]$^+$ 567.26; found: 567.23. |
| 93 | 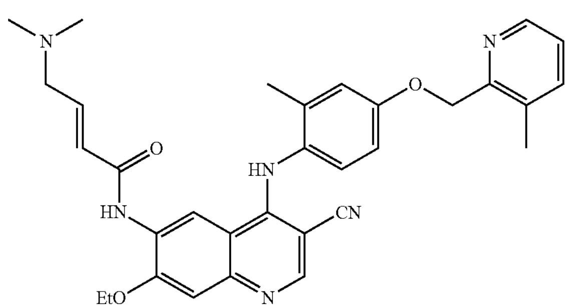 [SMILES: CCOc1cc2ncc(C#N)c(Nc3ccc(OCc4ncccc4C)cc3C)c2cc1NC(=O)/C=C/CN(C)C] | $^1$H NMR (400 MHz, Methanol-d$_4$) δ 9.26 (s, 1H), 8.77 (s, 1H), 8.62 (d, J = 5.7 Hz, 2H), 8.32 (d, J = 7.9 Hz, 2H), 7.84 (dd, J = 7.9, 5.6 Hz, 2H), 7.41 (t, J = 4.3 Hz, 3H), 7.26-7.13 (m, 3H), 7.00 (dt, J = 14.4, 7.1 Hz, 1H), 6.89-6.83 (m, 1H), 5.53 (s, 2H), 4.44 (q, J = 7.0 Hz, 3H), 4.04 (d, J = 7.2 Hz, 3H), 2.95 (s, 7H), 2.57 (s, 4H), 2.35 (s, 4H), 1.60 (t, J = 7.0 Hz, 5H); MS-ESI (m/z) calcd for [$C_{32}H_{34}N_6O_3$ + H]$^+$ 551.27; found: 276.38 (z = 2). |

| Ex. | Structure | Analytical Data |
|---|---|---|
| 94 | 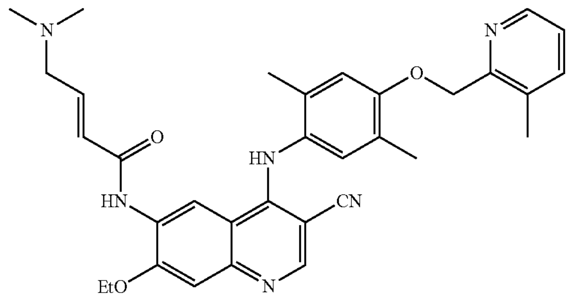 [SMILES: CCOc1cc2ncc(C#N)c(Nc3cc(C)c(OCc4ncccc4C)cc3C)c2cc1NC(=O)/C=C/CN(C)C] | $^1$H NMR (400 MHz, Methanol-$d_4$) δ 9.20 (s, 1H), 8.71 (s, 1H), 8.54-8.48 (m, 1H), 8.10 (d, J = 8.0 Hz, 1H), 7.65 (dd, J = 7.9, 5.3 Hz, 1H), 7.36 (s, 1H), 7.17 (s, 1H), 7.09 (s, 1H), 7.02-6.89 (m, 1H), 6.80 (dt, J = 15.2, 1.0 Hz, 1H), 5.40 (s, 2H), 4.88 (s, 1H), 4.39 (q, J = 7.0 Hz, 2H), 3.99 (dd, J = 7.2, 1.2 Hz, 2H), 3.31 (s, 1H), 2.91 (d, J = 2.2 Hz, 6H), 2.52 (s, 4H), 2.24 (d, J = 17.8 Hz, 7H), 1.56 (t, J = 7.0 Hz, 3H); MS-ESI (m/z) calcd for [$C_{33}H_{36}N_6O_3$ + H]$^+$ 565.28; found: 283.39 (z = 2). |

Example 95

Synthesis of N-(4-(3-chloro-4-(pyridin-2-yl-methoxy)phenylamino)-3-cyano-7-ethoxyquinolin-6-yl)-4-(pyrrolidin-1-yl)butanamide (11)

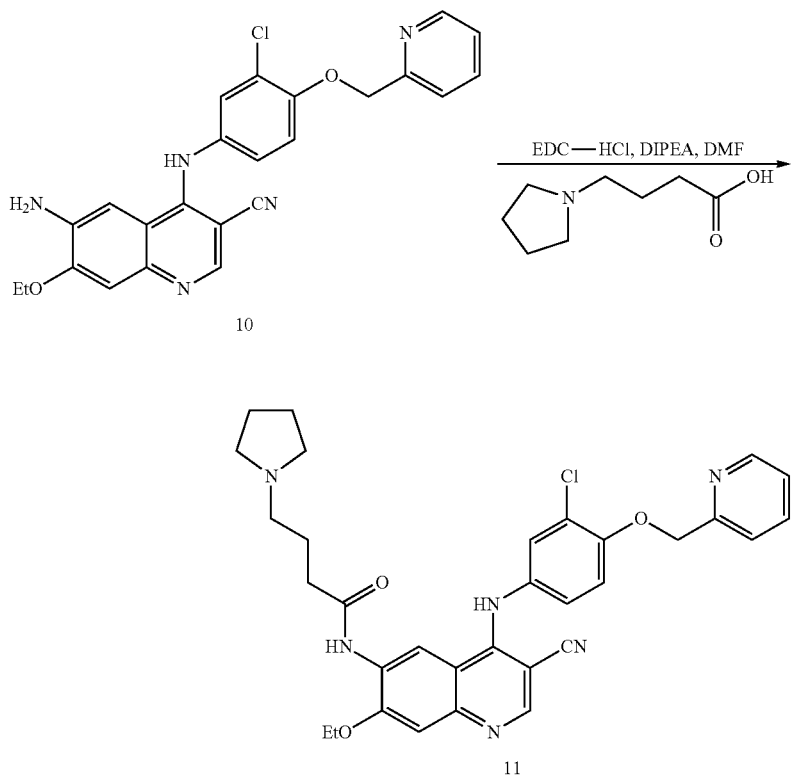

A 1 dram vial with a stir bar is charged with compound 10 (30 mg, 0.067 mmol, 1.0 equiv), 4-(pyrrolidin-1-yl)butanoic acid hydrochloride (27 mg, 0.14 mmol, 2.0 equiv), EDC-HCl (33 mg, 0.17 mmol, 2.5 equiv), 48 mg DIPEA (0.37 mmol, 5.5 equiv) and $CH_2Cl_2$. DMAP (1.5 mg, 0.012 mmol, 0.2 equiv) is added, the reaction vial is capped and stirred for at room temperature for 18 h. The reaction is quenched with the addition of 2 mL of saturated $NH_4Cl$ and is extracted with $CH_2Cl_2$ (2×2 mL). The combined organic layer is washed with brine and evaporated. The crude residue is purified by gradient flash column chromatography (2 to 20% MeOH in $CH_2Cl_2$) to yield the product as a yellow solid (32 mg, 82%). $^1$H NMR (400 MHz, $CDCl_3$) δ 9.06 (s, 1H), 8.60 (d, J=4.3 Hz, 1H), 8.46 (s, 1H), 8.38 (s, 1H), 7.90 (s, 1H), 7.77 (td, J=7.6, 1.7 Hz, 1H), 7.66 (d, J=7.8 Hz, 1H), 7.29-7.18 (m, 3H), 6.99 (d, J=8.4 Hz, 1H), 6.90 (d, J=8.5 Hz, 1H), 5.27 (s, 2H), 4.26 (q, J=6.9 Hz, 2H), 2.70-2.45 (m, 8H), 1.95 (p, J=7.2 Hz, 2H), 1.85-1.71 (m, 4H), 1.55 (t, J=6.9 Hz, 3H); MS-ESI (m/z) calcd for [$C_{32}H_{33}ClN_6O_3$+H]$^+$ 585.24; found: 293.19 (z=2).

Examples 96-106 were prepared according to a similar procedure as described for example 95:

| Ex. | Structure | Analytical Data |
|---|---|---|
| 96 | 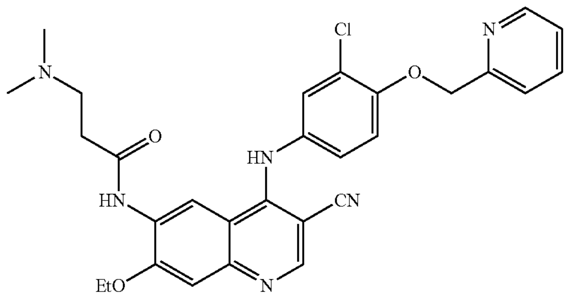 [SMILES: CCOc1cc2ncc(C#N)c(Nc3ccc(OCc4ccccn4)c(Cl)c3)c2cc1NC(=O)CCN(C)C] | $^1$H NMR (400 MHz, CDCl$_3$) δ 9.06 (s, 1H), 8.61 (d, J = 4.5 Hz, 1H), 8.50 (s, 1H), 7.82-7.65 (m, 3H), 7.34-7.24 (m, 3H), 7.08 (dd, J = 8.7, 2.6 Hz, 1H), 6.97 (d, J = 8.8 Hz, 1H), 5.30 (s, 2H), 4.28 (q, J = 7.0 Hz, 2H), 2.88 (s, 2H), 2.77 (s, 2H), 2.51 (s, 6H), 1.61-1.52 (m, 3H); MS-ESI (m/z) calcd for [C$_{29}$H$_{29}$ClN$_6$O$_3$ + H]$^+$ 545.21; found: 545.16. |
| 97 | 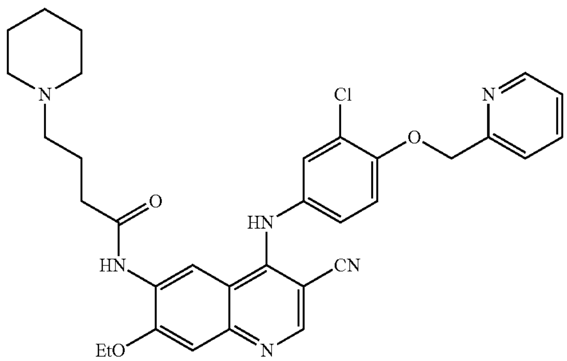 [SMILES: CCOc1cc2ncc(C#N)c(Nc3ccc(OCc4ccccn4)c(Cl)c3)c2cc1NC(=O)CCCN1CCCCC1] | $^1$H NMR (400 MHz, Methanol-d$_4$) δ 9.09 (s, 1H), 8.79 (s, 1H), 8.61 (d, J = 5.1 Hz, 1H), 7.99 (td, J = 7.8, 1.8 Hz, 1H), 7.77 (d, J = 7.8 Hz, 1H), 7.59 (d, J = 2.5 Hz, 1H), 7.50-7.45 (m, 1H), 7.41-7.36 (m, 2H), 7.29 (d, J = 8.9 Hz, 1H), 5.37 (s, 2H), 4.41 (q, J = 6.9 Hz, 2H), 3.58 (d, J = 12.3 Hz, 2H), 3.24-3.15 (m, 2H), 2.95 (t, J = 12.5 Hz, 2H), 2.73 (t, J = 6.9 Hz, 2H), 2.20-2.07 (m, 2H), 1.96 (d, J = 14.8 Hz, 2H), 1.80 (dd, J = 35.2, 14.7 Hz, 3H), 1.59 (t, J = 7.0 Hz, 3H), 1.52 (d, J = 14.9 Hz, 1H); MS-ESI (m/z) calcd for [C$_{33}$H$_{35}$ClN$_6$O$_3$ + H]$^+$ 599.25; found: 599.21. |
| 98 | 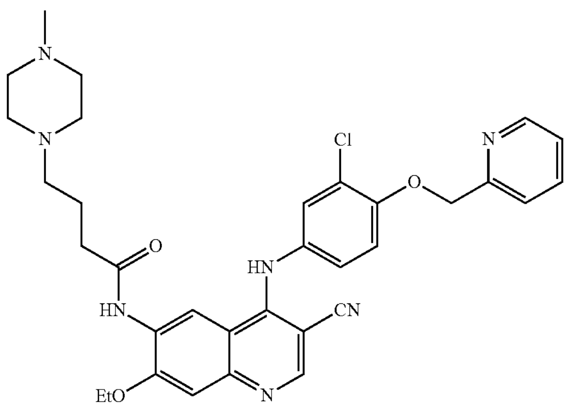 [SMILES: CCOc1cc2ncc(C#N)c(Nc3ccc(OCc4ccccn4)c(Cl)c3)c2cc1NC(=O)CCCN1CCN(C)CC1] | $^1$H NMR (400 MHz, Methanol-d$_4$) δ 9.14 (s, 1H), 8.81 (s, 1H), 8.68 (d, J = 4.9 Hz, 1H), 8.15 (td, J = 7.8, 1.7 Hz, 1H), 7.88 (d, J = 7.9 Hz, 1H), 7.67-7.58 (m, 2H), 7.45-7.38 (m, 2H), 7.32 (d, J = 8.8 Hz, 1H), 5.44 (s, 2H), 4.41 (q, J = 7.0 Hz, 2H), 3.46 (s, 4H), 3.34 (s, 4H), 3.06 (dd, J = 9.0, 6.5 Hz, 2H), 2.90 (s, 3H), 2.71 (t, J = 7.0 Hz, 2H), 2.08 (p, J = 7.1 Hz, 2H), 1.59 (t, J = 7.0 Hz, 3H); MS-ESI (m/z) calcd for [C$_{33}$H$_{36}$ClN$_7$O$_3$ + H]$^+$ 614.26; found: 614.31. |
| 99 | 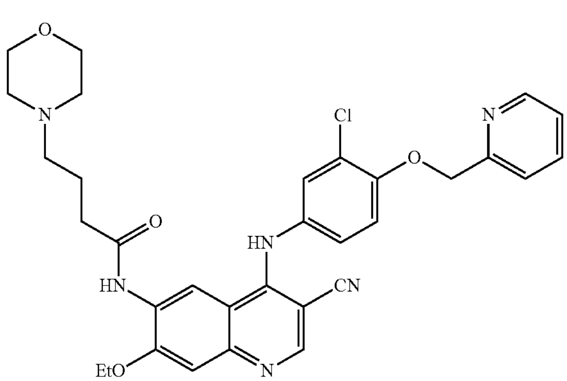 [SMILES: CCOc1cc2ncc(C#N)c(Nc3ccc(OCc4ccccn4)c(Cl)c3)c2cc1NC(=O)CCCN1CCOCC1] | $^1$H NMR (400 MHz, Methanol-d$_4$) δ 9.13 (s, 1H), 8.81 (s, 1H), 8.67 (d, J = 4.4 Hz, 1H), 8.12 (td, J = 7.8, 1.7 Hz, 1H), 7.86 (d, J = 7.9 Hz, 1H), 7.64-7.56 (m, 2H), 7.45-7.38 (m, 2H), 7.31 (d, J = 8.8 Hz, 1H), 5.43 (s, 2H), 4.41 (q, J = 7.0 Hz, 2H), 4.06 (d, J = 12.9 Hz, 2H), 3.78 (t, J = 12.5 Hz, 2H), 3.55 (d, J = 12.4 Hz, 2H), 3.31-3.24 (m, 2H), 3.23-3.08 (m, 2H), 2.74 (t, J = 6.9 Hz, 2H), 2.22-2.07 (m, 2H), 1.59 (t, J = 6.9 Hz, 3H); MS-ESI (m/z) calcd for [C$_{32}$H$_{33}$ClN$_6$O$_4$ + H]$^+$ 601.23; found: 601.21. |

| Ex. | Structure | Analytical Data |
|---|---|---|
| 100 | 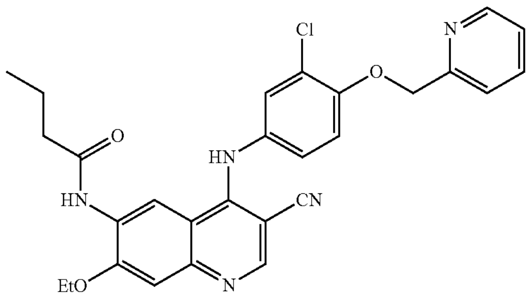 [SMILES: CCCC(=O)Nc1cc2c(Nc3ccc(OCc4ccccn4)c(Cl)c3)c(C#N)cnc2cc1OCC] | ¹H NMR (400 MHz, Methanol-d₄) δ 9.07 (s, 1H), 8.80 (s, 1H), 8.63 (d, J = 4.4 Hz, 1H), 8.04 (td, J = 7.8, 1.7 Hz, 1H), 7.81 (d, J = 7.9 Hz, 1H), 7.60 (d, J = 2.6 Hz, 1H), 7.56-7.46 (m, 1H), 7.41 (dd, J = 8.7, 2.6 Hz, 1H), 7.35 (s, 1H), 7.29 (d, J = 8.8 Hz, 1H), 5.39 (s, 2H), 4.40 (q, J = 7.0 Hz, 2H), 2.53 (t, J = 7.3 Hz, 2H), 1.77 (h, J = 7.4 Hz, 2H), 1.59 (t, J = 7.0 Hz, 3H), 1.04 (t, J = 7.4 Hz, 3H); MS-ESI (m/z) calcd for [C₂₈H₂₆ClN₅O₃ + H]⁺ 516.18; found: 516.25. |
| 101 | 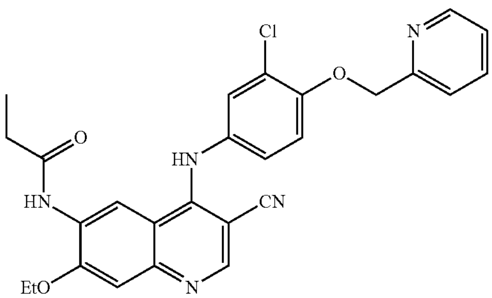 [SMILES: CCOc1cc2ncc(C#N)c(Nc3ccc(OCc4ccccn4)c(Cl)c3)c2cc1NC(=O)CC] | ¹H NMR (400 MHz, Methanol-d₄) δ 9.10 (s, 1H), 8.80 (s, 1H), 8.63 (d, J = 4.3 Hz, 1H), 8.04 (td, J = 7.8, 1.7 Hz, 1H), 7.85-7.77 (m, 1H), 7.61 (d, J = 2.5 Hz, 1H), 7.52 (ddd, J = 7.7, 5.1, 1.2 Hz, 1H), 7.41 (dd, J = 8.7, 2.6 Hz, 1H), 7.35 (s, 1H), 7.30 (d, J = 8.8 Hz, 1H), 5.40 (s, 2H), 4.40 (q, J = 7.0 Hz, 2H), 2.57 (q, J = 7.5 Hz, 2H), 1.59 (t, J = 7.0 Hz, 3H), 1.24 (t, J = 7.5 Hz, 3H); MS-ESI (m/z) calcd for [C₂₇H₂₄ClN₅O₃ + H]⁺ 502.16; found: 502.16. |
| 102 | 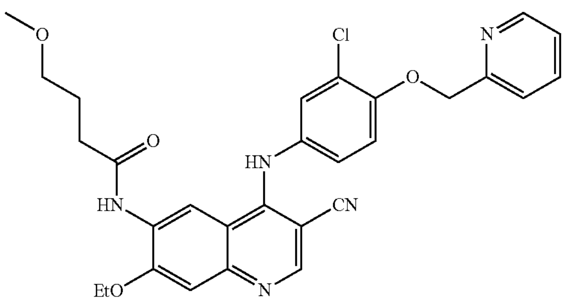 [SMILES: CCOc1cc2ncc(C#N)c(Nc3ccc(OCc4ccccn4)c(Cl)c3)c2cc1NC(=O)CCCOC] | ¹H NMR (400 MHz, Methanol-d₄) δ 9.07 (s, 1H), 8.77 (s, 1H), 8.60 (d, J = 5.0 Hz, 1H), 7.97 (td, J = 7.7, 1.8 Hz, 1H), 7.76 (d, J = 7.9 Hz, 1H), 7.58 (d, J = 2.6 Hz, 1H), 7.49-7.42 (m, 1H), 7.39 (dd, J = 8.8, 2.6 Hz, 1H), 7.34 (s, 1H), 7.28 (d, J = 8.8 Hz, 1H), 5.36 (s, 2H), 4.40 (q, J = 7.0 Hz, 2H), 3.49 (t, J = 6.2 Hz, 2H), 3.35 (s, 3H), 2.62 (t, J = 7.3 Hz, 2H), 2.03-1.92 (m, 2H), 1.59 (t, J = 7.0 Hz, 3H); MS-ESI (m/z) calcd for [C₂₉H₂₈ClN₅O₄ + H]⁺ 546.19; found: 546.23. |
| 103 | 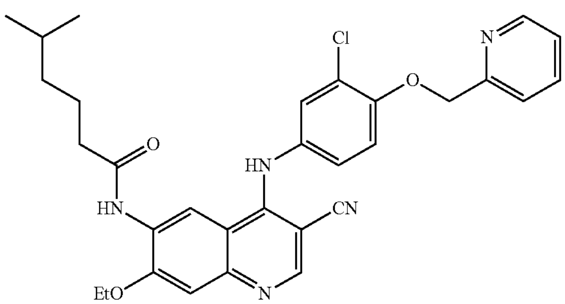 [SMILES: CCOc1cc2ncc(C#N)c(Nc3ccc(OCc4ccccn4)c(Cl)c3)c2cc1NC(=O)CCCC(C)C] | ¹H NMR (400 MHz, Methanol-d₄) δ 9.02 (s, 1H), 8.73 (s, 1H), 8.58 (d, J = 5.1 Hz, 1H), 7.94 (td, J = 7.6, 1.7 Hz, 1H), 7.74 (d, J = 8.0 Hz, 1H), 7.56 (d, J = 2.6 Hz, 1H), 7.46-7.40 (m, 1H), 7.37 (dd, J = 8.7, 2.6 Hz, 1H), 7.33 (s, 1H), 7.27 (d, J = 8.8 Hz, 1H), 5.35 (s, 2H), 4.39 (q, J = 6.9 Hz, 2H), 2.53 (t, J = 7.4 Hz, 2H), 1.81-1.68 (m, 2H), 1.66-1.52 (m, 4H), 1.38-1.22 (m, 2H), 0.92 (d, J = 6.6 Hz, 6H); MS-ESI (m/z) calcd for [C₃₃H₃₂ClN₅O₃ + H]⁺ 558.23; found: 558.29. |
| 104 | 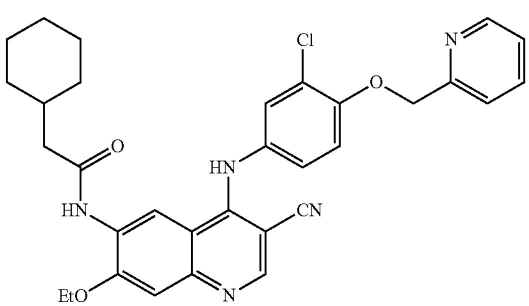 [SMILES: CCOc1cc2ncc(C#N)c(Nc3ccc(OCc4ccccn4)c(Cl)c3)c2cc1NC(=O)CC1CCCCC1] | ¹H NMR (400 MHz, Methanol-d₄) δ 8.98 (s, 1H), 8.74 (s, 1H), 8.59 (d, J = 5.2 Hz, 1H), 7.95 (td, J = 7.8, 1.7 Hz, 1H), 7.74 (d, J = 8.0 Hz, 1H), 7.56 (d, J = 2.5 Hz, 1H), 7.46-7.41 (m, 1H), 7.37 (dd, J = 8.7, 2.6 Hz, 1H), 7.33 (s, 1H), 7.27 (d, J = 8.8 Hz, 1H), 5.35 (s, 2H), 4.38 (q, J = 7.0 Hz, 2H), 2.41 (d, J = 6.9 Hz, 2H), 1.94-1.64 (m, 5H), 1.58 (t, J = 7.0 Hz, 3H), 1.40-1.16 (m, 4H), 1.09 (d, J = 11.8 Hz, 2H); MS-ESI (m/z) calcd for [C₃₂H₃₂ClN₅O₃ + H]⁺ 570.23; found: 570.35. |

| Ex. | Structure | Analytical Data |
|---|---|---|
| 105 | 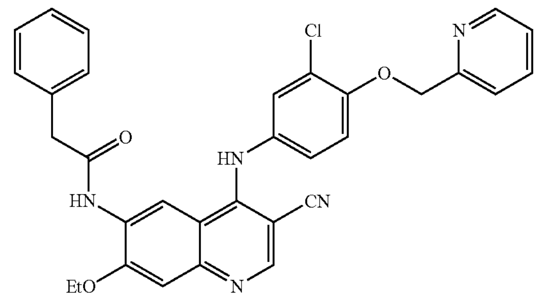 [SMILES: CCOc1cc2ncc(C#N)c(Nc3ccc(OCc4ccccn4)c(Cl)c3)c2cc1NC(=O)Cc1ccccc1] | $^1$H NMR (400 MHz, CDCl$_3$) δ 9.11 (s, 1H), 8.60 (d, J = 4.5 Hz, 1H), 8.38 (s, 1H), 8.12 (s, 1H), 7.77 (td, J = 7.7, 1.8 Hz, 1H), 7.66 (d, J = 7.9 Hz, 1H), 7.48-7.36 (m, 5H), 7.34-7.23 (m, 2H), 7.20-7.13 (m, 2H), 6.89 (dd, J = 8.7, 2.3 Hz, 1H), 6.83 (d, J = 8.8 Hz, 1H), 5.26 (s, 2H), 4.03 (q, J = 6.9 Hz, 2H), 3.84 (s, 2H), 1.26 (t, J = 6.9 Hz, 3H); MS-ESI (m/z) calcd for [C$_{32}$H$_{26}$ClN$_5$O$_3$ + H]$^+$ 564.18; found: 282.66 (z = 2). |
| 106 | 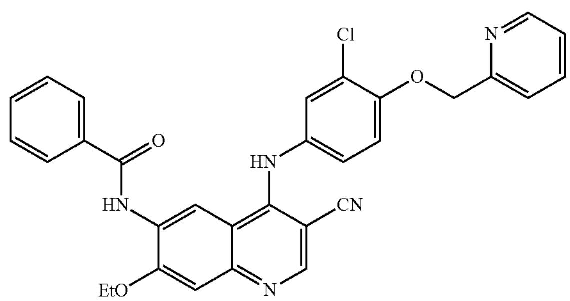 [SMILES: CCOc1cc2ncc(C#N)c(Nc3ccc(OCc4ccccn4)c(Cl)c3)c2cc1NC(=O)c1ccccc1] | $^1$H NMR (400 MHz, CDCl$_3$) δ 9.29 (s, 1H), 8.84 (s, 1H), 8.59 (d, J = 4.5 Hz, 1H), 8.44 (s, 1H), 7.87 (d, J = 7.4 Hz, 2H), 7.76 (td, J = 7.6, 1.8 Hz, 1H), 7.70-7.57 (m, 2H), 7.57-7.44 (m, 2H), 7.33-7.19 (m, 2H), 7.04 (dd, J = 8.7, 2.6 Hz, 1H), 6.88 (d, J = 8.7 Hz, 1H), 5.25 (s, 2H), 4.33 (q, J = 6.9 Hz, 2H), 1.58 (t, J = 7.0 Hz, 3H); MS-ESI (m/z) calcd for [C$_{31}$H$_{24}$ClN$_5$O$_3$ + H]$^+$ 550.16; found: 275.67 (z = 2). |

Example 107

Synthesis of N-(4-(3-chloro-4-(2-(pyridin-2-yl)ethyl)phenylamino)-3-cyano-7-ethoxyquinolin-6-yl)-4-(dimethylamino)butanamide (14)

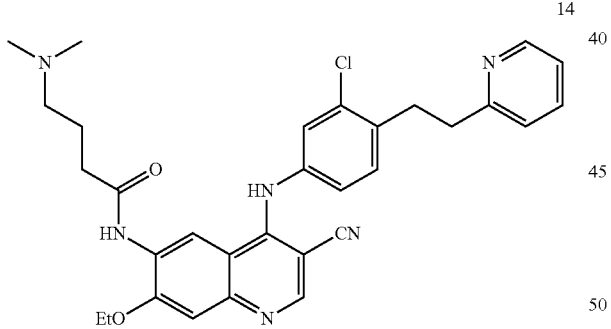

14

Step 1: 3-chloro-4-(pyridin-2-ylethynyl)aniline (12)

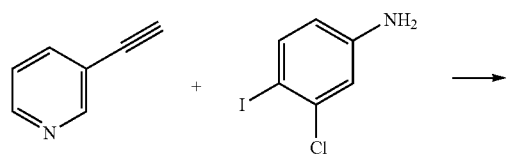

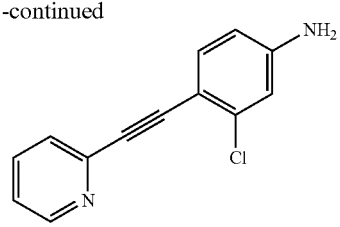

12

2-Ethynylpyridine (0.57 mL, 5.6 mmol), 4-iodo-3-chloroaniline (1.01 g, 4.0 mmol), PdCl$_2$(PPh$_3$)$_2$ (281 mg, 0.4 mmol), copper (I) iodide (152 mg, 0.8 mmol), trimethylamine (5.6 mL, 40 mmol) and DMF (4.5 mL) were added to a vial with a stirbar and the mixture was sparged with Argon. The reaction mixture was heated in a 90° C. heating block for 45 min then cooled to ambient temperature. The mixture was partitioned between water and ethyl acetate, and the organic layer was washed with brine, dried over Na$_2$SO$_4$, filtered and evaporated under reduced pressure. The crude product was purified by gradient flash column chromatography from 0-100% EtOAc in hexanes to yield 660 mg (72%) of 3-chloro-4-(pyridin-2-ylethynyl)aniline (12) as a yellow solid. $^1$H NMR (400 MHz, CDCl$_3$) δ 8.61 (s, 1H), 7.69 (t, J=7.7 Hz, 1H), 7.54 (d, J=7.8 Hz, 1H), 7.41 (d, J=8.4 Hz, 1H), 7.26-7.21 (m, 1H), 6.72 (s, 1H), 6.53 (d, J=8.4 Hz, 1H), 3.95 (br s, 2H).

Step 2: 3-chloro-4-(2-(pyridin-2-yl)ethyl)aniline (13)

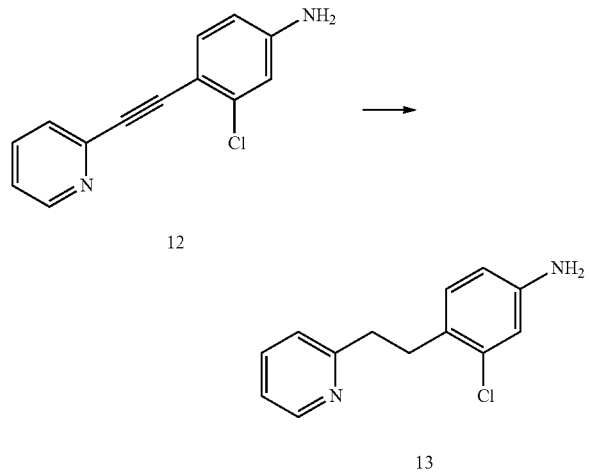

To a Parr shaker hydrogenation apparatus was added 12 (650 mg, 2.47 mmol), 10% Pd/C (50 mg) and EtOAc (15 mL). The reaction flask was filled to 80 psi with $H_2$ and the reaction was shaken for 16 h. After offgassing the $H_2$, the reaction mixture was passed through a pad of Celite then the crude product was purified by gradient flash column chromatography from 0-100% EtOAc in hexane. 3-chloro-4-(2-(pyridin-2-yl)ethyl)aniline (13) was isolated as a yellow solid, 343 mg (1.47 mmol, 60%). $^1$H NMR (400 MHz, CDCl$_3$) δ 8.58 (ddd, J=5.0, 1.9, 0.9 Hz, 1H), 7.63 (td, J=7.7, 1.9 Hz, 1H), 7.21-7.11 (m, 2H), 6.95 (d, J=8.2 Hz, 1H), 6.72 (d, J=2.4 Hz, 1H), 6.49 (dd, J=8.1, 2.4 Hz, 1H), 3.79 (br s, 2H), 3.16-2.99 (m, 4H).

Step 3: N-(4-(3-chloro-4-(2-(pyridin-2-yl)ethyl)phenylamino)-3-cyano-7-ethoxyquinolin-6-yl)-4-(dimethylamino)butanamide (14)

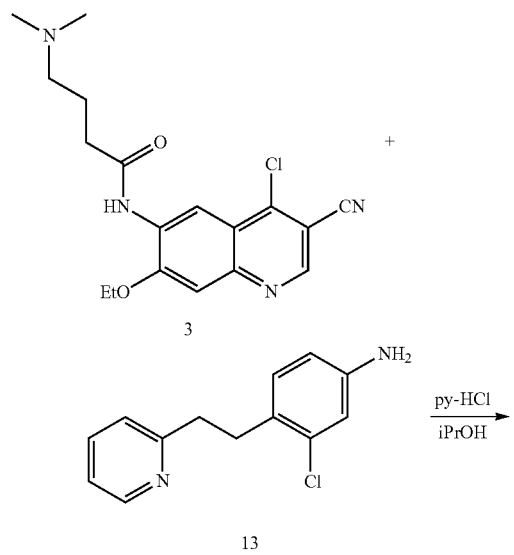

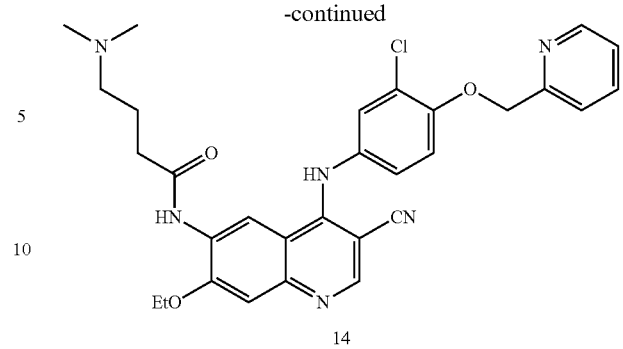

N-(4-(3-chloro-4-(2-(pyridin-2-yl)ethyl)phenylamino)-3-cyano-7-ethoxyquinolin-6-yl)-4-(dimethylamino)butanamide (14) was prepared by a similar procedure to that described for example 1 by coupling Compound 3 with Compound 13. $^1$H NMR (400 MHz, Methanol-d$_4$) δ 9.11 (s, 1H), 8.78 (s, 1H), 8.67 (d, J=5.8 Hz, 1H), 8.38 (tt, J=8.0, 2.0 Hz, 1H), 7.88-7.81 (m, 1H), 7.81-7.75 (m, 1H), 7.50 (s, 1H), 7.42 (s, 1H), 7.36-7.27 (m, 2H), 4.41 (q, J=6.7 Hz, 2H), 3.46-3.39 (m, 2H), 3.38-3.33 (m, 2H), 3.28-3.20 (m, 2H), 2.92 (s, 6H), 2.73 (t, J=6.9 Hz, 2H), 2.12 (p, J=7.1 Hz, 2H), 1.58 (t, J=7.0 Hz, 3H). MS-ESI (m/z) calcd for [C$_{31}$H$_{33}$ClN$_6$O$_2$+H]$^+$ 557.24; found: 279.24 (z=2).

Example 108

Synthesis of N-(2-chloro-4-(3-cyano-6-(4-(dimethylamino)butanamido)-7-ethoxyquinolin-4-ylamino)phenyl)-3-methylpicolinamide (15)

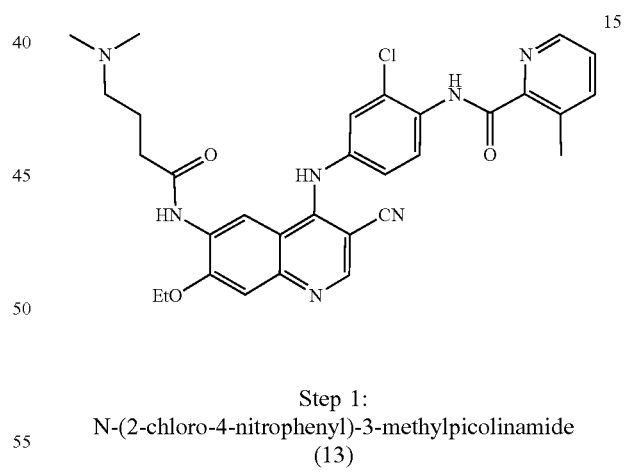

Step 1: N-(2-chloro-4-nitrophenyl)-3-methylpicolinamide (13)

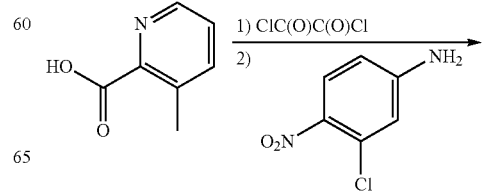

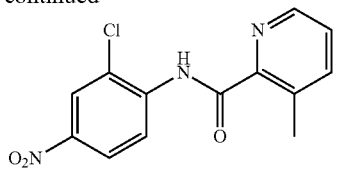

13

3-Methylpyridine-2-carboxylic acid (206 mg, 1.5 mmol) was stirred in dry $CH_2Cl_2$ (3 mL) under argon in a 0° C. ice-water bath. Oxalyl chloride (570 mg, 4.5 mmol) was added dropwise by syringe and the reaction was allowed to warm to ambient temperature and stir for 16 h, at which point the solvent was evaporated under reduced pressure and the residue was redissolved in 5 mL of $CH_2Cl_2$. 2-Chloro-4-nitroaniline (172 mg, 1 mmol) was added as a solid and the reaction mixture was stirred at ambient temperature under argon for 2.5 h. The solvent was removed under reduced pressure and the resulting crude product was purified by gradient flash column chromatography with 0-100% EtOAc in hexanes to yield N-(2-chloro-4-nitrophenyl)-3-methylpicolinamide (13) as a yellow solid (98 mg, 34%). $^1$H NMR (400 MHz, $CDCl_3$) δ 11.38 (s, 1H), 8.91 (d, J=9.2 Hz, 1H), 8.59-8.48 (m, 1H), 8.35 (d, J=2.6 Hz, 1H), 8.21 (dd, J=9.2, 2.6 Hz, 1H), 7.70 (dd, J=7.7, 1.5 Hz, 1H), 7.45 (dd, J=7.8, 4.6 Hz, 1H), 2.82 (s, 3H).

Step 2:
N-(4-amino-2-chlorophenyl)-3-methylpicolinamide (14)

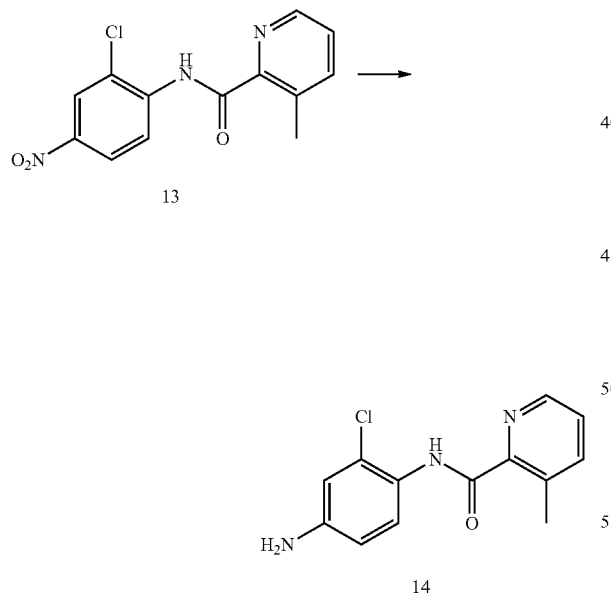

Compound 13 (98 mg, 0.34 mmol), zinc dust (230 mg, 3.5 mmol), ammonium chloride (45 mg, 0.85 mmol), methanol (5 mL) and water (1 mL) were stirred in a vial at ambient temperature for 16 h, then the mixture was filtered through filter paper and the solvents were removed under reduced pressure. The crude product was purified by gradient flash column chromatography with 0-100% EtOAc in hexanes with 0.1% triethylamine, to give N-(4-amino-2-chlorophenyl)-3-methylpicolinamide (14) (28 mg, 31%) as a yellow solid. LCMS (found 262.1, M+H$^+$).

Step 3: N-(2-chloro-4-(3-cyano-6-(4-(dimethylamino)butanamido)-7-ethoxyquinolin-4-ylamino)phenyl)-3-methylpicolinamide (15)

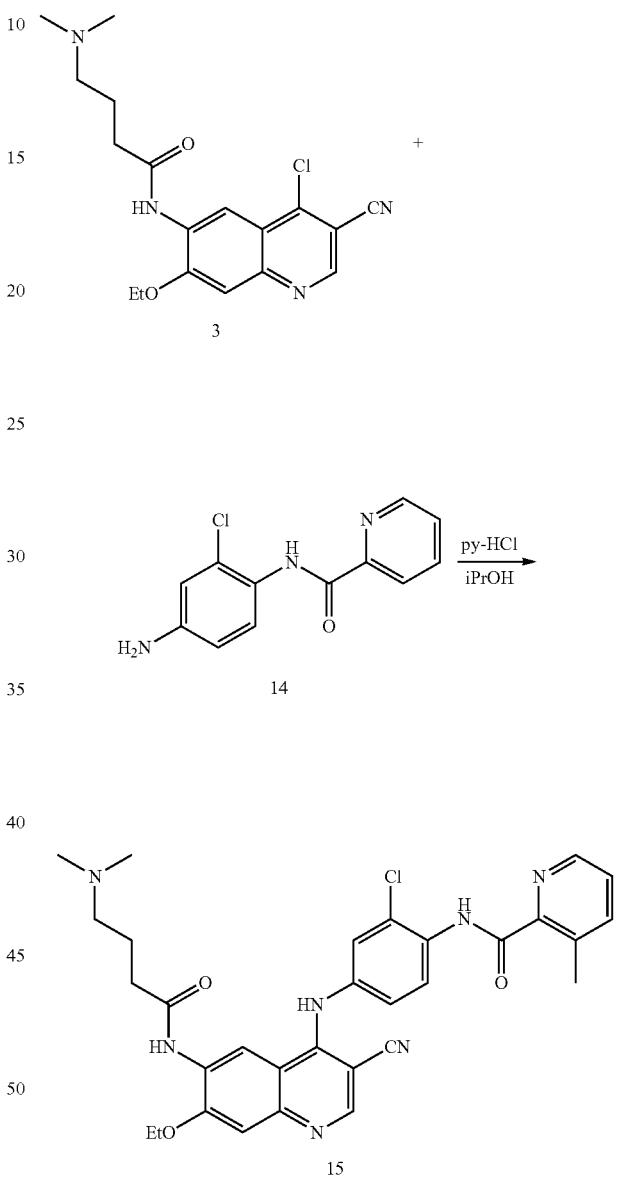

N-(2-chloro-4-(3-cyano-6-(4-(dimethylamino)butanamido)-7-ethoxyquinolin-4-ylamino)phenyl)-3-methylpicolinamide (15) was prepared by a similar procedure to that described for example 1 by coupling Compound 3 with Compound 14. $^1$H NMR (400 MHz, Methanol-d$_4$) δ 9.06 (s, 1H), 8.74 (s, 1H), 8.67 (d, J=8.8 Hz, 1H), 8.58 (d, J=4.5 Hz, 1H), 7.85 (d, J=7.7 Hz, 1H), 7.62-7.51 (m, 2H), 7.45-7.37 (m, 2H), 4.42 (q, J=7.2 Hz, 2H), 2.94 (s, 6H), 2.81 (s, 3H), 2.75 (t, J=6.8 Hz, 2H), 2.20-2.06 (m, 2H), 1.60 (t, J=7.0 Hz, 3H), 2H are unresolved and under the MeOD peak; MS-ESI (m/z) calcd for $[C_{31}H_{32}ClN_7O_3+H]^+$ 586.24; found: 586.2 (z=2).

Example 109

Synthesis of N-(2-chloro-4-(3-cyano-6-(4-(dimethylamino)butanamido)-7-ethoxyquinolin-4-ylamino)phenylbenzamide

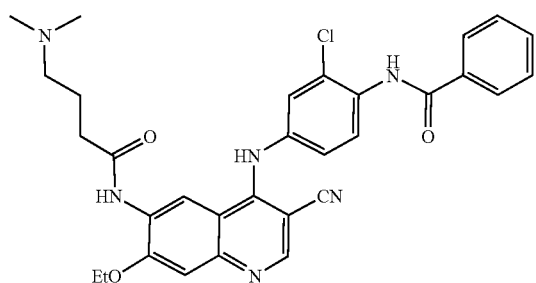 [SMILES: CCOc1cc2ncc(C#N)c(Nc3ccc(NC(=O)c4ccccc4)c(Cl)c3)c2cc1NC(=O)CCCN(C)C]

N-(2-chloro-4-(3-cyano-6-(4-(dimethylamino)butanamido)-7-ethoxyquinolin-4-ylamino)phenyl)benzamide was prepared by a similar procedure to that described for example 108 starting with benzoic acid in step 1. $^1$H NMR (400 MHz, Methanol-$d_4$) δ 9.09 (s, 1H), 8.79 (s, 1H), 8.08-7.97 (m, 3H), 7.68-7.48 (m, 4H), 7.48-7.38 (m, 2H), 4.41 (q, J=6.9 Hz, 2H), 3.27-3.21 (m, 2H), 2.92 (s, 6H), 2.74 (t, J=6.9 Hz, 2H), 2.19-2.04 (m, 2H), 1.59 (t, J=7.0 Hz, 3H); MS-ESI (m/z) calcd for [$C_{31}H_{31}ClN_6O_3$+H]$^+$ 571.22; found: 286.26 (z=2).

Example 110

Synthesis of N-(4-(6-acetamido-3-cyano-7-ethoxyquinolin-4-ylamino)-2-chlorophenyl)benzamide

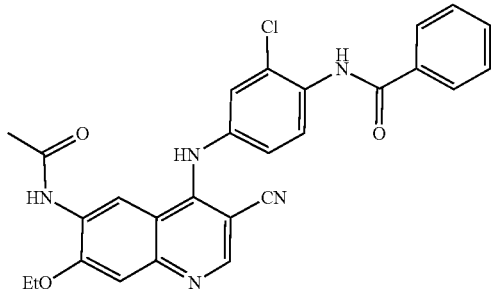 [SMILES: CCOc1cc2ncc(C#N)c(Nc3ccc(NC(=O)c4ccccc4)c(Cl)c3)c2cc1NC(C)=O]

N-(4-(6-acetamido-3-cyano-7-ethoxyquinolin-4-ylamino)-2-chlorophenyl)benzamide was prepared by a similar procedure to that described for example 1 by coupling Compound 1 with Compound 14. $^1$H NMR (400 MHz, Methanol-$d_4$) δ 9.13 (s, 1H), 8.87 (s, 1H), 8.09 (d, J=8.6 Hz, 1H), 8.01 (d, J=7.6 Hz, 2H), 7.70 (d, J=2.4 Hz, 1H), 7.63 (d, J=7.3 Hz, 1H), 7.56 (t, J=7.6 Hz, 2H), 7.52-7.46 (m, 1H), 7.35 (s, 1H), 4.42 (q, J=7.0 Hz, 2H), 2.29 (s, 3H), 1.61 (t, J=7.0 Hz, 3H); MS-ESI (m/z) calcd for [$C_{27}H_{22}ClN_5O_3$+H]$^+$ 500.15; found: 500.29.

Example 111

Synthesis of N-(4-(3-chloro-4-(pyridin-2-ylmethylamino)phenylamino)-3-cyano-7-ethoxyquinolin-6-yl)-4-(dimethylamino)butanamide (16)

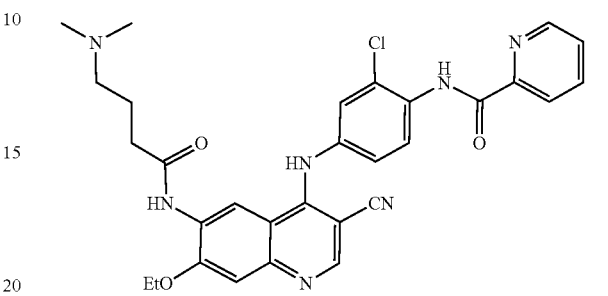

Step 1: 2-Chloro-4-nitro-N-(pyridin-2-ylmethyl)aniline (B)

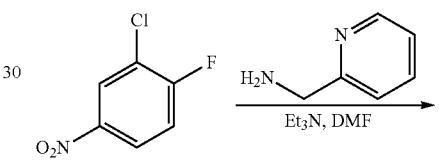

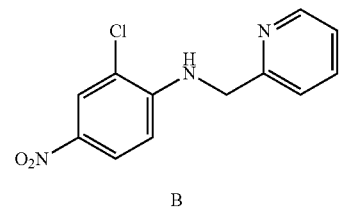

3-Chloro-4-fluoronitrobenzene (3.51 g, 20.0 mmol) and triethylamine (4.18 mL, 30.0 mmol) are dissolved in 20 mL of DMF in a round bottom flask charged with a stir bar. 2-(aminomethyl)pyridine is added via syringe and the reaction is allowed to stir under argon for 18 h. The reaction is stopped by the addition of water (100 mL) and the resulting mixture is filtered and washed with more water to yield 5.149 g of compound B as a yellow solid which is taken onto the next step without further purification.

Step 2: 2-Chloro-N1-(pyridin-2-ylmethyl)benzene-1,4-diamine (C)

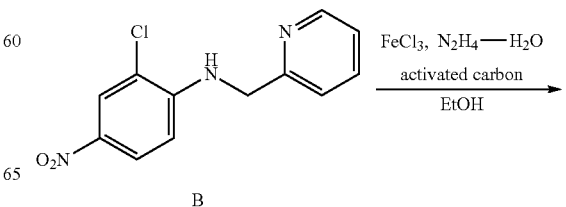

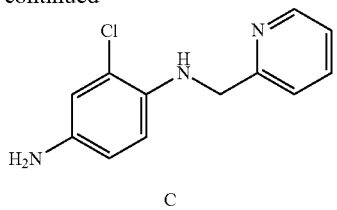

A round bottom flask is charged with 527 mg (2.0 mmol) of compound B, 500 mg of activated carbon, 16.2 mg (0.1 mmol) of FeCl$_3$, and 20 mL of ethanol and the flask is sparged with argon. Hydrazine monohydrate (400 mg, 8.0 mmol) is added by syringe and the reaction mixture is stirred under argon at 60° C. After 17 h, the reaction is cooled to room temperature and filtered through Celite, washing with methanol. The filtrate is evaporated and the resulting residue is purified by automated flash column chromatography (0 to 100% EtOAc in hexanes) to yield 113 mg (24%) of compound C as an off-white solid. 1H NMR (400 MHz, CDCl$_3$) δ 8.67-8.49 (m, 1H), 7.71-7.53 (m, 1H), 7.33 (t, J=6.4 Hz, 1H), 7.18 (dt, J=7.3, 4.8 Hz, 1H), 6.75 (d, J=2.3 Hz, 1H), 6.50 (dt, J=13.6, 8.7 Hz, 2H), 4.47 (d, J=5.0 Hz, 2H), 4.07-3.62 (m, 3H).

Step 3: N-(4-(3-chloro-4-(pyridin-2-ylmethylamino) phenylamino)-3-cyano-7-ethoxyquinolin-6-yl)-4-(dimethylamino)butanamide (16)

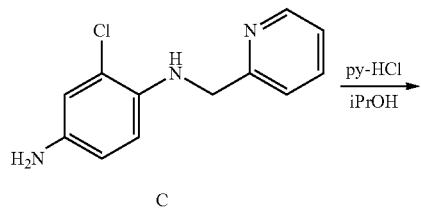

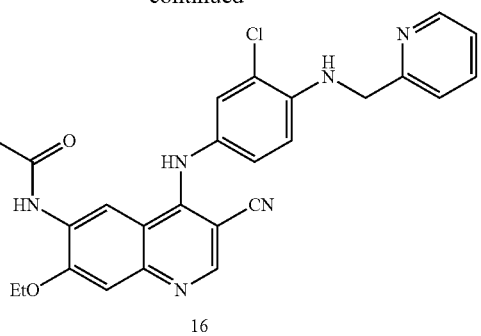

N-(4-(3-chloro-4-(pyridin-2-ylmethylamino)phenylamino)-3-cyano-7-ethoxyquinolin-6-yl)-4-(dimethylamino)butanamide (16) was prepared by a similar procedure to that described for example 1 by coupling Compound 3 with Compound C. $^1$H NMR (400 MHz, Methanol-d$_4$) δ 9.10 (s, 1H), 8.74 (s, 1H), 8.65 (d, J=4.8 Hz, 1H), 8.22-8.11 (m, 1H), 7.74 (d, J=8.2 Hz, 1H), 7.64 (t, J=6.5 Hz, 1H), 7.50-7.43 (m, 1H), 7.36 (s, 1H), 7.22-7.14 (m, 1H), 6.65 (d, J=8.8 Hz, 1H), 4.80 (s, 2H), 4.40 (q, J=7.1 Hz, 2H), 3.30-3.20 (m, 2H), 2.93 (s, 6H), 2.73 (t, J=6.9 Hz, 2H), 2.12 (p, J=7.3 Hz, 2H), 1.58 (t, J=6.9 Hz, 3H); MS-ESI (m/z) calcd for [C$_{30}$H$_{32}$ClN$_7$O$_2$+H]$^+$ 558.24; found: 279.78 (z=2).

Examples 112-114 were prepared according to a similar procedure as described for example 111:

| Ex. | Structure | Analytical Data |
|---|---|---|
| 112 | 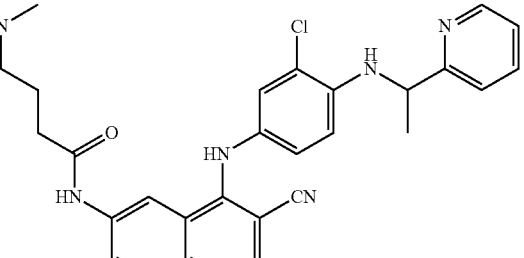 | $^1$H NMR (400 MHz, Methanol-d$_4$) δ 9.06 (s, 1H), 8.71 (d, J = 1.4 Hz, 1H), 8.58 (ddd, J = 5.2, 1.7, 0.9 Hz, 1H), 7.96 (td, J = 7.8, 1.7 Hz, 1H), 7.62 (dt, J = 7.9, 1.0 Hz, 1H), 7.48-7.40 (m, 2H), 7.34 (s, 1H), 7.10 (dd, J = 8.7, 2.4 Hz, 1H), 6.56 (d, J = 8.8 Hz, 1H), 4.85 (q, J = 7.0 Hz, 1H), 4.39 (q, J = 7.0 Hz, 2H), 3.27-3.20 (m, 2H), 2.92 (d, J = 1.7 Hz, 6H), 2.73 (t, J = 6.9 Hz, 2H), 2.17-2.06 (m, 2H), 1.67 (d, J = 6.8 Hz, 3H), 1.57 (t, J = 7.0 Hz, 3H); MS-ESI (m/z) calcd for [C$_{31}$H$_{34}$ClN$_7$O$_2$ + H]$^+$ 572.25; found: 572.20. |
| 113 | 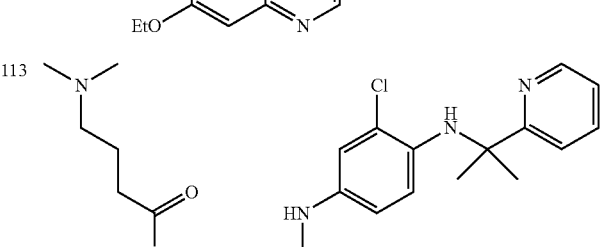 | $^1$H NMR (400 MHz, Methanol-d$_4$) δ 9.04 (s, 1H), 8.69 (s, 1H), 8.59 (ddd, J = 5.1, 1.7, 0.9 Hz, 1H), 7.98 (t, J = 7.8 Hz, 1H), 7.78 (d, J = 8.1 Hz, 1H), 7.49-7.40 (m, 2H), 7.33 (s, 1H), 6.98-6.91 (m, 1H), 6.11 (d, J = 8.8 Hz, 1H), 4.38 (q, J = 7.0 Hz, 2H), 3.27-3.19 (m, 2H), 2.92 (s, 6H), 2.72 (t, J = 7.0 Hz, 2H), 2.11 (dt, J = 15.0, 7.1 Hz, 2H), 1.81 (s, 6H), 1.57 (t, J = 7.0 Hz, 3H); MS-ESI (m/z) calcd for [C$_{32}$H$_{36}$ClN$_7$O$_2$ + H]$^+$ 586.27; found: 586.21. |

| Ex. | Structure | Analytical Data |
|---|---|---|
| 114 | 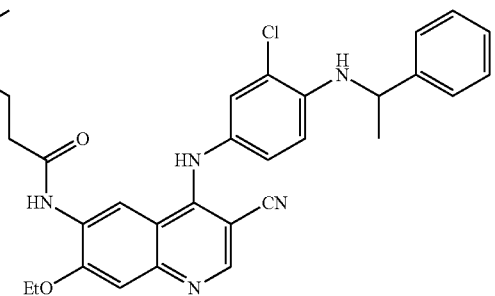 | $^1$H NMR (400 MHz, Methanol-$d_4$) δ 8.77 (s, 1H), 8.34 (s, 1H), 7.38 (d, J = 7.1 Hz, 2H), 7.34-7.28 (m, 3H), 7.26 (d, J = 2.4 Hz, 1H), 7.24-7.18 (m, 1H), 6.95 (dd, J = 8.7, 2.4 Hz, 1H), 6.50 (d, J = 8.8 Hz, 1H), 4.67-4.57 (m, 1H), 4.32 (q, J = 7.1 Hz, 2H), 2.72 (t, J = 7.8 Hz, 2H), 2.60 (t, J = 7.1 Hz, 2H), 2.51 (s, 6H), 2.02-1.93 (m, 2H), 1.62-1.50 (m, 6H); MS-ESI (m/z) calcd for $[C_{32}H_{35}ClN_6O_2 + H]^+$ 571.26; found: 571.28. |

Example 115

Synthesis of N-(3-cyano-7-ethoxy-4-(phenylamino)quinolin-6-yl)acetamide

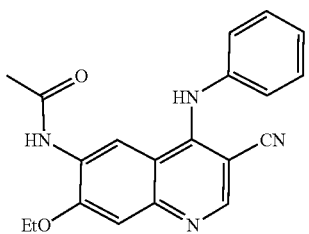 [SMILES: CCOc1cc2ncc(C#N)c(Nc3ccccc3)c2cc1NC(C)=O]

N-(3-cyano-7-ethoxy-4-(phenylamino)quinolin-6-yl)acetamide was prepared by a similar procedure to that described for example 1 by coupling Compound 1 with aniline. $^1$H NMR (400 MHz, Methanol-$d_4$) δ 9.06 (s, 1H), 8.74 (s, 1H), 7.55-7.41 (m, 5H), 7.34 (s, 1H), 4.40 (q, J=7.0 Hz, 2H), 2.28 (s, 3H), 1.59 (t, J=7.0 Hz, 3H).

Examples 116-136 were prepared according to a similar procedure as described for example 115:

| Ex. | Structure | Analytical Data |
|---|---|---|
| 116 | 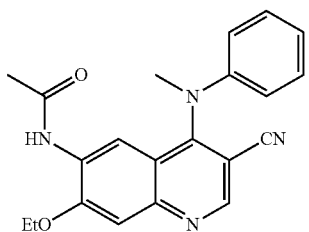 [SMILES: CCOc1cc2ncc(C#N)c(N(C)c3ccccc3)c2cc1NC(C)=O] | $^1$H NMR (400 MHz, Methanol-$d_4$) δ 10.44 (s, 1H), 10.37 (s, 1H), 9.02 (s, 1H), 8.85 (dd, J = 8.7, 7.3 Hz, 2H), 8.56 (t, J = 7.4 Hz, 1H), 8.49 (d, J = 7.7 Hz, 2H), 5.95 (q, J = 7.0 Hz, 2H), 5.26 (s, 3H), 3.75 (s, 3H), 3.13 (t, J = 7.0 Hz, 3H). |
| 117 | 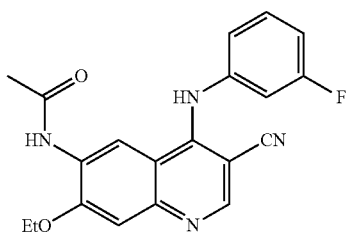 [SMILES: CCOc1cc2ncc(C#N)c(Nc3cccc(F)c3)c2cc1NC(C)=O] | $^1$H NMR (400 MHz, Methanol-$d_4$) δ 9.04 (s, 1H), 8.76 (s, 1H), 7.50 (td, J = 8.1, 6.2 Hz, 1H), 7.36 (s, 1H), 7.27-7.12 (m, 3H), 4.40 (q, J = 7.0 Hz, 2H), 2.28 (s, 3H), 1.59 (t, J = 7.0 Hz, 3H); MS-ESI (m/z) calcd for $[C_{20}H_{17}FN_4O_2 + H]^+$ 365.14; found: 365.21. |
| 118 | 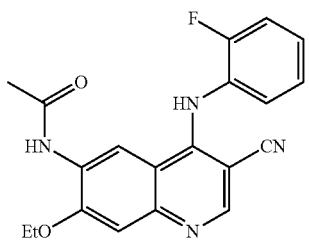 [SMILES: CCOc1cc2ncc(C#N)c(Nc3ccccc3F)c2cc1NC(C)=O] | $^1$H NMR (400 MHz, Methanol-$d_4$) δ 9.08 (s, 1H), 8.76 (s, 1H), 7.56-7.46 (m, 2H), 7.36 (s, 1H), 7.35-7.28 (m, 2H), 4.40 (q, J = 7.0 Hz, 2H), 2.28 (s, 3H), 1.59 (t, J = 7.0 Hz, 3H). |

-continued

| Ex. | Structure | Analytical Data |
|---|---|---|
| 119 | 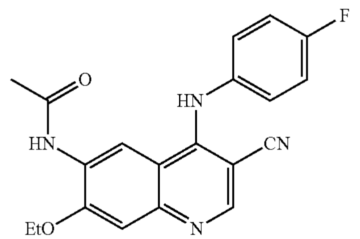 [SMILES: CCOc1cc2ncc(C#N)c(Nc3ccc(F)cc3)c2cc1NC(C)=O] | ¹H NMR (400 MHz, Methanol-d₄) δ 9.06 (s, 1H), 8.74 (s, 1H), 7.52-7.44 (m, 2H), 7.33 (s, 1H), 7.25 (t, J = 8.6 Hz, 2H), 4.40 (q, J = 7.0 Hz, 2H), 2.28 (s, 3H), 1.59 (t, J = 7.0 Hz, 3H); MS-ESI (m/z) calcd for [C₂₀H₁₇FN₄O₂ + H]⁺ 365.14; found: 365.21. |
| 120 | 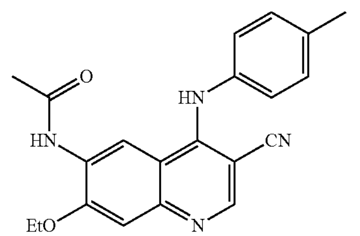 [SMILES: CCOc1cc2ncc(C#N)c(Nc3ccc(C)cc3)c2cc1NC(C)=O] | ¹H NMR (400 MHz, Methanol-d₄) δ 9.08 (s, 1H), 8.75 (s, 1H), 7.34 (s, 4H), 7.33 (s, 1H), 4.40 (q, J = 7.0 Hz, 2H), 2.44 (s, 3H), 2.28 (s, 3H), 1.59 (t, J = 7.0 Hz, 3H); MS-ESI (m/z) calcd for [C₂₁H₂₀N₄O₂ + H]⁺ 361.17; found: 361.24. |
| 121 | 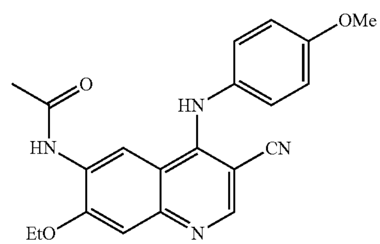 [SMILES: CCOc1cc2ncc(C#N)c(Nc3ccc(OC)cc3)c2cc1NC(C)=O] | ¹H NMR (400 MHz, Methanol-d₄) δ 9.05 (s, 1H), 8.71 (s, 1H), 7.37 (d, J = 8.9 Hz, 2H), 7.32 (s, 1H), 7.05 (d, J = 8.9 Hz, 2H), 4.39 (q, J = 7.0 Hz, 2H), 3.87 (s, 3H), 2.28 (s, 3H), 1.59 (t, J = 7.0 Hz, 3H); MS-ESI (m/z) calcd for [C₂₁H₂₀N₄O₃ + H]⁺ 377.16; found: 377.21. |
| 122 | 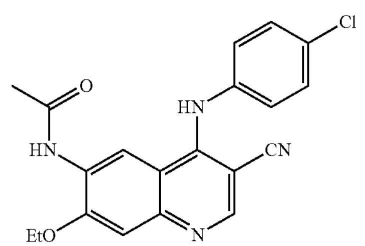 [SMILES: CCOc1cc2ncc(C#N)c(Nc3ccc(Cl)cc3)c2cc1NC(C)=O] | ¹H NMR (400 MHz, Methanol-d₄) δ 9.07 (s, 1H), 8.78 (s, 1H), 7.52 (d, J = 8.7 Hz, 2H), 7.43 (d, J = 8.7 Hz, 2H), 7.35 (s, 1H), 4.40 (q, J = 7.0 Hz, 2H), 2.28 (s, 3H), 1.59 (t, J = 7.0 Hz, 3H); MS-ESI (m/z) calcd for [C₂₀H₁₇ClN₄O₂ + H]⁺ 381.11; found: 381.11. |
| 123 | 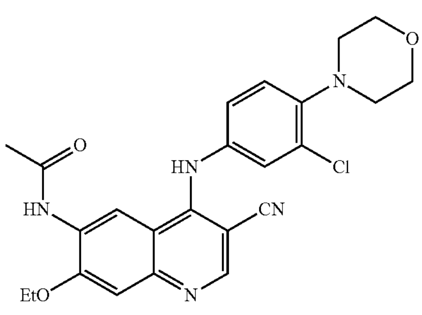 [SMILES: CCOc1cc2ncc(C#N)c(Nc3ccc(N4CCOCC4)c(Cl)c3)c2cc1NC(C)=O] | ¹H NMR (400 MHz, Methanol-d₄) δ 9.08 (s, 1H), 8.79 (d, J = 1.4 Hz, 1H), 7.53 (d, J = 2.3 Hz, 1H), 7.39 (dd, J = 8.5, 2.5 Hz, 1H), 7.34 (s, 1H), 7.26 (d, J = 8.6 Hz, 1H), 4.40 (q, J = 7.0 Hz, 2H), 3.91-3.82 (m, 4H), 3.14-3.08 (m, 4H), 2.28 (s, 3H), 1.59 (t, J = 7.0 Hz, 3H); MS-ESI (m/z) calcd for [C₂₄H₂₄ClN₅O₃ + H]⁺ 466.16; found: 466.18. |
| 124 | 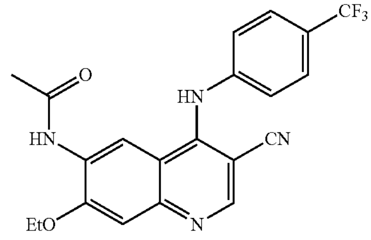 [SMILES: CCOc1cc2ncc(C#N)c(Nc3ccc(C(F)(F)F)cc3)c2cc1NC(C)=O] | ¹H NMR (400 MHz, Methanol-d₄) δ 9.10 (s, 1H), 8.85 (s, 1H), 7.80 (d, J = 8.3 Hz, 2H), 7.59 (d, J = 8.1 Hz, 2H), 7.39 (s, 1H), 4.41 (q, J = 7.0 Hz, 2H), 2.28 (s, 3H), 1.60 (t, J = 7.0 Hz, 3H); MS-ESI (m/z) calcd for [C₂₁H₁₇F₃N₄O₂ + H]⁺ 415.14; found: 415.21. |

| Ex. | Structure | Analytical Data |
|---|---|---|
| 125 | 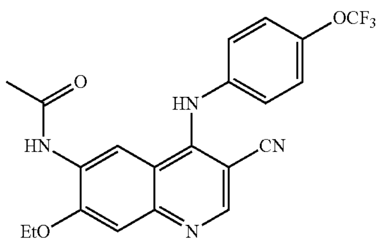 [SMILES: CCOc1cc2ncc(C#N)c(Nc3ccc(OC(F)(F)F)cc3)c2cc1NC(C)=O] | ¹H NMR (400 MHz, Methanol-d₄) δ 9.09 (s, 1H), 8.81 (s, 1H), 7.57 (d, J = 8.9 Hz, 2H), 7.43 (d, J = 8.3 Hz, 2H), 7.39 (d, J = 2.6 Hz, 1H), 4.40 (q, J = 7.0 Hz, 2H), 2.28 (s, 3H), 1.59 (t, J = 7.0 Hz, 3H); MS-ESI (m/z) calcd for [$C_{21}H_{17}F_3N_4O_3$ +H]⁺ 431.13; found: 431.18. |
| 126 | 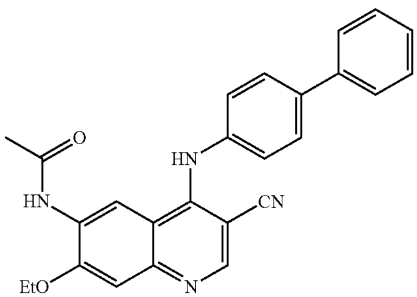 [SMILES: CCOc1cc2ncc(C#N)c(Nc3ccc(-c4ccccc4)cc3)c2cc1NC(C)=O] | ¹H NMR (400 MHz, Methanol-d₄) δ 9.08 (s, 1H), 8.76 (s, 1H), 7.76 (d, J = 8.5 Hz, 2H), 7.69 (dd, J = 8.3, 1.3 Hz, 2H), 7.54-7.43 (m, 4H), 7.41-7.31 (m, 2H), 4.40 (q, J = 7.0 Hz, 2H), 2.28 (s, 3H), 1.60 (t, J = 7.0 Hz, 3H); MS-ESI (m/z) calcd for [$C_{26}H_{22}N_4O_2$ + H]⁺ 423.18; found: 423.16. |
| 127 | 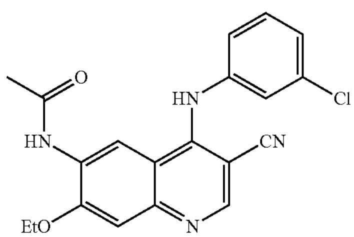 [SMILES: CCOc1cc2ncc(C#N)c(Nc3cccc(Cl)c3)c2cc1NC(C)=O] | ¹H NMR (400 MHz, Methanol-d₄) δ 9.11 (s, 1H), 8.83 (d, J = 1.4 Hz, 1H), 7.55-7.32 (m, 5H), 4.41 (q, J = 7.0 Hz, 2H), 2.28 (d, J = 1.4 Hz, 3H), 1.64-1.54 (m, 3H); MS-ESI (m/z) calcd for [$C_{20}H_{17}ClN_4O_2$ + H]⁺ 381.11; found: 381.18. |
| 128 | 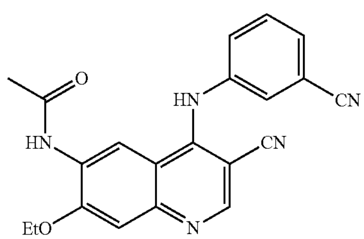 [SMILES: CCOc1cc2ncc(C#N)c(Nc3cccc(C#N)c3)c2cc1NC(C)=O] | ¹H NMR (400 MHz, Methanol-d₄) δ 9.11 (s, 1H), 8.85 (s, 1H), 7.86 (t, J = 1.9 Hz, 1H), 7.82-7.66 (m, 3H), 7.39 (s, 1H), 4.42 (q, J = 7.0 Hz, 2H), 2.28 (s, 3H), 1.60 (t, J = 7.0 Hz, 3H); MS-ESI (m/z) calcd for [$C_{21}H_{17}N_5O_2$ + H]⁺ 372.15; found: 372.19. |
| 129 | 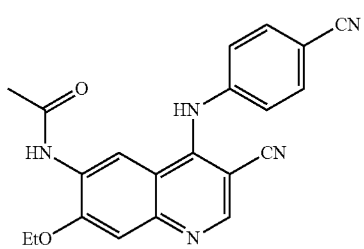 [SMILES: CCOc1cc2ncc(C#N)c(Nc3ccc(C#N)cc3)c2cc1NC(C)=O] | ¹H NMR (400 MHz, Methanol-d₄) δ 9.05 (s, 1H), 8.85 (s, 1H), 7.81 (d, J = 8.4 Hz, 2H), 7.48 (d, J = 8.2 Hz, 2H), 7.41 (s, 1H), 4.41 (q, J = 6.9 Hz, 2H), 2.27 (s, 3H), 1.59 (t, J = 7.0 Hz, 3H). |
| 130 | 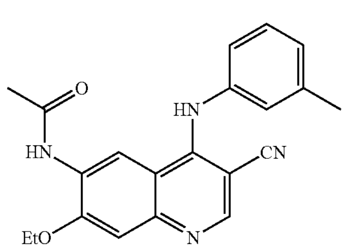 [SMILES: CCOc1cc2ncc(C#N)c(Nc3cccc(C)c3)c2cc1NC(C)=O] | ¹H NMR (400 MHz, Methanol-d₄) δ 9.05 (s, 1H), 8.72 (s, 1H), 7.39 (t, J = 7.7 Hz, 1H), 7.33 (s, 1H), 7.31-7.18 (m, 3H), 4.39 (q, J = 7.0 Hz, 2H), 2.42 (s, 3H), 2.28 (s, 3H), 1.59 (t, J = 7.0 Hz, 3H); MS-ESI (m/z) calcd for [$C_{21}H_{20}N_4O_2$ + H]⁺ 361.17; found: 361.24. |

-continued

| Ex. | Structure | Analytical Data |
|---|---|---|
| 131 | 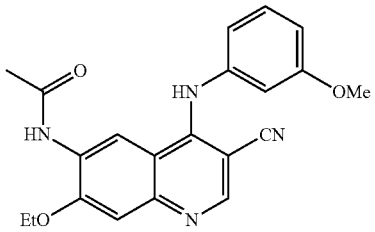 [SMILES: CCOc1cc2ncc(C#N)c(Nc3cccc(OC)c3)c2cc1NC(C)=O] | ¹H NMR (400 MHz, Methanol-d₄) δ 9.06 (s, 1H), 8.73 (s, 1H), 7.43-7.32 (m, 2H), 7.04-6.92 (m, 3H), 4.37 (q, J = 7.0 Hz, 2H), 3.83 (s, 3H), 2.29 (s, 3H), 1.59 (t, J = 7.0 Hz, 3H); MS-ESI (m/z) calcd for [C₂₁H₂₀N₄O₃ + H]⁺ 377.16; found: 377.21. |
| 132 | 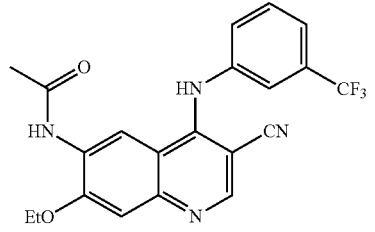 [SMILES: CCOc1cc2ncc(C#N)c(Nc3cccc(C(F)(F)F)c3)c2cc1NC(C)=O] | ¹H NMR (400 MHz, Methanol-d₄) δ 9.13 (s, 1H), 8.84 (s, 1H), 7.84-7.67 (m, 4H), 7.42 (s, 1H), 4.41 (q, J = 6.9 Hz, 2H), 2.29 (s, 3H), 1.60 (t, J = 7.0 Hz, 3H); MS-ESI (m/z) calcd for [C₂₁H₁₇F₃N₄O₂ + H]⁺ 415.14; found: 415.21. |
| 133 | 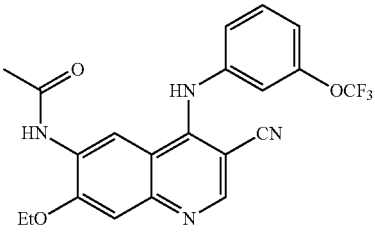 [SMILES: CCOc1cc2ncc(C#N)c(Nc3cccc(OC(F)(F)F)c3)c2cc1NC(C)=O] | ¹H NMR (400 MHz, Methanol-d₄) δ 9.12 (s, 1H), 8.85 (s, 1H), 7.62 (t, J = 8.1 Hz, 1H), 7.53-7.36 (m, 4H), 4.41 (q, J = 6.9 Hz, 2H), 2.28 (s, 3H), 1.60 (t, J = 6.9 Hz, 3H); MS-ESI (m/z) calcd for [C₂₁H₁₇F₃N₄O₃ + H]⁺ 431.13; found: 431.11. |
| 134 | 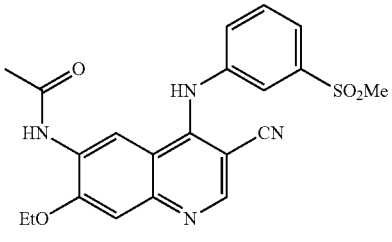 [SMILES: CCOc1cc2ncc(C#N)c(Nc3cccc(S(C)(=O)=O)c3)c2cc1NC(C)=O] | ¹H NMR (400 MHz, Methanol-d₄) δ 9.08 (s, 1H), 8.80 (s, 1H), 8.03-7.92 (m, 2H), 7.82-7.69 (m, 2H), 7.37 (s, 1H), 4.41 (q, J = 7.0 Hz, 2H), 3.16 (s, 3H), 2.28 (s, 3H), 1.60 (t, J = 7.0 Hz, 3H); MS-ESI (m/z) calcd for [C₂₁H₂₀N₄O₄S + H]⁺ 425.13; found: 425.11. |
| 135 | 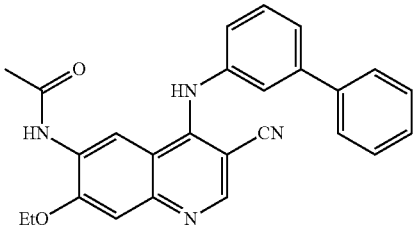 [SMILES: CCOc1cc2ncc(C#N)c(Nc3cccc(-c4ccccc4)c3)c2cc1NC(C)=O] | ¹H NMR (400 MHz, Methanol-d₄) δ 9.10 (s, 1H), 8.75 (s, 1H), 7.73-7.63 (m, 4H), 7.58 (t, J = 7.8 Hz, 1H), 7.49-7.33 (m, 5H), 4.39 (q, J = 7.0 Hz, 2H), 2.28 (s, 3H), 1.59 (t, J = 6.9 Hz, 3H); MS-ESI (m/z) calcd for [C₂₆H₂₂N₄O₂ + H]⁺ 423.18; found: 423.16. |
| 136 | 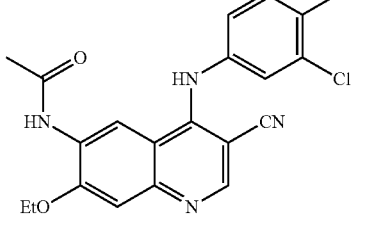 | ¹H NMR (400 MHz, Methanol-d₄) δ 9.07 (s, 1H), 8.76 (s, 1H), 7.51 (d, J = 2.6 Hz, 1H), 7.39 (dd, J = 8.7, 2.6 Hz, 1H), 7.33 (s, 1H), 7.20 (d, J = 8.8 Hz, 1H), 4.40 (q, J = 7.0 Hz, 2H), 3.97 (s, 3H), 2.28 (s, 3H), 1.59 (t, J = 7.0 Hz, 3H); MS-ESI (m/z) calcd for [C₂₁H₁₉ClN₄O₃ + H]⁺ 411.12; found: 411.17. |

Example 137

Synthesis of N-(4-(3-chlorophenylamino)-3-cyano-7-ethoxyquinolin-6-yl)-4-(dimethylamino)butanamide (18)

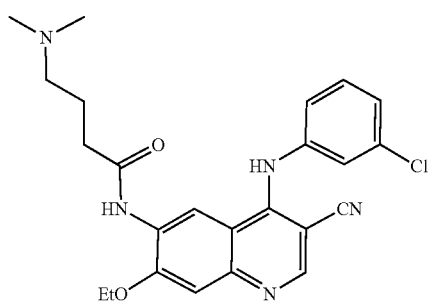

Step 1: 6-Amino-4-(3-chlorophenylamino)-7-ethoxyquinoline-3-carbonitrile (17)

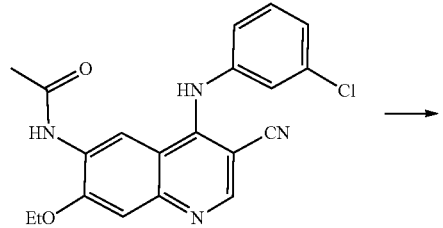

Compound 17 was prepared according to a similar procedure as described for Compound 2 (example 1) beginning with the compound described as Example 127. Compound 17 was used without further purification.

Step 2: N-(4-(3-Chlorophenylamino)-3-cyano-7-ethoxyquinolin-6-yl)-4-(dimethylamino)butanamide (18)

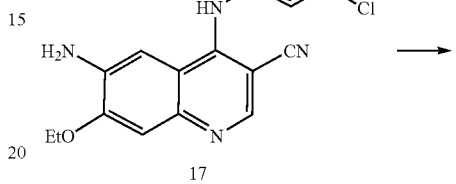

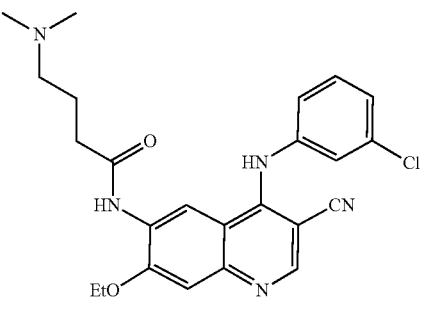

N-(4-(3-Chlorophenylamino)-3-cyano-7-ethoxyquinolin-6-yl)-4-(dimethylamino)butanamide (18) was prepared according to a similar procedure as described for intermediate 3 (example 1) beginning with Compound 17. $^1$H NMR (400 MHz, Methanol-$d_4$) δ 9.10 (s, 1H), 8.78 (s, 1H), 7.52-7.44 (m, 3H), 7.43 (s, 1H), 7.38 (dt, J=7.5, 1.8 Hz, 1H), 4.39 (q, J=7.0 Hz, 2H), 3.28-3.20 (m, 2H), 2.92 (s, 6H), 2.74 (t, J=6.9 Hz, 2H), 2.18-2.06 (m, 2H), 1.58 (t, J=7.0 Hz, 3H); MS-ESI (m/z) calcd for $[C_{24}H_{26}ClN_5O_2+H]^+$ 452.18; found: 452.17.

Examples 138-139 were prepared according to a similar procedure as described for example 137:

| Ex. | Structure | Analytical Data |
|---|---|---|
| 138 | 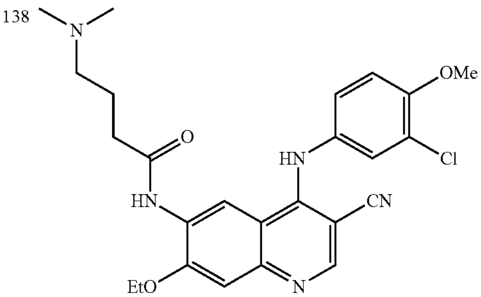 | ¹H NMR (400 MHz, Methanol-d₄) δ 9.08 (s, 1H), 8.75 (s, 1H), 7.59-7.47 (m, 1H), 7.46-7.31 (m, 2H), 7.28-7.16 (m, 1H), 4.40 (q, J = 7.8, 7.0 Hz, 2H), 3.97 (s, 3H), 2.93 (s, 6H), 2.79-2.68 (m, 2H), 2.13 (dd, J = 14.9, 7.7 Hz, 2H), 1.58 (t, J = 8.3 Hz, 3H), 1.40-1.29 (m, 2H). |
| 139 | 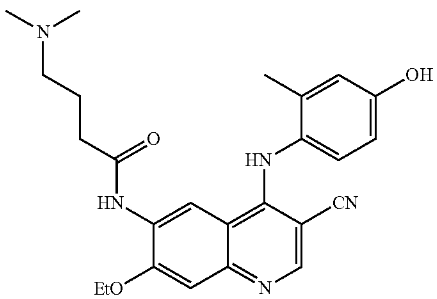 [SMILES: CCOc1cc2ncc(C#N)c(Nc3ccc(O)cc3C)c2cc1NC(=O)CCCN(C)C] | ¹H NMR (400 MHz, Methanol-d₄) δ 9.13 (s, 1H), 8.72 (d, J = 0.7 Hz, 1H), 8.53 (d, J = 5.3 Hz, 1H), 8.12 (d, J = 7.9 Hz, 1H), 7.71-7.63 (m, 1H), 7.36 (d, J = 8.9 Hz, 2H), 7.17 (d, J = 2.8 Hz, 1H), 7.09 (dd, J = 8.6, 2.7 Hz, 1H), 5.43 (s, 2H), 4.40 (q, J = 7.0 Hz, 2H), 3.31 (dq, J = 3.2, 1.6 Hz, 23H), 2.93 (d, J = 0.8 Hz, 6H), 2.74 (t, J = 6.9 Hz, 2H), 2.53 (s, 3H), 2.32 (s, 3H), 2.14 (q, J = 7.4 Hz, 2H), 1.58 (t, J = 7.0 Hz, 3H); MS-ESI (m/z) calcd for [C₂₅H₂₉N₅O₃ + H]⁺ 448.23; found: 277.83. |

Example 140

Synthesis of 4-(3-chloro-4-(pyridin-2-ylmethoxy)phenylamino)-7-ethoxy-6-(methylamino)quinoline-3-carbonitrile (20)

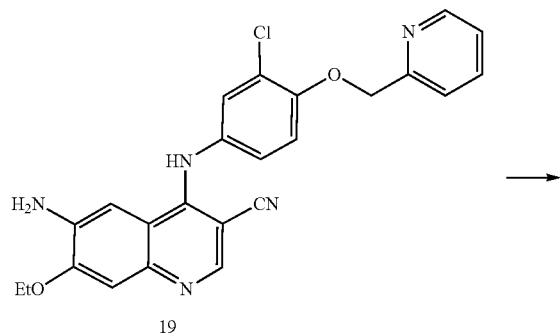

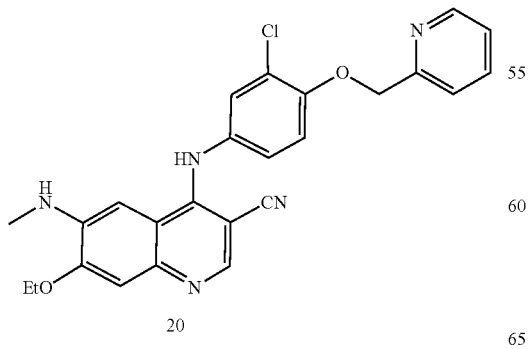

To a stirred suspension of 6-amino-4-((3-chloro-4-(pyridin-2-ylmethoxy)phenyl)amino)-7-ethoxyquinoline-3-carbonitrile (19) (30 mg, 0.067 mmol) and sodium bicarbonate (6 mg, 0.07 mmol) in DMF (0.75 mL) is added iodomethane (11 mg, 0.08 mmol) and the reaction is stirred at room temperature. After 2 h, the reaction is stopped with the addition of water (2 mL) and extracted into CH₂Cl₂ (2×2 mL). The combined organic layer is washed with brine and evaporated. The resulting crude residue is purified by automatic flash column chromatography (2% to 8% methanol in CH₂Cl₂) to give 4-(3-chloro-4-(pyridin-2-ylmethoxy)phenylamino)-7-ethoxy-6-(methylamino)quinoline-3-carbonitrile (20) (1.8 mg, 6%) as a yellow solid. ¹H NMR (400 MHz, Methanol-d₄) δ 8.58 (d, J=5.3 Hz, 1H), 8.26 (s, 1H), 7.96-7.89 (m, 1H), 7.74 (d, J=7.9 Hz, 1H), 7.44-7.37 (m, 2H), 7.25-7.13 (m, 3H), 7.02 (s, 1H), 5.31 (s, 2H), 4.30 (q, J=7.0 Hz, 2H), 2.95 (s, 3H), 1.55 (t, J=6.9 Hz, 3H); MS-ESI (m/z) calcd for [C₂₅H₂₂ClN₅O₂+H]⁺ 460.15; found: 230.55 (z=2).

Examples 141-142 were prepared according to a similar procedure as described for example 140:

| Ex. | Structure | Analytical Data |
|---|---|---|
| 141 | 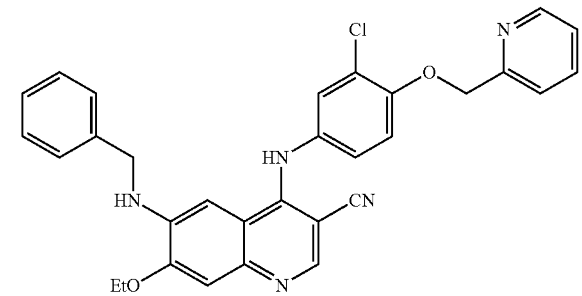 [SMILES: CCOc1cc2ncc(C#N)c(Nc3ccc(OCc4ccccn4)c(Cl)c3)c2cc1NCc1ccccc1] | $^1$H NMR (400 MHz, CDCl$_3$) δ 8.60 (d, J = 4.8 Hz, 1H), 7.88-7.66 (m, 3H), 7 55 (s, 1H), 7 39 (dd, J = 11.7, 7 0 Hz, 3H), 7.22 (d, J = 7.5 Hz, 3H), 7.05 (d, J = 2.5 Hz, 1H), 6.95 (d, J = 8.6 Hz, 1H), 6.81 (dd, J = 8.3, 2.5 Hz, 1H), 6.50 (s, 1H), 5.30 (s, 2H), 5.16 (s, 2H), 3.90 (q, J = 7.0 Hz, 2H), 1.37 (t, J = 6.9 Hz, 3H); MS-ESI (m/z) calcd for [C$_{31}$H$_{26}$ClN$_5$O$_2$ + H]$^+$ 536.18; found: 268.68 (z = 2). |
| 142 | 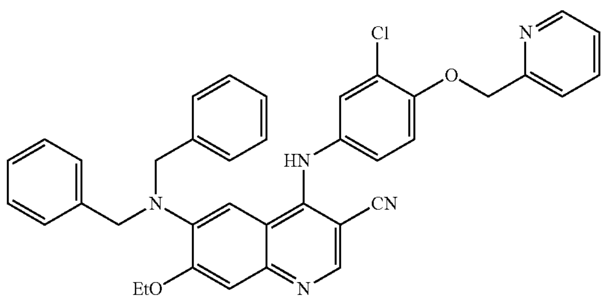 [SMILES: CCOc1cc2ncc(C#N)c(Nc3ccc(OCc4ccccn4)c(Cl)c3)c2cc1N(Cc1ccccc1)Cc1ccccc1] | $^1$H NMR (400 MHz, CDCl$_3$) δ 8.59 (dt, J = 4.8, 1.4 Hz, 1H), 7.91-7.64 (m, 3H), 7.57 (s, 1H), 7.46-7.05 (m, 13H), 6.99-6.81 (m, 2H), 6.54 (s, 1H), 5.30 (s, 2H), 5.21 (s, 2H), 4.70 (s, 1H), 4.47 (s, 2H), 3.93 (q, J = 7.0 Hz, 2H), 1.33 (t, J = 7.0 Hz, 3H); MS-ESI (m/z) calcd for [C$_{38}$H$_{32}$ClN$_5$O$_2$ + H]$^+$ 626.23; found: 313.67 (z = 2). |

Example 143

Synthesis of N-(4-(3-chloro-4-(3-methylpyridin-2-yloxy)phenylamino)-3-cyano-7-ethoxyquinolin-6-yl)-4-(dimethylamino)butanamide (22)

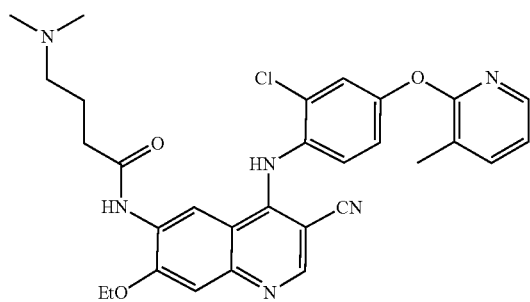

22

Step 1: 2-Chloro-4-(3-methylpyridin-2-yloxy)aniline (21)

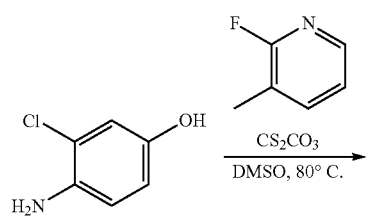

-continued

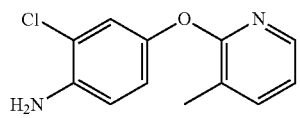

21

4-amino-3-chlorophenol (0.5 g, 3.5 mmol) was combined with 2-Fluoro-3-methylpyridine (0.387 g, 3.5 mmol), DMSO (10 mL) and cesium carbonate (1.47 g, 4.17 mmol). The reaction mixture was stirred at 80° C. for 15 h. The reaction was cooled to room temperature and the suspension was filtered. The filtrate partitioned between ethyl acetate (25 mL) and water (20 mL), the organic layer was washed with brine (20 mL), dried over sodium sulfate, and concentrated in vacuum. The resulting was purified by automatic flash column chromatography (1 to 5% methanol in CH$_2$Cl$_2$) yielding the product; m/z of 235.1 (M+1$^+$) was observed. This product was taken to the next step without further characterization.

Step 2: N-(4-(3-chloro-4-(3-methylpyridin-2-yloxy) phenylamino)-3-cyano-7-ethoxyquinolin-6-yl)-4-(dimethylamino)butanamide (22)

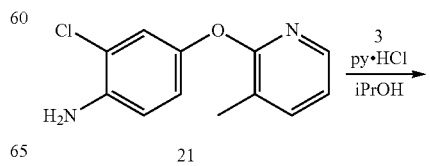

21

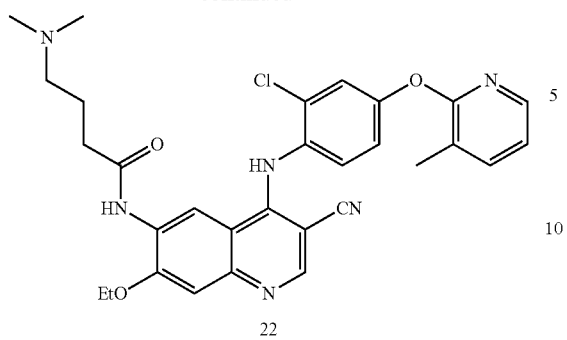

22

N-(4-(3-chloro-4-(3-methylpyridin-2-yloxy)phenylamino)-3-cyano-7-ethoxyquinolin-6-yl)-4-(dimethylamino)butanamide (22) was prepared by a similar procedure to that described for example 1 by coupling Compound 3 with 2-chloro-4-((3-methylpyridin-2-yl)oxy)aniline (21). $^1$H NMR (400 MHz, Methanol-$d_4$) δ 9.15 (s, 1H), 8.77 (s, 1H), 8.05-7.98 (m, 1H), 7.75 (ddd, J=7.4, 1.9, 1.0 Hz, 1H), 7.57 (d, J=8.7 Hz, 1H), 7.38 (s, 1H), 7.32 (d, J=2.6 Hz, 1H), 7.19-7.10 (m, 2H), 4.97-4.73 (m, 3H), 4.40 (q, J=7.0 Hz, 2H), 3.30-3.19 (m, 2H), 2.92 (s, 6H), 2.73 (t, J=6.9 Hz, 2H), 2.33 (s, 3H), 2.18-2.06 (m, 2H), 1.57 (t, J=7.0 Hz, 3H); MS-ESI (m/z) calcd for $[C_{30}H_{31}ClN_6O_3+H]^+$ 559.21; found: 280.32 (z=2).

Example 144

Synthesis of N-(4-(2-chloro-4-((3-methylpyridin-2-yl)methoxy)phenylamino)-3-cyanoquinolin-6-yl)-4-(dimethylamino)butanamide (30)

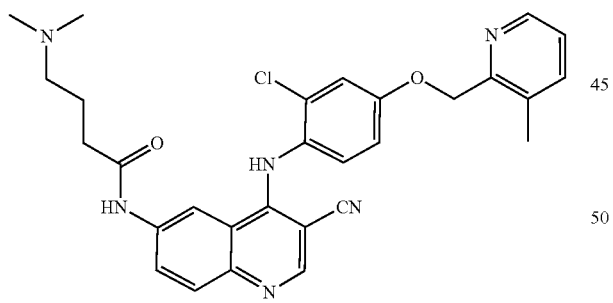

30

Step 1: N-(4-(((2,2-Dimethyl-4,6-dioxo-1,3-dioxan-5-ylidene)methyl)amino)phenyl)acetamide (23)

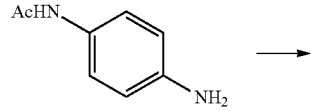

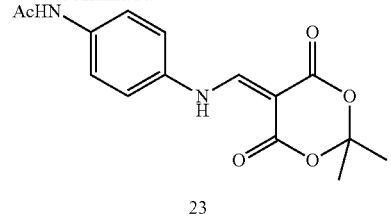

23

A suspension of N-(4-aminophenyl)acetamide (5 g, 33.3 mmol) in 100 mL of isopropanol was heated at 50° C. for 10 min at which point 5-(methoxymethylene)-2,2-dimethyl-1,3-dioxane-4,6-dione (6.2 g, 33.3 mmol) was added. The resulting suspension was heated at 80° C. for 1 h before being cooled to room temperature. The solid was filtered, washed well with ether, and dried in vacuo to provide compound 23 (8 g, 78%) as a brown solid that was immediately used in the next step.

Step 2: N-(4-Oxo-1,4-dihydroquinolin-6-yl)acetamide (24)

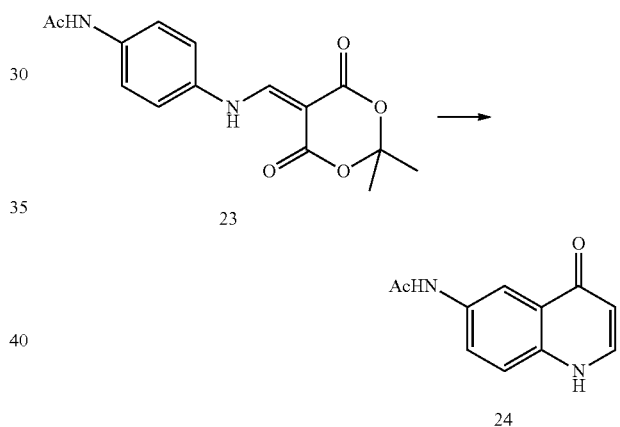

A suspension of compound 23 (8 g, 26.3 mmol) in 135 mL of diphenyl ether was heated at 240° C. for 18 h. The mixture was cooled to room temperature and filtered. The resulting brown solid was washed with ether and dried in vacuo to provide N-(4-oxo-1,4-dihydroquinolin-6-yl)acetamide (24) (2 g, 37%) as a brown solid that was used without further purification.

Step 3: N-(3-bromo-4-oxo-1,4-dihydroquinolin-6-yl)acetamide (25)

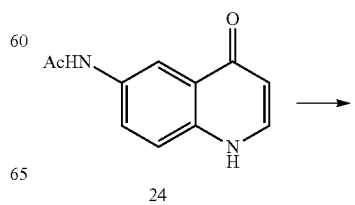

24

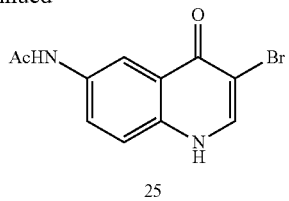

25

To a stirred suspension of compound 24 (2 g, 9.89 mmol) in AcOH (30 mL) was added dropwise a solution of Br$_2$ (0.5 mL, 9.89 mmol) over 10 min, the resulting reaction mixture was stirred at rt for 1 h. The resulting solid was collected, washed with cooled EtOH (30 mL), and dried under reduced pressure to give to provide compound 25 as a faint brown solid; m/z of 281.9 (M+1$^+$). This product was taken to the next step without further characterization.

Step 4: N-(3-cyano-4-oxo-1,4-dihydroquinolin-6-yl)acetamide (26)

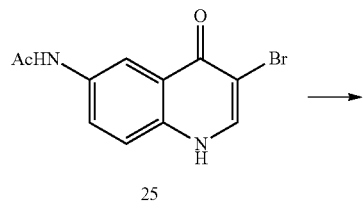

Compound 25 (1 g, 3.55 mmol), CuCN (636 mg, 7.11 mmol) and CuI (169 mg, 0.887 mmol) were suspended in DMF (15 mL) under nitrogen. The reaction mixture stirred and heated 130-140° C. for 6 h and then cooled rt. The resulting mixture filtered through a celite pad and celite pad was washed with 50 Ml of DMF. The combined filtrate was concentrated. The residue was suspended in 50% EtOH/EtOAc (50 mL), stirred and heated to 70° C. for 1 h. After cooled to room temperature, the resulting solid was collected washed with 50% EtOH/EtOAc (25 mL) and dried at 50° C. to give N-(3-cyano-4-oxo-1,4-dihydroquinolin-6-yl)acetamide (26); m/z of 215.1 (M+1$^+$). This product was taken to the next step without further characterization.

Step 5: N-(4-chloro-3-cyanoquinolin-6-yl)acetamide (27)

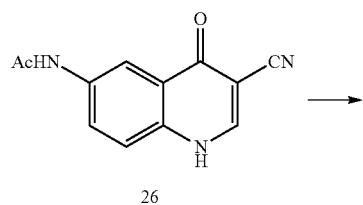

N-(3-cyano-4-oxo-1,4-dihydroquinolin-6-yl)acetamide (800 mg, 3.52 mmol) was added to 10 mL of thionyl chloride. Three drops of DMF were added, and the mixture was heated at 125° C. for 3 h. The mixture was cooled to room temperature, and the solvent was removed in vacuo. The derived solid was taken up in CH$_2$Cl$_2$ (50 mL) and poured into saturated NaHCO$_3$ (100 mL). The layers were separated, and the aqueous layer was extracted with CH$_2$Cl$_2$ (50 mL). The combined organic layers were washed with brine, dried over sodium sulfate, filtered, and concentrated to provide provide the title compound; m/z of 245.74 (M+1$^+$). This product was used in next step without further purification.

Step 6: N-(4-((2-Chloro-4-((3-methylpyridin-2-yl)methoxy)phenyl)amino)-3-cyanoquinolin-6-yl)acetamide (28)

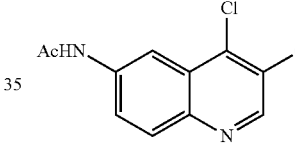

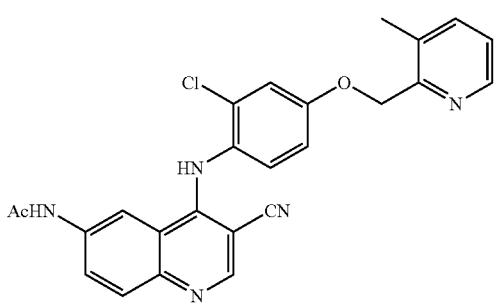

N-(4-((2-Chloro-4-((3-methylpyridin-2-yl)methoxy)phenyl)amino)-3-cyanoquinolin-6-yl)acetamide (28) was prepared by a similar procedure to that described for example 1 by coupling Compound 27 with Compound 8. $^1$H NMR (400 MHz, Methanol-d$_4$) δ 9.06 (s, 1H), 8.73 (s, 1H), 8.60 (d, J=4.9 Hz, 1H), 7.96 (td, J=7.8, 1.8 Hz, 1H), 7.75 (d, J=7.9 Hz, 1H), 7.58 (d, J=2.6 Hz, 1H), 7.45 (dd, J=7.3, 5.0 Hz, 1H), 7.38 (dd, J=8.7, 2.6 Hz, 1H), 7.35 (s, 1H), 7.28 (d, J=8.8 Hz, 1H), 5.36 (s, 2H), 2.30 (s, 3H), 2.06 (s, 3H); MS-ESI (m/z) calcd for [C$_{25}$H$_{20}$ClN$_5$O$_2$+H]$^+$ 458.13; found: 458.1

Step 7: 6-Amino-4-((2-chloro-4-((3-methylpyridin-2-yl)methoxy)phenyl)amino)quinoline-3-carbonitrile (29)

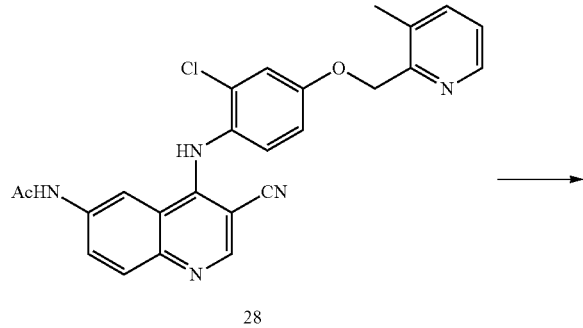

28

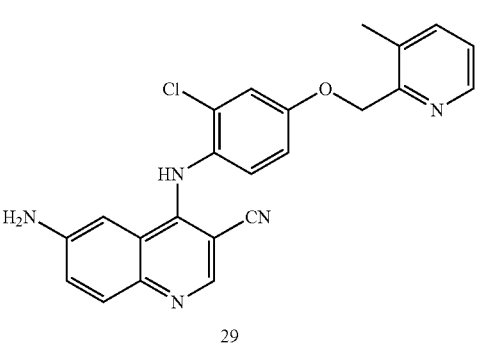

29

6-Amino-4-((2-chloro-4-((3-methylpyridin-2-yl)methoxy)phenyl)amino)quinoline-3-carbonitrile (29) was prepared by a similar procedure that described in example 1 step 1. The crude 6-amino-4-((2-chloro-4-((3-methylpyridin-2-yl) methoxy)phenyl)amino)quinoline-3-carbonitrile (29) was taken on to the next step without further purification.

Step 8: N-(4-(2-Chloro-4-((3-methylpyridin-2-yl)methoxy)phenylamino)-3-cyanoquinolin-6-yl)-4-(dimethylamino)butanamide (30)

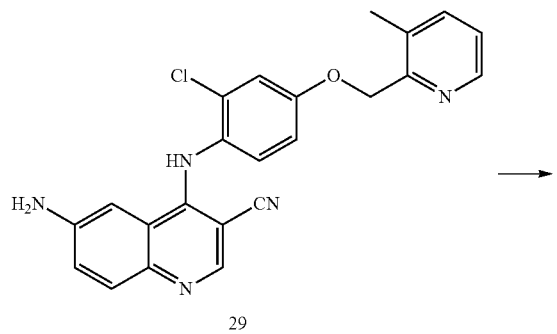

29

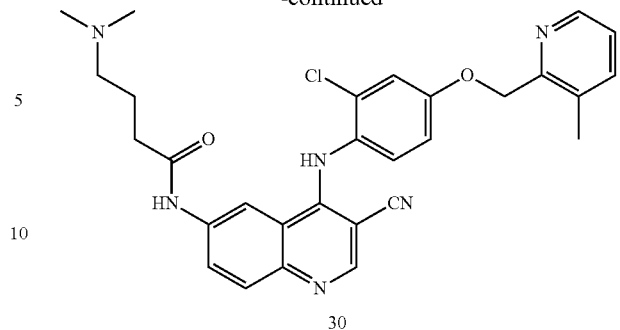

30

N-(4-(2-Chloro-4-((3-methylpyridin-2-yl)methoxy)phenylamino)-3-cyanoquinolin-6-yl)-4-(dimethylamino)butanamide (30) was prepared according to a similar procedure as described for example 95. $^1$H NMR (400 MHz, Methanol-$d_4$) δ 8.86 (s, 1H), 8.68-8.58 (m, 1H), 8.51-8.47 (m, 1H), 8.21-8.15 (m, 1H), 8.00 (d, J=8.7 Hz, 1H), 7.93 (s, 1H), 7.55 (dd, J=22.9, 9.0 Hz, 2H), 7.43-7.36 (m, 2H), 7.30 (s, 1H), 7.21 (s, 1H), 7.16-7.10 (m, 1H), 5.41 (s, 2H), 2.67 (dt, J=15.2, 7.3 Hz, 3H), 2.50 (d, J=3.2 Hz, 3H), 2.10 (dd, J=18.5, 9.3 Hz, 4H), 1.28 (s, 5H); MS-ESI (m/z) calcd for $[C_{29}H_{29}ClN_6O_2+H]^+$ 529.20; found: 529.7.

Example 145

Synthesis of N-(4-(2-chloro-4-((3-methylpyridin-2-yl)methoxy)phenylamino)-7-ethoxy-3-formylquinolin-6-yl)-4-(dimethylamino)butanamide (31)

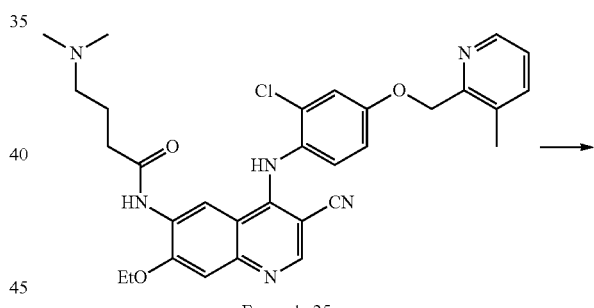

Example 25

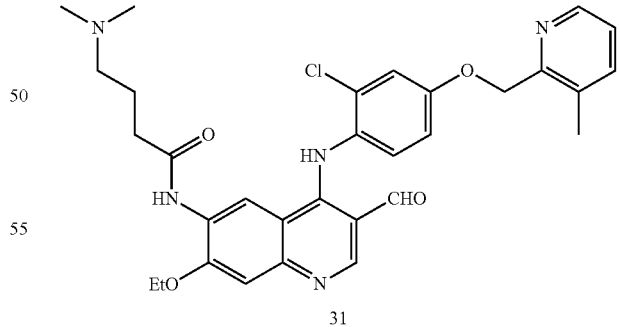

31

Diisobutylaluminium hydride solution (0.1 mL of 2 M solution in hexane) was added drop wise over a period of 5 min to a vigorously stirred solution of N-(4-((2-chloro-4-((3-methyl-pyridin-2-yl)methoxy)phenyl)amino)-3-cyano-7-ethoxyquinolin-6-yl)-4-(dimethylamino)butanamide (example 25) (50 mg, 0.08 mmol) in anhydrous dichloromethane (10 mL) under nitrogen at −78° C. After the mixture was stirred for an additional 30 min. excess reagent was quenched by addition of methanol (1 mL) followed by 5% HCl (5 mL). The resulting mixture was allowed to warm to rt and the organic layer was removed. The aqueous layer was extracted with dichloromethane (10 mL), the combined organic layers, washed with brine (10 mL), dried over anhydrous $Na_2SO_4$ and the solvent was evaporated under vacuum, to afford the crude aldehyde which was purified by prep-HPLC to N-(4-(2-chloro-4-((3-methylpyridin-2-yl)methoxy)phenylamino)-7-ethoxy-3-formylquinolin-6-yl)-4-(dimethylamino)butanamide (31). $^1$H NMR (400 MHz, Methanol-$d_4$) δ 10.00 (s, 1H), 9.03 (s, 1H), 8.68 (s, 1H), 8.48 (d, J=4.9 Hz, 1H), 7.88 (d, J=7.8 Hz, 1H), 7.55-7.40 (m, 3H), 7.35 (s, 1H), 7.21 (dd, J=8.8, 2.8 Hz, 1H), 5.36 (s, 2H), 4.92 (d, J=8.4 Hz, 1H), 4.39 (q, J=7.0 Hz, 2H), 3.19-3.10 (m, 2H), 2.87 (s, 6H), 2.62-2.46 (m, 5H), 1.98 (dt, J=15.1, 6.9 Hz, 2H), 1.55 (t, J=7.0 Hz, 3H); MS-ESI (m/z) calcd for $[C_{31}H_{34}ClN_5O_4+H]^+$ 576.23; found: 576.29.

Example 146

Synthesis of N-(4-(2-chloro-4-((3-methylpyridin-2-yl)methoxy)phenylamino)-7-ethoxyquinazolin-6-yl)-4-(dimethylamino)butanamide (36)

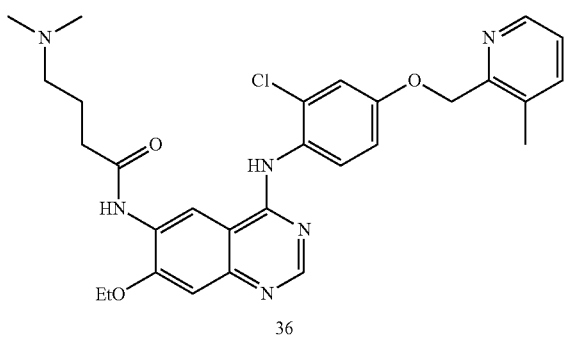 [SMILES: CCOc1cc2ncnc(Nc3ccc(OCc4ncccc4C)cc3Cl)c2cc1NC(=O)CCCN(C)C]

Step 1: 4-Chloro-7-ethoxy-6-nitroquinazoline (33)

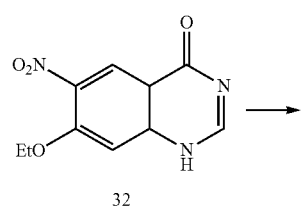

A suspension of 7-ethoxy-6-nitro-1,8a-dihydroquinazolin-4(4aH)-one (32) (314 mg, 1.34 mmol) in $POCl_3$ (15 mL) was heated to reflux for 1 h. The clear solution was then evaporated by $N_2$ stream and the residue was dissolved in $CH_2Cl_2$ and washed with aqueous $NaHCO_3$. The organic layer was dried and the solvent removed to obtain 4-chloro-7-ethoxy-6-nitroquinazoline (33); $^1$H NMR ($CDCl_3$, 400 MHz) δ 9.07 (s, 1H), 8.62 (s, 1H), 7.54 (s, 1H), 4.37 (q, J=7.0 Hz, 2H), 1.57 (t, J=7.0 Hz, 3H).

Step 2:
N-(4-Oxo-1,4-dihydroquinolin-6-yl)acetamide (34)

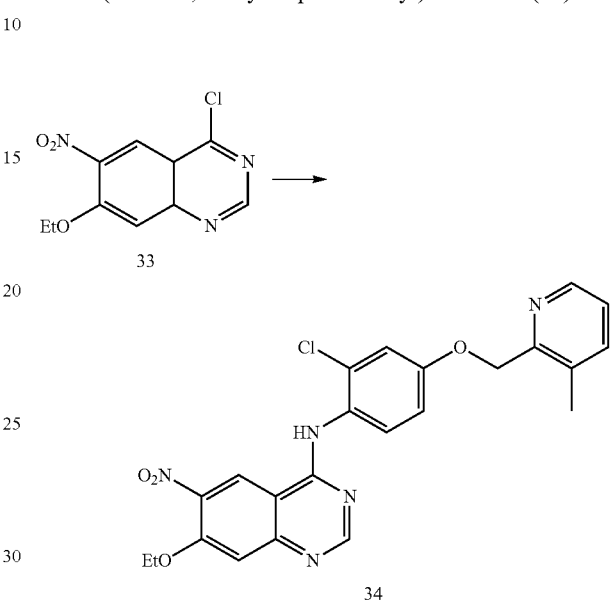

4-Chloro-7-ethoxy-6-nitroquinazoline (33) (100 mg, 0.214 mmol) and compound 8 (98 mg, 0.395 mmol) in i-PrOH (16 mL) were heated to reflux and conc HCl (3 drops) was added. The mixture was stirred and refluxed for 6 h and then basified by addition of $Et_3N$. The solvent was removed under reduced pressure, the solid residue was dissolved in $Et_2O$ and filtered, then the solvent was removed under reduced pressure and the residue was further dissolved in AcOEt and washed with $H_2O$. The organic layer was evaporated to dryness to give N-(4-Oxo-1,4-dihydroquinolin-6-yl)acetamide (34) that was used in the next step without further purifications.

Step 3: $N^4$-(2-Chloro-4-((3-methylpyridin-2-yl)methoxy)phenyl)-7-ethoxyquinazoline-4,6-diamine (35)

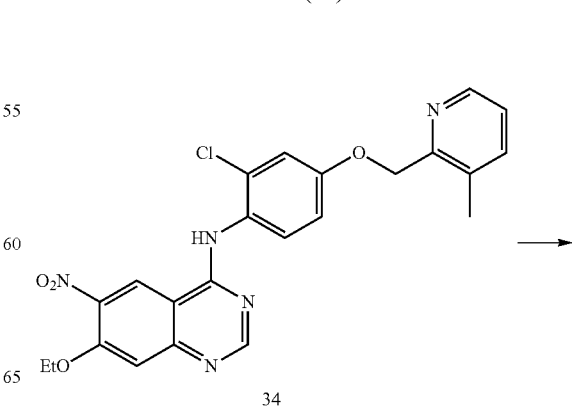

-continued

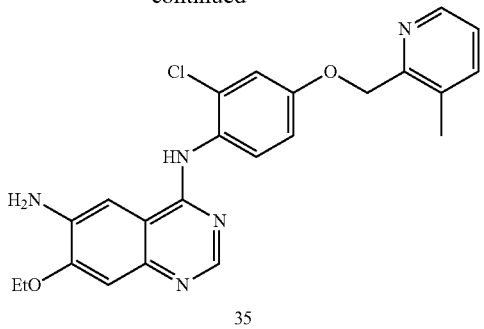

35

N-(4-Oxo-1,4-dihydroquinolin-6-yl)acetamide (34) (100 mg, 1.00 mmol) was dissolved in acetone/saturated aqueous NH$_4$Cl (5 mL each) at room temperature. Zinc nanopowder (42 mg, 0.643) was added, and the mixture was stirred vigorously for 30 min. The mixture was diluted with EtOAc (50 mL) and filtered to remove the Zn salts. The organic phase was washed with saturated aqueous NaHCO$_3$ (20 mL) and saturated aqueous NaCl (10 mL). The aqueous phase was extracted with EtOAc (2×10 mL), and the combined organic extracts were dried over Na$_2$SO$_4$ and concentrated to obtain N$^4$-(2-chloro-4-((3-methylpyridin-2-yl)methoxy) phenyl)-7-ethoxyquinazoline-4,6-diamine (35).

Step 4: N-(4-(2-chloro-4-((3-methylpyridin-2-yl) methoxy)phenylamino)-7-ethoxyquinazolin-6-yl)-4-(dimethylamino)butanamide (36)

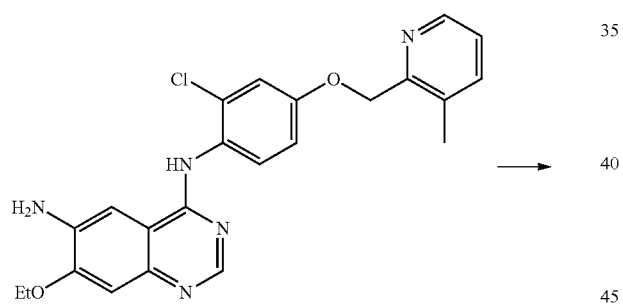

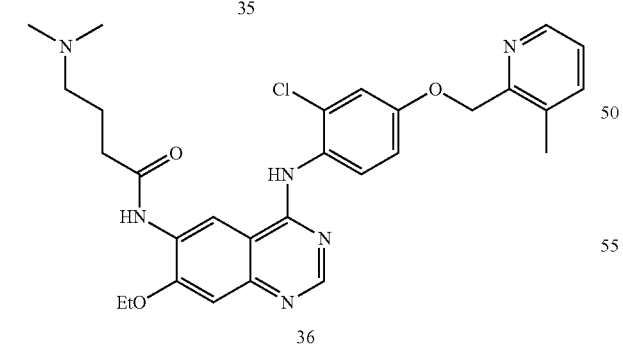

36

N-(4-(2-chloro-4-((3-methylpyridin-2-yl)methoxy)phenylamino)-7-ethoxyquinazolin-6-yl)-4-(dimethylamino)butanamide (36) was prepared according to a similar procedure as described for example 95. $^1$H NMR (400 MHz, Methanol-d$_4$) δ 9.17 (s, 1H), 8.62 (s, 1H), 8.50 (d, J=5.0 Hz, 1H), 7.97 (d, J=7.8 Hz, 1H), 7.60-7.46 (m, 2H), 7.40 (d, J=2.8 Hz, 1H), 7.29 (s, 1H), 7.21 (dd, J=8.9, 2.8 Hz, 1H), 5.39 (s, 2H), 4.42 (q, J=7.0 Hz, 2H), 3.32-3.23 (m, 2H), 2.95 (s, 6H), 2.76 (t, J=6.9 Hz, 2H), 2.52 (s, 3H), 2.15 (dt, J=15.1, 7.1 Hz, 2H), 1.60 (t, J=7.0 Hz, 3H); MS-ESI (m/z) calcd for [C$_{29}$H$_{33}$ClN$_6$O$_3$+H]$^+$ 549.23; found: 549.2.

Example 147

Synthesis of N-(4-(2-chloro-4-((3-methylpyridin-2-yl)methoxy)phenylamino)quinolin-6-yl)-4-(dimethylamino)butanamide

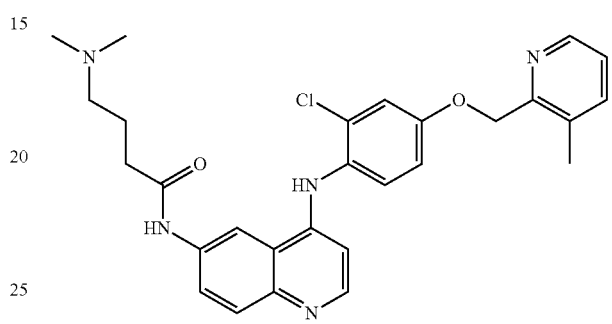

N-(4-(2-chloro-4-((3-methylpyridin-2-yl)methoxy)phenylamino)quinolin-6-yl)-4-(dimethylamino)butanamide (147) was prepared according to a similar procedure as described for example 144. $^1$H NMR (400 MHz, Methanol-d$_4$) δ 8.87 (d, J=2.0 Hz, 1H), 8.52 (d, J=5.3 Hz, 1H), 8.32 (dd, J=7.0, 1.8 Hz, 1H), 8.06-7.95 (m, 2H), 7.91 (dd, J=9.2, 1.7 Hz, 1H), 7.65-7.55 (m, 2H), 7.52-7.38 (m, 2H), 6.82 (dd, J=6.9, 1.8 Hz, 1H), 5.49-5.44 (m, 2H), 3.32-3.21 (m, 7H), 2.96-2.91 (m, 6H), 2.67 (td, J=7.0, 1.7 Hz, 2H), 2.59-2.53 (m, 3H), 2.20-2.07 (m, 2H); MS-ESI (m/z) calcd for [C$_{28}$H$_{30}$ClN$_5$O$_2$+H]$^+$ 504.21; found: 504.2.

Example 148

Synthesis of 1-(4-(3-chloro-4-(pyridin-2-ylmethoxy) phenylamino)-3-cyano-7-ethoxyquinolin-6-yl)-3-cyclohexylurea (37)

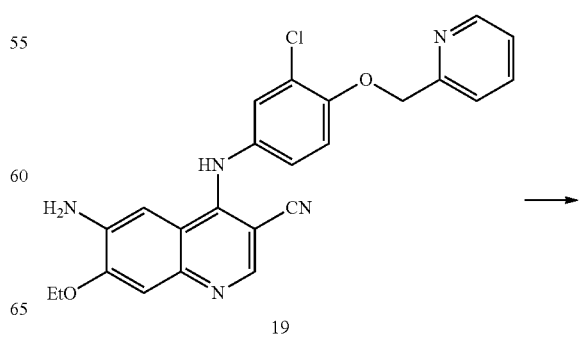

19

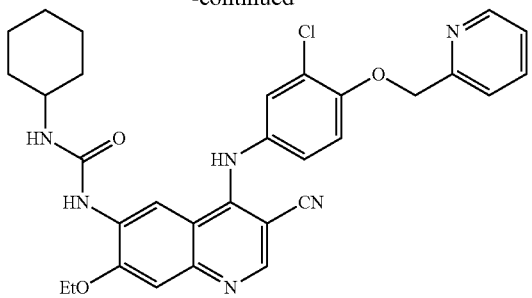

37

To a stirred solution of 6-amino-4-((3-chloro-4-(pyridin-2-ylmethoxy)phenyl)amino)-7-ethoxyquinoline-3-carbonitrile (19) and DIPEA (31 mg, 0.23 mmol) in THF (0.75 mL) is added cyclohexyl isocyanate (0.05 mL) and the reaction is stirred at room temperature for 2 days. At this point, the reaction is evaporated and purified by preparative HPLC (10% to 60% MeCN in water, +0.1% TFA). The starting material is reisolated as well as a very minor peak corresponding to the desired product, yielding 0.8 mg (2%) of 1-(4-(3-chloro-4-(pyridin-2-ylmethoxy)phenylamino)-3-cyano-7-ethoxyquinolin-6-yl)-3-cyclohexylurea (37) as a solid. $^1$H NMR (400 MHz, Methanol-$d_4$) δ 8.99 (s, 1H), 8.73 (s, 1H), 8.59 (d, J=5.0 Hz, 1H), 7.96 (td, J=7.8, 1.8 Hz, 1H), 7.75 (d, J=8.0 Hz, 1H), 7.59 (d, J=2.5 Hz, 1H), 7.47-7.42 (m, 1H), 7.39 (dd, J=8.7, 2.6 Hz, 1H), 7.31-7.26 (m, 2H), 5.36 (s, 2H), 4.40 (q, J=7.0 Hz, 2H), 3.70-3.55 (m, 1H), 2.01-1.90 (m, 2H), 1.82-1.70 (m, 2H), 1.61 (t, J=6.9 Hz, 3H), 1.47-1.34 (m, 2H), 1.34-1.20 (m, 4H).

Example 149

MST1/MST2 Biochemical LanthaScreen Eu Kinase Binding Assay

MST1 and MST2 biochemical LanthaScreen Eu Kinase Binding Assay was based on the binding and displacement of kinase tracer to the kinase of interest. Compounds in 1000×DMSO stock solution was dispensed using automated dispensing system (Labcyte) to 384 well Corning Microplate at 15 nL, 5 uL of Kinase buffer A was added to each well. Plates were shaken and incubated for 1 min to ensure well dissolution of compounds. Kinase/Antibody mixture was added at a final concentration of 5 nM and 2 nM and kinase tracer 222 solution at a final concentration of 100 nM in a total volume of 20 uL. Plates were incubated for 1.5 hrs in dark at room temperature and assay plates were scanned on Envision plate reader with excitation: 340 nM and kinase Tracer Emission at 665 nM. $IC_{50}$ data is shown in Table 1.

TABLE 1

MST1/EGFR/MAP4K4 Binding Assays

| Ex | Kinase Binding assay-MST1 $IC_{50}$ (nM) | Kinase Binding assay-MST2 $IC_{50}$ (nM) | Ex | Kinase Binding assay-MST1 $IC_{50}$ (nM) | Kinase Binding assay-MST2 $IC_{50}$ (nM) | Ex | Kinase Binding assay-MST1 $IC_{50}$ (nM) | Kinase Binding assay-MST2 $IC_{50}$ (nM) |
|---|---|---|---|---|---|---|---|---|
| 1 | A | A | 2 | A | A | 3 | A | A |
| 4 | A | A | 5 | A | B | 6 | B | B |
| 7 | A | A | 8 | A | B | 9 | B | B |
| 10 | A | B | 11 | B | A | 12 | A | A |
| 13 | B | B | 14 | B | B | 15 | A | A |
| 16 | A | A | 17 | A | A | 18 | A | B |
| 19 | A | A | 20 | A | B | 21 | A | B |
| 22 | A | A | 23 | A | A | 24 | A | A |
| 25 | A | A | 26 | A | A | 27 | B | C |
| 28 | A | A | 29 | B | B | 30 | A | B |
| 31 | A | A | 32 | A | B | 33 | A | A |
| 34 | A | A | 35 | A | A | 36 | B | B |
| 37 | A | B | 38 | B | B | 39 | A | B |
| 40 | B | B | 41 | A | A | 42 | A | B |
| 43 | B | C | 44 | B | B | 45 | A | A |
| 46 | B | NT | 47 | B | NT | 48 | B | NT |
| 49 | C | NT | 50 | C | NT | 51 | C | NT |
| 52 | NT | NT | 53 | B | NT | 54 | B | NT |
| 55 | B | NT | 56 | B | NT | 57 | B | NT |
| 58 | B | NT | 59 | C | NT | 60 | B | NT |
| 61 | C | NT | 62 | B | NT | 63 | B | NT |
| 64 | B | NT | 65 | C | NT | 66 | B | NT |
| 67 | B | B | 68 | B | NT | 69 | B | NT |
| 70 | B | NT | 71 | B | NT | 72 | B | NT |
| 73 | B | NT | 74 | A | A | 75 | A | A |
| 76 | A | A | 77 | A | A | 78 | A | A |
| 79 | A | A | 80 | B | B | 81 | A | A |
| 82 | B | B | 83 | A | A | 84 | A | A |
| 85 | A | C | 86 | NT | NT | 87 | NT | NT |
| 88 | NT | NT | 89 | NT | NT | 90 | A | A |
| 91 | A | A | 92 | A | A | 93 | A | A |
| 94 | A | A | 95 | A | B | 96 | A | NT |
| 97 | A | B | 98 | A | NT | 99 | B | B |
| 100 | NT | NT | 101 | C | NT | 102 | B | B |
| 103 | NT | NT | 104 | NT | NT | 105 | NT | NT |
| 106 | NT | NT | 107 | B | B | 108 | B | B |
| 109 | B | NT | 110 | NT | NT | 111 | B | NT |
| 112 | C | NT | 113 | C | NT | 114 | C | NT |

TABLE 1-continued

MST1/EGFR/MAP4K4 Binding Assays

| Ex | Kinase Binding assay- MST1 IC$_{50}$ (nM) | Kinase Binding assay- MST2 IC$_{50}$ (nM) | Ex | Kinase Binding assay- MST1 IC$_{50}$ (nM) | Kinase Binding assay- MST2 IC$_{50}$ (nM) | Ex | Kinase Binding assay- MST1 IC$_{50}$ (nM) | Kinase Binding assay- MST2 IC$_{50}$ (nM) |
|---|---|---|---|---|---|---|---|---|
| 115 | C | NT | 116 | C | NT | 117 | NT | NT |
| 118 | B | NT | 119 | NT | NT | 120 | B | NT |
| 121 | B | NT | 122 | C | NT | 123 | NT | NT |
| 124 | NT | NT | 125 | NT | NT | 126 | NT | NT |
| 127 | A | A | 128 | NT | NT | 129 | C | NT |
| 130 | C | NT | 131 | B | NT | 132 | NT | NT |
| 133 | NT | NT | 134 | C | NT | 135 | NT | NT |
| 136 | B | NT | 137 | C | NT | 138 | C | NT |
| 139 | B | C | 140 | B | C | 141 | NT | NT |
| 142 | NT | NT | 143 | A | A | 144 | B | B |
| 145 | C | C | 146 | C | NT | 147 | C | C |
| 148 | NT | NT | | | | | | |

A = IC$_{50}$ less than 100 nM;
B = IC$_{50}$ greater than or equal to 100 nM and less than 1 μM;
C = IC$_{50}$ greater than or equal to 1 μM and less than 10 μM;
NT = not tested

Example 150

Nucview488 Cell Based Assay

Nucview488 cell based assay was carried out in INS1 beta cells, using a membrane-permeable fluorogenic caspase substrate to detect caspase-3/7 activity in living cells without inhibiting activity of the caspase. Compounds in 1000× DMSO stock solution was dispensed using automated dispensing system (Labcyte) to 384 well Corning Microplate at 25 nL, cells were added to the assay plate at 10 k cells/well in 25 uL of the completed growth media, 24 hours later, Nucview488 substrate/Thapsigargin mixture in cell growth media was added to a final concentration of 1 uM and 25 nM, respectively at 25 uL total volume. 16 hours later, cells were fixed with 3% PFA and stained with 0.2 ug/mL Hoechst33342 and plates were scanned and fluorescence was detected and qualitied through imaging software Cellomics.

Example 151

Figure 8:
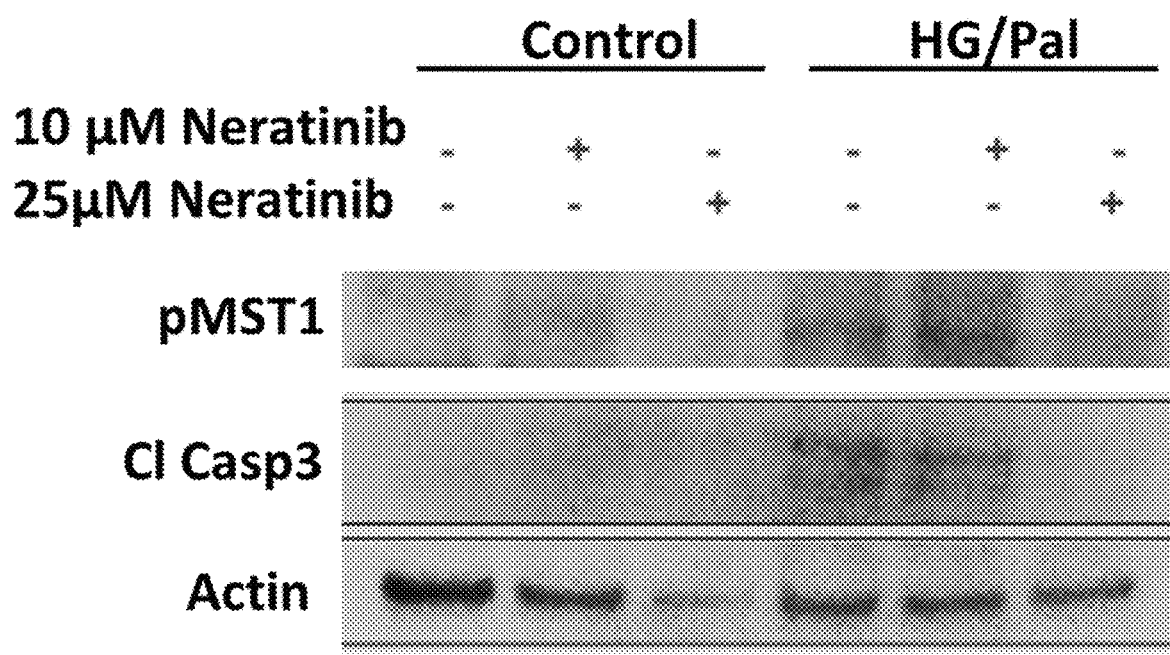
FIG. 8 shows anti-apoptotic activity of neratinib in beta cells.

Neratinib Inhibits High Glucose/Palmitate Induced Apoptotic Activity in Beta Cells Freshly isolated human islets from a single donor were exposed to high glucose and palmitate (HG/Pal) to induce apoptosis. Phosphorylated MST1 (pMST1) and cleaved caspase 3 (Cl Casp3) was readily induced under these conditions, indicating apoptotic activity was triggered by the treatment (FIG. 8, Lane 4). However, MST1 phosphorylation and induction of cleaved caspase 3 was inhibited by 25 μM neratinib, indicating neratinib anti-apoptotic activity (FIG. 8, Lane 6).

Example 152

Neratinib Inhibits Cytokine Induced Apoptotic Activity in Beta Cells

Figure 9:
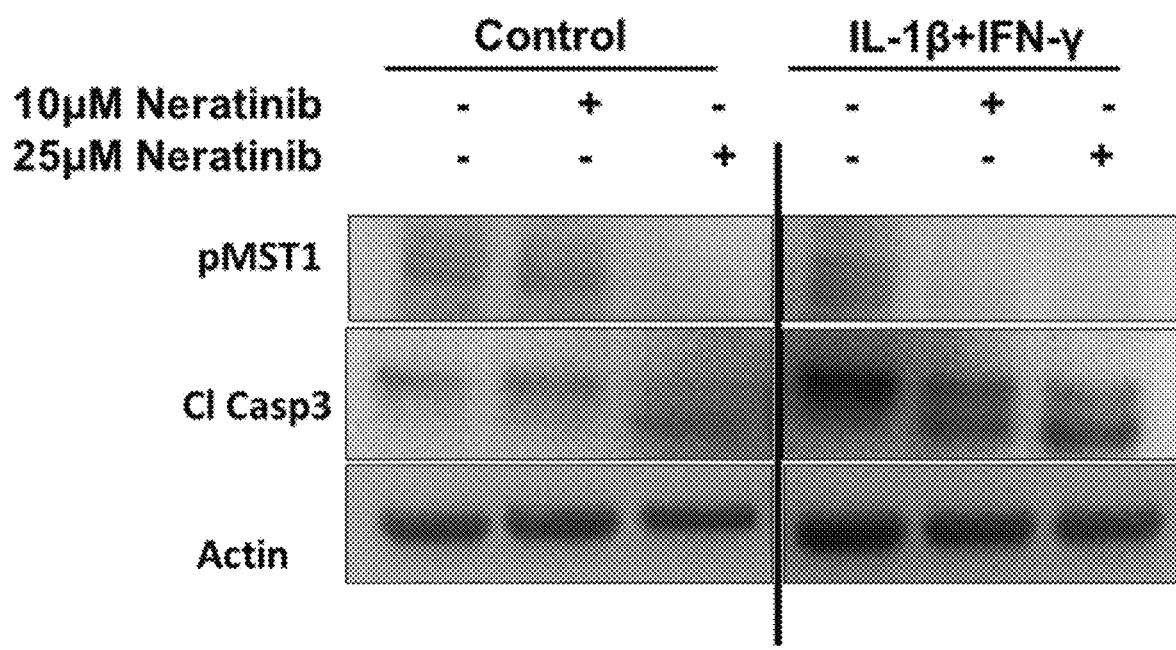
FIG. 9 shows anti-apoptotic activity of neratinib in beta cells.

Freshly isolated human islets from a single donor were stressed with a combination of proinflammatory cytokines interleukin 1 beta (IL-1β) and interferon gamma (IFN-γ). Islets exhibited an increase in MST1 phosphorylation and strong increase in Caspase 3 cleavage (Cl Casp3) (FIG. 9, lane 4). Both 10 μM and 25 μM neratinib treatment inhibited MST1 phosphorylation and Caspase 3 cleavage (FIG. 9, lanes 5 and 6).

What is claimed is:

1. A method of liver regeneration in a subject by binding MST1 comprising administering to the subject a compound of Formula (I) having the structure:

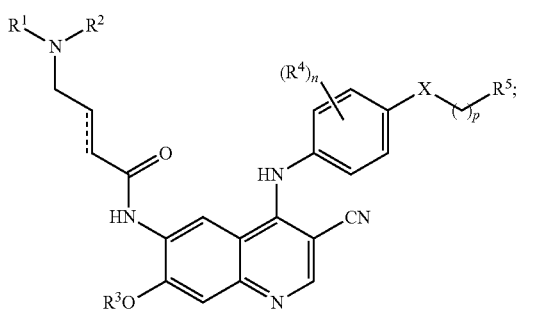

Formula (I)

wherein:
   --- is a single bond;
   X is —O—;
   $R^1$ and $R^2$ are each independently $C_{1-6}$alkyl; or $R^1$ and $R^2$ together with the nitrogen to which they are attached are combined to form a heterocycloalkyl ring;
   $R^3$ is $C_{1-6}$alkyl;
   each $R^4$ is independently halogen, $C_{1-6}$alkyl, $C_{1-6}$alkoxy, $C_{1-6}$haloalkyl, or —CN;
   $R^5$ is aryl or heteroaryl, wherein aryl and heteroaryl are unsubstituted or substituted by one or more substituents selected from halogen, $C_{1-6}$alkyl, $C_{1-6}$alkoxy, $C_{1-6}$haloalkyl, $C_{1-6}$haloalkoxy, —OH, —CH$_2$OH, —CN, —CO$_2$R$^6$, $C_{3-6}$cycloalkyl, and phenyl;

$R^6$ is H or $C_{1-6}$alkyl;
n is 0, 1, 2, or 3; and
p is 1, 2, or 3;
or a pharmaceutically acceptable salt or solvate thereof.

2. The method of claim 1, wherein p is 1.
3. The method of claim 2, wherein n is 1 or 2.
4. The method of claim 3, wherein each $R^4$ is independently halogen or $C_{1-6}$alkyl.
5. The method of claim 4 having the structure of Formula (Ia) or Formula (Ib):

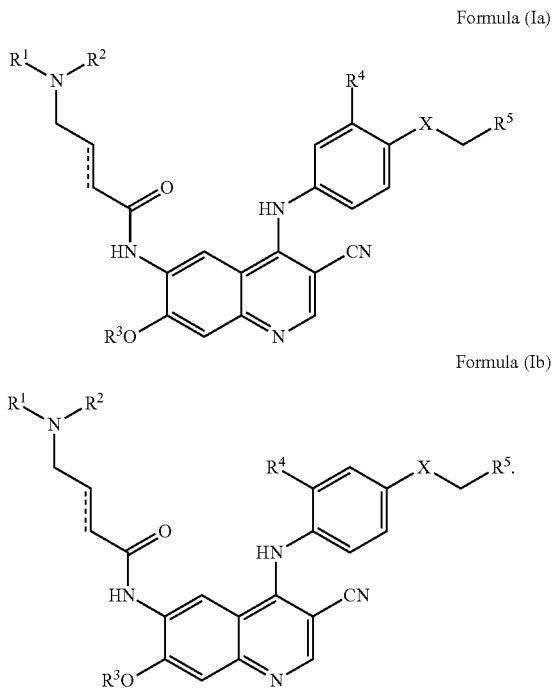

6. The method of claim 5, wherein $R^1$ and $R^2$ are each independently $C_{1-6}$alkyl.
7. The method of claim 6, wherein $R^1$ and $R^2$ are each —$CH_3$.
8. The method of claim 7, wherein $R^5$ is heteroaryl and wherein heteroaryl is unsubstituted or substituted by one or more substituents selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl.
9. The method of claim 8, wherein $R^5$ is unsubstituted pyridyl.
10. The method of claim 8, wherein $R^5$ is pyridyl substituted by one substituent selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl.
11. The method of claim 10, wherein $R^5$ is pyridyl substituted by $C_{1-6}$alkyl.
12. The method of claim 11, wherein $R^5$ is pyridyl substituted by —$CH_3$.
13. The method of claim 7, wherein $R^5$ is aryl and wherein aryl is unsubstituted or substituted by one or more substituents selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl.
14. The method of claim 13, wherein $R^5$ is unsubstituted phenyl.
15. The method of claim 13, wherein $R^5$ is phenyl and wherein phenyl is substituted by one substituent selected from halogen, $C_{1-6}$alkyl, $C_{1-6}$alkoxy, $C_{1-6}$haloalkyl, $C_{1-6}$haloalkoxy, —OH, —$CH_2OH$, —CN, —$CO_2R^6$, $C_{3-6}$cycloalkyl, and phenyl.
16. The method of claim 1, wherein $R^4$ is halogen.
17. The method of claim 16, wherein $R^4$ is —Cl.
18. The method of claim 1, wherein n is 1.
19. The method of claim 1, wherein the compound is selected from:

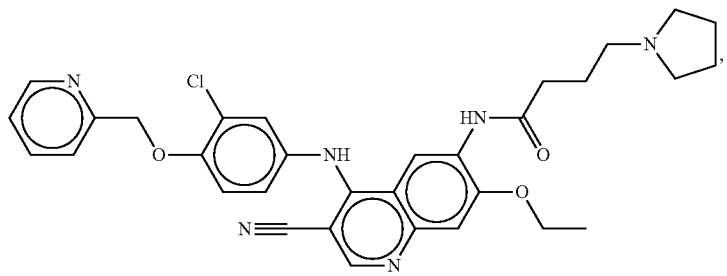

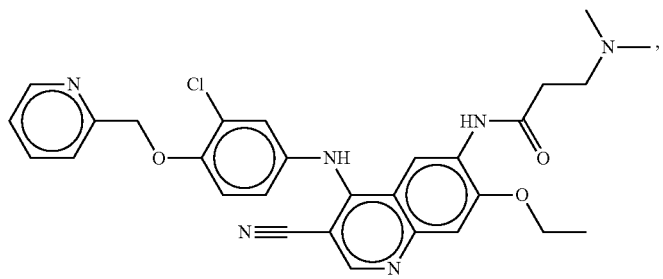

-continued
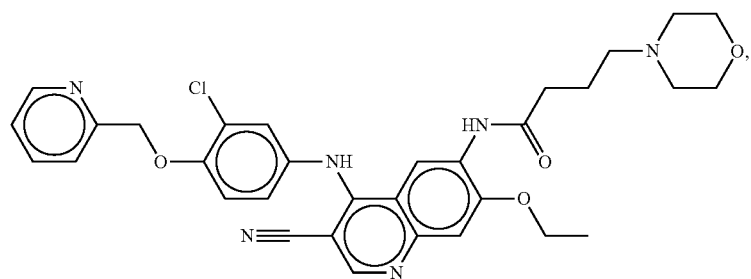
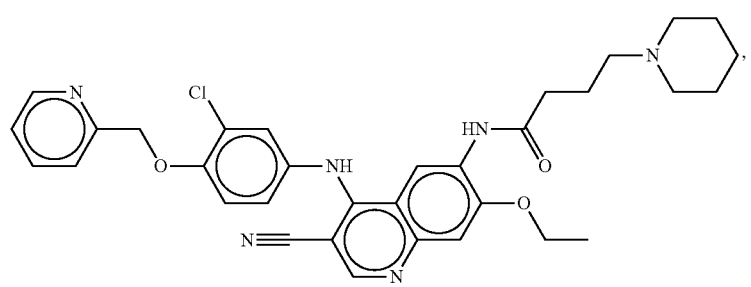
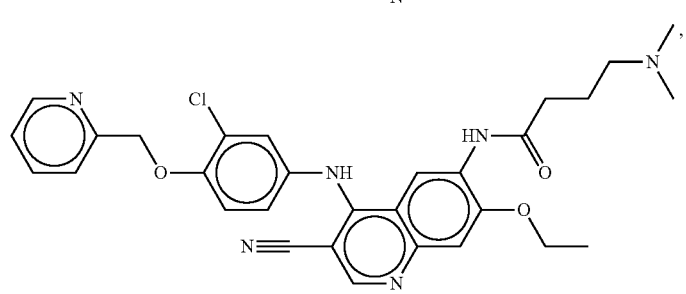
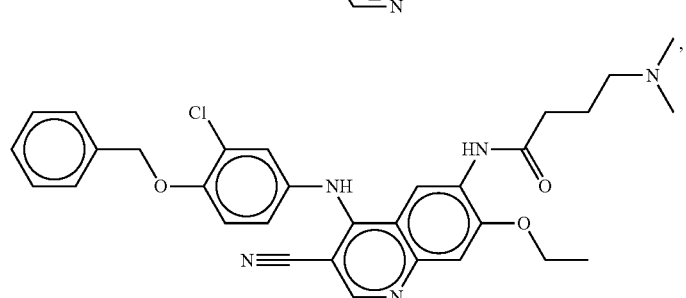
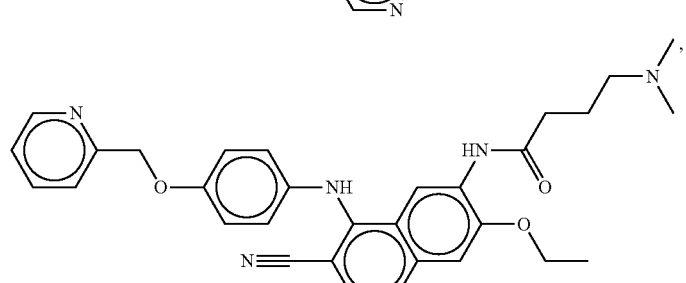
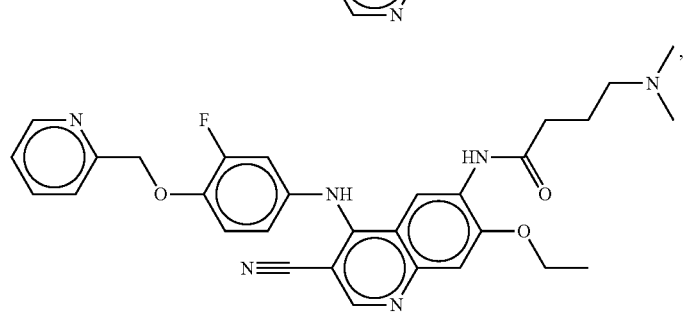

-continued
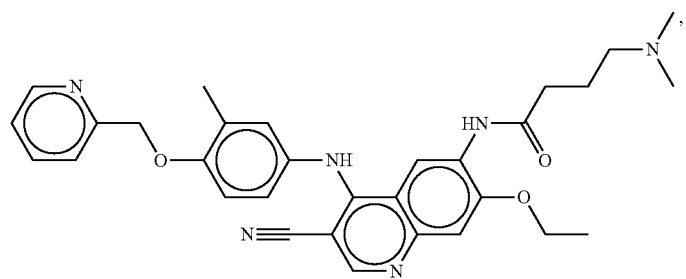
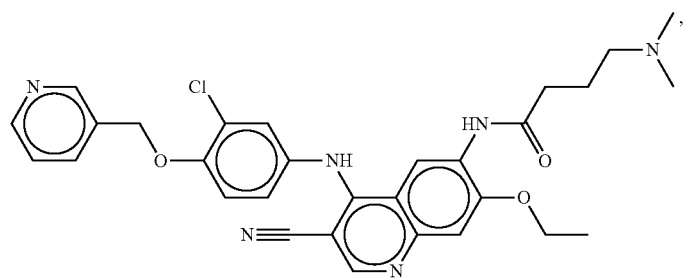
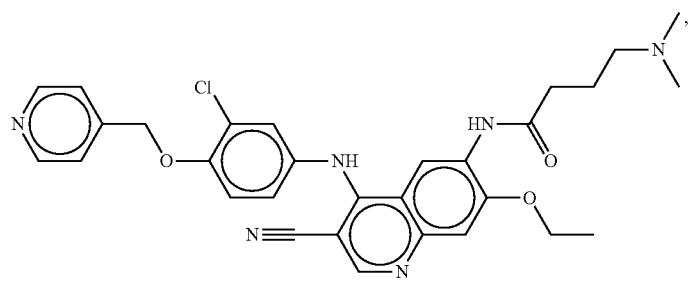
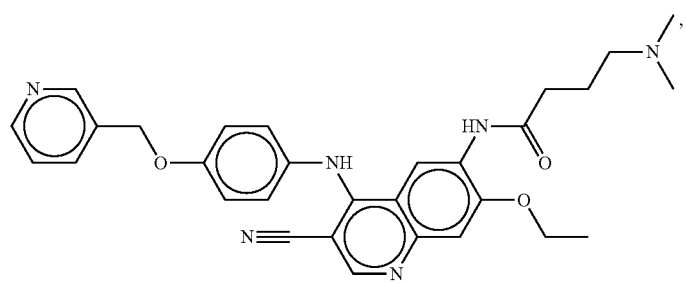
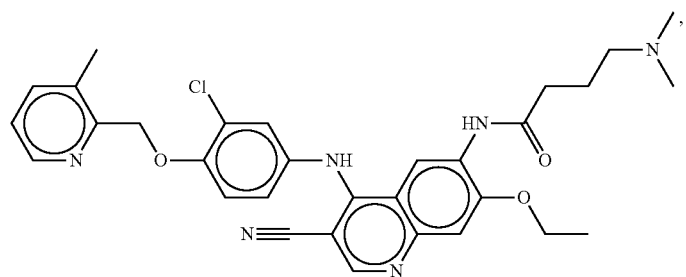
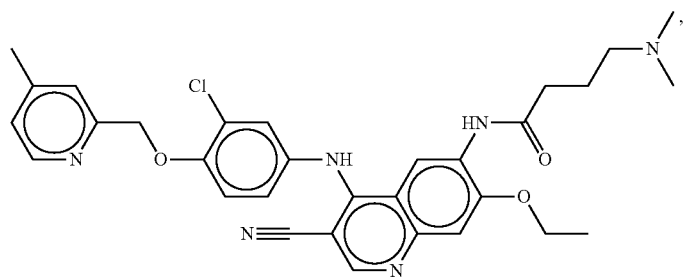

-continued
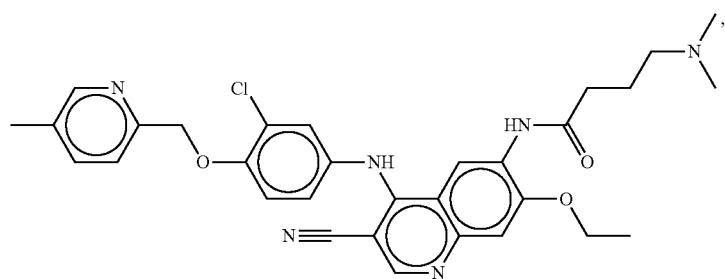
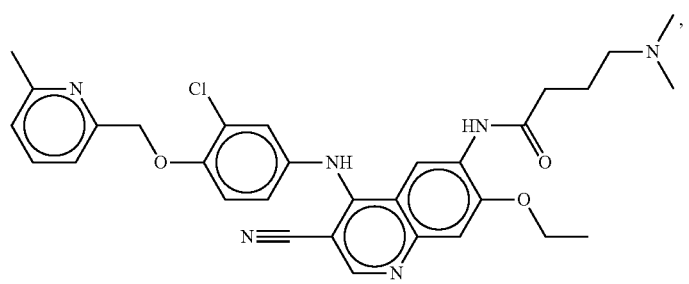
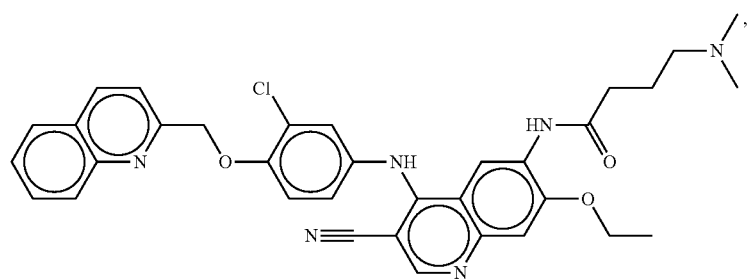
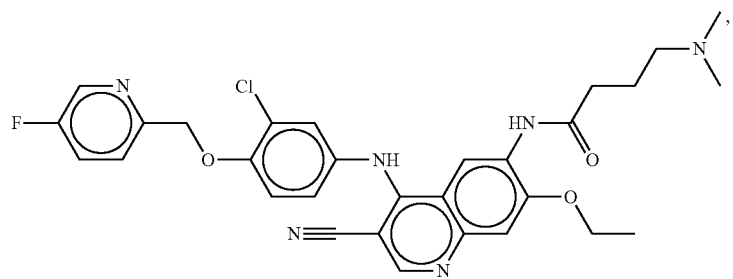
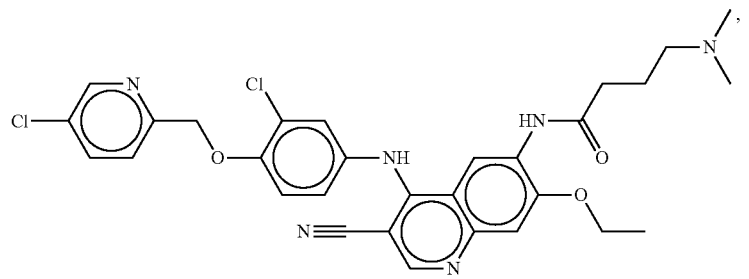
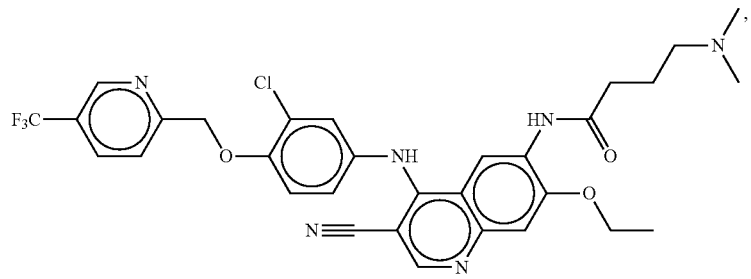

-continued
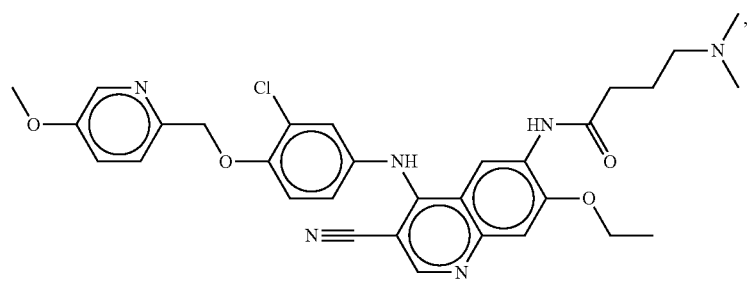
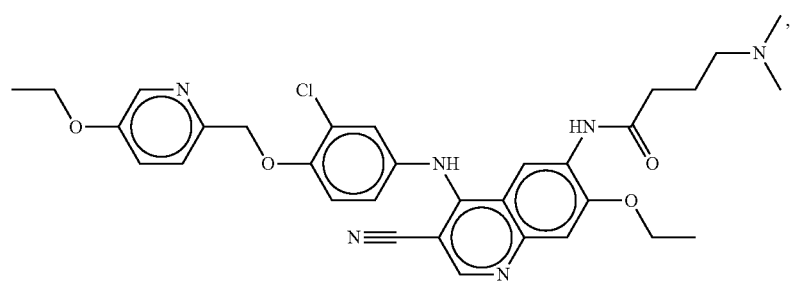
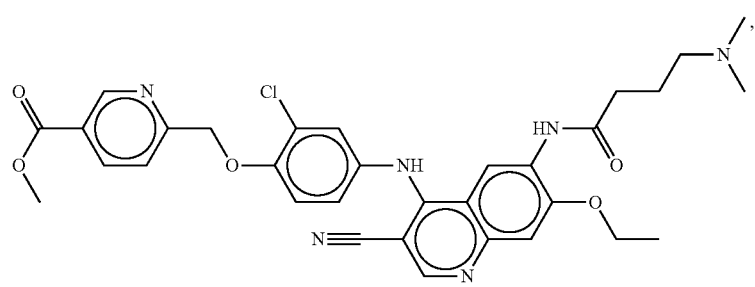
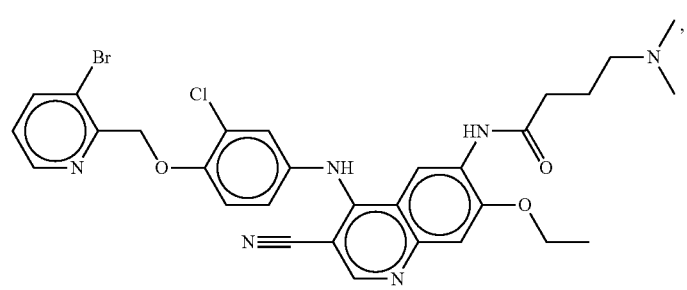
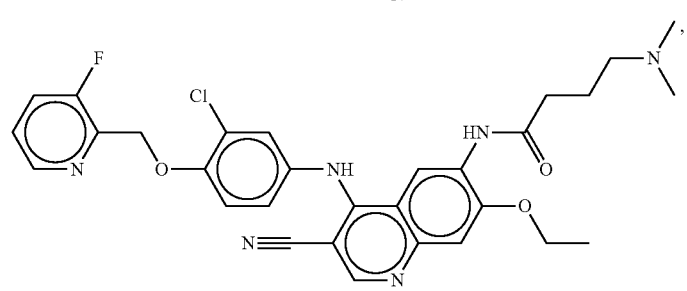
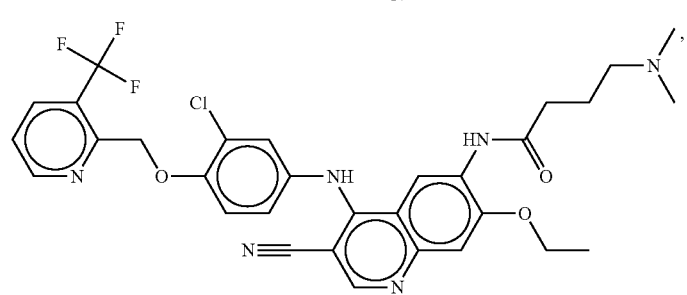

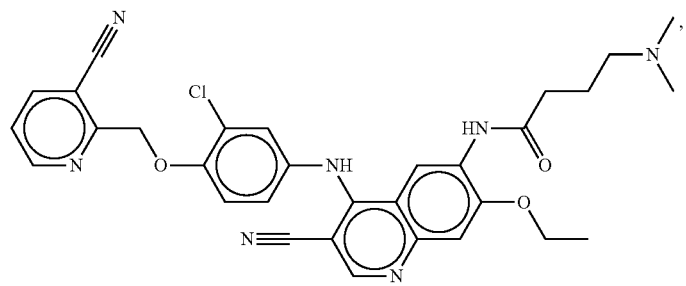
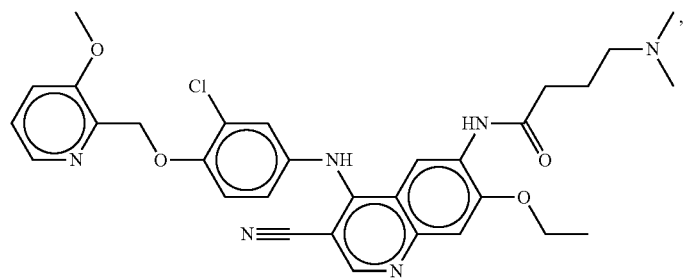
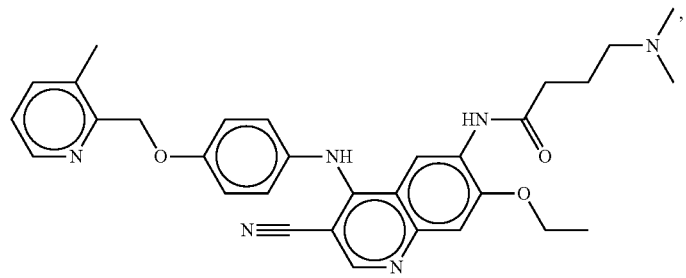
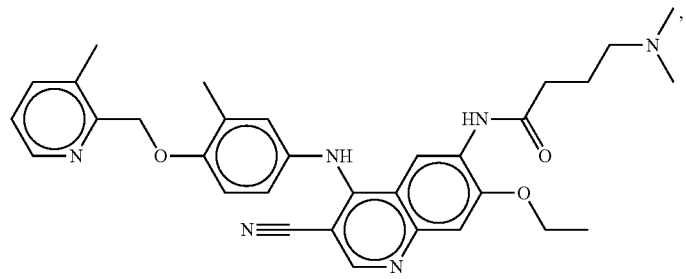
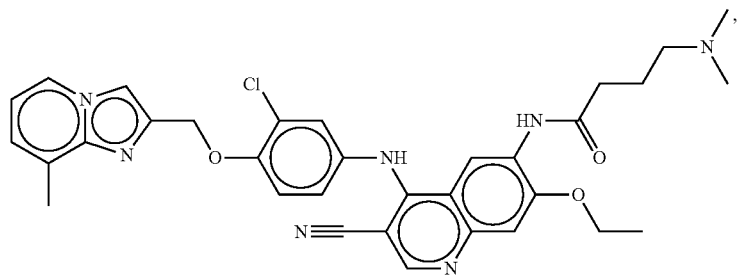
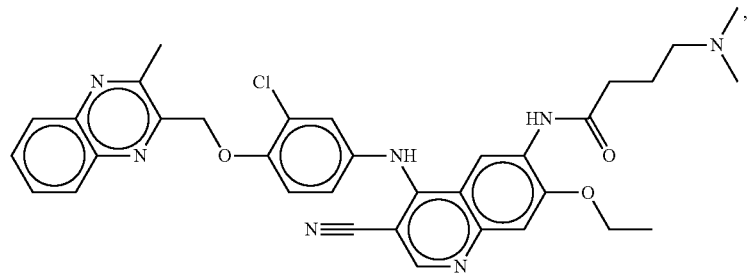

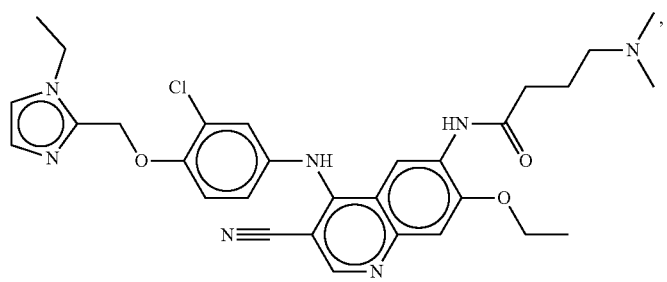
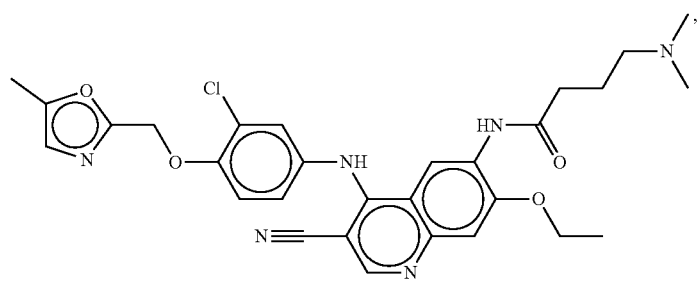
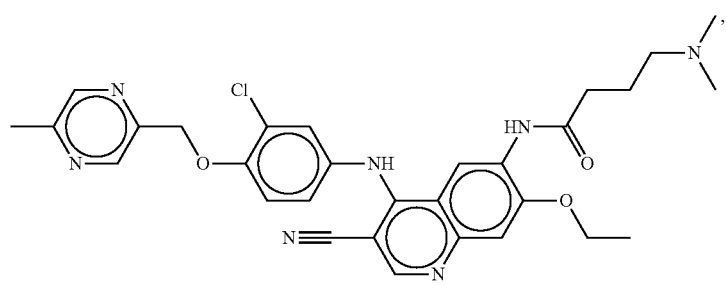
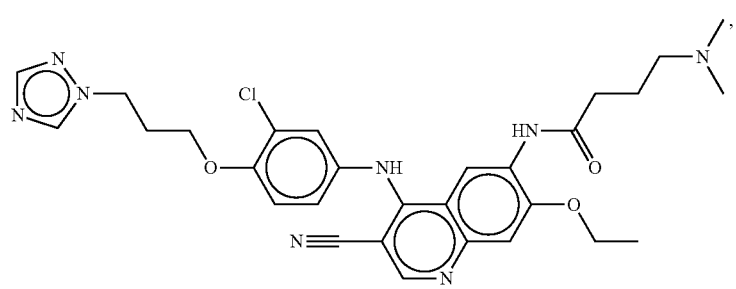
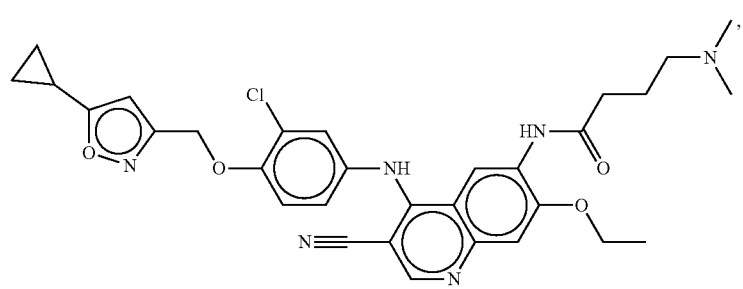
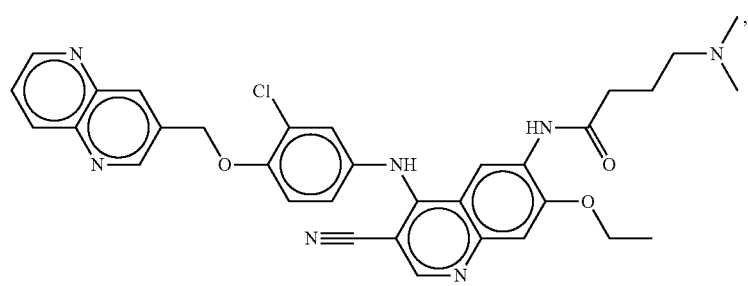

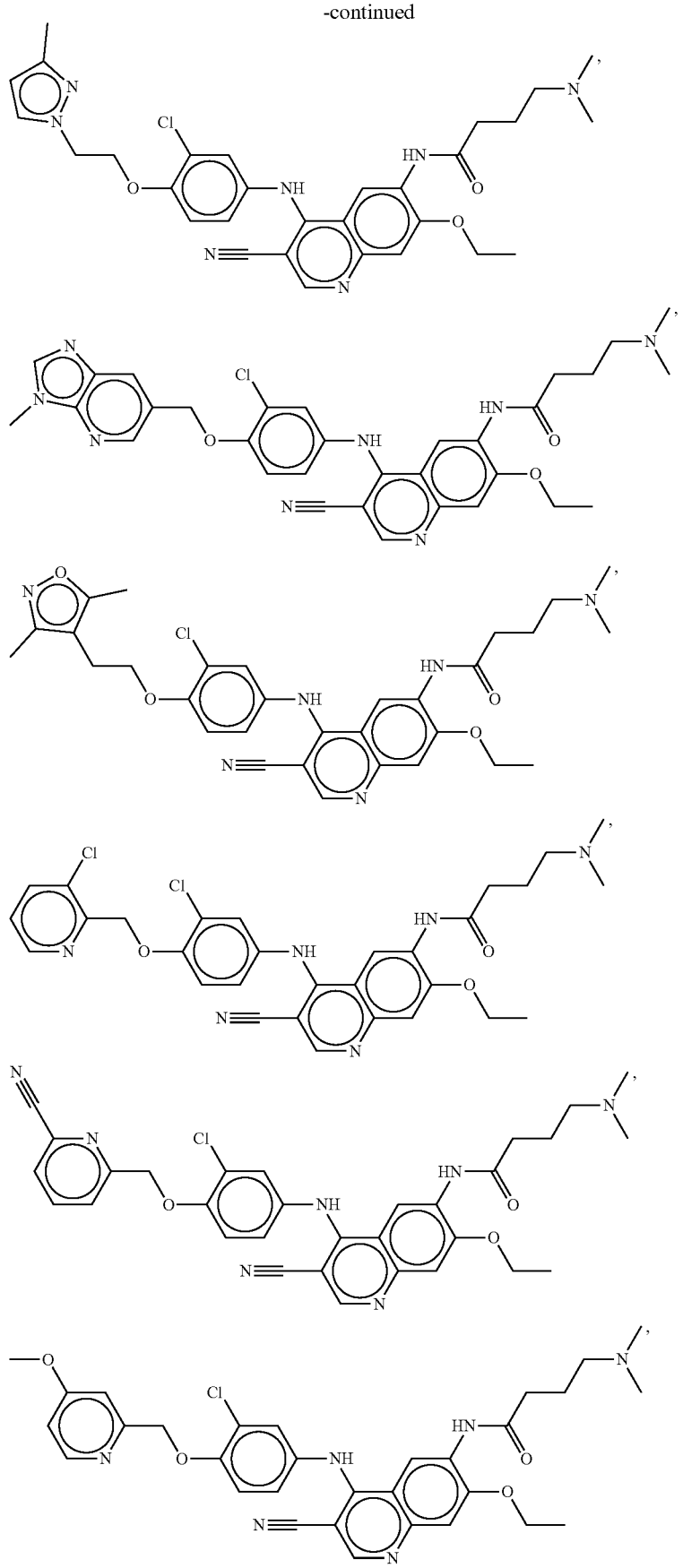

-continued
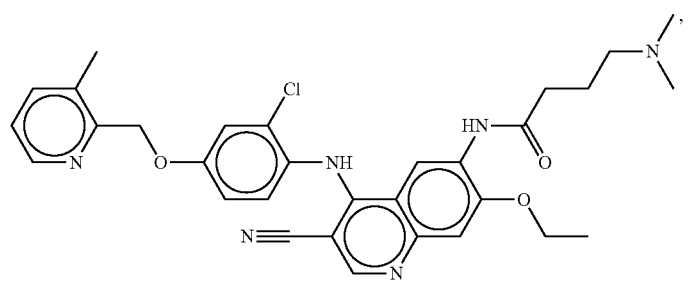
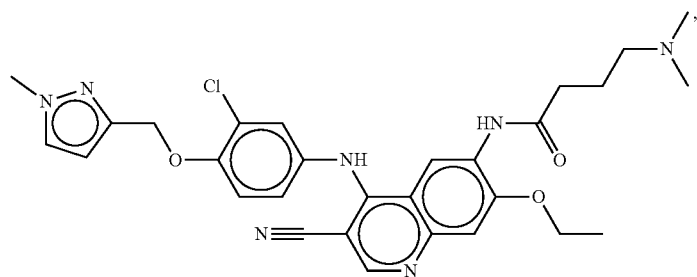
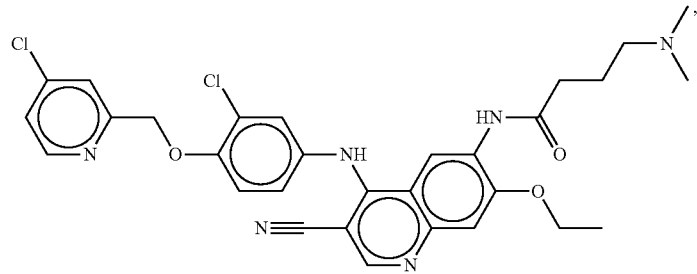
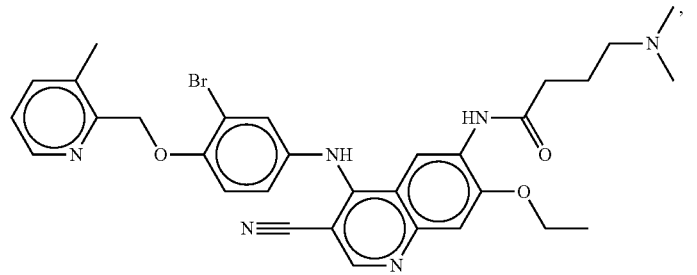
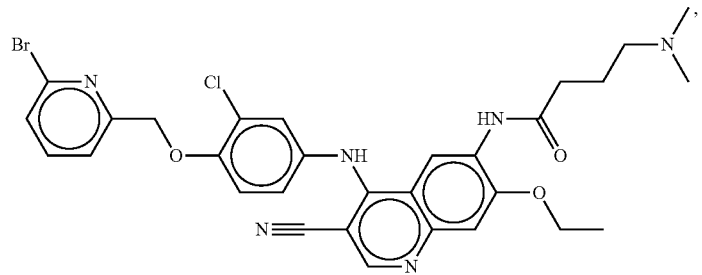
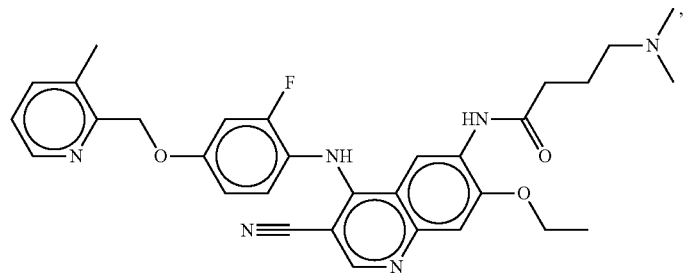

-continued
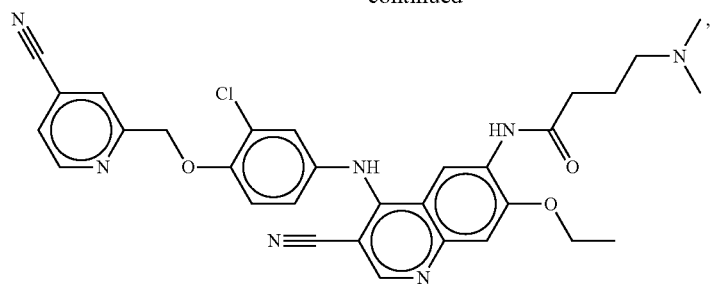
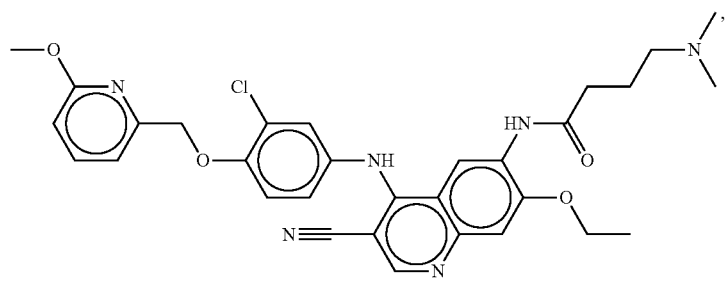
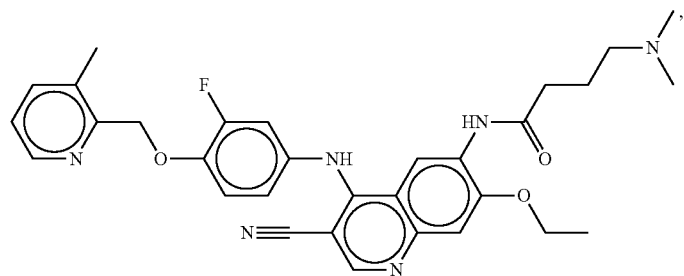
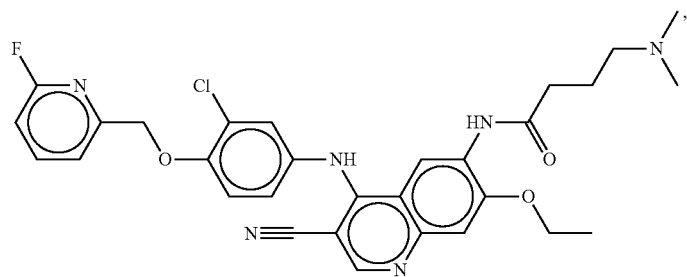
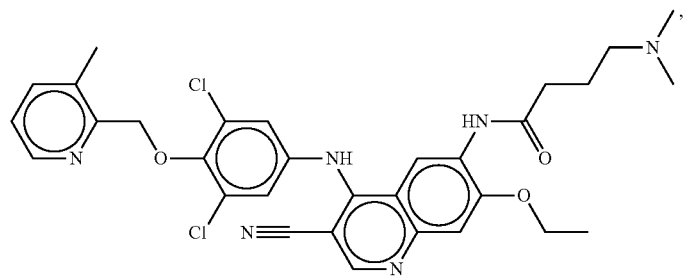
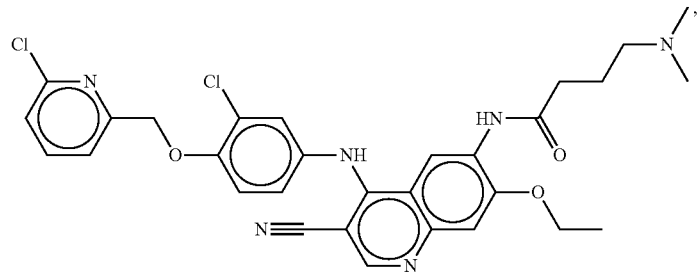

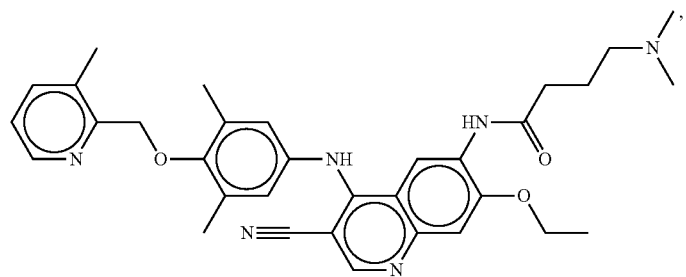
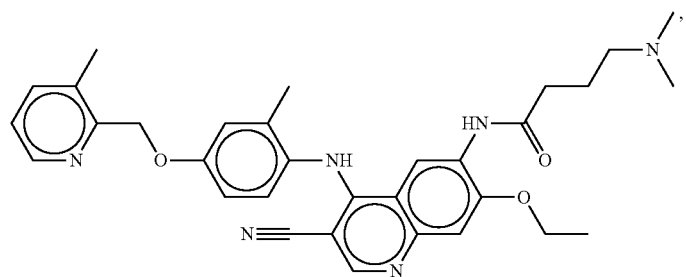
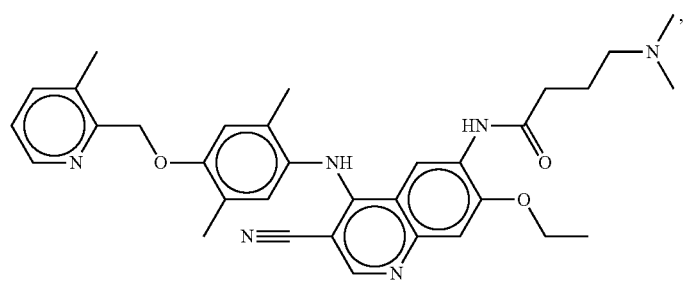
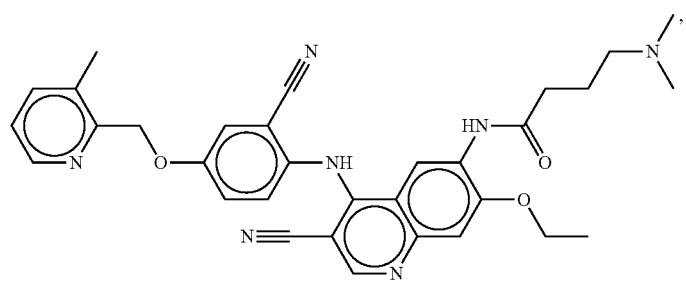
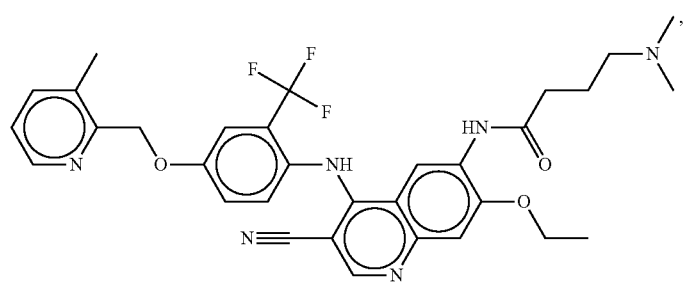
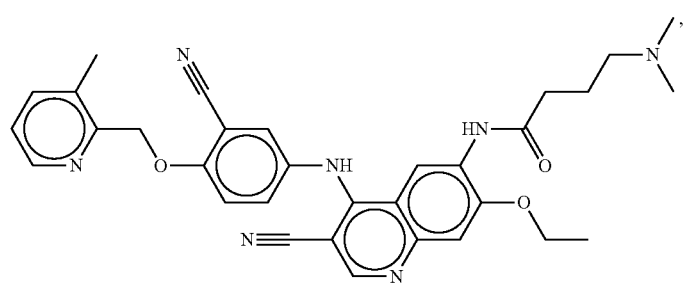

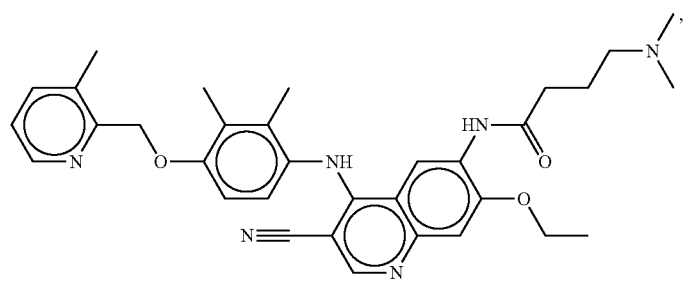
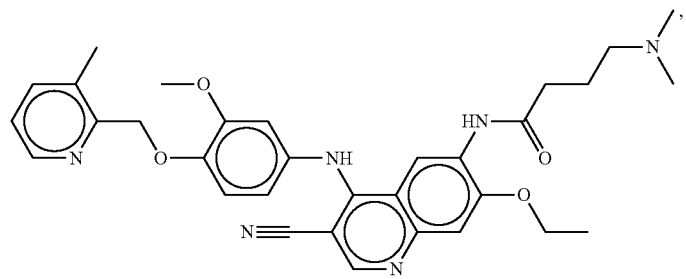
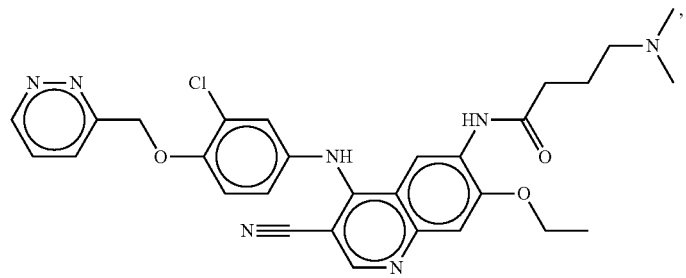
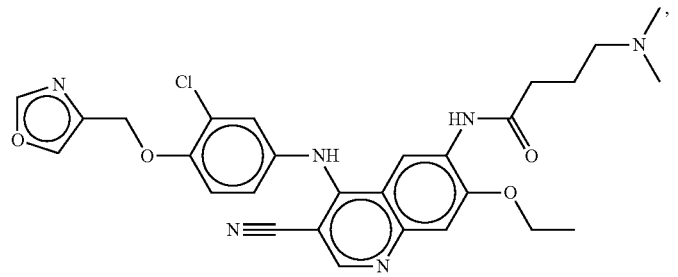
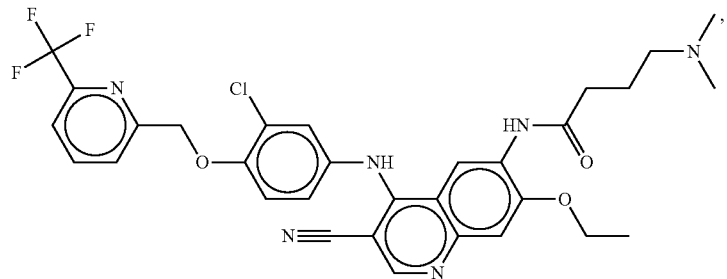
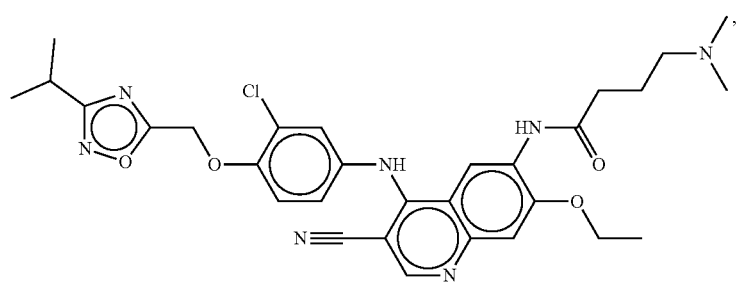

-continued
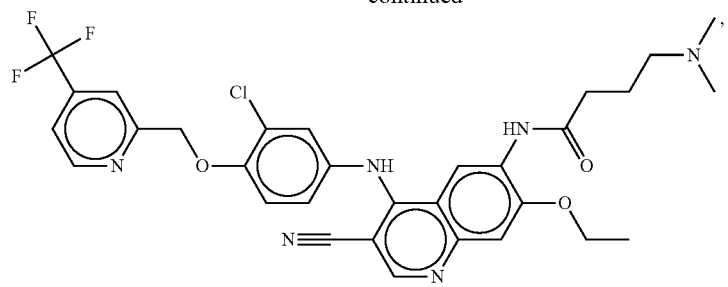
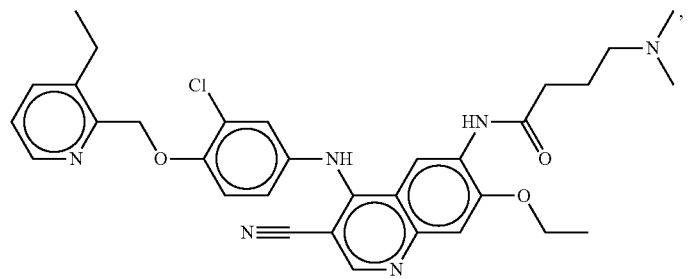
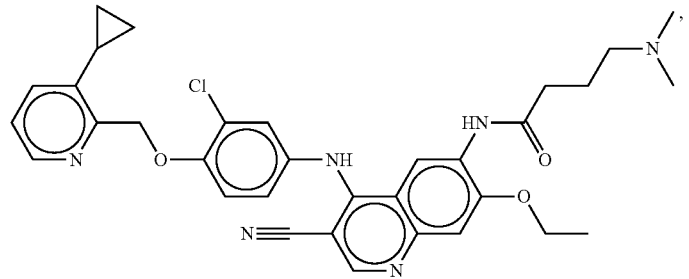
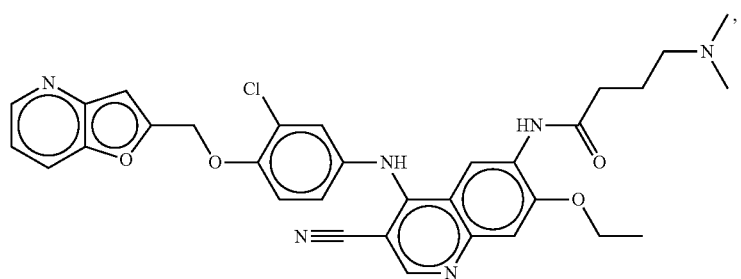
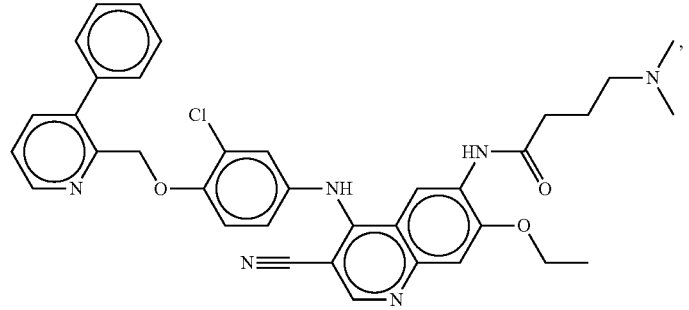
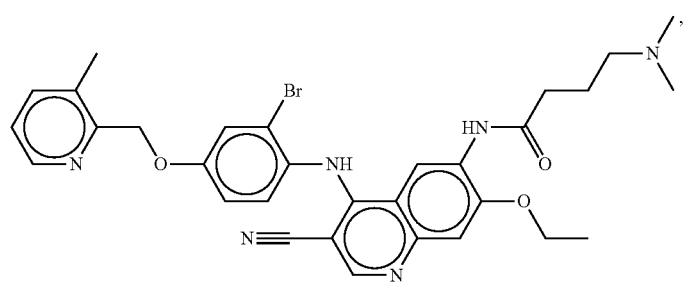

-continued
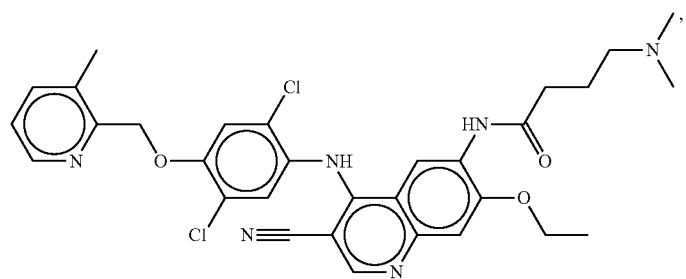
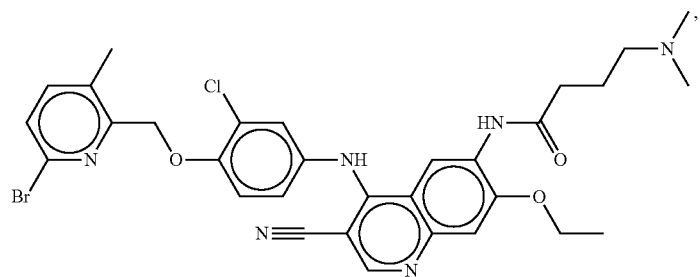
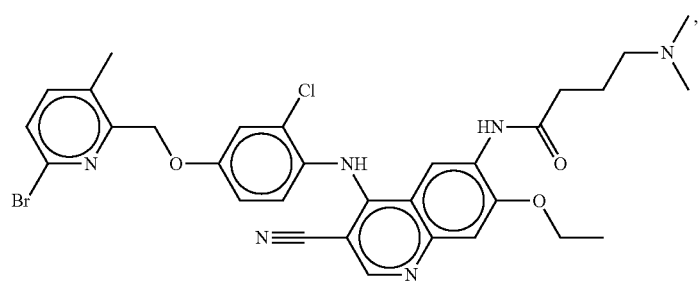
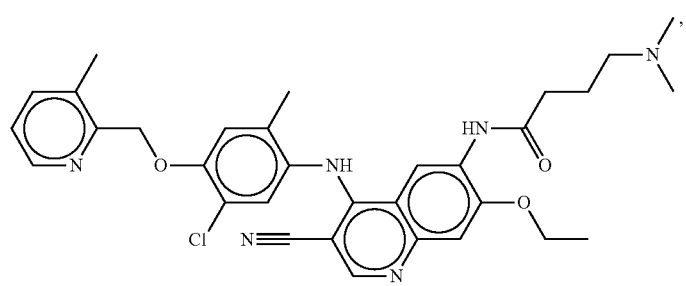
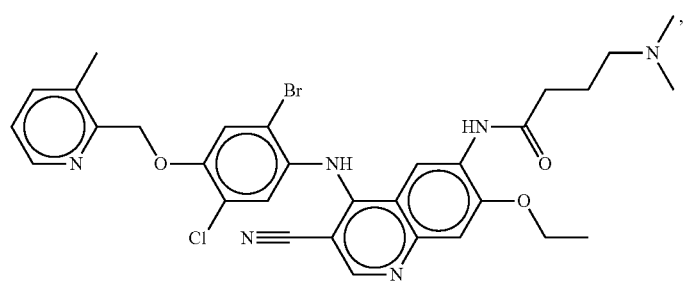
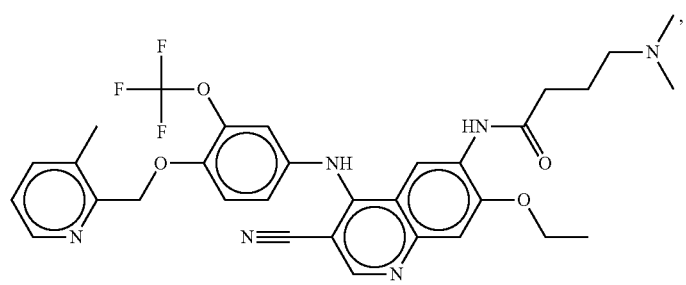

-continued
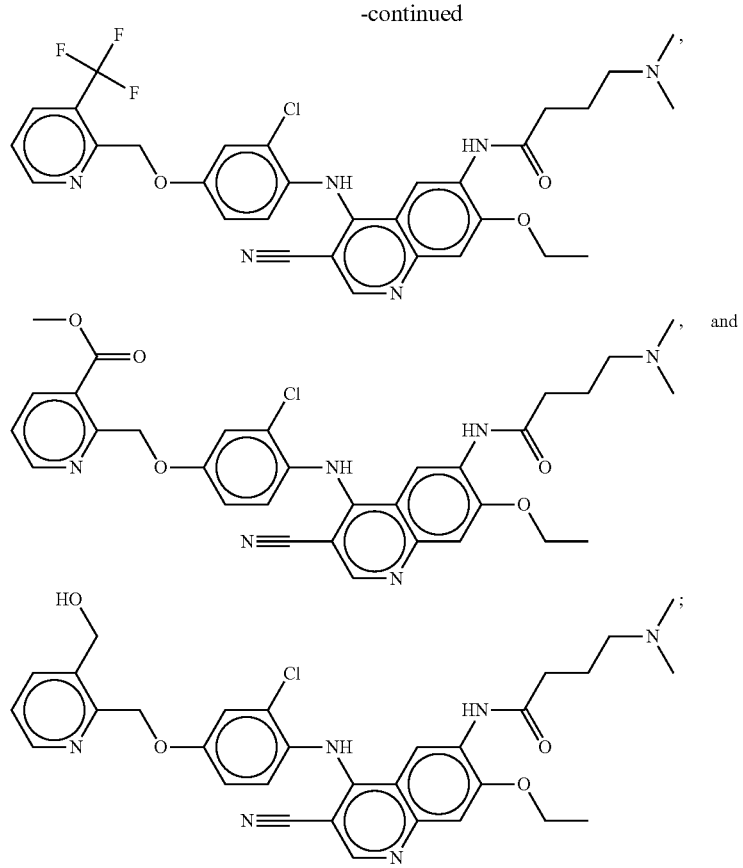
or a pharmaceutically acceptable salt or solvate thereof.
* * * * *